US012435323B2

(12) United States Patent
Alexander et al.

(10) Patent No.: US 12,435,323 B2
(45) Date of Patent: Oct. 7, 2025

(54) ENZYMES WITH RUVC DOMAINS

(71) Applicant: Metagenomi, Inc., Emeryville, CA (US)

(72) Inventors: Lisa Alexander, Albany, CA (US); Daniela S. A. Goltsman, Oakland, CA (US); Sarah Laperriere, Berkeley, CA (US); Morayma Temoche-Diaz, Oakland, CA (US)

(73) Assignee: Metagenomi, Inc., Emeryville, CA (US)

( * ) Notice: Subject to any disclaimer, the term of this patent is extended or adjusted under 35 U.S.C. 154(b) by 0 days.

(21) Appl. No.: 18/586,929

(22) Filed: Feb. 26, 2024

(65) Prior Publication Data

US 2024/0200047 A1 Jun. 20, 2024

Related U.S. Application Data

(63) Continuation of application No. PCT/US2022/041755, filed on Aug. 29, 2022.

(60) Provisional application No. 63/369,858, filed on Jul. 29, 2022, provisional application No. 63/322,944, filed on Mar. 23, 2022, provisional application No. 63/319,681, filed on Mar. 14, 2022, provisional application No. 63/316,895, filed on Mar. 4, 2022, provisional application No. 63/282,909, filed on Nov. 24, 2021, provisional application No. 63/252,956, filed on Oct. 6, 2021, provisional application No. 63/245,629, filed on Sep. 17, 2021, provisional application No. 63/237,791, filed on Aug. 27, 2021.

(51) Int. Cl.
*C12N 9/22* (2006.01)
*C12N 15/10* (2006.01)
*C12N 15/11* (2006.01)

(52) U.S. Cl.
CPC ............ *C12N 9/22* (2013.01); *C12N 15/102* (2013.01); *C12N 15/11* (2013.01); *C12N 2310/20* (2017.05)

(58) Field of Classification Search
CPC ........................................................ C12N 9/22
See application file for complete search history.

(56) References Cited

U.S. PATENT DOCUMENTS

| | | | |
|---|---|---|---|
| 5,858,988 | A | 1/1999 | Wang |
| 6,291,438 | B1 | 9/2001 | Wang |
| 8,889,418 | B2 | 11/2014 | Zhang et al. |
| 10,011,849 | B1 | 7/2018 | Gill et al. |
| 10,253,365 | B1 | 4/2019 | Doudna et al. |
| 10,392,607 | B2 | 8/2019 | Sternberg et al. |
| 10,913,941 | B2 | 2/2021 | Thomas et al. |
| 10,982,200 | B2 | 4/2021 | Thomas et al. |
| 11,946,039 | B2 | 4/2024 | Thomas et al. |
| 12,024,727 | B2 | 7/2024 | Thomas et al. |
| 2014/0186919 | A1 | 7/2014 | Zhang et al. |
| 2014/0186958 | A1 | 7/2014 | Zhang et al. |
| 2014/0273234 | A1 | 9/2014 | Zhang et al. |
| 2015/0045546 | A1 | 2/2015 | Siksnys et al. |
| 2016/0138046 | A1 | 5/2016 | Wu et al. |
| 2016/0289700 | A1 | 10/2016 | Barrangou et al. |
| 2016/0362667 | A1 | 12/2016 | Donohoue et al. |
| 2018/0312824 | A1 | 11/2018 | Zhang et al. |
| 2018/0371498 | A1 | 12/2018 | Gill et al. |
| 2019/0010471 | A1 | 1/2019 | Zhang et al. |
| 2019/0062735 | A1 | 2/2019 | Welstead et al. |
| 2019/0249200 | A1 | 8/2019 | Seebeck et al. |
| 2019/0264232 | A1 | 8/2019 | Hou et al. |
| 2020/0032240 | A1 | 1/2020 | Wang et al. |
| 2020/0080067 | A1 | 3/2020 | Zhang et al. |
| 2020/0263165 | A1 | 8/2020 | Bendezu et al. |
| 2020/0302240 | A1 | 9/2020 | Murata et al. |
| 2020/0332273 | A1 | 10/2020 | Thomas et al. |
| 2022/0033791 | A1 | 2/2022 | Thomas et al. |
| 2022/0220460 | A1 | 7/2022 | Thomas et al. |
| 2022/0298494 | A1 | 9/2022 | Thomas et al. |
| 2022/0364067 | A1 | 11/2022 | Lin et al. |
| 2022/0403357 | A1 | 12/2022 | Zhang et al. |
| 2024/0110167 | A1 | 4/2024 | Thomas et al. |
| 2024/0117330 | A1 | 4/2024 | Thomas et al. |
| 2024/0209332 | A1 | 6/2024 | Thomas et al. |
| 2024/0309356 | A1 | 9/2024 | Thomas et al. |
| 2024/0344045 | A1 | 10/2024 | Thomas et al. |

FOREIGN PATENT DOCUMENTS

| | | | |
|---|---|---|---|
| CA | 3091267 | A1 | 8/2019 |
| CN | 104520429 | A | 4/2015 |
| CN | 105142669 | A | 12/2015 |
| CN | 105209621 | A | 12/2015 |
| CN | 112126661 | A | 12/2020 |
| EP | 3141604 | A1 | 3/2017 |
| EP | 3617311 | A1 | 3/2020 |
| EP | 3699268 | A1 | 8/2020 |
| EP | 3854877 | A1 | 7/2021 |

(Continued)

OTHER PUBLICATIONS

Adronescu, M. et al., "Efficient Parameter Estimation for RNA Secondary Structure Prediction", Bioinformatics, 2007, vol. 23, pp. i19-i28.

(Continued)

*Primary Examiner* — Suzanne M Noakes

(74) *Attorney, Agent, or Firm* — Wilson Sonsini Goodrich & Rosati

(57) ABSTRACT

The present disclosure provides for endonuclease enzymes having distinguishing domain features, as well as methods of using such enzymes or variants thereof.

30 Claims, 36 Drawing Sheets

Specification includes a Sequence Listing.

(56) References Cited

FOREIGN PATENT DOCUMENTS

| | | | |
|---|---|---|---|
| EP | 4308699 | A1 | 1/2024 |
| JP | 2019507599 | A | 3/2019 |
| JP | 2019534695 | A | 12/2019 |
| JP | 2022520428 | A | 3/2022 |
| WO | WO-2015066119 | A1 | 5/2015 |
| WO | WO-2015161276 | A2 | 10/2015 |
| WO | WO-2016073990 | A2 | 5/2016 |
| WO | WO-2016141224 | A1 | 9/2016 |
| WO | WO-2016160721 | A1 | 10/2016 |
| WO | WO-2016183041 | A2 | 11/2016 |
| WO | WO-2016186953 | A1 | 11/2016 |
| WO | WO-2016196655 | A1 | 12/2016 |
| WO | WO-2017093969 | A1 | 6/2017 |
| WO | WO-2017152015 | A1 | 9/2017 |
| WO | WO-2017155714 | A1 | 9/2017 |
| WO | WO-2017193107 | A2 | 11/2017 |
| WO | WO-2018035250 | A1 | 2/2018 |
| WO | WO-2018041120 | A1 | 3/2018 |
| WO | WO-2018064352 | A1 | 4/2018 |
| WO | WO-2018064594 | A2 | 4/2018 |
| WO | WO-2018073393 | A2 | 4/2018 |
| WO | WO-2018074979 | A1 | 4/2018 |
| WO | WO-2018129346 | A1 | 7/2018 |
| WO | WO-2018172556 | A1 | 9/2018 |
| WO | WO-2018209712 | A1 | 11/2018 |
| WO | WO-2019094791 | A2 | 5/2019 |
| WO | WO-2019097305 | A2 | 5/2019 |
| WO | WO-2019118516 | A1 | 6/2019 |
| WO | WO-2019161290 | A1 | 8/2019 |
| WO | WO-2019165168 | A1 | 8/2019 |
| WO | WO-2019178421 | A1 | 9/2019 |
| WO | WO-2019195492 | A1 | 10/2019 |
| WO | WO-2019200306 | A1 | 10/2019 |
| WO | WO-2020041120 | A1 | 2/2020 |
| WO | WO-2020055941 | A1 | 3/2020 |
| WO | WO-2020057486 | A1 | 3/2020 |
| WO | WO-2020081613 | A1 | 4/2020 |
| WO | WO-2020084580 | A1 | 4/2020 |
| WO | WO-2020150534 | A2 | 7/2020 |
| WO | WO-2020168122 | A1 | 8/2020 |
| WO | WO-2020168234 | A1 | 8/2020 |
| WO | WO-2020168291 | A1 | 8/2020 |
| WO | WO-2020168300 | A1 | 8/2020 |
| WO | WO-2020236967 | A1 | 11/2020 |
| WO | WO-2021097118 | A1 | 5/2021 |
| WO | WO-2021202559 | A1 | 10/2021 |
| WO | WO-2021202568 | A1 | 10/2021 |
| WO | WO-2021226363 | A1 | 11/2021 |
| WO | WO-2021226369 | A1 | 11/2021 |
| WO | WO-2022056324 | A1 | 3/2022 |
| WO | WO-2022087494 | A1 | 4/2022 |
| WO | WO-2022132765 | A1 | 6/2022 |
| WO | WO-2022159758 | A1 | 7/2022 |
| WO | WO-2022232638 | A2 | 11/2022 |
| WO | WO-2023028348 | A1 | 3/2023 |
| WO | WO-2023097262 | A1 | 6/2023 |
| WO | WO-2023097282 | A1 | 6/2023 |

OTHER PUBLICATIONS

Co-pending U.S. Appl. No. 18/435,779, inventors Thomas; Brian et al., filed Feb. 7, 2024.

Co-pending U.S. Appl. No. 18/668,543, inventors Thomas; Brian C. et al., filed May 20, 2024.

Corley , et al. How RNA-Binding Proteins Interact with RNA: Molecules and Mechanisms. Molecular Cell. 78(1):9-29 (2020).

GenPept Accession No. CAH11307. Version No. CAH11307.1. hypothetical protein lpp0160 [*Legionella pneumophila* str. *Paris*]. Record created Oct. 3, 2004. pp. 1-2. Retrieved Jun. 10, 2024 at URL: https://www.ncbi.nlm.nih.gov/protein/CAH11307.1.

GenPept Accession No. WP_127108862. Version No. WP_127108862.1. type II-B CRISPR-associated RNA-guided endonuclease Cas9/Csx12 [*Legionella* sp. km535]. Record created Jan. 6, 2019. pp. 1-2. Retrieved Jun. 10, 2024 at URL: https://www.ncbi.nlm.nih.gov/protein/WP_127108862.1.

Paix, et al. Precision genome editing using synthesis-dependent repair of Cas9-induced DNA breaks. Proceedings of the National Academy of Sciences of the United States of America 114,50:E10745-E10754 (2017).

Shmakov et al., Diversity and evolution of class 2 CRISPR-Cas systems. Nat Rev. Microbiol. 15(3): 169-182 (2017).

Singh, et al. Protein Engineering Approaches in the Post-Genomic Era. Current Protein and Peptide Science 18:1-11 (2017).

UniProtKB Accession No. A0A3B9GP868. CRISPR-associated endonuclease Cas9. Record created Jan. 16, 2019. p. 1, Retrieved Jun. 10, 2024 at URL: https://www.uniprot.org/uniprotkb/A0A3B9GP86/entry.

U.S. Appl. No. 17/193,173 Notice of Allowance dated Feb. 21, 2024.

U.S. Appl. No. 17/431,135 Office Action dated Jun. 4, 2024.

Xu, Daohua. Tigit Cas9-KO Strategy. GenPharmatech Co, Ltd., Retrieved at URL: https://oss.gempharmatech.com/upload/file/20240324/T012735.Tigit%20Cas9-KO%20%20Strategy-EN.pdf, 11 pages (2019).

Xu, et al. Efficient genome engineering in eukaryotes using Cas9 from *Streptococcus thermophilus*. Cellular and Molecular Life Sciences 72(2):383-399 (2014).

Zhang et al. Propagated Perturbations from a Peripheral Mutation Show Interactions Supporting WW Domain Thermostability. Structure 26(11):1474-1485 (2018).

Zhou, X.M. et al. Intrinsic Expression of Immune Checkpoint Molecule TIGIT Could Help Tumor Growth in vivo by Suppressing the Function of NK and CD8+ T Cells. Front. Immunol. vol. 9, Article 2821: 1-11 (2018).

Altae-Tran et al.: The widespread IS200/IS605 transposon family encodes diverse programmable RNA-guided endonucleases. Science. 374(6563):57-65 doi:10.1126/science.abj6856 (2021).

Andronescu et al. Efficient Parameter Estimation for RNA Secondary Structure Prediction. Bioinformatics 23(13):i19-28 (2007).

Bitard-Feildel, T. et al., Order in Disorder as Observed by the Hydrophobic Cluster Analysis of Protein Sequences, Proteomics, 2018, vol. 18, E1800054, pp. 1-12.

Brinkman et al.: Easy quantitative assessment of genome editing by sequence trace decomposition. Nucleic Acids Research 42(22):e168 , pp. 1-8 doi: 10.1093/nar/gku936 (2014).

Burstein et al.: New CRISPR-Cas systems from uncultivated microbes. Nature. 542(7640):237-241 (2017).

Carugo, O., Amino Acid Composition and Protein Dimension, Protein Science, Oct. 2008, vol. 17, No. 12, pp. 2187-2191.

Co-pending U.S. Appl. No. 18/053,232, inventors Thomas; Brian et al., filed Nov. 7, 2022.

CtSKENNERTON: Mining CRISPRs in Environmental Datasets: Minced. GitHub URL:www.github.com/ctSkennerton/minced [1-4](2019).

Ding et al.: Recent Advances in Genome Editing Using CRISPR/Cas9. Front Plant Sci. 7:703:1-12 doi: 10.3389/fpls.2016.00703 (2016).

Dyson, H.J., Roles of intrinsic disorder in protein-nucleic acid interactions, Mol Biosyst, 2011, vol. 8, No. 1, pp. 97-104.

Fang et al.: CRISPR/Cas9-mediated Genome Editing Technology. Progress in Biochemistry and Biophysics, 40(8):691-702 [with English Machine Translation] (2013).

Gasiunas et al., A catalogue of biochemically diverse CRISPR-Cas9 orthologs. Nat Commun. 11: 5512, pp. 1-10 (2020).

Gasiunas, et al., Cas9-crRNA ribonucleoprotein complex mediates specific DNA cleavage for adaptive immunity in bacteria. Proceedings of the National Academy of Sciences of the United States of America 109:E2579-E2586 (2012).

Goltsman et al.: Compact Cas9d and HEARO enzymes for genome editing discovered from uncultivated microbes. Nat Commun. 13(1):7602:1-11. doi: 10.1038/s41467-022-35257-7 (2022).

Guo et al.: Off-target effects and optimization strategies of CRISPR/Cas9 technology. Progress in Biochemistry and Biophysics, 45(8):798-807 [with English Machine Translation] (2018).

(56) References Cited

OTHER PUBLICATIONS

Harms, M. et al., Analyzing protein structure and function using ancestral gene reconstruction, Current Opinion in Structural Biology, 2010, vol. 20, No. 6, pp. 360-366.
Harrington, Lucas, et al., Programmed DNA Destruction by Miniature CRISPR-Cas14 Enzymes. Science 362(6416):839-842 (2018).
Harris, K.A et al., Large Noncoding RNAs in Bacteria, Microbiol Spectr, 2018, vol. 6, No. 4, pp. 1-18.
Hayashi et al.: Efficient viral delivery of Cas9 into human safe harbor. Scientific Reports 10(1):21474:1-14 doi:10.1038/s41598-020-78450-8 (2020).
Herdewijn: Heterocyclic modifications of oligonucleotides and antisense technology. Antisense & Nucleic Acid Drug Dev 10:297-310 (2000).
Huber et al. Orchestrating High-Throughput Genomic Analysis With Bioconductor. Nat Methods 12(2):115-21 (2015).
Jiang, F., et al., CRISPR—Cas9 Structures and Mechanisms, Annual Reviews Biophys., (2017), 46:505-529.
Jinek, Martin, et al., A programmable dual-RNA-guided DNA endonuclease in adaptive bacterial immunity. Science 337(6096):816-821 (2012).
Kapitonov et al.: ISC, a Novel Group of Bacterial and Archaeal DNA Transposons That Encode Cas9 Homologs. J Bacteriol. 198(5):797-807 doi:10.1128/JB.00783-15 (2015).
Karvelis et al. Methods for Decoding Cas9 Protospacer Adjacent Motif (PAM) Sequences: A Brief Overview. Methods 121-122:3-8 (2017).
Katoh, K. et al., MAFFT Multiple Sequence Alignment Software Version 7: Improvements in Performance and Usability, Molecular Biology and Evolution, 2013, vol. 30, No. 4, pp. 772-780.
Koonin et al. (2017) Diversity, classification and evolution of CRISPR-Cas systems. Current Opinion in Microbiology, 37:67-78 (Year : 2017).
Madshus, I.H . . . Regulation of intracellular pH in eukaryotic cells, Biochemical Journal, 1988, vol. 250, No. 1, pp. 1-8.
Makarova et al. Evolutionary classification of CRISPR-Cas systems: a burst of class 2 and derived variants. Nat Rev Microbiol. 18(2):67-83 (2020).
Mali, Prashant, et al., RNA-Guided Human Genome Engineering Via Cas9. Science 339(6121):823-826 (2013).
Mir et al.: Type II-C CRISPR-Cas9 Biology, Mechanism, and Application. ACS Chem Biol. 13(2):357-365 (2018).
Moon et al.: Recent advances in the CRISPR genome editing tool set. Exp Mol Med. 51(11):1-11 (2019).
Murthy, A.C. et al., "Molecular interactions underlying liquid-liquid phase separation of the FUS low complexity domain", Nat Struct Mol Biol, 2019, vol. 26, No. 7, pp. 637-648.
NCBI GenBank Accession No. HHR99113.1, TPA: type II CRISPR RNA-guided endonuclease Cas9 [Acidobacteria bacterium] [1-2](2020).
NCBI GenBank Accession No. WP_061212298.1, HNH endonuclease [Dermabacter hominis] [1-2](2016).
NCBI GenBank: GBR72910.1—CRISPR-associated protein Csn1 family [Candidatus Termititenax aidoneus], pp. 1-3 (Oct. 31, 2019).
NCBI GenBank: WP_070675185.1—Multispecies: HNH endonuclease [unclassified Rothia (in: high G+C Gram-positive bacteria)], pp. 1-2 (Jan. 20, 2023).
NCBI GenBank: WP_070690139.1—HNH endonuclease [*Rothia* sp. HMSC076D04], pp. 1-3 (Jan. 20, 2023).
NCBI GenBank: WP_070847477.1—HNH endonuclease [*Rothia* sp. HMSC065C03], pp. 1-2 (May 16, 2022).
NCBI Reference Sequence: RMH36335.1, hypothetical protein D66910_06140 [Nitrospirae bacterium], https://www.ncbi.nlm.nih.gov/protein/RMH36335.1/ [1-2] (Published on Oct. 29, 2018).
Nowak et al. Guide RNA engineering for versatile Cas9 functionality. Nucleic Acids Res. 44(20):9555-9564 (2016).
Osorio, D. et al., Peptides: A Package for Data Mining of Antimicrobial Peptides, The R. Journal, 2015, 7(1), 4-14, pp. 1-11.
PCT/US2020/018353 International Search Report and Written Opinion dated Jun. 30, 2020.
PCT/US2020/018432 International Search Report and Written Opinion dated Jun. 30, 2020.
PCT/US2021/024927 International Search Report and Written Opinion dated Jul. 21, 2021.
PCT/US2021/024945 International Search Report and Written Opinion mailed Jul. 20, 2021.
PCT/US2021/031136 International Search Report and Written Opinion dated Aug. 25, 2021.
PCT/US2021/031143 International Search Report and Written Opinion dated Aug. 25, 2021.
PCT/US2022/027124 International Preliminary Report on Patentability dated Nov. 9, 2023.
PCT/US2022/027124 International Search Report and Written Opinion dated Oct. 26, 2022.
PCT/US2022/041755 International Preliminary Report on Patentability dated Mar. 7, 2024.
PCT/US2022/041755 International Search Report and Written Opinion dated Dec. 2, 2022.
PCT/US2022/080411 International Search Report and Written Opinion dated Apr. 19, 2023.
PCT/US2022/080437 International Search Report and Written Opinion dated Feb. 28, 2023.
Price, M.N. et al., Fast Tree2—Approximately Maximum-Likelihood Trees for Large Alignments, PLOS One, 2010, vol. 5, No. 3, e9490, pp. 1-10.
Ran, F. et al., In vivo genome editing using *Staphylococcus aureus* Cas 9, Nature, 2015, vol. 520, pp. 1-18.
Rautela et al.: Efficient genome editing of human natural killer cells by CRISPR RNP. bioRxiv prePrint doi: https://doi.org/10.1101/406934 [1-24] (2018).
Schneider et al. Sequence logos: a new way to display consensus sequences. Nucleic acids research 18(20):6097-6100 (1990).
Shmakov et al., Discovery and Functional Characterization of Diverse Class 2 CRISPR-Cas Systems. Mol Cell 60(3):385-397 (2015).
Shmakov, et al.: Diversity and evolution of class 2 CRISPR-Cas systems. Nature Reviews Microbiology 15(3): 169-182 (2017).
Stamatakis, A., RAxML Version 8: a tool for phylogenetic analysis and post-analysis of large phylogenies, Bioinformatics, 2014, vol. 30, No. 9, pp. 1312-1313.
Tang et al.: Class 2 CRISPR/Cas: an expanding biotechnology toolbox for and beyond genome editing. Cell Biosci. 8:59 doi:10.1186/s13578-018-0255-x [1-13](2018).
Tareen et al.: Logomaker: beautiful sequence logos in Python. Bioinformatics 6(7):2272-2274 (2020).
UniProtKB, [online] Accession No. A0A1F8ZSN4, HNH nuclease domain-containing protein, Dec. 11, 2019, p. 1 [retrieved online Apr. 24, 2024], URL: https://rest.uniprot.org/unisave/A0A1F8ZSN4?format=txt&versions=11.
UniProtKB, [online] Accession No. AA0A3D 5Y812 and HNHc domain-containingprotein, Dec. 11, 2019, p. 1 [retrieved online Apr. 24, 2024], URL: https://rest.uniprot.org/unisave/A0A3D5Y812?format=txt&versions=6.
Uniprotkb/trembl: A0A1F0KNW4 • A0A1F0KNW4_9MICC HNHc domain-containing protein. *Rothia* sp. HMSC066H02, pp. 1-5 [retrieved online Dec. 1, 2022] URL: https://www.uniprot.org/uniprotkb/A0A1F0KNW4/entry (Feb. 15, 2017).
Uniprotkb/trembl: A0A1S1DAD0 • A0A1S1DAD0_9MICC HNH Cas9-type domain-containing protein. *Rothia* sp. HMSC065C03, pp. 1-5 [retrieved online Dec. 1, 2022] URL: https://www.uniprot.org/uniprotkb/A0A1S1DAD0/entry (Apr. 12, 2017).
Uniprotkb/trembl: A1F0PN46 • A0A1F0PN46_9MICC HNH Cas9-type domain-containing protein. *Rothia* sp. HMSC076D04, pp. 1-5 [retrieved online Dec. 1, 2022] URL: https://www.uniprot.org/uniprotkb/A0A1F0PN46/entry (Feb. 15, 2017).
U.S. Appl. No. 17/193,173 Final Office Action dated Apr. 17, 2023.
U.S. Appl. No. 17/193,173 Non-Final Office Action dated Oct. 7, 2022.
U.S. Appl. No. 17/857,923 Advisory Action dated Aug. 8, 2023.
U.S. Appl. No. 17/857,923 Final Office Action dated Jun. 13, 2023.
U.S. Appl. No. 17/857,923 Non-Final Office Action dated Feb. 28, 2023.
U.S. Appl. No. 16/917,837 Office Action dated Aug. 26, 2020.

(56) References Cited

OTHER PUBLICATIONS

U.S. Appl. No. 16/917,838 Office Action dated Jul. 28, 2020.
U.S. Appl. No. 17/431,135 Office Action dated Feb. 16, 2024.
Weinberg, Z. et al, Extraordinary Structured Noncoding RNAs Revealed by Bacterial Metagenome Analysis, Nature 2009, vol. 462, No. 7273, pp. 656-659.
Xiao, N. et la., protr/ProtrWeb: R package and web server for generating various numerical representation schemes of protein sequences, Bioinformatics, 2015, vol. 31, No. 11, pp. 1857-1859.
Yan et al., Functionally diverse type V CRISPR-Cas systems. Science 363: 88-91 (2019).
Yang et al.: New CRISPR-Cas systems discovered. Cell Res. 27(3):313-314 doi:10.1038/cr.2017.21 (2017).
Yang, Z., PAML 4: Phylogenetic Analysis by Maximum Likelihood, Molecular Biology and Evolution, 2007, vol. 24, No. 8, pp. 1586-1591.
Kortleve, D. et al. Orthotopic editing of T-cell receptors. Cell Therapy vol. 3: 949-950 (2019).
NCBI GenBank: OGP48943.1—MAG: hypothetical protein A2022_01700 [Deltaproteobacteria bacterium GWF2_42_12], pp. 1-2 (Oct. 20, 2016).
Co-pending U.S. Appl. No. 19/028,339, inventors Thomas; Brian C. et al., filed Jan. 17, 2025.
Makarova, Kira S. et al. Unification of Cas protein families and a simple scenario for the origin and evolution of CRISPR-Cas systems. Biology Direct 6:38, 1-27 (2011).

*FIG. 25*
J3F280_CAS9_ACTNH_4ogc
J7RUA5_CAS9_STAAU
Q99ZW2_CAS9_SPY
MG15-169
MG15-170
MG15-175
MG15-177
MG15-181
MG15-172
MG15-176
MG15-174
MG15-171
MG15-184
MG15-182
MG15-187
MG15-191
MG15-180
MG15-166
MG15-167
MG15-168
MG15-165
MG15-164
MG15-193
MG15-216
MG15-218
MG15-215
MG15-217
MG15-157
MG15-2
MG15-3
MG15-159
MG15-14
MG15-146
MG15-149
MG15-118
MG15-13
MG15-107
MG15-97
MG15-213
MG15-95
MG15-209
MG15-133
MG15-210
MG15-64
MG15-208
MG15-124
MG15-94
MG15-211
MG15-10
MG15-141
MG15-140
MG15-135
MG15-138
MG15-203
MG15-136
MG15-115
MG15-205
MG15-137
MG15-214
MG15-204
MG15-66
MG15-67
MG15-196
MG15-112
MG15-201
MG15-199
MG15-200
MG15-197
MG15-198
MG15-202
MG15-4
MG15-212
MG15-45
MG15-130
MG15-162
MG15-177
MG15-87
MG15-84 and 4 others (0.003)
MG15-102
MG15-63
MG15-20
MG15-1
MG15-100
MG15-85
MG15-79
MG15-207
MG15-48
MG15-116
MG15-31
MG15-61
MG15-88 and 12 others (0.032)
0.5

MG123-1

MG124-2

MG125-1

MG125-2

MG125-3

MG125-4

MG125-5

MG150-5

MG150-6

MG150-7

MG150-8

MG150-9

MG3-18

MG3-89

MG3-90

MG3-91

MG3-92

MG3-93

MG3-95

MG3-96

MG3-103

MG15-130

MG15-146

MG15-164

MG15-166

MG15-171

MG15-172

MG15-174

MG15-184

MG15-187

MG15-191

MG15-193

MG15-195

MG15-217

MG15-218

MG15-219

MG15-177

ENZYMES WITH RUVC DOMAINS

RELATED APPLICATIONS

This application is related to PCT application no. PCT/US2021/031136, which is incorporated by reference in its entirety herein.

CROSS-REFERENCE

This application is a continuation of International Application No. PCT/US2022/041755, filed on Aug. 29, 2022, which claims the benefit of U.S. Provisional Application Nos: 63/237,791, filed on Aug. 27, 2021; 63/245,629 filed on Sep. 17, 2021; 63/252,956, filed on Oct. 6, 2021; 63/282,909, filed on Nov. 24, 2021; 63/316,895, filed on Mar. 4, 2022; 63/319,681, filed on Mar. 14, 2022; 63/322,944, filed on Mar. 23, 2022; and 63/369,858, filed on Jul. 29, 2022; each of which is incorporated by reference herein in its entirety.

BACKGROUND

Cas enzymes along with their associated Clustered Regularly Interspaced Short Palindromic Repeats (CRISPR) guide ribonucleic acids (RNAs) appear to be a pervasive (~45% of bacteria, ~84% of archaea) component of prokaryotic immune systems, serving to protect such microorganisms against non-self nucleic acids, such as infectious viruses and plasmids by CRISPR-RNA guided nucleic acid cleavage. While the deoxyribonucleic acid (DNA) elements encoding CRISPR RNA elements may be relatively conserved in structure and length, their CRISPR-associated (Cas) proteins are highly diverse, containing a wide variety of nucleic acid-interacting domains. While CRISPR DNA elements have been observed as early as 1987, the programmable endonuclease cleavage ability of CRISPR/Cas complexes has only been recognized relatively recently, leading to the use of recombinant CRISPR/Cas systems in diverse DNA manipulation and gene editing applications.

SEQUENCE LISTING

The instant application contains a Sequence Listing which has been submitted electronically in XML format and is hereby incorporated by reference in its entirety. Said XML copy, created on Feb. 22, 2024, is named 55921-731_301.xml and is 26,079,403 bytes in size.

SUMMARY

In some aspects, the present disclosure provides for a method of disrupting a Beta-2-Microglobulin (B2M) locus in a cell, comprising contacting to the cell (a) an RNA-guided endonuclease; and (b) an engineered guide RNA, wherein the engineered guide RNA is configured to form a complex with the endonuclease and the engineered guide RNA comprises a spacer sequence configured to hybridize to a region of the B2M locus, wherein the region of the B2M locus comprises a targeting sequence having at least 85% identity to at least 18 consecutive nucleotides of any one of SEQ ID NOs: 6387-6468. In some embodiments, the RNA-guided endonuclease is a class 2, type II Cas endonuclease. In some embodiments, the RNA-guided endonuclease comprises a RuvCIII domain comprising a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 2242 or SEQ ID NO: 2244. In some embodiments, the RNA-guided endonuclease further comprises an HNH domain. In some embodiments, the engineered guide RNA comprises a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 6305-6386. In some embodiments, the region of the B2M locus comprises a sequence at least 75%, 80%, or 90% identical to at least 19 of the non-degenerate nucleotides of any one of SEQ ID NOs: 6388, 6399, 6401, 6403, 6410, 6413, 6421, 6446, and 6448.

In some aspects, the present disclosure provides for a method of editing a T Cell Receptor Alpha Constant (TRAC) locus in a cell, comprising contacting to the cell: (a) an RNA-guided endonuclease; and (b) an engineered guide RNA, wherein the engineered guide RNA is configured to form a complex with the endonuclease and the engineered guide RNA comprises a spacer sequence configured to hybridize to a region of the TRAC locus, wherein the region of the TRAC locus comprises a targeting sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to at least 18 consecutive nucleotides of any one of SEQ ID NOs: 6509-6548 or 6805. In some embodiments, the RNA-guided endonuclease is a class 2, type II Cas endonuclease. In some embodiments, the RNA-guided endonuclease comprises a RuvCIII domain comprising a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 2242 or SEQ ID NO: 2244. In some embodiments, the RNA-guided endonuclease further comprises an HNH domain. In some embodiments, the engineered guide RNA comprises a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 6469-6508 or 6804. In some embodiments, the region of the TRAC locus comprises a sequence at least 75%, 80%, or 90% identical to at least 19 of the non-degenerate nucleotides of any one of SEQ ID NOs: 6517, 6520, and 6523.

In some aspects, the present disclosure provides for a method of disrupting a Hypoxanthine Phosphoribosyltransferase 1 (HPRT) locus in a cell, comprising contacting to the cell: (a) an RNA-guided endonuclease; and (b) an engineered guide RNA, wherein the engineered guide RNA is configured to form a complex with the endonuclease and the engineered guide RNA comprises a spacer sequence configured to hybridize to a region of the HPRT locus, wherein the region of the HPRT locus comprises a targeting sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to at least 18 consecutive nucleotides of any one of SEQ ID NOs: 6616-6682. In some embodiments, the RNA-guided endonuclease is a class 2, type II Cas endonuclease. In some embodiments, the RNA-guided endonuclease comprises a RuvCIII domain comprising a sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 2242 or SEQ ID NO: 2244. In some embodiments, the RNA-guided endonuclease further comprises an HNH domain. In some embodiments, the engineered guide RNA comprises a sequence having at least 80% identity to any one of SEQ ID NOs: 6549-6615. In some embodiments, the region of the HPRT locus comprises a sequence at least 75%, 80%, or 90% identical to at least 19 of the non-degenerate nucleotides of any one of SEQ ID NOs: 6619, 6634, 6673, 6675, and 6679.

In some aspects, the present disclosure provides for a method of editing a T Cell Receptor Beta Constant 1 or T Cell Receptor Beta Constant 2 (TRBC1/2) locus in a cell, comprising contacting to the cell: (a) an RNA-guided endonuclease; and (b) an engineered guide RNA, wherein the engineered guide RNA is configured to form a complex with the endonuclease and the engineered guide RNA comprises a spacer sequence configured to hybridize to a region of the TRBC1/2 locus, wherein the region of the TRBC1/2 locus comprises a targeting sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to at least 18 consecutive nucleotides of any one of SEQ ID NOs: 6722-6760 or 6782-6802. In some embodiments, the RNA-guided endonuclease is a class 2, type II Cas endonuclease. In some embodiments, the RNA-guided endonuclease comprises a RuvCIII domain comprising a sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 2242 or SEQ ID NO: 2244. In some embodiments, the RNA-guided endonuclease further comprises an HNH domain. In some embodiments, the engineered guide RNA comprises a sequence having at least 80% identity to any one of SEQ ID NOs: 6683-6721 and 6761-6781. In some embodiments, the region of the TRBC1/2 locus comprises a sequence at least 75%, 80%, or 90% identical to at least 19 of the non-degenerate nucleotides of any one of SEQ ID NOs: 6734, 6753, 6790, and 6800.

In some aspects, the present disclosure provides for a method of editing an Hydroxyacid Oxidase 1 (HAO1) locus in a cell, comprising contacting to the cell: (a) an RNA-guided endonuclease; and (b) an engineered guide RNA, wherein the engineered guide RNA is configured to form a complex with the endonuclease and the engineered guide RNA comprises a spacer sequence configured to hybridize to a region of the HAO1 locus, wherein the region of the HAO1 locus comprises a targeting sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to at least 18 consecutive nucleotides of any one of SEQ ID NOs: 11802-11820. In some embodiments, the RNA-guided endonuclease is a class 2, type II Cas endonuclease. In some embodiments, the RNA-guided endonuclease comprises a RuvCIII domain comprising a sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 2242. In some embodiments, the RNA-guided endonuclease further comprises an HNH domain. In some embodiments, the region of the HAO1 locus comprises a sequence at least 75%, 80%, or 90% identical to at least 19 of the non-degenerate nucleotides of any one of SEQ ID NOs: 11806, 11813, 11816, and 11819.

In some aspects, the present disclosure provides for an engineered nuclease system comprising: (a) an RNA-guided endonuclease; and (b) an engineered guide RNA, wherein the engineered guide RNA comprises (i) a 2'-O-methyl nucleotide; (ii) a 2'-fluoro nucleotide; or (iii) a phosphorothioate bond; wherein the RNA-guided endonuclease has at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 421-431 or a variant thereof. In some embodiments, the RNA-guided endonuclease comprises a sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 421.

In some aspects, the present disclosure provides for an engineered nuclease system comprising: (a) an endonuclease having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 421-431 or a variant thereof; and (b) an engineered guide RNA, wherein the engineered guide RNA is configured to form a complex with the endonuclease and the engineered guide RNA comprises a spacer sequence configured to hybridize to a target nucleic acid sequence, wherein the system has reduced immunogenicity when administered to a human subject compared to an equivalent system comprising a Cas9 enzyme. In some embodiments, the Cas9 enzyme is an SpCas9 enzyme. In some embodiments, the immunogenicity is antibody immunogenicity. In some embodiments, the engineered guide RNA comprises a sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to non-degenerate nucleotides of any one of SEQ ID NOs: 5466-5467 and 11160-11162. In some embodiments, the engineered nuclease has at least about 75% sequence identity at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 421 or 423 or a variant thereof.

In some aspects, the present disclosure provides for a method of editing a locus in a cell, comprising contacting to the cell: (a) an RNA-guided endonuclease or a nucleic acid encoding the RNA-guided endonuclease; and (b) an engineered guide RNA, wherein the engineered guide RNA is configured to form a complex with the RNA-guided endonuclease and the engineered guide RNA comprises a spacer sequence configured to hybridize to a region of the locus; wherein the cell is a peripheral blood mononuclear cell (PBMC), a hematopoietic stem cell (HSC), or an induced pluripotent stem cell (iPSC). In some embodiments, the RNA-guided endonuclease is a class 2, type II Cas endonuclease. In some embodiments, the RNA-guided endonuclease comprises a RuvCIII domain comprising a sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 2242, or a variant thereof. In some embodiments, the RNA-guided endonuclease further comprises an HNH domain. In some embodiments, the RNA-guided endonuclease has at least about 75% sequence identity at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 421 or a variant thereof. In some embodiments, the engineered guide RNA comprises a sequence at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 6804, 6806, and 6808. In some embodiments, the nucleic acid encoding the RNA-guided endonuclease comprises a sequence comprising at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 6803 or a variant thereof. In some embodiments, the region of the locus comprises a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to at least 18 nucleotides of any one of SEQ ID NOs: 6805, 6807, and 6809.

In some aspects, the present disclosure provides for a method of editing a CD2 Molecule (CD2) locus in a cell, comprising contacting to the cell: (a) an RNA-guided endonuclease; and (b) an engineered guide RNA, wherein the engineered guide RNA is configured to form a complex with the endonuclease and the engineered guide RNA comprises a spacer sequence configured to hybridize to a region of the CD2 locus, wherein the engineered guide RNA comprises or is configured to hybridize to a sequence having at least 18-22 consecutive nucleotides complementary to a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 6853-6894; or wherein the engineered guide RNA comprises a nucleotide sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to the non-degenerate nucleotides of any one of SEQ ID NOs: 6811-6852. In some embodiments, the RNA-guided endonuclease is a class 2, type II Cas endonuclease. In some embodiments, the RNA-guided endonuclease comprises a RuvCIII domain comprising a sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 2242 or SEQ ID NO: 2244, or a variant thereof. In some embodiments, the RNA-guided endonuclease further comprises an HNH domain. In some embodiments, the RNA-guided endonuclease comprises a sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 421-431. In some embodiments, the RNA-guided endonuclease comprises a sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 421, or a variant thereof. In some embodiments, the engineered guide RNA comprises a sequence at least about 80%, at least about 85%, at least about 90%, at least about 91%, at least about 92%, at least about 93%, at least about 94%, at least about 95%, at least about 96%, at least about 97%, at least about 98%, or at least about 99% identical to the non-degenerate nucleotides of any one of SEQ ID NOs: 6813, 6841, 6843-6847, 6852, or 6852. In some embodiments, the engineered guide RNA further comprises a pattern of nucleotide modifications recited in any of the guide RNAs recited in Table 6A. In some embodiments, the engineered guide RNA comprises or is configured to hybridize to a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to at least 18 consecutive nucleotides of any one of SEQ ID NOs: 6855, 6883, 6885-6889, 6892, or 6984.

In some aspects, the present disclosure provides for an isolated RNA molecule comprising a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 6811-6852. In some embodiments, the RNA molecule further comprises a pattern of nucleotide modifications recited in any of the guide RNAs recited in Table 6A.

In some aspects, the present disclosure provides for a method of editing a CD5 Molecule (CD5) locus in a cell comprising contacting to the cell: (a) an RNA-guided endonuclease; and (b) an engineered guide RNA, wherein the engineered guide RNA is configured to form a complex with the endonuclease and the engineered guide RNA comprises a spacer sequence configured to hybridize to a region of the CD5 locus, wherein the engineered guide RNA comprises or is configured to hybridize to a sequence having at least 18-22 consecutive nucleotide complementary to a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID Nos: 6959-7022; or wherein the engineered guide RNA comprises a nucleotide sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity the non-degenerate nucleotides of any one of SEQ ID NOs: 5466 or 6895-6958. In some embodiments, the RNA-guided endonuclease is a class 2, type II Cas endonuclease. In some embodiments, the RNA-guided endonuclease comprises a RuvCIII domain comprising a sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 2242 or SEQ ID NO: 2244, or a variant thereof. In some embodiments, the RNA-guided endonuclease further comprises an HNH domain. In some embodiments, the RNA-guided endonuclease comprises an endonuclease comprising a sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 421-431 or a variant thereof. In some embodiments, the RNA-guided endonuclease comprises a sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 421. In some embodiments, the engineered guide RNA comprises a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to non-degenerate nucleotides of SEQ ID NO: 5466. In some embodiments, the engineered guide RNA comprises a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity the non-degenerate nucleotides of any one of SEQ ID NOs: 6897, 6904, 6906, 6911, 6928, 6930, 6932, 6934, 6938, 6945, 6950, 6952, and 6958. In some embodiments, the engineered guide RNA further comprises a pattern of nucleotide modification recited in any of the guide RNAs recited in Table 7A. In some embodiments, the engineered guide RNA is configured to hybridize to a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to at least 18 consecutive nucleotides of any one of SEQ ID NOs: 6961, 6968, 6970, 6975, 6992, 6994, 6996, 6998, 7002, 7009, 7014, 7016, and 7022.

In some aspects, the present disclosure provides for an isolated RNA molecule comprising a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 6895-6958. In some embodiments, the RNA molecule further comprises a pattern of nucleotide modifications recited in any of the guide RNAs recited in Table 7A.

In some aspects, the present disclosure provides for a method of editing an RNA locus in a cell, comprising contacting to the cell: (a) an RNA-guided endonuclease comprising a sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 2242 or SEQ ID NO: 2244, or a variant thereof; and (b) an engineered guide RNA, wherein the engineered guide RNA is configured to form a complex with the endonuclease and the engineered guide RNA comprises a spacer sequence configured to hybridize to a region of the RNA locus, wherein the RNA locus does not comprise bacterial or microbial RNA. In some embodiments, the guide RNA comprises a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to non-degenerate nucleotides of SEQ ID NO: 5466 or SEQ ID NO: 5539.

In some aspects, the present disclosure provides for a method of disrupting a Fas Cell Surface Death Receptor (FAS) locus in a cell, comprising introducing to the cell: (a) an RNA-guided endonuclease; and (b) an engineered guide RNA, wherein the engineered guide RNA is configured to form a complex with the endonuclease and the engineered guide RNA comprises a spacer sequence configured to hybridize to a region of the human FAS locus, wherein the engineered guide RNA comprises or is configured to hybridize to a sequence having at least 18-22 consecutive nucleotides complementary to a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 7057-7090; or wherein the engineered guide RNA comprises a nucleotide sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 7023-7056. In some embodiments, the RNA-guided endonuclease is a class 2, type II Cas endonuclease. In some embodiments, the RNA-guided endonuclease comprises a RuvCIII domain comprising a sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 2242, or a variant thereof. In some embodiments, the RNA-guided endonuclease further comprises an HNH domain. In some embodiments, the engineered guide RNA comprises a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to non-degenerate nucleotides of SEQ ID NO: 5466. In some embodiments, the engineered guide RNA comprises or is configured to hybridize to a sequence having at least 80% identity to at least 18 consecutive nucleotides of any one of SEQ ID NOs: 7059, 7061, 7069, 7070, 7076, 7080, 7083, 7084, 7085, or 7088. In some embodiments, the RNA-guided endonuclease comprises a sequence at least 75%, 80%, or 90% identical to SEQ ID NO: 421, or a variant thereof. In some embodiments, the guide RNA comprises a sequence having at least 80% identity to any one of SEQ ID NOs: 7025, 7027, 7035, 7036, 7042, 7046, 7049-7051, or 7054. In some embodiments, the guide RNA further comprises a pattern of nucleotide modifications recited in any of the guide RNAs recited in Table 8.

In some aspects, the present disclosure provides for an isolated RNA molecule comprising a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 7023-7056. In some embodiments, the RNA molecule further comprises a pattern of nucleotide modifications recited in any of the guide RNAs recited in Table 8.

In some aspects, the present disclosure provides for a method of disrupting a Programmed Cell Death 1 (PD-1) locus in a cell, comprising introducing to the cell: (a) an RNA-guided endonuclease; and (b) an engineered guide RNA, wherein the engineered guide RNA is configured to form a complex with the endonuclease and the engineered guide RNA comprises a spacer sequence configured to hybridize to a region of the human PD-1 locus, wherein the engineered guide RNA comprises or is configured to hybridize to a sequence having at least 18-22 consecutive nucleotides complementary to a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 7129-7166; or wherein the engineered guide RNA comprises a nucleotide sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 7091-7128. In some embodiments, the RNA-guided endonuclease is a class 2, type II Cas endonuclease. In some embodiments, the RNA-guided endonuclease comprises a RuvCIII domain comprising a sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 2242, or a variant thereof. In some embodiments, the RNA-guided endonuclease further comprises an HNH domain. In some embodiments, the engineered guide RNA comprises a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to non-degenerate nucleotides of SEQ ID NO: 5466. In some embodiments, the engineered guide RNA comprises or is configured to hybridize to a sequence having at least 80% identity to at least 18 consecutive nucleotides of any one of SEQ ID NOs: 7135, 7137, 7146, 7149, 7152, 7156, 7160, 7161, 7164, 7165, or 7166. In some embodiments, the RNA-guided endonuclease comprises a sequence at least 75%, 80%, or 90% identical to SEQ ID NO: 421, or a variant thereof. In some embodiments, the guide RNA comprises a sequence having at least 80% identity to any one of SEQ ID NOs: 7097, 7099, 7108, 7111, 7114, 7118, 7122, 7123, 7126, 7127, or 7128. In some embodiments, the guide RNA further comprises a pattern of nucleotide modifications recited in any of the guide RNAs recited in Table 9.

In some aspects, the present disclosure provides for an isolated RNA molecule comprising a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 7091-7128. In some embodiments, the RNA molecule further comprises a pattern of nucleotide modifications recited in any of the guide RNAs recited in Table 9.

In some aspects, the present disclosure provides for a method of disrupting an human Rosa26 (hRosa26) locus in a cell, comprising introducing to the cell: (a) an RNA-guided endonuclease; and (b) an engineered guide RNA, wherein the engineered guide RNA is configured to form a complex with the endonuclease and the engineered guide RNA comprises a spacer sequence configured to hybridize to a region of the hRosa26 locus, wherein the engineered guide RNA comprises or is configured to hybridize to a sequence having at least 18-22 consecutive nucleotides complementary to a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 7199-7230; or wherein the engineered guide RNA comprises a nucleotide sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 7167-7198. In some embodiments, the RNA-guided endonuclease is a class 2, type II Cas endonuclease. In some embodiments, the RNA-guided endonuclease comprises a RuvCIII domain comprising a sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 2242, or a variant thereof. In some embodiments, the RNA-guided endonuclease further comprises an HNH domain. In some embodiments, the engineered guide RNA comprises a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to non-degenerate nucleotides of SEQ ID NO: 5466. In some embodiments, the engineered guide RNA comprises or is configured to hybridize to a sequence having at least 80% identity to at least 18 consecutive nucleotides of any one of SEQ ID NOs: 7205-7206, 7215, 7220, 7223, or 7225. In some embodiments, the RNA-guided endonuclease comprises a sequence at least 75%, 80%, or 90% identical to SEQ ID NO: 421, or a variant thereof. In some embodiments, the guide RNA comprises a sequence having at least 80% identity to any one of SEQ ID NOs: 7173, 7174, 7183, 7188, 7191, or 7193. In some embodiments, the guide RNA further comprises a pattern of nucleotide modifications recited in any of the guide RNAs recited in Table 10.

In some aspects, the present disclosure provides for an isolated RNA molecule comprising a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 7167-7198. In some embodiments, the RNA molecule further comprises a pattern of nucleotide modifications recited in any of the guide RNAs recited in Table 10.

In some aspects, the present disclosure provides for a method of disrupting an T Cell Receptor Alpha Constant (TRAC) locus in a cell, comprising introducing to the cell: (a) an RNA-guided endonuclease; and (b) an engineered guide RNA, wherein the engineered guide RNA is configured to form a complex with the endonuclease and the engineered guide RNA comprises a spacer sequence configured to hybridize to a region of the TRAC locus, wherein the engineered guide RNA comprises or is configured to hybridize to a sequence having at least 18-22 consecutive nucleotides complementary to a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 7235-7238, 7248-7256, 7270, or 7278-7284; or wherein the engineered guide RNA comprises a nucleotide sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 7231-7234, 7239-7247, 7269, or 7271-7277. In some embodiments, the RNA-guided endonuclease is a class 2, type II Cas endonuclease. In some embodiments, the RNA-guided endonuclease comprises a sequence at least 75%, 80%, or 90% identical to SEQ ID NO: 1512, 1756, 11711-11713, or a variant thereof. In some embodiments, the engineered guide RNA comprises a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to non-degenerate nucleotides of SEQ ID NO: 5473, 5475, 11145, 11714, or 11715. In some embodiments, the engineered guide RNA comprises or is configured to hybridize to a sequence having at least 80% identity to at least 18 consecutive nucleotides of any one of SEQ ID NOs: 7235-7238, 7248-7256, 7270, or 7278-7284. In some embodiments, the guide RNA comprises a sequence having at least 80% identity to any one of SEQ ID NOs: 7231-7234, 7239-7244, 7269, or 7271-7277. In some embodiments, the engineered guide RNA further comprises a pattern of nucleotide modifications recited in any of the guide RNAs recited in Table 11.

In some aspects, the present disclosure provides for an isolated RNA molecule comprising a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 7231-7234, 7239-7247, 7269, or 7271-7277. In some embodiments, the RNA molecule further comprises a pattern of nucleotide modifications recited in any of the guide RNAs recited in Table 11.

In some aspects, the present disclosure provides for a method of disrupting an Adeno-Associated Virus Integration Site 1 (AAVS1) locus in a cell, comprising introducing to the cell: (a) a class 2, type II Cas endonuclease; and (b) an engineered guide RNA, wherein the engineered guide RNA is configured to form a complex with the endonuclease and the engineered guide RNA comprises a spacer sequence configured to hybridize to a region of the AAVS1 locus, wherein the engineered guide RNA comprises or is configured to hybridize to a sequence having at least 18-22 consecutive nucleotides complementary to a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 7261-7264 or 7267-7268; or wherein the engineered guide RNA comprises a nucleotide sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 7257-7260 or 7265-7266. In some embodiments, the RNA-guided endonuclease is a class 2, type II Cas endonuclease. In some embodiments, the RNA-guided endonuclease comprises a sequence at least 75%, 80%, or 90% identical to SEQ ID NO: 1756 or 11711, or a variant thereof. In some embodiments, the engineered guide RNA comprises a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to non-degenerate nucleotides of SEQ ID NO: 5475 or 11715. In some embodiments, the engineered guide RNA comprises or is configured to hybridize to a sequence having at least 80% identity to at least 18 consecutive nucleotides of any one of SEQ ID NOs: 7261-7263 or 7267-7268. In some embodiments, the guide RNA comprises a sequence having at least 80% identity to any one of SEQ ID NOs: 7257-7260 or 7265-7266. In some embodiments, the engineered guide RNA further comprises a pattern of nucleotide modifications recited in any of the guide RNAs recited in Table 12.

In some aspects, the present disclosure provides for an isolated RNA molecule comprising a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 7257-7260 or 7265-7266. In some embodiments, the RNA molecule further comprises a pattern of nucleotide modifications recited in any of the guide RNAs recited in Table 12.

In some aspects, the present disclosure provides for a method of disrupting an Hydroxyacid Oxidase 1 (HAO-1) locus in a cell, comprising introducing to the cell: (a) an RNA-guided endonuclease; and (b) an engineered guide RNA, wherein the engineered guide RNA is configured to form a complex with the endonuclease and the engineered guide RNA comprises a spacer sequence configured to hybridize to a region of the HAO-1 locus, wherein the engineered guide RNA comprises or is configured to hybridize to a sequence having at least 18-22 consecutive nucleotides complementary to a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 11773-11793. In some embodiments, the RNA-guided endonuclease is a class 2, type II Cas endonuclease. In some embodiments, the RNA-guided endonuclease comprises a RuvCIII domain comprising a sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 2242, or a variant thereof. In some embodiments, the RNA-guided endonuclease further comprises an HNH domain. In some embodiments, the engineered guide RNA comprises a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to non-degenerate nucleotides of SEQ ID NO: 5466. In some embodiments, the engineered guide RNA comprises or is configured to hybridize to a sequence having at least 80% identity to at least 18 consecutive nucleotides of any one of SEQ ID NOs: 11773, 11780, 11786, or 11787. In some embodiments, the RNA-guided endonuclease comprises a sequence at least 75%, 80%, or 90% identical to SEQ ID NO: 421, or a variant thereof.

In some aspects, the present disclosure provides for an isolated RNA molecule comprising a spacer sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 11773-11793 and a scaffold sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 5466.

In some aspects, the present disclosure provides for a method of disrupting a human G Protein-Coupled Receptor 146 (GPR146) locus in a cell, comprising introducing to the cell: (a) an RNA-guided endonuclease; and (b) an engineered guide RNA, wherein the engineered guide RNA is configured to form a complex with the endonuclease and the engineered guide RNA comprises a spacer sequence configured to hybridize to a region of the GPR146 locus, wherein the engineered guide RNA comprises or is configured to hybridize to a sequence having at least 18-22 consecutive nucleotides complementary to a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 11406-11437; or wherein the engineered guide RNA comprises a nucleotide sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 11374-11405. In some embodiments, the RNA-guided endonuclease is a class 2, type II Cas endonuclease. In some embodiments, the RNA-guided endonuclease comprises a RuvCIII domain comprising a sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 2242, or a variant thereof. In some embodiments, the RNA-guided endonuclease further comprises an HNH domain. In some embodiments, the engineered guide RNA comprises a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to non-degenerate nucleotides of SEQ ID NO: 5466. In some embodiments, the engineered guide RNA comprises or is configured to hybridize to a sequence having at least 80% identity to at least 18 consecutive nucleotides of SEQ ID NO: 11425. In some embodiments, the RNA-guided endonuclease comprises a sequence at least 75%, 80%, or 90% identical to SEQ ID NO: 421, or a variant thereof. In some embodiments, the guide RNA comprises a sequence having at least 80% identity to SEQ ID NO: 11393. In some embodiments, the engineered guide RNA further comprises a pattern of nucleotide modifications recited in any of the guide RNAs recited in Table 15.

In some aspects, the present disclosure provides for an isolated RNA molecule comprising a spacer sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 11374-11405. In some embodiments, the RNA molecule further comprises a pattern of nucleotide modifications recited in any of the guide RNAs recited in Table 15.

In some aspects, the present disclosure provides for a method of disrupting a mouse G Protein-Coupled Receptor 146 (GPR146) locus in a cell, comprising introducing to the cell: (a) an RNA-guided endonuclease; and (b) an engineered guide RNA, wherein the engineered guide RNA is configured to form a complex with the endonuclease and the engineered guide RNA comprises a spacer sequence configured to hybridize to a region of the GPR146 locus, wherein the engineered guide RNA comprises or is configured to hybridize to a sequence having at least 18-22 consecutive nucleotides complementary to a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 11473-11507; or wherein the engineered guide RNA comprises a nucleotide sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 11438-11472. In some embodiments, the RNA-guided endonuclease is a class 2, type II Cas endonuclease. In some embodiments, the RNA-guided endonuclease comprises a RuvCIII domain comprising a sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 2242, or a variant thereof. In some embodiments, the RNA-guided endonuclease further comprises an HNH domain. In some embodiments, the engineered guide RNA comprises a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to non-degenerate nucleotides of SEQ ID NO: 5466. In some embodiments, the engineered guide RNA comprises or is configured to hybridize to a sequence having at least 80% identity to at least 18 consecutive nucleotides of any one of SEQ ID NOs: 11482, 11488, or 11490. In some embodiments, the RNA-guided endonuclease comprises a sequence at least 75%, 80%, or 90% identical to SEQ ID NO: 421, or a variant thereof. In some embodiments, the guide RNA comprises a sequence having at least 80% identity to SEQ ID NO: 11447, 11453, or 11455. In some embodiments, the engineered guide RNA further comprises a pattern of nucleotide modifications recited in any of the guide RNAs recited in Table 16.

In some aspects, the present disclosure provides for an isolated RNA molecule comprising a spacer sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 11438-11472. In some embodiments, the RNA molecule further comprises a pattern of nucleotide modifications recited in any of the guide RNAs recited in Table 16.

In some aspects, the present disclosure provides for a method of disrupting a T Cell Receptor Alpha Constant (TRAC) locus in a cell, comprising introducing to the cell: (a) an RNA-guided endonuclease; and (b) an engineered guide RNA, wherein the engineered guide RNA is configured to form a complex with the endonuclease and the engineered guide RNA comprises a spacer sequence configured to hybridize to a region of the TRAC locus, wherein the engineered guide RNA comprises or is configured to hybridize to a sequence having at least 18-22 consecutive nucleotides complementary to a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 11516-11517; or wherein the engineered guide RNA comprises a nucleotide sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 11514-11515. In some embodiments, the RNA-guided endonuclease is a class 2, type II Cas endonuclease. In some embodiments, the engineered guide RNA comprises a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to non-degenerate nucleotides of SEQ ID NO: 11153. In some embodiments, the engineered guide RNA comprises or is configured to hybridize to a sequence having at least 80% identity to at least 18 consecutive nucleotides of any one of SEQ ID NOs: 11516. In some embodiments, the RNA-guided endonuclease comprises a sequence at least 75%, 80%, or 90% identical to SEQ ID NO: 11716, or a variant thereof. In some embodiments, the guide RNA comprises a sequence having at least 80% identity to SEQ ID NO: 11514. In some embodiments, the engineered guide RNA further comprises a pattern of nucleotide modifications recited in any of the guide RNAs recited in Table 17.

In some aspects, the present disclosure provides for an isolated RNA molecule comprising a spacer sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 11514-11515. In some embodiments, the RNA molecule further comprises a pattern of nucleotide modifications recited in any of the guide RNAs recited in Table 17.

In some aspects, the present disclosure provides for a method of disrupting an Adeno-Associated Virus Integration Site 1 (AAVS1) locus in a cell, comprising introducing to the cell: (a) an RNA-guided endonuclease; and (b) an engineered guide RNA, wherein the engineered guide RNA is configured to form a complex with the endonuclease and the engineered guide RNA comprises a spacer sequence configured to hybridize to a region of the AAVS1 locus, wherein the engineered guide RNA comprises or is configured to hybridize to a sequence having at least 18-22 consecutive nucleotides complementary to a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 11511-11513; or wherein the engineered guide RNA comprises a nucleotide sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 11508-11510. In some embodiments, the RNA-guided endonuclease is a class 2, type II Cas endonuclease. In some embodiments, the engineered guide RNA comprises a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to non-degenerate nucleotides of SEQ ID NO: 11717. In some embodiments, the engineered guide RNA comprises or is configured to hybridize to a sequence having at least 80% identity to at least 18 consecutive nucleotides of SEQ ID NO: 11511. In some embodiments, the RNA-guided endonuclease comprises a sequence at least 75%, 80%, or 90% identical to SEQ ID NO: 914, or a variant thereof. In some embodiments, the guide RNA comprises a sequence having at least 80% identity to SEQ ID NO: 11508. In some embodiments, the engineered guide RNA further comprises a pattern of nucleotide modifications recited in any of the guide RNAs recited in Table 17.

In some aspects, the present disclosure provides for an isolated RNA molecule comprising a spacer sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any one of SEQ ID NOs: 11508-11510. In some embodiments, the RNA molecule further comprises a pattern of nucleotide modifications recited in any of the guide RNAs recited in Table 17.

In some aspects, the present disclosure provides for an engineered nuclease system comprising: (a) an endonuclease having at least at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% sequence identity to a PI domain of any of the Cas effector protein sequences described herein, or a variant thereof; and (b) an engineered guide RNA, wherein the engineered guide RNA is configured to form a complex with the endonuclease and the engineered guide RNA comprises a spacer sequence configured to hybridize to a target nucleic acid sequence, wherein the engineered guide RNA comprises a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to non-degenerate nucleotides of any of the sgRNA sequences described herein. In some embodiments, the endonuclease further comprises a RuvCIII domain or a HNH domain having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to RuvCIII domains or HNH domains of any of the Cas effector nucleases described herein. In some embodiments, the endonuclease is configured to have selectivity for any of the PAM sequences described herein. In some embodiments, the endonuclease further comprises a sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to any of the Cas effector sequences described herein.

In some aspects, the present disclosure provides for use of any of the methods described herein for disrupting a B2M locus in a cell.

In some aspects, the present disclosure provides for use of any of the methods described herein or any of the RNA molecules described herein for disrupting a TRAC locus in a cell.

In some aspects, the present disclosure provides for use of any of the methods described herein for disrupting an HPRT locus in a cell.

In some aspects, the present disclosure provides for use of any of the methods described herein for disrupting a TRBC1/2 locus in a cell.

In some aspects, the present disclosure provides for use of any of the methods described herein or any of the RNA molecules described herein for disrupting an HAO-1 locus in a cell.

In some aspects, the present disclosure provides for use of any of the methods described herein or any of the RNA molecules described herein for disrupting a CD2 locus in a cell.

In some aspects, the present disclosure provides for use of any of the methods described herein or any of the RNA molecules described herein for disrupting a CD5 locus in a cell.

In some aspects, the present disclosure provides for use of any of the methods described herein or any of the RNA molecules described herein for disrupting a FAS locus in a cell.

In some aspects, the present disclosure provides for use of any of the methods described herein or any of the RNA molecules described herein for disrupting a PD-1 locus in a cell.

In some aspects, the present disclosure provides for use of any of the methods described herein or any of the RNA molecules described herein for disrupting an hRosa26 locus in a cell.

In some aspects, the present disclosure provides for use of any of the methods described herein or any of the RNA molecules described herein for disrupting an AAVS1 locus in a cell.

In some aspects, the present disclosure provides for use of any of the methods described herein or any of the RNA molecules described herein for disrupting a GPR146 locus in a cell.

In some aspects, the present disclosure provides for an engineered nuclease system, comprising: (a) an endonuclease comprising a RuvC_III domain and an HNH domain, wherein the endonuclease is derived from an uncultivated microorganism, wherein the endonuclease is a class 2, type II Cas endonuclease; and (b) an engineered guide ribonucleic acid structure configured to form a complex with the endonuclease comprising: (i) a guide ribonucleic acid sequence configured to hybridize to a target deoxyribonucleic acid sequence; and (ii) a tracr ribonucleic acid sequence configured to bind to the endonuclease. In some embodiments, the RuvC_III domain comprises a sequence with at least 70%, at least 75%, at least 80%, at least 85%, at least 88%, at least 90%, at least 92%, at least 95%, or at least 98% sequence identity to any one of SEQ ID NOs: 1827-3637.

In some aspects, the present disclosure provides for an engineered nuclease system comprising: (a) an endonuclease comprising a RuvC_III domain having at least 70%, at least 75%, at least 80%, at least 85%, at least 88%, at least 90%, at least 92%, at least 95%, or at least 98% sequence identity to any one of SEQ ID NOs: 1827-3637; and (b) an engineered guide ribonucleic acid structure configured to form a complex with the endonuclease comprising: (i) a guide ribonucleic acid sequence configured to hybridize to a target deoxyribonucleic acid sequence; and (ii) a tracr ribonucleic acid sequence configured to bind to the endonuclease.

In some aspects, the present disclosure provides for an engineered nuclease system comprising: (a) an endonuclease configured to bind to a protospacer adjacent motif (PAM) sequence comprising SEQ ID NOs: 5512-5537, wherein the endonuclease is a class 2, type II Cas endonuclease; and (b) an engineered guide ribonucleic acid structure configured to form a complex with the endonuclease comprising: (i) a guide ribonucleic acid sequence configured to hybridize to a target deoxyribonucleic acid sequence; and (ii) a tracr ribonucleic acid sequence configured to bind to the endonuclease.

In some embodiments, the endonuclease is derived from an uncultivated microorganism. In some embodiments, the endonuclease has not been engineered to bind to a different PAM sequence. In some embodiments, the endonuclease is not a Cas9 endonuclease, a Cas14 endonuclease, a Cas12a endonuclease, a Cas12b endonuclease, a Cas 12c endonuclease, a Cas12d endonuclease, a Cas12e endonuclease, a Cas13a endonuclease, a Cas13b endonuclease, a Cas13c endonuclease, or a Cas 13d endonuclease. In some embodiments, the endonuclease has less than 80% identity to a Cas9 endonuclease. In some embodiments, the endonuclease further comprises an HNH domain. In some embodiments, the tracr ribonucleic acid sequence comprises a sequence with at least 80% sequence identity to about 60 to 90 consecutive nucleotides selected from any one of SEQ ID NOs: 5476-5511 and SEQ ID NO: 5538.

In some aspects, the present disclosure provides for an engineered nuclease system comprising, (a) an engineered guide ribonucleic acid structure comprising: (i) a guide ribonucleic acid sequence configured to hybridize to a target deoxyribonucleic acid sequence; and (ii) a tracr ribonucleic acid sequence configured to bind to an endonuclease, wherein the tracr ribonucleic acid sequence comprises a sequence with at least 80% sequence identity to about 60 to 90 consecutive nucleotides selected from any one of SEQ ID NOs: 5476-5511 and SEQ ID NO: 5538; and (b) a class 2, type II Cas endonuclease configured to bind to the engineered guide ribonucleic acid. In some embodiments, the endonuclease is configured to bind to a protospacer adjacent motif (PAM) sequence selected from the group comprising SEQ ID NOs: 5512-5537.

In some embodiments, the engineered guide ribonucleic acid structure comprises at least two ribonucleic acid polynucleotides. In some embodiments, the engineered guide ribonucleic acid structure comprises one ribonucleic acid polynucleotide comprising the guide ribonucleic acid sequence and the tracr ribonucleic acid sequence.

In some embodiments, the guide ribonucleic acid sequence is complementary to a prokaryotic, bacterial, archaeal, eukaryotic, fungal, plant, mammalian, or human genomic sequence. In some embodiments, the guide ribonucleic acid sequence is 15-24 nucleotides in length. In some embodiments, the endonuclease comprises one or more nuclear localization sequences (NLSs) proximal to an N- or C-terminus of the endonuclease. In some embodiments, the NLS comprises a sequence selected from SEQ ID NOs: 5597-5612.

In some embodiments, the engineered nuclease system further comprises a single- or double-stranded DNA repair template comprising from 5' to 3': a first homology arm comprising a sequence of at least 20 nucleotides 5' to the target deoxyribonucleic acid sequence, a synthetic DNA sequence of at least 10 nucleotides, and a second homology arm comprising a sequence of at least 20 nucleotides 3' to the target sequence. In some embodiments, the first or second homology arm comprises a sequence of at least 40, 80, 120, 150, 200, 300, 500, or 1,000 nucleotides.

In some embodiments, the system further comprises a source of Mg2+.

In some embodiments, the endonuclease and the tracr ribonucleic acid sequence are derived from distinct bacterial species within a same phylum. In some embodiments, the endonuclease is derived from a bacterium belonging to a genus Dermabacter. In some embodiments, the endonuclease is derived from a bacterium belonging to Phylum Verrucomicrobia, Phylum Candidatus Peregrinibacteria, or Phylum Candidatus Melainabacteria. In some embodiments, the endonuclease is derived from a bacterium comprising a 16S rRNA gene having at least 90% identity to any one of SEQ ID NOs: 5592-5595.

In some embodiments, the HNH domain comprises a sequence with at least 70% or at least 80% identity to any one of SEQ ID NOs: 5638-5460. In some embodiments, the endonuclease comprises SEQ ID NOs: 1-1826 or a variant thereof having at least 55% identity thereto. In some embodiments, the endonuclease comprises a sequence at least 70%, 80%, or 90% identical to a sequence selected from the group consisting of SEQ ID NOs: 1827-1830 or SEQ ID NOs: 1827-2140.

In some embodiments, the endonuclease comprises a sequence at least 70%, 80%, or 90% identical to a sequence selected from the group consisting of SEQ ID NOs: 3638-3641 or SEQ ID NOs: 3638-3954. In some embodiments, the endonuclease comprises at least 1, at least 2, at least 3, at least 4, or at least 5 peptide motifs selected from the group consisting of SEQ ID NOs: 5615-5632. In some embodiments, the endonuclease comprises a sequence at least 70%, 80%, or 90% identical to a sequence selected from the group consisting of SEQ ID NOs: 1-4 or SEQ ID NOs: 1-319.

In some embodiments, the guide RNA structure comprises a sequence at least 70%, 80%, or 90% identical to a sequence selected from the group consisting of SEQ ID NOs: 5461-5464, SEQ ID NOs: 5476-5479, or SEQ ID NOs: 5476-5489. In some embodiments, the guide RNA structure comprises an RNA sequence predicted to comprise a hairpin consisting of a stem and a loop, wherein the stem comprises at least 10, at least 12 or at least 14 base-paired ribonucleotides, and an asymmetric bulge within 4 base pairs of the loop.

In some embodiments, the endonuclease is configured to bind to a PAM comprising a sequence selected from the group consisting of SEQ ID NOs: 5512-5515 or SEQ ID NOs: 5527-5530.

In some embodiments: (a) the endonuclease comprises a sequence at least 70%, at least 80%, or at least 90% identical to SEQ ID NO: 1827; (b) the guide RNA structure comprises a sequence at least 70%, at least 80%, or at least 90% identical to at least one of SEQ ID NO: 5461 or SEQ ID NO: 5476; and (c) the endonuclease is configured to bind to a PAM comprising SEQ ID NO: 5512 or SEQ ID NO: 5527. In some embodiments: (a) the endonuclease comprises a sequence at least 70%, at least 80%, or at least 90% identical to SEQ ID NO: 1828; (b) the guide RNA structure comprises a sequence at least 70%, at least 80%, or at least 90% identical to at least one of SEQ ID NO: 5462 or SEQ ID NO: 5477; and (c) the endonuclease is configured to bind to a PAM comprising SEQ ID NO: 5513 or SEQ ID NO: 5528. In some embodiments: (a) the endonuclease comprises a sequence at least 70%, at least 80%, or at least 90% identical to SEQ ID NO: 1829; (b) the guide RNA structure comprises a sequence at least 70%, at least 80%, or at least 90% identical to at least one of SEQ ID NO: 5463 or SEQ ID NO: 5478; and (c) the endonuclease is configured to bind to a PAM comprising SEQ ID NO: 5514 or SEQ ID NO: 5529. In some embodiments: (a) the endonuclease comprises a sequence at least 70%, at least 80%, or at least 90% identical to SEQ ID NO: 1830; (b) the guide RNA structure comprises a sequence at least 70%, at least 80%, or at least 90% identical to at least one of SEQ ID NO: 5464 or SEQ ID NO: 5479; and (c) the endonuclease is configured to bind to a PAM comprising SEQ ID NO: 5515 or SEQ ID NO: 5530.

In some embodiments, the endonuclease comprises a sequence at least 70%, 80%, or 90% identical to a sequence selected from the group consisting of SEQ ID NOs: 2141-2142 or SEQ ID NOs: 2141-2241. In some embodiments, the endonuclease comprises a sequence at least 70%, 80%, or 90% identical to a sequence selected from the group consisting of SEQ ID NOs: 3955-3956 or SEQ ID NOs: 3955-4055. In some embodiments, the endonuclease comprises at least 1, at least 2, at least 3, at least 4, or at least 5 peptide motifs selected from the group consisting of SEQ ID NOs: 5632-5638. In some embodiments, the endonuclease comprises a sequence at least 70%, 80%, or 90% identical to a sequence selected from the group consisting of SEQ ID NOs: 320-321 or SEQ ID NOs: 320-420. In some embodiments, the guide RNA structure comprises a sequence at least 70%, 80%, or 90% identical to a sequence selected from the group consisting of SEQ ID NO: 5465, SEQ ID NOs: 5490-5491 or SEQ ID NOs: 5490-5494. In some embodiments, the guide RNA structure comprises a tracr ribonucleic acid sequence comprising a hairpin comprising at least 8, at least 10, or at least 12 base-paired ribonucleotides. In some embodiments, the endonuclease is configured to bind to a PAM comprising a sequence selected from the group consisting of SEQ ID NOs: 5516 and SEQ ID NOs: 5531. In some embodiments: (a) the endonuclease comprises a sequence at least 70%, 80%, or 90% identical to SEQ ID NO: 2141; (b) the guide RNA structure comprises a sequence at least 70%, 80%, or 90% identical to SEQ ID NO: 5490; and (c) the endonuclease is configured to binding to a PAM comprising SEQ ID NO: 5531. In some embodiments: (a) the endonuclease comprises a sequence at least 70%, 80%, or 90% identical to SEQ ID NO: 2142; (b) the guide RNA structure comprises a sequence at least 70%, 80%, or 90% identical to SEQ ID NO: 5465 or SEQ ID NO: 5491; and (c) the endonuclease is configured to binding to a PAM comprising SEQ ID NO: 5516.

In some embodiments, the endonuclease comprises a sequence at least 70%, 80%, or 90% identical to a sequence selected from the group consisting of SEQ ID NOs: 2245-2246. In some embodiments, the endonuclease comprises a sequence at least 70%, 80%, or 90% identical to a sequence selected from the group consisting of SEQ ID NOs: 4059-4060. In some embodiments, the endonuclease comprises at least 1, at least 2, at least 3, at least 4, or at least 5 peptide motifs selected from the group consisting of SEQ ID NOs: 5639-5648. In some embodiments, the endonuclease comprises a sequence at least 70%, 80%, or 90% identical to a sequence selected from the group consisting of SEQ ID NOs: 424-425. In some embodiments, the guide RNA structure comprises a sequence at least 70%, 80%, or 90% identical to a sequence selected from the group consisting of SEQ ID NOs: 5498-5499 and SEQ ID NO: 5539. In some embodiments, the guide RNA structure comprises a guide ribonucleic acid sequence predicted to comprise a hairpin with an uninterrupted base-paired region comprising at least 8 nucleotides of a guide ribonucleic acid sequence and at least 8 nucleotides of a tracr ribonucleic acid sequence, and wherein the tracr ribonucleic acid sequence comprises, from 5' to 3', a first hairpin and a second hairpin, wherein the first hairpin has a longer stem than the second hairpin.

In some embodiments, the endonuclease comprises a sequence at least 70%, 80%, or 90% identical to a sequence selected from the group consisting of SEQ ID NOs: 2242-2244 or SEQ ID NOs: 2247-2249. In some embodiments, the endonuclease comprises a sequence at least 70%, 80%, or 90% identical to a sequence selected from the group consisting of SEQ ID NOs: 4056-4058 and SEQ ID NOs 4061-4063. In some embodiments, the endonuclease comprises at least 1, at least 2, at least 3, at least 4, or at least 5 peptide motifs selected from the group consisting of SEQ ID NOs: 5639-5648. In some embodiments, the endonuclease comprises a sequence at least 70%, 80%, or 90% identical to a sequence selected from the group consisting of SEQ ID NOs: 421-423 or SEQ ID NOs: 426-428. In some embodiments, the guide RNA structure comprises a sequence at least 70%, 80%, or 90% identical to a sequence selected from the group consisting of SEQ ID NOs: 5466-5467, SEQ ID NOs: 5495-5497, SEQ ID NO: 5500-5502, and SEQ ID NO: 5539. In some embodiments, the guide RNA structure comprises a guide ribonucleic acid sequence predicted to comprise a hairpin with an uninterrupted base-paired region comprising at least 8 nucleotides of a guide ribonucleic acid sequence and at least 8 nucleotides of a tracr ribonucleic acid sequence, and wherein the tracr ribonucleic acid sequence comprises, from 5' to 3', a first hairpin and a second hairpin, wherein the first hairpin has a longer stem than the second hairpin. In some embodiments, the endonuclease is configured to binding to a PAM comprising a sequence selected from the group consisting of SEQ ID NOs: 5517-5518 or SEQ ID NOs: 5532-5534. In some embodiments: (a) the endonuclease comprises a sequence at least 70%, 80%, or 90% identical to SEQ ID NO: 2247; (b) the guide RNA structure comprises a sequence at least 70%, 80%, or 90% identical to SEQ ID NO: 5500; and (c) the endonuclease is configured to binding to a PAM comprising SEQ ID NO: 5517 or SEQ ID NO: 5532. In some embodiments: (a) the endonuclease comprises a sequence at least 70%, 80%, or 90% identical to SEQ ID NO: 2248; (b) the guide RNA structure comprises a sequence at least 70%, 80%, or 90% identical to SEQ ID NO: 5501; and (c) the endonuclease is configured to binding to a PAM comprising SEQ ID NO: 5518 or SEQ ID NOs: 5533. In some embodiments: (a) the endonuclease comprises a sequence at least 70%, 80%, or 90% identical to SEQ ID NO: 2249; (b) the guide RNA structure comprises a sequence at least 70%, 80%, or 90% identical to SEQ ID NO: 5502; and (c) the endonuclease is configured to binding to a PAM comprising SEQ ID NO: 5534.

In some embodiments, the endonuclease comprises a sequence at least 70%, 80%, or 90% identical to a sequence selected from the group consisting of SEQ ID NO: 2253 or SEQ ID NOs: 2253-2481. In some embodiments, the endonuclease comprises a sequence at least 70%, 80%, or 90% identical to a sequence selected from the group consisting of SEQ ID NO: 4067 or SEQ ID NOs: 4067-4295. In some embodiments, the endonuclease comprises a peptide motif according to SEQ ID NO: 5649. In some embodiments, the endonuclease comprises a sequence at least 70%, 80%, or 90% identical to a sequence selected from the group consisting of SEQ ID NO: 432 or SEQ ID NOs: 432-660. In some embodiments, the guide RNA structure comprises a sequence at least 70%, 80%, or 90% identical to a sequence selected from the group consisting of SEQ ID NO: 5468 or SEQ ID NO: 5503. In some embodiments, the endonuclease is configured to binding to a PAM comprising a sequence selected from the group consisting of SEQ ID NOs: 5519. In some embodiments: (a) the endonuclease comprises a sequence at least 70%, 80%, or 90% identical to SEQ ID NO: 2253; (b) the guide RNA structure comprises a sequence at least 70%, 80%, or 90% identical to SEQ ID NO: 5468 or SEQ ID NO: 5503; and (c) the endonuclease is configured to binding to a PAM comprising SEQ ID NO: 5519.

In some embodiments, the endonuclease comprises a sequence at least 70%, 80%, or 90% identical to a sequence selected from the group consisting of SEQ ID NOs: 2482-2489. In some embodiments, the endonuclease comprises a sequence at least 70%, 80%, or 90% identical to a sequence selected from the group consisting of SEQ ID NOs: 4296-4303. In some embodiments, the endonuclease comprises a sequence at least 70%, 80%, or 90% identical to a sequence selected from the group consisting of or SEQ ID NOs: 661-668. In some embodiments, the endonuclease comprises a sequence at least 70%, 80%, or 90% identical to a sequence selected from the group consisting of or SEQ ID NOs: 2490-2498. In some embodiments, the endonuclease comprises a sequence at least 70%, 80%, or 90% identical to a sequence selected from the group consisting of SEQ ID NOs: 4304-4312. In some embodiments, the endonuclease comprises a sequence at least 70%, 80%, or 90% identical to a sequence selected from the group consisting of SEQ ID NOs: 669-677. In some embodiments, the guide RNA structure comprises a sequence at least 70%, 80%, or 90% identical to a sequence selected from the group consisting of SEQ ID NO: 5504.

In some embodiments, the endonuclease comprises a sequence at least 70%, 80%, or 90% identical to a sequence selected from the group consisting of SEQ ID NO: 2499 or SEQ ID NOs: 2499-2750. In some embodiments, the endonuclease comprises a sequence at least 70%, 80%, or 90% identical to a sequence selected from the group consisting of SEQ ID NO: 4313 or SEQ ID NOs: 4313-4564. In some embodiments, the endonuclease comprises at least 1, at least 2, at least 3, at least 4, or at least 5 peptide motifs selected from the group consisting of SEQ ID NOs: 5650-5667. In some embodiments, the endonuclease comprises a sequence at least 70%, 80%, or 90% identical to a sequence selected from the group consisting of SEQ ID NO: 678 or SEQ ID NOs: 678-929. In some embodiments, the guide RNA structure comprises a sequence at least 70%, 80%, or 90% identical to SEQ ID NO: 5469 or SEQ ID NO: 5505. In some embodiments, the endonuclease is configured to binding to a PAM comprising SEQ ID NOs: 5520 or SEQ ID NOs: 5535. In some embodiments: (a) the endonuclease comprises a sequence at least 70%, 80%, or 90% identical to SEQ ID NO: 2499; (b) the guide RNA structure comprises a sequence at least 70%, 80%, or 90% identical to SEQ ID NO: 5469 or SEQ ID NO: 5505; and (c) the endonuclease is configured to binding to a PAM comprising SEQ ID NO: 5520 or SEQ ID NO: 5535.

In some embodiments, the endonuclease comprises a sequence at least 70%, 80%, or 90% identical to a sequence selected from the group consisting of SEQ ID NO: 2751 or SEQ ID NOs: 2751-2913. In some embodiments, the endonuclease comprises a sequence at least 70%, 80%, or 90% identical to a sequence selected from the group consisting of SEQ ID NO: 4565 or SEQ ID NOs: 4565-4727. In some embodiments, the endonuclease comprises at least 1, at least 2, at least 3, at least 4, or at least 5 peptide motifs selected from the group consisting of SEQ ID NOs: 5668-5678. In some embodiments, the endonuclease comprises a sequence at least 70%, 80%, or 90% identical to a sequence selected from the group consisting of SEQ ID NO: 930 or SEQ ID NOs: 930-1092. In some embodiments, the guide RNA structure comprises a sequence at least 70%, 80%, or 90% identical to SEQ ID NO: 5470 or SEQ ID NOs: 5506. In some embodiments, the endonuclease is configured to binding to a PAM comprising a sequence selected from the group consisting of SEQ ID NOs: 5521 or SEQ ID NOs: 5536. In some embodiments: (a) the endonuclease comprises a sequence at least 70%, 80%, or 90% identical to SEQ ID NO: 2751; (b) the guide RNA structure comprises a sequence at least 70%, 80%, or 90% identical to SEQ ID NO: 5470 or SEQ ID NO: 5506; and (c) the endonuclease is configured to binding to a PAM comprising SEQ ID NO: 5521 or SEQ ID NO: 5536.

In some embodiments, the endonuclease comprises a sequence at least 70%, 80%, or 90% identical to a sequence selected from the group consisting of SEQ ID NO: 2914 or SEQ ID NOs: 2914-3174. In some embodiments, the endonuclease comprises a sequence at least 70%, 80%, or 90% identical to a sequence selected from the group consisting of SEQ ID NO: 4728 or SEQ ID NOs: 4728-4988. In some embodiments, the endonuclease comprises at least 1, at least 2, or at least 3 peptide motifs selected from the group consisting of SEQ ID NOs: 5676-5678. In some embodiments, the endonuclease comprises a sequence at least 70%, 80%, or 90% identical to a sequence selected from the group consisting of SEQ ID NO: 1093 or SEQ ID NOs: 1093-1353. In some embodiments, the guide RNA structure comprises a sequence at least 70%, 80%, or 90% identical to a sequence selected from the group consisting of SEQ ID NO: 5471, SEQ ID NO: 5507, and SEQ ID NOs: 5540-5542. In some embodiments, the guide RNA structure comprises a tracr ribonucleic acid sequence predicted to comprise at least two hairpins comprising less than 5 base-paired ribonucleotides. In some embodiments, the endonuclease is configured to binding to a PAM comprising SEQ ID NO: 5522. In some embodiments: (a) the endonuclease comprises a sequence at least 70%, 80%, or 90% identical to SEQ ID NO: 2914; (b) the guide RNA structure comprises a sequence at least 70%, 80%, or 90% identical to SEQ ID NO: 5471 or SEQ ID NO: 5507; and (c) the endonuclease is configured to binding to a PAM comprising SEQ ID NO: 5522.

In some embodiments, the endonuclease comprises a sequence at least 70%, 80%, or 90% identical to a sequence selected from the group consisting of SEQ ID NO: 3175 or SEQ ID NOs: 3175-3330. In some embodiments, the endonuclease comprises a sequence at least 70%, 80%, or 90% identical to a sequence selected from the group consisting of SEQ ID NO: 4989 or SEQ ID NOs: 4989-5146. In some embodiments, the endonuclease comprises at least 1, at least 2, at least 3, at least 4, or at least 5 peptide motifs selected from the group consisting of SEQ ID NOs: 5679-5686. In some embodiments, the endonuclease comprises a sequence at least 70%, 80%, or 90% identical to a sequence selected from the group consisting of SEQ ID NO: 1354 or SEQ ID NOs: 1354-1511. In some embodiments, the guide RNA structure comprises a sequence at least 70%, 80%, or 90% identical to a sequence selected from the group consisting of SEQ ID NOs: 5472 or SEQ ID NOs: 5508. In some embodiments, the endonuclease is configured to binding to a PAM comprising a sequence selected from the group consisting of SEQ ID NO: 5523 or SEQ ID NO: 5537. In some embodiments: (a) the endonuclease comprises a sequence at least 70%, 80%, or 90% identical to SEQ ID NO: 3175; (b) the guide RNA structure comprises a sequence at least 70%, 80%, or 90% identical to SEQ ID NO: 5472 or SEQ ID NO: 5508; and (c) the endonuclease is configured to binding to a PAM comprising SEQ ID NO: 5523 or SEQ ID NO: 5537.

In some embodiments, the endonuclease comprises a sequence at least 70%, 80%, or 90% identical to a sequence selected from the group consisting of SEQ ID NOs: 3331 or SEQ ID NOs: 3331-3474. In some embodiments, the endonuclease comprises a sequence at least 70%, 80%, or 90% identical to a sequence selected from the group consisting of SEQ ID NOs: 5147 or SEQ ID NOs: 5147-5290. In some embodiments, the endonuclease comprises at least 1, at least 2, at least 3, at least 4, or at least 5 peptide motifs selected from the group consisting of SEQ ID NOs: 5674-5675 and SEQ ID NOs: 5687-5693. In some embodiments, the endonuclease comprises a sequence at least 70%, 80%, or 90% identical to a sequence selected from the group consisting of SEQ ID NO: 1512 or SEQ ID NOs: 1512-1655. In some embodiments, the guide RNA structure comprises a sequence at least 70%, 80%, or 90% identical to a sequence selected from the group consisting of SEQ ID NO: 5473 or SEQ ID NO: 5509. In some embodiments, the endonuclease is configured to binding to a PAM comprising SEQ ID NO: 5524. In some embodiments: (a) the endonuclease comprises a sequence at least 70%, 80%, or 90% identical to SEQ ID NO: 3331; (b) the guide RNA structure comprises a sequence at least 70%, 80%, or 90% identical to SEQ ID NO: 5473 or SEQ ID NO: 5509; and (c) the endonuclease is configured to binding to a PAM comprising SEQ ID NO: 5524.

In some embodiments, the endonuclease comprises a sequence at least 70%, 80%, or 90% identical to a sequence selected from the group consisting of SEQ ID NO: 3475 or SEQ ID NOs: 3475-3568. In some embodiments, the endonuclease comprises a sequence at least 70%, 80%, or 90% identical to a sequence selected from the group consisting of SEQ ID NO: 5291 or SEQ ID NOs: 5291-5389. In some embodiments, the endonuclease comprises at least 1, at least 2, at least 3, at least 4, or at least 5 peptide motifs selected from the group consisting of SEQ ID NOs: 5694-5699. In some embodiments, the endonuclease comprises a sequence at least 70%, 80%, or 90% identical to a sequence selected from the group consisting of SEQ ID NO: 1656 or SEQ ID NOs: 1656-1755. In some embodiments, the guide RNA structure comprises a sequence at least 70%, 80%, or 90% identical to SEQ ID NO: 5474 or SEQ ID NO: 5510. In some embodiments, the endonuclease is configured to binding to a PAM comprising SEQ ID NOs: 5525. In some embodiments: (a) the endonuclease comprises a sequence at least 70%, 80%, or 90% identical to SEQ ID NO: 3475; (b) the guide RNA structure comprises a sequence at least 70%, 80%, or 90% identical to SEQ ID NO: 5474 or SEQ ID NO: 5510; and (c) the endonuclease is configured to binding to a PAM comprising SEQ ID NO: 5525.

In some embodiments, the endonuclease comprises a sequence at least 70%, 80%, or 90% identical to a sequence selected from the group consisting of SEQ ID NO: 3569 or SEQ ID NOs: 3569-3637. In some embodiments, the endonuclease comprises a sequence at least 70%, 80%, or 90% identical to a sequence selected from the group consisting of SEQ ID NO: 5390 or SEQ ID NOs: 5390-5460. In some embodiments, the endonuclease comprises at least 1, at least 2, at least 3, at least 4, or at least 5 peptide motifs selected from the group consisting of SEQ ID NOs: 5700-5717. In some embodiments, the endonuclease comprises a sequence at least 70%, 80%, or 90% identical to a sequence selected from the group consisting of SEQ ID NO: 1756 or SEQ ID NOs: 1756-1826. In some embodiments, the guide RNA structure comprises a sequence at least 70%, 80%, or 90% identical to SEQ ID NO: 5475 or SEQ ID NOs: 5511. In some embodiments, the endonuclease is configured to binding to a PAM comprising SEQ ID NO: 5526. In some embodiments: (a) the endonuclease comprises a sequence at least 70%, 80%, or 90% identical to SEQ ID NO: 3569; (b) the guide RNA structure comprises a sequence at least 70%, 80%, or 90% identical to SEQ ID NO: 5475 or SEQ ID NO: 5511; and (c) the endonuclease is configured to binding to a PAM comprising SEQ ID NO: 5526. In some embodiments, the sequence identity is determined by a BLASTP, CLUSTALW, MUSCLE, MAFFT, or CLUSTALW with the parameters of the Smith-Waterman homology search algorithm. In some embodiments, the sequence identity is determined by the BLASTP homology search algorithm using parameters of a wordlength (W) of 3, an expectation (E) of 10, and a BLOSUM62 scoring matrix setting gap costs at existence of 11, extension of 1, and using a conditional compositional score matrix adjustment.

In some aspects, the present disclosure provides for an engineered guide ribonucleic acid polynucleotide comprising: (a) a DNA-targeting segment comprising a nucleotide sequence that is complementary to a target sequence in a target DNA molecule; and (b) a protein-binding segment comprising two complementary stretches of nucleotides that hybridize to form a double-stranded RNA (dsRNA) duplex, wherein the two complementary stretches of nucleotides are covalently linked to one another with intervening nucleotides, and wherein the engineered guide ribonucleic acid polynucleotide is configured to forming a complex with an endonuclease comprising a RuvC_III domain having at least 70%, at least 75%, at least 80%, at least 85%, at least 88%, at least 90%, at least 92%, at least 95%, or at least 98% sequence identity to any one of SEQ ID NOs: 1827-3637 and targeting the complex to the target sequence of the target DNA molecule. In some embodiments, the DNA-targeting segment is positioned 5' of both of the two complementary stretches of nucleotides.

In some embodiments: (a) the protein binding segment comprises a sequence having at least 70%, at least 75%, at least 80%, at least 85%, at least 88%, at least 90%, at least 92%, at least 95%, or at least 98% identity to a sequence selected from the group consisting of SEQ ID NOs: 5476-5479 or SEQ ID NOs: 5476-5489; (b) the protein binding segment comprises a sequence having at least 70%, at least 80%, or at least 90% identity to a sequence selected from the group consisting of (SEQ ID NOs: 5490-5491 or SEQ ID NOs: 5490-5494) and SEQ ID NO: 5538; (c) the protein binding segment comprises a sequence having at least 70%, at least 80%, or at least 90% identity to a sequence selected from the group consisting of SEQ ID NOs: 5498-5499; (d) the protein binding segment comprises a sequence having at least 70%, at least 80%, or at least 90% identity to a sequence selected from the group consisting of SEQ ID NOs: 5495-5497 and SEQ ID NOs: 5500-5502; (e) the protein binding segment comprises a sequence having at least 70%, at least 80%, or at least 90% identity to SEQ ID NO: 5503; (f) the protein binding segment comprises a sequence having at least 70%, at least 80%, or at least 90% identity to SEQ ID NO: 5504; (g) the protein binding segment comprises a sequence having at least 70%, at least 80%, or at least 90% identity to SEQ ID NOs: 5505; (h) protein binding segment comprises a sequence having at least 70%, at least 80%, or at least 90% identity to SEQ ID NO: 5506; (i) protein binding segment comprises a sequence having at least 70%, at least 80%, or at least 90% identity to SEQ ID NO: 5507; (j) the protein binding segment comprises a sequence having at least 70%, at least 80%, or at least 90% identity to SEQ ID NO: 5508; (k) the protein binding segment comprises a sequence having at least 70%, at least 80%, or at least 90% identity to SEQ ID NO: 5509; (1) the protein binding segment comprises a sequence having at least 70%, at least 80%, or at least 90% identity to SEQ ID NO: 5510; or (m) the protein binding segment comprises a sequence having at least 70%, at least 80%, or at least 90% identity to SEQ ID NO: 5511.

In some embodiments: (a) the guide ribonucleic acid polynucleotide comprises an RNA sequence comprising a hairpin comprising a stem and a loop, wherein the stem comprises at least 10, at least 12, or at least 14 base-paired ribonucleotides, and an asymmetric bulge within 4 base pairs of the loop; (b) the guide ribonucleic acid polynucleotide comprises a tracr ribonucleic acid sequence predicted to comprise a hairpin comprising at least 8, at least 10, or at least 12 base-paired ribonucleotides; (c) the guide ribonucleic acid polynucleotide comprises a guide ribonucleic acid sequence predicted to comprise a hairpin with an uninterrupted base-paired region comprising at least 8 nucleotides of a guide ribonucleic acid sequence and at least 8 nucleotides of a tracr ribonucleic acid sequence, and wherein the tracr ribonucleic acid sequence comprises, from 5' to 3', a first hairpin and a second hairpin, wherein the first hairpin has a longer stem than the second hairpin; or (d) the guide ribonucleic acid polynucleotide comprises a tracr ribonucleic acid sequence predicted to comprise at least two hairpins comprising less than 5 base-paired ribonucleotides.

In some aspects, the present disclosure provides for a deoxyribonucleic acid polynucleotide encoding any of the engineered guide ribonucleic acid polynucleotides described herein.

In some aspects, the present disclosure provides for a nucleic acid comprising an engineered nucleic acid sequence optimized for expression in an organism, wherein the nucleic acid encodes a class 2, type II Cas endonuclease comprising a RuvC_III domain and an HNH domain, and wherein the endonuclease is derived from an uncultivated microorganism.

In some aspects, the present disclosure provides for a nucleic acid comprising an engineered nucleic acid sequence optimized for expression in an organism, wherein the nucleic acid encodes an endonuclease comprising a RuvC_III domain having at least 70% sequence identity to any one of SEQ ID NOs: 1827-3637. In some embodiments, the endonuclease comprises an HNH domain having at least 70% or at least 80% sequence identity to any one of SEQ ID NOs: 3638-5460. In some embodiments, the endonuclease comprises SEQ ID NOs: 5572-5591 or a variant thereof having at least 70% sequence identity thereto. In some embodiments, the endonuclease comprises a sequence encoding one or more nuclear localization sequences (NLSs) proximal to an N- or C-terminus of the endonuclease. In some embodiments, the NLS comprises a sequence selected from SEQ ID NOs: 5597-5612.

In some embodiments, the organism is prokaryotic, bacterial, eukaryotic, fungal, plant, mammalian, rodent, or human. In some embodiments, the organism is *E. coli*, and: (a) the nucleic acid sequence has at least 70%, 80%, or 90% identity to a sequence selected from the group consisting of SEQ ID NOs: 5572-5575; (b) the nucleic acid sequence has at least 70%, 80%, or 90% identity to a sequence selected from the group consisting of SEQ ID NOs: 5576-5577; (c) the nucleic acid sequence has at least 70%, 80%, or 90% identity to a sequence selected from the group consisting of SEQ ID NOs: 5578-5580; (d) the nucleic acid sequence has at least 70%, 80%, or 90% identity to SEQ ID NO: 5581; (e) the nucleic acid sequence has at least 70%, 80%, or 90% identity to SEQ ID NO: 5582; (f) the nucleic acid sequence has at least 70%, 80%, or 90% identity to SEQ ID NO: 5583; (g) the nucleic acid sequence has at least 70%, 80%, or 90% identity to SEQ ID NO: 5584; (h) the nucleic acid sequence has at least 70%, 80%, or 90% identity to SEQ ID NO: 5585; (i) the nucleic acid sequence has at least 70%, 80%, or 90% identity to SEQ ID NO: 5586; or (j) the nucleic acid sequence has at least 70%, 80%, or 90% identity to SEQ ID NO: 5587. In some embodiments, the organism is human, and: (a) the nucleic acid sequence has at least 70%, 80%, or 90% identity to SEQ ID NO: 5588 or SEQ ID NO: 5589; or (b) the nucleic acid sequence has at least 70%, 80%, or 90% identity to SEQ ID NO: 5590 or SEQ ID NO: 5591.

In some aspects, the present disclosure provides for a vector comprising a nucleic acid sequence encoding a class 2, type II Cas endonuclease comprising a RuvC_III domain and an HNH domain, wherein the endonuclease is derived from an uncultivated microorganism.

In some aspects, the present disclosure provides for a vector comprising the any of the nucleic acids described herein. In some embodiments, the vector further comprises a nucleic acid encoding an engineered guide ribonucleic acid structure configured to form a complex with the endonuclease comprising: (a) a guide ribonucleic acid sequence configured to hybridize to a target deoxyribonucleic acid sequence; and (b) a tracr ribonucleic acid sequence configured to binding to the endonuclease. In some embodiments, the vector is a plasmid, a minicircle, a CELiD, an adeno-associated virus (AAV) derived virion, or a lentivirus.

In some aspects, the present disclosure provides for a cell comprising any of the vectors described herein.

In some aspects, the present disclosure provides for a method of manufacturing an endonuclease, comprising cultivating any of the cells described herein.

In some aspects, the present disclosure provides for a method for binding, cleaving, marking, or modifying a double-stranded deoxyribonucleic acid polynucleotide, comprising: (a) contacting the double-stranded deoxyribonucleic acid polynucleotide with a class 2, type II Cas endonuclease in complex with an engineered guide ribonucleic acid structure configured to bind to the endonuclease and the double-stranded deoxyribonucleic acid polynucleotide; (b) wherein the double-stranded deoxyribonucleic acid polynucleotide comprises a protospacer adjacent motif (PAM); and (c) wherein the PAM comprises a sequence selected from the group consisting of SEQ ID NOs: 5512-5526 or SEQ ID NOs: 5527-5537. In some embodiments, the double-stranded deoxyribonucleic acid polynucleotide comprises a first strand comprising a sequence complementary to a sequence of the engineered guide ribonucleic acid structure and a second strand comprising the PAM. In some embodiments, the PAM is directly adjacent to the 3' end of the sequence complementary to the sequence of the engineered guide ribonucleic acid structure.

In some embodiments, the class 2, type II Cas endonuclease is not a Cas9 endonuclease, a Cas14 endonuclease, a Cas12a endonuclease, a Cas12b endonuclease, a Cas 12c endonuclease, a Cas12d endonuclease, a Cas12e endonuclease, a Cas13a endonuclease, a Cas13b endonuclease, a Cas13c endonuclease, or a Cas 13d endonuclease. In some embodiments, the class 2, type II Cas endonuclease is derived from an uncultivated microorganism. In some embodiments, the double-stranded deoxyribonucleic acid polynucleotide is a eukaryotic, plant, fungal, mammalian, rodent, or human double-stranded deoxyribonucleic acid polynucleotide.

In some embodiments: (a) the PAM comprises a sequence selected from the group consisting of SEQ ID NOs: 5512-5515 and SEQ ID NOs: 5527-5530; (b) the PAM comprises SEQ ID NO: 5516 or SEQ ID NO: 5531; (c) the PAM comprises SEQ ID NO: 5539; (d) the PAM comprises SEQ ID NO: 5517 or SEQ ID NO: 5518; (e) the PAM comprises SEQ ID NO: 5519; (f) the PAM comprises SEQ ID NO: 5520 or SEQ ID NO: 5535; (g) the PAM comprises SEQ ID NO: 5521 or SEQ ID NO: 5536; (h) the PAM comprises SEQ ID NO: 5522; (i) the PAM comprises SEQ ID NO: 5523 or SEQ ID NO: 5537; (j) the PAM comprises SEQ ID NO: 5524; (k) the PAM comprises SEQ ID NO: 5525; or (l) the PAM comprises SEQ ID NO: 5526.

In some aspects, the present disclosure provides for a method of modifying a target nucleic acid locus, the method comprising delivering to the target nucleic acid locus any of the engineered nuclease systems described herein, wherein the endonuclease is configured to form a complex with the engineered guide ribonucleic acid structure, and wherein the complex is configured such that upon binding of the complex to the target nucleic acid locus, the complex modifies the target nucleic locus. In some embodiments, modifying the target nucleic acid locus comprises binding, nicking, cleaving, or marking the target nucleic acid locus. In some embodiments, the target nucleic acid locus comprises deoxyribonucleic acid (DNA) or ribonucleic acid (RNA). In some embodiments, the target nucleic acid comprises genomic DNA, viral DNA, viral RNA, or bacterial DNA. In some embodiments, the target nucleic acid locus is in vitro. In some embodiments, the target nucleic acid locus is within a cell. In some embodiments, the cell is a prokaryotic cell, a bacterial cell, a eukaryotic cell, a fungal cell, a plant cell, an animal cell, a mammalian cell, a rodent cell, a primate cell, or a human cell.

In some embodiments, delivering the engineered nuclease system to the target nucleic acid locus comprises delivering any of the nucleic acids described herein or any of the vectors described herein. In some embodiments, delivering the engineered nuclease system to the target nucleic acid locus comprises delivering a nucleic acid comprising an open reading frame encoding the endonuclease. In some embodiments, the nucleic acid comprises a promoter to which the open reading frame encoding the endonuclease is operably linked. In some embodiments, the engineered nuclease system to the target nucleic acid locus comprises delivering a capped mRNA containing the open reading frame encoding the endonuclease. In some embodiments, the engineered nuclease system to the target nucleic acid locus comprises delivering a translated polypeptide. In some embodiments, the engineered nuclease system to the target nucleic acid locus comprises delivering a deoxyribonucleic acid (DNA) encoding the engineered guide ribonucleic acid structure operably linked to a ribonucleic acid (RNA) pol III promoter. In some embodiments, the endonuclease induces a single-stranded break or a double-stranded break at or proximal to the target locus.

In some aspects, the present disclosure provides for an engineered nuclease system comprising: (a) an endonuclease comprising a sequence having at least 75% sequence identity to any one of SEQ ID NOs: 5718-5846 or 6257; and (b) an engineered guide ribonucleic acid structure configured to form a complex with said endonuclease comprising: (i) a ribonucleic acid sequence configured to hybridize to a target deoxyribonucleic acid sequence; and (ii) a ribonucleic acid sequence configured to bind to said endonuclease. In some aspects, the present disclosure provides for an engineered nuclease system comprising: (a) an endonuclease configured to bind to a protospacer adjacent motif (PAM) sequence comprising SEQ ID NOs: 5847-5861 or 6258-6278, wherein said endonuclease is a class 2, type II Cas endonuclease; and (b) an engineered guide ribonucleic acid structure configured to form a complex with said endonuclease comprising: (i) a ribonucleic acid sequence configured to hybridize to a target deoxyribonucleic acid sequence; and (ii) a ribonucleic acid sequence configured to bind to said endonuclease. In some embodiments, said endonuclease is derived from an uncultivated microorganism. In some embodiments, said endonuclease has not been engineered to bind to a different PAM sequence. In some embodiments, said endonuclease is not a Cas9 endonuclease, a Cas14 endonuclease, a Cas12a endonuclease, a Cas12b endonuclease, a Cas 12c endonuclease, a Cas12d endonuclease, a Cas12e endonuclease, a Cas13a endonuclease, a Cas13b endonuclease, a Cas13c endonuclease, or a Cas 13d endonuclease. In some embodiments, said endonuclease has less than 80% identity to a Cas9 endonuclease. In some embodiments, said ribonucleic acid sequence comprises a sequence with at least 80% sequence identity to (a) any one of SEQ ID NOs: 5886-5887, 5891, 5893, or 5894; or (b) the non-degenerate nucleotides of any one of SEQ ID NOs: 5862-5885, 5888-5890, 5892, 5895-5896, or 6279-6301. In some aspects, the present disclosure provides for an engineered nuclease system comprising, (a) an engineered guide ribonucleic acid structure comprising: (i) a ribonucleic acid sequence configured to hybridize to a target deoxyribonucleic acid sequence; and (ii) a ribonucleic acid sequence configured to bind to an endonuclease, wherein said ribonucleic acid sequence comprises a sequence with at least 80% sequence identity (a) any one of SEQ ID NOs: 5886-5887, 5891, 5893, or 5894; or (b) the non-degenerate nucleotides of any one of SEQ ID NOs: 5862-5885, 5888-5890, 5892, 5895-5896, or 6279-6301; and a class 2, type II Cas endonuclease configured to bind to said engineered guide ribonucleic acid. In some embodiments, endonuclease is configured to bind to a protospacer adjacent motif (PAM) sequence selected from the group comprising SEQ ID NOs: 5847-5861 or 6258-6278. In some embodiments, said guide ribonucleic acid sequence is 15-24 nucleotides in length or 19-24 nucleotides in length. In some embodiments, said endonuclease comprises one or more nuclear localization sequences (NLSs) proximal to an N- or C-terminus of said endonuclease. In some embodiments, said NLS comprises a sequence selected from SEQ ID NOs: 5597-5612. In some embodiments, the system further comprises a single- or double-stranded DNA repair template comprising from 5' to 3': a first homology arm comprising a sequence of at least 20 nucleotides 5' to said target deoxyribonucleic acid sequence, a synthetic DNA sequence of at least 10 nucleotides, and a second homology arm comprising a sequence of at least 20 nucleotides 3' to said target sequence. In some embodiments, said first or second homology arm comprises a sequence of at least 40, 80, 120, 150, 200, 300, 500, or 1,000 nucleotides. In some embodiments, said sequence identity is determined by a BLASTP, CLUSTALW, MUSCLE, MAFFT, or CLUSTALW with the parameters of the Smith-Waterman homology search algorithm. In some embodiments, said sequence identity is determined by said BLASTP homology search algorithm using parameters of a wordlength (W) of 3, an expectation (E) of 10, and a BLOSUM62 scoring matrix setting gap costs at existence of 11, extension of 1, and using a conditional compositional score matrix adjustment.

In some aspects, the present disclosure provides for an engineered guide ribonucleic acid polynucleotide comprising: (a) a DNA-targeting segment comprising a nucleotide sequence that is complementary to a target sequence in a target DNA molecule; and (b) a protein-binding segment comprising two complementary stretches of nucleotides that hybridize to form a double-stranded RNA (dsRNA) duplex, wherein said two complementary stretches of nucleotides are covalently linked to one another with intervening nucleotides, and wherein said engineered guide ribonucleic acid polynucleotide is configured to form a complex with an endonuclease comprising sequence having at least 75% sequence identity to any one of SEQ ID NOs: 5718-5846 or 6257 and target said complex to said target sequence of said target DNA molecule. In some embodiments, said DNA-targeting segment is positioned 5' of both of said two complementary stretches of nucleotides.

In some aspects, the present disclosure provides for a deoxyribonucleic acid polynucleotide encoding any of the engineered guide ribonucleic acid polynucleotides described herein.

In some aspects, the present disclosure provides for a nucleic acid comprising an engineered nucleic acid sequence optimized for expression in an organism, wherein said nucleic acid encodes an endonuclease comprising a sequence having at least 75% sequence identity to any one of SEQ ID NOs: 5718-5846 or 6257. In some embodiments, said endonuclease comprises a sequence encoding one or more nuclear localization sequences (NLSs) proximal to an N- or C-terminus of said endonuclease. In some embodiments, said NLS comprises a sequence selected from SEQ ID NOs: 5597-5612. In some embodiments, said organism is prokaryotic, bacterial, eukaryotic, fungal, plant, mammalian, rodent, or human.

In some aspects, the present disclosure provides for a vector comprising any of the nucleic acids described herein. In some embodiments, the vector further comprises a nucleic acid encoding an engineered guide ribonucleic acid structure configured to form a complex with said endonuclease comprising: (a) a ribonucleic acid sequence configured to hybridize to a target deoxyribonucleic acid sequence; and (b) a ribonucleic acid sequence configured to bind to said endonuclease. In some embodiments, the vector is a plasmid, a minicircle, a CELiD, an adeno-associated virus (AAV) derived virion, or a lentivirus.

In some aspects, the present disclosure provides for a cell comprising any of the vectors described herein In some aspects, the present disclosure provides for a method of manufacturing an endonuclease, comprising cultivating any of the cells described herein.

In some aspects, the present disclosure provides for a method for binding, cleaving, marking, or modifying a double-stranded deoxyribonucleic acid polynucleotide, comprising: contacting said double-stranded deoxyribonucleic acid polynucleotide with a class 2, type II Cas endonuclease in complex with an engineered guide ribonucleic acid structure configured to bind to said endonuclease and said double-stranded deoxyribonucleic acid polynucleotide; wherein said double-stranded deoxyribonucleic acid polynucleotide comprises a protospacer adjacent motif (PAM); and wherein said PAM comprises a sequence selected from the group consisting of SEQ ID NOs: 5847-5861 or 6258-6278. In some embodiments, said double-stranded deoxyribonucleic acid polynucleotide comprises a first strand comprising a sequence complementary to a sequence of said engineered guide ribonucleic acid structure and a second strand comprising said PAM. In some embodiments, said PAM is directly adjacent to the 3' end of said sequence complementary to said sequence of said engineered guide ribonucleic acid structure. In some embodiments, said class 2, type II Cas endonuclease is not a Cas9 endonuclease, a Cas14 endonuclease, a Cas12a endonuclease, a Cas12b endonuclease, a Cas 12c endonuclease, a Cas12d endonuclease, a Cas12e endonuclease, a Cas13a endonuclease, a Cas13b endonuclease, a Cas13c endonuclease, or a Cas 13d endonuclease. In some embodiments, said double-stranded deoxyribonucleic acid polynucleotide is a eukaryotic, plant, fungal, mammalian, rodent, or human double-stranded deoxyribonucleic acid polynucleotide.

In some aspects, the present disclosure provides for a method of modifying a target nucleic acid locus, said method comprising delivering to said target nucleic acid locus any of the engineered nuclease systems described herein, wherein said endonuclease is configured to form a complex with said engineered guide ribonucleic acid structure, and wherein said complex is configured such that upon binding of said complex to said target nucleic acid locus, said complex modifies said target nucleic locus. In some embodiments, said target nucleic acid locus comprises binding, nicking, cleaving, or marking said target nucleic acid locus. In some embodiments, said target nucleic acid locus comprises deoxyribonucleic acid (DNA) or ribonucleic acid (RNA). In some embodiments, said target nucleic acid comprises genomic DNA, viral DNA, viral RNA, or bacterial DNA. In some embodiments, said target nucleic acid locus is in vitro. In some embodiments, said target nucleic acid locus is within a cell. In some embodiments, said cell is a prokaryotic cell, a bacterial cell, a eukaryotic cell, a fungal cell, a plant cell, an animal cell, a mammalian cell, a rodent cell, a primate cell, or a human cell. In some embodiments, said engineered nuclease system to said target nucleic acid locus comprises delivering any of the nucleic acids described herein or any of the vectors described herein. In some embodiments, delivering said engineered nuclease system to said target nucleic acid locus comprises delivering a nucleic acid comprising an open reading frame encoding said endonuclease. In some embodiments, said nucleic acid comprises a promoter to which said open reading frame encoding said endonuclease is operably linked. In some embodiments, delivering said engineered nuclease system to said target nucleic acid locus comprises delivering a capped mRNA containing said open reading frame encoding said endonuclease. In some embodiments, delivering said engineered nuclease system to said target nucleic acid locus comprises delivering a translated polypeptide. In some embodiments, delivering said engineered nuclease system to said target nucleic acid locus comprises delivering a deoxyribonucleic acid (DNA) encoding said engineered guide ribonucleic acid structure operably linked to a ribonucleic acid (RNA) pol III promoter. In some embodiments, said endonuclease induces a single-stranded break or a double-stranded break at or proximal to said target locus.

In some aspects, the present disclosure provides for a method of editing a TRAC locus in a cell, comprising contacting to said cell (a) an RNA-guided endonuclease; and (b) an engineered guide RNA, wherein said engineered guide RNA is configured to form a complex with said endonuclease and said engineered guide RNA comprises a spacer sequence configured to hybridize to a region of said TRAC locus, wherein said engineered guide RNA comprises a targeting sequence having at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to at least 19, at least 20, at least 21, at least 22, at least 23, or at least 24 consecutive nucleotides of any one of SEQ ID NOs: 5950-5958 or 5959-5965. In some embodiments, said RNA-guided endonuclease is a class II, type II Cas endonuclease. In some embodiments, said RNA-guided endonuclease comprises a RuvCIII domain comprising a sequence having at least 75% identity, at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to SEQ ID NO: 2242 or SEQ ID NO: 2244. In some embodiments, said RNA-guided endonuclease further comprises an HNH domain. In some embodiments, said RNA-guided endonuclease comprises a sequence having at least 75% identity, at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to SEQ ID NO: 421 or SEQ ID NO: 423. In some embodiments, said engineered guide RNA comprises a targeting sequence having at least 85% identity to at least 18 consecutive nucleotides of any one of SEQ ID NOs: 5950-5958 and said endonuclease comprises a sequence having at least 75% identity to SEQ ID NO:421. In some embodiments, said engineered guide RNA comprises a targeting sequence having at least 85% identity to at least 18 consecutive nucleotides of any one of SEQ ID NOs: 5959-5965 and said endonuclease comprises a sequence having at least 75% identity to SEQ ID NO: 423. In some embodiments, said engineered guide RNA comprises a targeting sequence having at least 85% identity to at least 18 consecutive nucleotides of any one of SEQ ID NOs: 5953-5957. In some embodiments, said engineered guide RNA comprises a targeting sequence having at least 85% identity to at least 18 consecutive nucleotides of any one of SEQ ID NOs: 5960-5961 or 5963-5964.

In some aspects, the present disclosure provides for a method of editing a TRBC locus in a cell, comprising contacting to said cell (a) an RNA-guided endonuclease; and (b) an engineered guide RNA, wherein said engineered guide RNA is configured to form a complex with said endonuclease and said engineered guide RNA comprises a spacer sequence configured to hybridize to a region of said TRBC locus, wherein said engineered guide RNA comprises a targeting sequence having at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to at least 19, at least 20, at least 21, at least 22, at least 23, or at least 24 consecutive nucleotides of any one of SEQ ID NOs: 5966-6004 or 6005-6025. In some embodiments, said RNA-guided endonuclease is a class II, type II Cas endonuclease. In some embodiments, said RNA-guided endonuclease comprises a RuvCIII domain comprising a sequence having at least 75% identity, at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to SEQ ID NO: 2242 or SEQ ID NO: 2244. In some embodiments, said RNA-guided endonuclease further comprises an HNH domain. In some embodiments, said RNA-guided endonuclease comprises a sequence having at least 75% identity, at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to SEQ ID NO: 421 or SEQ ID NO: 423. In some embodiments, said engineered guide RNA comprises a targeting sequence having at least 85% identity to at least 18 consecutive nucleotides of any one of SEQ ID NOs: 5966-6004 and said endonuclease comprises a sequence having at least 75% identity to SEQ ID NO: 421. In some embodiments, said engineered guide RNA comprises a targeting sequence having at least 85% identity to at least 18 consecutive nucleotides of any one of SEQ ID NOs: 6005-6025 and said endonuclease comprises a sequence having at least 75% identity to SEQ ID NO: 423. In some embodiments, said engineered guide RNA comprises a targeting sequence having at least 85% identity to at least 18 consecutive nucleotides of any one of SEQ ID NOs: 5970, 5971, 5983, or 5984. In some embodiments, said engineered guide RNA comprises a targeting sequence having at least 85% identity to at least 18 consecutive nucleotides of any one of SEQ ID NOs: 6006, 6010, 6011, or 6012.

In some aspects, the present disclosure provides for a method of editing a GR (NR3C1) locus in a cell, comprising contacting to said cell (a) an RNA-guided endonuclease; and (b) an engineered guide RNA, wherein said engineered guide RNA is configured to form a complex with said endonuclease and said engineered guide RNA comprises a spacer sequence configured to hybridize to a region of said GR (NR3C1) locus, wherein said engineered guide RNA comprises a targeting sequence having at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to at least 19, at least 20, at least 21, at least 22, at least 23, or at least 24 consecutive nucleotides consecutive nucleotides of any one of SEQ ID NOs: 6026-6090 or 6091-6121. In some embodiments, said RNA-guided endonuclease is a class II, type II Cas endonuclease. In some embodiments, said RNA-guided endonuclease comprises a RuvCIII domain comprising a sequence having at least 75% identity, at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to SEQ ID NO: 2242 or SEQ ID NO: 2244. In some embodiments, said RNA-guided endonuclease further comprises an HNH domain. In some embodiments, said RNA-guided endonuclease comprises a sequence having at least 75% identity to SEQ ID NO: 421 or SEQ ID NO: 423. In some embodiments, said engineered guide RNA comprises a targeting sequence having at least 85% identity to at least 18 consecutive nucleotides of any one of SEQ ID NOs: 6026-6090 and said endonuclease comprises a sequence having at least 75% identity to SEQ ID NO: 421. In some embodiments, said engineered guide RNA comprises a targeting sequence having at least 85% identity to at least 18 consecutive nucleotides of any one of SEQ ID NOs: 6091-6121 and said endonuclease comprises a sequence having at least 75% identity to SEQ ID NO: 423. In some embodiments, said engineered guide RNA comprises a targeting sequence having at least 85% identity to at least 18 consecutive nucleotides of any one of SEQ ID NOs: 6027-6028, 6029, 6038, 6043, 6049, 6076, 6080, 6081, or 6086. In some embodiments, said engineered guide RNA comprises a targeting sequence having at least 85% identity to at least 18 consecutive nucleotides of any one of SEQ ID NOs: 6092, 6115, or 6119.

In some aspects, the present disclosure provides for a method of editing an AAVS1 locus in a cell, comprising contacting to said cell (a) an RNA-guided endonuclease; and (b) an engineered guide RNA, wherein said engineered guide RNA is configured to form a complex with said endonuclease and said engineered guide RNA comprises a spacer sequence configured to hybridize to a region of said AAVS1 locus, wherein said engineered guide RNA comprises a targeting sequence having at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to at least 19, at least 20, at least 21, at least 22, at least 23, or at least 24 consecutive nucleotides of any one of SEQ ID NOs: 6122-6152. In some embodiments, said RNA-guided endonuclease is a class II, type II Cas endonuclease. In some embodiments, said RNA-guided endonuclease comprises a RuvCIII domain comprising a sequence having at least 75% identity, at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to SEQ ID NO: 2242 or SEQ ID NO: 2244. In some embodiments, said RNA-guided endonuclease further comprises an HNH domain. In some embodiments, said RNA-guided endonuclease comprises a sequence having at least 75% identity, at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to SEQ ID NO: 421 or SEQ ID NO: 423. In some embodiments, said engineered guide RNA comprises a targeting sequence having at least 85% identity to at least 18 consecutive nucleotides of any one of SEQ ID NOs: 6122, 6125-6126, 6128, 6131, 6133, 6136, 6141, 6143, or 6148.

In some aspects, the present disclosure provides for a method of editing an TIGIT locus in a cell, comprising contacting to said cell (a) an RNA-guided endonuclease; and (b) an engineered guide RNA, wherein said engineered guide RNA is configured to form a complex with said endonuclease and said engineered guide RNA comprises a spacer sequence configured to hybridize to a region of said TIGIT locus, wherein said engineered guide RNA comprises a targeting sequence having at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to at least 19, at least 20, at least 21, at least 22, at least 23, or at least 24 consecutive nucleotides of any one of SEQ ID NOs: 6153-6181. In some embodiments, said RNA-guided endonuclease is a class II, type II Cas endonuclease. In some embodiments, said RNA-guided endonuclease comprises a sequence having at least 75% identity, at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to SEQ ID NO: 421 or SEQ ID NO: 423. In some embodiments, said RNA-guided endonuclease comprises a RuvCIII domain comprising a sequence having at least 75% identity, at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to SEQ ID NO: 2242 or SEQ ID NO: 2244. In some embodiments, said RNA-guided endonuclease further comprises an HNH domain. In some embodiments, said engineered guide RNA comprises a targeting sequence having at least 85% identity to at least 18 consecutive nucleotides of any one of SEQ ID NOs: 66155, 6159, 616, or 6172.

In some aspects, the present disclosure provides for a method of editing an CD38 locus in a cell, comprising contacting to said cell (a) an RNA-guided endonuclease; and (b) an engineered guide RNA, wherein said engineered guide RNA is configured to form a complex with said endonuclease and said engineered guide RNA comprises a spacer sequence configured to hybridize to a region of said CD38 locus, wherein said engineered guide RNA comprises a targeting sequence having at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to at least 19, at least 20, at least 21, at least 22, at least 23, or at least 24 consecutive nucleotides of any one of SEQ ID NOs: 6182-6248 or 6249-6256. In some embodiments, said RNA-guided endonuclease is a class II, type II Cas endonuclease. In some embodiments, said RNA-guided endonuclease comprises a RuvCIII domain comprising a sequence having at least 75% identity, at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to SEQ ID NO: 2242 or SEQ ID NO: 2244. In some embodiments, said RNA-guided endonuclease further comprises an HNH domain. In some embodiments, said RNA-guided endonuclease comprises a sequence having at least 75% identity, at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to SEQ ID NO: 421 or SEQ ID NO: 423. In some embodiments, said engineered guide RNA comprises a targeting sequence having at least 85% identity to at least 18 consecutive nucleotides of any one of SEQ ID NOs: 6182-6248 and said endonuclease comprises a sequence having at least 75% identity to SEQ ID NO: 421. In some embodiments, said engineered guide RNA comprises a targeting sequence having at least 85% identity to at least 18 consecutive nucleotides of any one of SEQ ID NOs: 6249-

6256 and said endonuclease comprises a sequence having at least 75% identity to SEQ ID NO: 423. In some embodiments, said engineered guide RNA comprises a targeting sequence having at least 85% identity to at least 18 consecutive nucleotides of any one of SEQ ID NOs: 6182-6183, 6189, 6191, 6208, 6210, 6211, or 6215. In some embodiments, said engineered guide RNA comprises a targeting sequence having at least 85% identity to at least 18 consecutive nucleotides of SEQ ID NO: 6251.

In some embodiments of any of the methods for editing particular loci in cells above, said cell is a peripheral blood mononuclear cell, a T-cell, an NK cell, a hematopoietic stem cell (HSCT), or a B-cell, or any combination thereof.

In some aspects, the present disclosure provides for an engineered guide ribonucleic acid polynucleotide comprising: (a) a DNA-targeting segment comprising a nucleotide sequence that is complementary to a target sequence in a target DNA molecule; and (b) a protein-binding segment comprising two complementary stretches of nucleotides that hybridize to form a double-stranded RNA (dsRNA) duplex, wherein said two complementary stretches of nucleotides are covalently linked to one another with intervening nucleotides, and wherein said engineered guide ribonucleic acid polynucleotide is configured to form a complex with a class 2, type II Cas endonuclease and target said complex to said target sequence of said target DNA molecule, wherein said DNA-targeting segment comprises a sequence having at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to at least 19, at least 20, at least 21, at least 22, at least 23, or at least 24 consecutive nucleotides of any one of SEQ ID NOs: 5950-5965, 5966-6025, 6026-6121, 6122-6152, 6153-6181, or 6182-6256. In some embodiments, said protein-binding segment comprises a sequence having at least 85% identity to any one of SEQ ID NOs: 5466 or 6304.

In some aspects, the present disclosure provides for a system for generating an edited immune cell, comprising: (a) an RNA-guided endonuclease; (b) an engineered guide ribonucleic acid polynucleotide configured to bind said RNA-guided endonuclease; and (c) a single- or double-stranded DNA repair template comprising first and second homology arms flanking a sequence encoding a chimeric antigen receptor (CAR). In some embodiments, said cell is a peripheral blood mononuclear cell, a T-cell, an NK cell, a hematopoietic stem cell (HSCT), or a B-cell, or any combination thereof. In some aspects, said RNA-guided endonuclease is a class II, type II Cas endonuclease. In some aspects, said RNA-guided endonuclease comprises a RuvCIII domain comprising a sequence having at least 75% identity, at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to SEQ ID NO: 2242 or SEQ ID NO: 2244. In some aspects, said RNA-guided endonuclease further comprises an HNH domain. In some aspects, said RNA-guided endonuclease comprises a sequence having at least 75% identity, at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity, at least 99% identity, or at least 100% identity to SEQ ID NO: 421 or SEQ ID NO: 423.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

In some aspects, the present disclosure provides for a method of editing a B2M locus in a cell, comprising contacting to said cell (a) an RNA-guided endonuclease; and (b) an engineered guide RNA, wherein said engineered guide RNA is configured to form a complex with said endonuclease and said engineered guide RNA comprises a spacer sequence configured to hybridize to a region of said B2M locus, wherein said region of said B2M locus comprises a targeting sequence having at least 85% identity to at least 18 consecutive nucleotides of any one of SEQ ID NOs: 6387-6468. In some embodiments, said RNA-guided endonuclease is a Cas endonuclease. In some embodiments, said Cas endonuclease is a class 2, type II Cas endonuclease. In some embodiments, said class 2, type II Cas endonuclease comprises an endonuclease having at least 75% sequence identity to any one of SEQ ID NOs: 421-431. In some embodiments, said RNA-guided endonuclease comprises a RuvCIII domain comprising a sequence having at least 75% sequence identity to SEQ ID NO: 2242 or SEQ ID NO: 2244. In some embodiments, said RNA-guided endonuclease further comprises an HNH domain. In some embodiments, said RNA-guided endonuclease comprises a sequence at least 75%, 80%, or 90% identical to SEQ ID NO: 421. In some embodiments, said engineered guide RNA comprises a sequence having at least 80% identity to any one of SEQ ID NOs: 6305-6386. In some embodiments, said region of said B2M locus comprises a sequence at least 75%, 80%, or 90% identical to at least 19 of the non-degenerate nucleotides of any one of SEQ ID NOs: 6388, 6399, 6401, 6403, 6410, 6413, 6421, 6446, and 6448. In some embodiments, said engineered guide RNA comprises a sequence at 80%, or at least 90% identical to any one of SEQ ID NOs: 6306, 6317, 6319, 6321, 6328, 6331, 6339, 6364, and 6366.

In some aspects, the present disclosure provides for a method of editing a TRAC locus in a cell, comprising contacting to said cell (a) an RNA-guided endonuclease; and (b) an engineered guide RNA, wherein said engineered guide RNA is configured to form a complex with said endonuclease and said engineered guide RNA comprises a spacer sequence configured to hybridize to a region of said TRAC locus, wherein said region of said TRAC locus comprises a targeting sequence having at least 85% identity to at least 18 consecutive nucleotides of any one of SEQ ID NOs: 6509-6548. In some embodiments, said RNA-guided endonuclease is a Cas endonuclease. In some embodiments, said Cas endonuclease is a class 2, type II Cas endonuclease. In some embodiments, said class 2, type II Cas endonuclease comprises an endonuclease having at least 75% sequence identity to any one of SEQ ID NOs: 421-431. In some embodiments, said RNA-guided endonuclease comprises a RuvCIII domain comprising a sequence having at least 75% sequence identity to SEQ ID NO: 2242 or SEQ ID NO: 2244. In some embodiments, said RNA-guided endonuclease further comprises an HNH domain. In some embodiments, said RNA-guided endonuclease comprises a sequence at least 75%, 80%, or 90% identical to SEQ ID NO: 421. In some embodiments, said engineered guide RNA comprises a sequence having at least 80% identity to any one of SEQ ID NOs: 6469-6508. In some embodiments, said region of said TRAC locus comprises a sequence at least 75%, 80%, or 90% identical to at least 19 of the non-degenerate nucleotides of any one of SEQ ID NOs: 6517, 6520, and 6523. In some embodiments, said engineered guide RNA comprises a sequence at 80%, or at least 90% identical to any one of SEQ ID NOs: 6477, 6480, and 6483.

In some aspects, the present disclosure provides for a method of editing a HPRT locus in a cell, comprising contacting to said cell (a) an RNA-guided endonuclease; and (b) an engineered guide RNA, wherein said engineered guide RNA is configured to form a complex with said endonuclease and said engineered guide RNA comprises a spacer sequence configured to hybridize to a region of said HPRT locus, wherein said region of said HPRT locus comprises a targeting sequence having at least 85% identity to at least 18 consecutive nucleotides of any one of SEQ ID NOs: 6616-6682. In some embodiments, said RNA-guided endonuclease is a Cas endonuclease. In some embodiments, said Cas endonuclease is a class 2, type II Cas endonuclease. In some embodiments, said class 2, type II Cas endonuclease comprises an endonuclease having at least 75% sequence identity to any one of SEQ ID NOs: 421-431. In some embodiments, said RNA-guided endonuclease comprises a RuvCIII domain comprising a sequence having at least 75% sequence identity to SEQ ID NO: 2242 or SEQ ID NO: 2244. In some embodiments, said RNA-guided endonuclease further comprises an HNH domain. In some embodiments, said RNA-guided endonuclease comprises a sequence at least 75%, 80%, or 90% identical to SEQ ID NO: 421 or SEQ ID NO: 423. In some embodiments, said engineered guide RNA comprises a sequence having at least 80% identity to any one of SEQ ID NOs: 6549-6615. In some embodiments, said region of said HPRT locus comprises a sequence at least 75%, 80%, or 90% identical to at least 19 of the non-degenerate nucleotides of any one of SEQ ID NOs: 6619, 6634, 6673, 6675, and 6679. In some embodiments, said engineered guide RNA comprises a sequence at 80%, or at least 90% identical to any one of SEQ ID NOs: 6552, 6567, 6606, 6608, and 6612.

In some aspects, the present disclosure provides for a method of editing a TRBC1/2 locus in a cell, comprising contacting to said cell (a) an RNA-guided endonuclease; and (b) an engineered guide RNA, wherein said engineered guide RNA is configured to form a complex with said endonuclease and said engineered guide RNA comprises a spacer sequence configured to hybridize to a region of said TRBC1/2 locus, wherein said region of said TRBC1/2 locus comprises a targeting sequence having at least 85% identity to at least 18 consecutive nucleotides of any one of SEQ ID NOs: 6722-6760 or 6782-6802. In some embodiments, said RNA-guided endonuclease is a Cas endonuclease. In some embodiments, said Cas endonuclease is a class 2, type II Cas endonuclease. In some embodiments, said class 2, type II Cas endonuclease comprises an endonuclease having at least 75% sequence identity to any one of SEQ ID NOs: 421-431. In some embodiments, said RNA-guided endonuclease comprises a RuvCIII domain comprising a sequence having at least 75% sequence identity to SEQ ID NO: 2242 or SEQ ID NO: 2244. In some embodiments, said RNA-guided endonuclease further comprises an HNH domain. In some embodiments, said RNA-guided endonuclease comprises a sequence at least 75%, 80%, or 90% identical to SEQ ID NO: 421 or SEQ ID NO: 423. In some embodiments, said engineered guide RNA comprises a sequence having at least 80% identity to any one of SEQ ID NOs: 6683-6721 and 6761-6781. In some embodiments, said region of said TRBC1/2 locus comprises a sequence at least 75%, 80%, or 90% identical to at least 19 of the non-degenerate nucleotides of any one of SEQ ID NOs: 6734, 6753, 6790, and 6800. In some embodiments, said engineered guide RNA comprises a sequence at 80%, or at least 90% identical to any one of SEQ ID NOs: 6695, 6714, 6769, and 6779.

In some aspects, the present disclosure provides for a method of editing a HAO1 locus in a cell, comprising contacting to said cell (a) an RNA-guided endonuclease; and (b) an engineered guide RNA, wherein said engineered guide RNA is configured to form a complex with said endonuclease and said engineered guide RNA comprises a spacer sequence configured to hybridize to a region of said HAO1 locus, wherein said region of said HAO1 locus comprises a targeting sequence having at least 85% identity to at least 18 consecutive nucleotides of any one of SEQ ID NOs: 11802-11820. In some embodiments, said RNA-guided endonuclease is a Cas endonuclease. In some embodiments, said Cas endonuclease is a class 2, type II Cas endonuclease. In some embodiments, said class 2, type II Cas endonuclease comprises an endonuclease having at least 75% sequence identity to any one of SEQ ID NOs: 421-431. In some embodiments, said RNA-guided endonuclease comprises a RuvCIII domain comprising a sequence having at least 75% sequence identity to SEQ ID NO: 2242. In some embodiments, said RNA-guided endonuclease further comprises an HNH domain. In some embodiments, said RNA-guided endonuclease comprises a sequence at least 75%, 80%, or 90% identical to SEQ ID NO: 421. In some embodiments, said region of said HAO1 locus comprises a sequence at least 75%, 80%, or 90% identical to at least 19 of the non-degenerate nucleotides of any one of SEQ ID NOs: 11806, 11813, 11816, and 11819. In some embodiments, said cell is a peripheral blood mononuclear cell (PBMC). In some embodiments, said cell is a T-cell or a precursor thereof or a hematopoietic stem cell (HSC).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

BRIEF DESCRIPTION OF THE SEQUENCE LISTING

Figure 1:
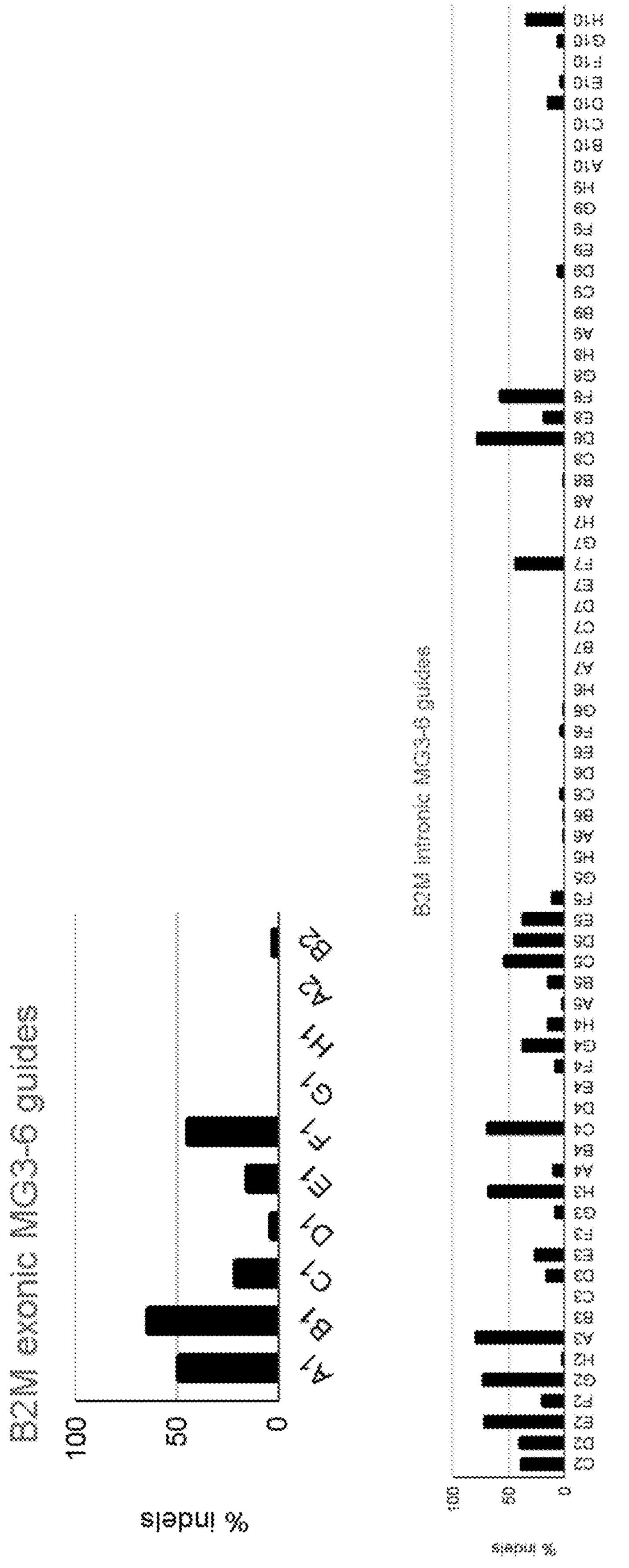
FIG. 1 depicts the gene editing outcomes at the DNA level for B2M.

The Sequence Listing filed herewith provides exemplary polynucleotide and polypeptide sequences for use in methods, compositions and systems according to the disclosure. Below are exemplary descriptions of sequences therein.

MG1

SEQ ID NOs: 1-319 and 7285-7293 show the full-length peptide sequences of MG1 nucleases.

SEQ ID NOs: 1827-2140 show the peptide sequences of RuvC_III domains of MG1 nucleases above.

SEQ ID NOs: 3638-3955 show the peptide of HNH domains of MG1 nucleases above.

SEQ ID NOs: 5476-5479 show the nucleotide sequences of MG1 tracrRNAs derived from the same loci as MG1 nucleases above (e.g., same loci as SEQ ID NO:1-4, respectively).

SEQ ID NOs: 5461-5464 and 11130 show the nucleotide sequences of sgRNAs engineered to function with an MG1 nuclease (e.g., SEQ ID NO:1-4, respectively), where Ns denote nucleotides of a targeting sequence.

SEQ ID NOs: 5572-5575 show nucleotide sequences for *E. coli* codon-optimized coding sequences for MG1 family enzymes (SEQ ID NOs: 1-4).

SEQ ID NOs: 5588-5589 show nucleotide sequences for human codon-optimized coding sequences for MG1 family enzymes (SEQ ID NOs: 1 and 3).

SEQ ID NOs: 5616-5632 show peptide motifs characteristic of MG1 family enzymes.

SEQ ID NOs: 9192-9255 show the peptide sequences of PAM-interacting domains of MG1 nucleases.

SEQ ID NOs: 11229-11269 show the nucleotide sequences of target sites of MG1 nucleases.

MG2

SEQ ID NOs: 320-420 and 7294-7358 show the full-length peptide sequences of MG2 nucleases.

SEQ ID NOs: 2141-2241 show the peptide sequences of RuvC_III domains of MG2 nucleases above.

SEQ ID NOs: 3955-4055 show the peptide of HNH domains of MG2 nucleases above.

SEQ ID NOs: 5490-5494 and 11159 show the nucleotide sequences of MG2 tracrRNAs derived from the same loci as MG2 nucleases above (e.g., same loci as SEQ ID NOs: 320, 321, 323, 325, and 326, respectively).

SEQ ID NO: 5465 shows the nucleotide sequence of an sgRNA engineered to function with an MG2 nuclease (e.g., SEQ ID NO: 321 above).

SEQ ID NOs: 5572-5575 show nucleotide sequences for *E. coli* codon-optimized coding sequences for MG2 family enzymes.

SEQ ID NOs: 5631-5638 show peptide sequences characteristic of MG2 family enzymes.

SEQ ID NOs: 9256-9322 show the peptide sequences of PAM-interacting domains of MG2 nucleases.

SEQ ID NOs: 11270-11275 show the nucleotide sequences of target sites of MG2 nucleases.

MG3

SEQ ID NOs: 421-431 show the full-length peptide sequences of MG3 nucleases.

SEQ ID NO: 6803 shows the nucleotide sequence of an MG3-6 nuclease containing 5' UTR, NLS, CDS, NLS, 3' UTR, and polyA tail.

SEQ ID NOs: 2242-2252 show the peptide sequences of RuvC_III domains of MG3 nucleases above.

SEQ ID NOs: 4056-4066 show the peptide of HNH domains of MG3 nucleases above.

SEQ ID NOs: 5495-5502 and 11160-11162 show the nucleotide sequences of MG3 tracrRNAs derived from the same loci as MG3 nucleases above (e.g., same loci as SEQ ID NOs: 421-428, respectively).

SEQ ID NOs: 5466-5467, 11131, and 11567-11576 show the nucleotide sequences of sgRNAs engineered to function with MG3 nucleases (e.g., SEQ ID NOs: 421-423).

SEQ ID NOs: 5578-5580 show nucleotide sequences for *E. coli* codon-optimized coding sequences for MG3 family enzymes.

SEQ ID NOs: 5639-5648 show peptide sequences characteristic of MG3 family enzymes.

SEQ ID NOs: 9323-9329 show the peptide sequences of PAM-interacting domains of MG3 nucleases.

SEQ ID NOs: 11108 and 11530-11538 show the nucleotide sequences of single guide PAMs of MG3 nucleases.

SEQ ID NOs: 11276-11294 show the nucleotide sequences of target sites of MG1 nucleases.

SEQ ID NO: 11373 shows the nucleotide sequence of a DNA sequence encoding MG3-6 mRNA.

MG3a

SEQ ID NOs: 7369-7375 show the full-length peptide sequences of MG3a nucleases.

SEQ ID NOs: 11099 show the peptide sequences of PAM-interacting domains of MG3a nucleases.

MG3b

SEQ ID NOs: 7376-7390 show the full-length peptide sequences of MG3b nucleases.

SEQ ID NOs: 11100-11107 show the peptide sequences of PAM-interacting domains of MG3b nucleases.

MG4

SEQ ID NOs: 432-660 and 7391-7535 show the full-length peptide sequences of MG4 nucleases.

SEQ ID NOs: 2253-2481 show the peptide sequences of RuvC_III domains of MG4 nucleases above.

SEQ ID NOs: 4067-4295 show the peptide of HNH domains of MG4 nucleases above.

SEQ ID NO: 5503 shows the nucleotide sequences of an MG4 tracrRNA derived from the same loci as MG4 nucleases above.

SEQ ID NO: 5468 shows the nucleotide sequence of sgRNAs engineered to function with an MG4 nuclease.

SEQ ID NO: 5649 shows a peptide sequence characteristic of MG4 family enzymes.

SEQ ID NOs: 9330-9485 show the peptide sequences of PAM-interacting domains of MG4 nucleases.

SEQ ID NOs: 11295-11303 show the nucleotide sequences of target sites of MG4 nucleases.

MG5

SEQ ID NOs: 7536-7583 show the full-length peptide sequences of MG5 nucleases.

SEQ ID NOs: 9486-9526 show the peptide sequences of PAM-interacting domains of MG5 nucleases.

MG6

SEQ ID NOs: 661-668 and 7584-7587 show the full-length peptide sequences of MG6 nucleases.

SEQ ID NOs: 2482-2489 show the peptide sequences of RuvC_III domains of MG6 nucleases above.

SEQ ID NOs: 4296-4303 show the peptide of HNH domains of MG3 nucleases above.

SEQ ID NOs: 9527-9531 show the peptide sequences of PAM-interacting domains of MG6 nucleases.

MG7

SEQ ID NOs: 669-677 show the full-length peptide sequences of MG7 nucleases.

SEQ ID NOs: 2490-2498 show the peptide sequences of RuvC_III domains of MG7 nucleases above.

SEQ ID NOs: 4304-4312 show the peptide of HNH domains of MG3 nucleases above.

SEQ ID NO: 5504 shows the nucleotide sequence of an MG7 tracrRNA derived from the same loci as MG7 nucleases above.

SEQ ID NOs: 9532-9535 show the peptide sequences of PAM-interacting domains of MG7 nucleases.

MG14

SEQ ID NOs: 678-929 and 7588-7597 show the full-length peptide sequences of MG14 nucleases.

SEQ ID NOs: 2499-2750 show the peptide sequences of RuvC_III domains of MG14 nucleases above.

SEQ ID NOs: 4313-4564 show the peptide of HNH domains of MG14 nucleases above.

SEQ ID NOs: 5505 and 11163-11167 show nucleotide sequences of MG14 tracrRNAs derived from the same loci as MG14 nucleases above.

SEQ ID NO: 5581 shows a nucleotide sequence for an *E. coli* codon-optimized coding sequences for an MG14 family enzyme.

SEQ ID NOs: 5650-5667 show peptide sequences characteristic of MG14 family enzymes.

SEQ ID NOs: 9536-9611 show the peptide sequences of PAM-interacting domains of MG14 nucleases.

SEQ ID NOs: 11109-11113 show the nucleotide sequences of single guide PAMs of MG14 nucleases.

SEQ ID NOs: 11132-11136 shows the nucleotide sequence of sgRNAs engineered to function with an MG14 nuclease.

SEQ ID NOs: 11304-11312 show the nucleotide sequences of target sites of MG14 nucleases.

MG15

SEQ ID NOs: 930-1092, 7598-7622, and 11593-11616 show the full-length peptide sequences of MG15 nucleases.

SEQ ID NOs: 2751-2913 show the peptide sequences of RuvC_III domains of MG15 nucleases above.

SEQ ID NOs: 4565-4727 show the peptide of HNH domains of MG15 nucleases above.

SEQ ID NOs: 5506 and 11168-11172 show nucleotide sequences of MG15 tracrRNAs derived from the same loci as MG15 nucleases above.

SEQ ID NOs: 5470 and 11577-11592 show the nucleotide sequences of sgRNAs engineered to function with MG15 nucleases.

SEQ ID NO: 5582 shows a nucleotide sequence for an *E. coli* codon-optimized coding sequences for an MG15 family enzyme.

SEQ ID NOs: 5668-5675 show peptide sequences characteristic of MG15 family enzymes.

SEQ ID NOs: 9612-9671 show the peptide sequences of PAM-interacting domains of MG15 nucleases.

SEQ ID NOs: 11539-11554 show the nucleotide sequences of single guide PAMs of MG15 nucleases.

MG16

SEQ ID NOs: 1093-1353 and 7623-7698 show the full-length peptide sequences of MG16 nucleases.

SEQ ID NOs: 2914-3174 show the peptide sequences of RuvC_III domains of MG16 nucleases above.

SEQ ID NOs: 4728-4988 show the peptide of HNH domains of MG16 nucleases above.

SEQ ID NOs: 5507 and 11173-11174 show nucleotide sequences of MG16 tracrRNAs derived from the same loci as MG16 nucleases above.

SEQ ID NOs: 5471 and 11137 show nucleotide sequences of sgRNAs engineered to function with an MG16 nuclease.

SEQ ID NO: 5583 shows a nucleotide sequence for an *E. coli* codon-optimized coding sequences for an MG16 family enzyme.

SEQ ID NOs: 5676-5678 show peptide sequences characteristic of MG16 family enzymes.

SEQ ID NOs: 9672-9842 show the peptide sequences of PAM-interacting domains of MG16 nucleases.

SEQ ID NO: 11114 shows the nucleotide sequence of a single guide PAM of an MG16 nuclease.

SEQ ID NOs: 11313-11320 show the nucleotide sequences of target sites of MG16 nucleases.

MG17

SEQ ID NOs: 7699-7715 show the full-length peptide sequences of MG17 nucleases.

SEQ ID NOs: 9843-9856 show the peptide sequences of PAM-interacting domains of MG17 nucleases.

SEQ ID NO: 11115 shows the nucleotide sequence of a single guide PAM of an MG17 nuclease.

SEQ ID NO: 11138 shows the nucleotide sequence of an sgRNA engineered to function with an MG17 nuclease.

SEQ ID NO: 11175 shows the nucleotide sequence of an MG17 tracrRNA derived from the same loci as MG17 nucleases above.

MG18

SEQ ID NOs: 1354-1511 show the full-length peptide sequences of MG18 nucleases.

SEQ ID NOs: 3175-3330 show the peptide sequences of RuvC_III domains of MG18 nucleases above.

SEQ ID NOs: 4989-5146 show the peptide of HNH domains of MG18 nucleases above.

SEQ ID NO: 5508 shows the nucleotide sequences of MG18 tracrRNA derived from the same loci as MG18 nucleases above.

SEQ ID NOs: 5472 shows the nucleotide sequence of an sgRNA engineered to function with an MG18 nuclease.

SEQ ID NO: 5584 shows a nucleotide sequence for an *E. coli* codon-optimized coding sequences for an MG18 family enzyme.

SEQ ID NOs: 5679-5686 show peptide sequences characteristic of MG18 family enzymes.

SEQ ID NOs: 9857-9891 show the peptide sequences of PAM-interacting domains of MG18 nucleases.

SEQ ID NOs: 11321-11327 show the nucleotide sequences of target sites of MG18 nucleases.

MG21

SEQ ID NOs: 1512-1655 and 7716-7733 show the full-length peptide sequences of MG21 nucleases.

SEQ ID NOs: 3331-3474 show the peptide sequences of RuvC_III domains of MG21 nucleases above.

SEQ ID NOs: 5147-5290 show the peptide of HNH domains of MG21 nucleases above.

SEQ ID NOs: 5509 and 11176-11178 show nucleotide sequences of MG21 tracrRNAs derived from the same loci as MG21 nucleases above.

SEQ ID NOs: 5473 and 11139 show nucleotide sequences of sgRNAs engineered to function with an MG21 nuclease.

SEQ ID NO: 5585 shows a nucleotide sequence for an *E. coli* codon-optimized coding sequences for an MG21 family enzyme.

SEQ ID NOs: 5687-5692 and 5674-5675 show peptide sequences characteristic of MG21 family enzymes.

SEQ ID NOs: 9892-9951 show the peptide sequences of PAM-interacting domains of MG21 nucleases.

SEQ ID NO: 11116 shows the nucleotide sequence of a single guide PAM of an MG21 nuclease.

SEQ ID NOs: 11328-11336 show the nucleotide sequences of target sites of MG21 nucleases.

MG22

SEQ ID NOs: 1656-1755 show the full-length peptide sequences of MG22 nucleases.

SEQ ID NOs: 3475-3568 show the peptide sequences of RuvC_III domains of MG22 nucleases above.

SEQ ID NOs: 5291-5389 show the peptide of HNH domains of MG22 nucleases above.

SEQ ID NOs: 5510 and 11179-11180 show nucleotide sequences of MG22 tracrRNAs derived from the same loci as MG22 nucleases above.

SEQ ID NOs: 5474 shows the nucleotide sequence of an sgRNAs engineered to function with an MG22 nuclease.

SEQ ID NO: 5586 shows a nucleotide sequence for an *E. coli* codon-optimized coding sequences for an MG22 family enzyme.

SEQ ID NOs: 5694-5699 show peptide sequences characteristic of MG22 family enzymes.

SEQ ID NOs: 9952-9982 show the peptide sequences of PAM-interacting domains of MG22 nucleases.

SEQ ID NOs: 11337-11344 show the nucleotide sequences of target sites of MG22 nucleases.

MG23

SEQ ID NOs: 1756-1826 and 7734-7735 show the full-length peptide sequences of MG23 nucleases.

SEQ ID NOs: 3569-3637 show the peptide sequences of RuvC_III domains of MG23 nucleases above.

SEQ ID NOs: 5390-5460 show the peptide of HNH domains of MG23 nucleases above.

SEQ ID NOs: 5511 and 11181-11182 show nucleotide sequences of MG23 tracrRNAs derived from the same loci as MG23 nucleases above.

SEQ ID NOs: 5475 and 11140 show nucleotide sequences of sgRNAs engineered to function with an MG23 nuclease.

SEQ ID NO: 5587 shows a nucleotide sequence for an *E. coli* codon-optimized coding sequences for an MG23 family enzyme.

SEQ ID NOs: 5700-5717 show peptide sequences characteristic of MG23 family enzymes.

SEQ ID NOs: 9983-10004 show the peptide sequences of PAM-interacting domains of MG23 nucleases.

SEQ ID NOs: 11345-11351 show the nucleotide sequences of target sites of MG23 nucleases.

MG24

SEQ ID NOs: 7736-8027 show the full-length peptide sequences of MG24 nucleases.

SEQ ID NOs: 10005-10162 show the peptide sequences of PAM-interacting domains of MG24 nucleases.

MG25

SEQ ID NOs: 8028-8091 show the full-length peptide sequences of MG25 nucleases.

SEQ ID NOs: 10163-10211 show the peptide sequences of PAM-interacting domains of MG25 nucleases.

MG38

SEQ ID NOs: 8092-8095 show the full-length peptide sequences of MG38 nucleases.

SEQ ID NOs: 10212-10214 show the peptide sequences of PAM-interacting domains of MG38 nucleases.

MG40

SEQ ID NOs: 5718-5750 and 8096-8163 show the full-length peptide sequences of MG40 nucleases.

SEQ ID NOs: 5847-5852 show protospacer adjacent motifs associated with MG 40 nucleases.

SEQ ID NOs: 5862-5873 show the nucleotide sequence of an sgRNA engineered to function with an MG40 nuclease.

SEQ ID NOs: 10215-10263 show the peptide sequences of PAM-interacting domains of MG40 nucleases.

SEQ ID NOs: 11183-11188 show nucleotide sequences of MG40 tracrRNAs derived from the same loci as MG40 nucleases above.

MG41

SEQ ID NOs: 8164-8286 show the full-length peptide sequences of MG41 nucleases.

SEQ ID NOs: 10264-10304 show the peptide sequences of PAM-interacting domains of MG41 nucleases.

MG42

SEQ ID NOs: 8287-8356 show the full-length peptide sequences of MG42 nucleases.

SEQ ID NOs: 10305-10355 show the peptide sequences of PAM-interacting domains of MG42 nucleases.

MG43

SEQ ID NOs: 8357-8453 show the full-length peptide sequences of MG43 nucleases.

SEQ ID NOs: 10356-10412 show the peptide sequences of PAM-interacting domains of MG43 nucleases.

SEQ ID NO: 11117 shows the nucleotide sequence of a single guide PAM of an MG43 nuclease.

SEQ ID NO: 11141 shows the nucleotide sequence of an sgRNA engineered to function with an MG43 nuclease.

SEQ ID NO: 11189 shows the nucleotide sequence of an MG43 tracrRNA derived from the same loci as MG43 nucleases above.

MG44

SEQ ID NOs: 8454-8496 show the full-length peptide sequences of MG44 nucleases.

SEQ ID NOs: 10413-10555 show the peptide sequences of PAM-interacting domains of MG44 nucleases.

SEQ ID NO: 11190 shows the nucleotide sequence of an MG44 tracrRNA derived from the same loci as MG44 nucleases above.

MG46

SEQ ID NOs: 8497-8634 show the full-length peptide sequences of MG46 nucleases.

SEQ ID NOs: 10556-10633 show the peptide sequences of PAM-interacting domains of MG46 nucleases.

SEQ ID NO: 11191 shows the nucleotide sequence of an MG46 tracrRNA derived from the same loci as MG46 nucleases above.

MG47

SEQ ID NOs: 5751-5768 and 8635-8664 show the full-length peptide sequences of MG47 nucleases.

SEQ ID NOs: 5853-5854 show protospacer adjacent motifs associated with MG47 nucleases.

SEQ ID NOs: 5878-5881 show the nucleotide sequence of an sgRNA engineered to function with an MG47 nuclease.

SEQ ID NOs: 10634-10656 show the peptide sequences of PAM-interacting domains of MG47 nucleases.

SEQ ID NOs: 11192-11193 show nucleotide sequences of MG47 tracrRNAs derived from the same loci as MG47 nucleases above.

MG48

SEQ ID NOs: 5769-5804 and 8665 show the full-length peptide sequences of MG48 nucleases.

SEQ ID NOs: 5855-5856 show protospacer adjacent motifs associated with MG48 nucleases.

SEQ ID NOs: 5886, 5890, 5893, and 11194 show the nucleotide sequences of MG48 tracrRNA derived from the same loci as MG48 nucleases above SEQ ID NOs: 5887, 5891 and 5894 show CRISPR repeats associated with MG48 nucleases described herein.

SEQ ID NOs: 5888-5889, 5892 and 5895-5896 show putative sgRNA designed to function with an MG48 nuclease.

SEQ ID NOs: 10657-10662 show the peptide sequences of PAM-interacting domains of MG48 nucleases.

SEQ ID NOs: 11142-11143 show nucleotide sequences of sgRNAs engineered to function with an MG48 nuclease.

MG49

SEQ ID NOs: 5805-5823 and 8666-8677 show the full-length peptide sequences of MG49 nucleases.

SEQ ID NOs: 5857-5858 show protospacer adjacent motifs associated with MG49 nucleases.

SEQ ID NOs: 5862-5873 show the nucleotide sequence of an sgRNA engineered to function with an MG40 nuclease.

SEQ ID NOs: 5876-5877 show the nucleotide sequence of an sgRNA engineered to function with an MG49 nuclease.

SEQ ID NOs: 10663-10675 show the peptide sequences of PAM-interacting domains of MG49 nucleases.

SEQ ID NOs: 11195-11196 show nucleotide sequences of MG49 tracrRNAs derived from the same loci as MG49 nucleases above.

MG50

SEQ ID NOs: 5824-5826 and 8678-8682 show the full-length peptide sequences of MG50 nucleases.

SEQ ID NO: 5859 shows a protospacer adjacent motif associated with MG50 nucleases.

SEQ ID NOs: 5884-5885 show the nucleotide sequence of an sgRNA engineered to function with an MG50 nuclease.

SEQ ID NOs: 10676-10682 show the peptide sequences of PAM-interacting domains of MG50 nucleases.

SEQ ID NO: 11197 shows the nucleotide sequence of an MG50 tracrRNA derived from the same loci as MG50 nucleases above.

MG51

SEQ ID NOs: 5827-5830 and 8683-8705 show the full-length peptide sequences of MG51 nucleases.

SEQ ID NO: 5860 shows a protospacer adjacent motif associated with MG51 nucleases.

SEQ ID NOs: 5882-5883 show the nucleotide sequence of an sgRNA engineered to function with an MG51 nuclease.

SEQ ID NOs: 10683-10704 show the peptide sequences of PAM-interacting domains of MG51 nucleases.

SEQ ID NO: 11198 shows the nucleotide sequence of an MG51 tracrRNA derived from the same loci as MG51 nucleases above.

MG52

SEQ ID NOs: 5831-5846 and 8706 show the full-length peptide sequences of MG52 nucleases.

SEQ ID NO: 5861 shows a protospacer adjacent motif associated with MG52 nucleases.

SEQ ID NOs: 5874-5875 show the nucleotide sequence of an sgRNA engineered to function with an MG52 nuclease.

SEQ ID NOs: 10705-10710 show the peptide sequences of PAM-interacting domains of MG52 nucleases.

SEQ ID NO: 11199 shows the nucleotide sequence of an MG52 tracrRNA derived from the same loci as MG52 nucleases above.

MG71

SEQ ID NOs: 10711-10712 show the peptide sequences of PAM-interacting domains of MG71 nucleases.

SEQ ID NOs: 11144-11145 show nucleotide sequences of sgRNAs engineered to function with an MG71 nuclease.

SEQ ID NOs: 11200-11201 show nucleotide sequences of MG71 tracrRNAs derived from the same loci as MG71 nucleases above.

MG72

SEQ ID NO: 11202 shows the nucleotide sequence of an MG72 tracrRNA derived from the same loci as MG72 nucleases above.

MG73

SEQ ID NOs: 10713-10718 show the peptide sequences of PAM-interacting domains of MG73 nucleases.

SEQ ID NOs: 11203-11204 show nucleotide sequences of MG73 tracrRNAs derived from the same loci as MG73 nucleases above.

MG74

SEQ ID NOs: 10719-10732 show the peptide sequences of PAM-interacting domains of MG74 nucleases.

SEQ ID NO: 11205 shows the nucleotide sequence of an MG74 tracrRNA derived from the same loci as MG74 nucleases above.

MG86

SEQ ID NOs: 8707-8737 show the full-length peptide sequences of MG86 nucleases.

SEQ ID NOs: 10733-10791 show the peptide sequences of PAM-interacting domains of MG86 nucleases.

SEQ ID NO: 11118 shows the nucleotide sequence of a single guide PAM of an MG86 nuclease.

SEQ ID NOs: 11206-11207 show nucleotide sequences of MG86 tracrRNAs derived from the same loci as MG86 nucleases above.

MG87

SEQ ID NOs: 8738-8747 show the full-length peptide sequences of MG87 nucleases.

SEQ ID NOs: 10792-10828 show the peptide sequences of PAM-interacting domains of MG87 nucleases.

SEQ ID NOs: 11208-11210 show nucleotide sequences of MG87 tracrRNAs derived from the same loci as MG87 nucleases above.

MG88

SEQ ID NOs: 10829-10841 show the peptide sequences of PAM-interacting domains of MG88 nucleases.

SEQ ID NOs: 11211-11213 show nucleotide sequences of MG88 tracrRNAs derived from the same loci as MG88 nucleases above.

MG89

SEQ ID NOs: 10842-10854 show the peptide sequences of PAM-interacting domains of MG89 nucleases.

SEQ ID NOs: 11214-11215 show nucleotide sequences of MG89 tracrRNAs derived from the same loci as MG89 nucleases above.

MG94

SEQ ID NOs: 8748-8781 show the full-length peptide sequences of MG94 nucleases.

SEQ ID NOs: 10855-10860 show the peptide sequences of PAM-interacting domains of MG94 nucleases.

SEQ ID NOs: 11119-11120 show the nucleotide sequences of single guide PAMs of MG94 nucleases.

SEQ ID NOs: 11146-11147 show nucleotide sequences of sgRNAs engineered to function with an MG94 nuclease.

SEQ ID NOs: 11216-11217 show nucleotide sequences of MG94 tracrRNAs derived from the same loci as MG94 nucleases above.

MG95

SEQ ID NOs: 8782-8785 show the full-length peptide sequences of MG95 nucleases.

SEQ ID NOs: 10861-10863 show the peptide sequences of PAM-interacting domains of MG95 nucleases.

SEQ ID NOs: 11121-11122 show the nucleotide sequences of single guide PAMs of MG95 nucleases.

SEQ ID NOs: 11148-11149 show nucleotide sequences of sgRNAs engineered to function with an MG95 nuclease.

SEQ ID NOs: 11218-11219 show nucleotide sequences of MG95 tracrRNAs derived from the same loci as MG95 nucleases above.

MG96

SEQ ID NOs: 8786-8814 show the full-length peptide sequences of MG96 nucleases.

SEQ ID NOs: 10864-10884 show the peptide sequences of PAM-interacting domains of MG96 nucleases.

SEQ ID NO: 11123 shows the nucleotide sequence of a single guide PAM of an MG96 nuclease.

SEQ ID NO: 11150 shows the nucleotide sequence of an sgRNA engineered to function with an MG96 nuclease.

SEQ ID NO: 11220 shows the nucleotide sequence of an MG96 tracrRNA derived from the same loci as MG96 nucleases above.

MG97

SEQ ID NOs: 8815-8818 show the full-length peptide sequences of MG97 nucleases.

SEQ ID NOs: 10885-10887 show the peptide sequences of PAM-interacting domains of MG97 nucleases.

MG98

SEQ ID NOs: 8819-8959 show the full-length peptide sequences of MG98 nucleases.

SEQ ID NOs: 10888-10936 show the peptide sequences of PAM-interacting domains of MG98 nucleases.

SEQ ID NOs: 11124-11125 show the nucleotide sequences of single guide PAMs of MG98 nucleases.

SEQ ID NOs: 11151-11152 show nucleotide sequences of sgRNAs engineered to function with an MG98 nuclease.

SEQ ID NOs: 11221-11222 show nucleotide sequences of MG98 tracrRNAs derived from the same loci as MG98 nucleases above.

MG99

SEQ ID NO: 11153 shows the nucleotide sequence of an sgRNA engineered to function with an MG99 nuclease.

SEQ ID NO: 11223 shows the nucleotide sequence of an MG99 tracrRNA derived from the same loci as MG99 nucleases above.

MG100

SEQ ID NOs: 8960-9036 show the full-length peptide sequences of MG100 nucleases.

SEQ ID NOs: 10937-10991 show the peptide sequences of PAM-interacting domains of MG100 nucleases.

SEQ ID NO: 11126 shows the nucleotide sequence of a single guide PAM of an MG100 nuclease.

SEQ ID NOs: 11154-11155 show nucleotide sequences of sgRNAs engineered to function with an MG100 nuclease.

SEQ ID NOs: 11224-11225 show nucleotide sequences of MG100 tracrRNAs derived from the same loci as MG100 nucleases above.

MG111

SEQ ID NOs: 9037-9126 show the full-length peptide sequences of MG111 nucleases.

SEQ ID NOs: 10992-11046 show the peptide sequences of PAM-interacting domains of MG111 nucleases.

SEQ ID NOs: 11127-11128 show the nucleotide sequences of single guide PAMs of MG111 nucleases.

SEQ ID NOs: 11156-11157 show nucleotide sequences of sgRNAs engineered to function with an MG111 nuclease.

SEQ ID NOs: 11226-11227 show nucleotide sequences of MG111 tracrRNAs derived from the same loci as MG111 nucleases above.

MG112

SEQ ID NOs: 9127-9149 show the full-length peptide sequences of MG112 nucleases.

SEQ ID NOs: 11047-11062 show the peptide sequences of PAM-interacting domains of MG112 nucleases.

MG116

SEQ ID NOs: 9150-9191 show the full-length peptide sequences of MG116 nucleases.

SEQ ID NOs: 11063-11098 show the peptide sequences of PAM-interacting domains of MG116 nucleases.

SEQ ID NO: 11129 shows the nucleotide sequence of a single guide PAM of an MG116 nuclease.

SEQ ID NO: 11158 shows the nucleotide sequence of an sgRNA engineered to function with an MG116 nuclease.

SEQ ID NO: 11228 shows the nucleotide sequence of an MG116 tracrRNA derived from the same loci as MG116 nucleases above.

MG123

SEQ ID NOs: 11617-11624 show the full-length peptide sequences of MG123 nucleases.

SEQ ID NO: 11518 shows the nucleotide sequence of a single guide PAM of an MG123 nuclease.

SEQ ID NO: 11555 shows the nucleotide sequence of an sgRNA engineered to function with an MG123 nuclease.

MG124

SEQ ID NOs: 11625-11626 show the full-length peptide sequences of MG124 nucleases.

SEQ ID NO: 11519 shows the nucleotide sequence of a single guide PAM of an MG124 nuclease.

SEQ ID NO: 11556 shows the nucleotide sequence of an sgRNA engineered to function with an MG124 nuclease.

MG125

SEQ ID NOs: 11627-11707 show the full-length peptide sequences of MG125 nucleases.

SEQ ID NOs: 11520-11524 show the nucleotide sequences of single guide PAMs of MG125 nucleases.

SEQ ID NOs: 11557-11561 show the nucleotide sequences of sgRNAs engineered to function with MG125 nucleases.

MG150

SEQ ID NOs: 7359-7368 and 11708-11710 show the full-length peptide sequences of MG150 nucleases.

SEQ ID NOs: 11525-11529 show the nucleotide sequences of single guide PAMs of MG150 nucleases.

SEQ ID NOs: 11562-11566 show the nucleotide sequences of sgRNAs engineered to function with MG150 nucleases.

B2M Targeting

SEQ ID NOs: 6305-6386 show the nucleotide sequences of sgRNAs engineered to function with an MG3-6 nuclease in order to target B2M.

SEQ ID NOs: 6387-6468 show the DNA sequences of B2M target sites.

TRAC Targeting

SEQ ID NOs: 6469-6508 and 6804 show the nucleotide sequences of sgRNAs engineered to function with an MG3-6 nuclease in order to target TRAC.

SEQ ID NOs: 6509-6548 and 6805 show the DNA sequences of TRAC target sites. HPRT Targeting SEQ ID NOs: 6549-6615 show the nucleotide sequences of sgRNAs engineered to function with an MG3-6 nuclease in order to target HPRT.

SEQ ID NOs: 6616-6682 show the DNA sequences of HPRT target sites.

MG3-6 TRBC1/2 Targeting

SEQ ID NOs: 6683-6721 show the nucleotide sequences of sgRNAs engineered to function with an MG3-6 nuclease in order to target TRBC1/2.

SEQ ID NOs: 6722-6760 show the DNA sequences of TRBC1/2 target sites.

MG3-8 TRBC1/2 Targeting

SEQ ID NOs: 6761-6781 show the nucleotide sequences of sgRNAs engineered to function with an MG3-8 nuclease in order to target TRBC1/2.

SEQ ID NOs: 6782-6802 show the DNA sequences of TRBC1/2 target sites.

MG3-6 CD2 Targeting

SEQ ID NOs: 6811-6852 show the nucleotide sequences of sgRNAs engineered to function with an MG3-6 nuclease in order to target CD2.

SEQ ID NOs: 6853-6894 show the DNA sequences of CD2 target sites.

MG3-6 CD5 Targeting

SEQ ID NOs: 6895-6958 show the nucleotide sequences of sgRNAs engineered to function with an MG3-6 nuclease in order to target CD5.

SEQ ID NOs: 6959-7022 show the DNA sequences of CD5 target sites.

MG3-6 FAS Targeting

SEQ ID NOs: 7023-7056 show the nucleotide sequences of sgRNAs engineered to function with an MG3-6 nuclease in order to target FAS.

SEQ ID NOs: 7057-7090 show the DNA sequences of FAS target sites.

MG3-6 PD-1 Targeting

SEQ ID NOs: 7091-7128 show the nucleotide sequences of sgRNAs engineered to function with an MG3-6 nuclease in order to target PD-1.

SEQ ID NOs: 7129-7166 show the DNA sequences of PD-1 target sites.

MG3-6 hRosa26 Targeting

SEQ ID NOs: 7167-7198 show the nucleotide sequences of sgRNAs engineered to function with an MG3-6 nuclease in order to target hRosa26.

SEQ ID NOs: 7199-7230 show the DNA sequences of hRosa26 target sites.

MG21-1 TRAC Targeting

SEQ ID NOs: 7231-7234 show the nucleotide sequences of sgRNAs engineered to function with an MG21-1 nuclease in order to target TRAC.

SEQ ID NOs: 7235-7238 show the DNA sequences of TRAC target sites.

MG23-1 TRAC Targeting

SEQ ID NOs: 7239-7247 show the nucleotide sequences of sgRNAs engineered to function with an MG23-1 nuclease in order to target TRAC.

SEQ ID NOs: 7248-7256 show the DNA sequences of TRAC target sites.

MG14-241 AAVS1 Targeting

SEQ ID NOs: 11508-11510 show the nucleotide sequences of sgRNAs engineered to function with an MG14-241 nuclease in order to target AAVS1.

SEQ ID NOs: 11511-11513 show the DNA sequences of AAVS1 target sites.

MG23-1 AAVS1 Targeting

SEQ ID NOs: 7257-7260 show the nucleotide sequences of sgRNAs engineered to function with an MG23-1 nuclease in order to target AAVS1.

SEQ ID NOs: 7261-7264 show the DNA sequences of AAVS1 target sites.

MG71-2 AAVS1 Targeting

SEQ ID NOs: 7265-7266 show the nucleotide sequences of sgRNAs engineered to function with an MG71-2 nuclease in order to target AAVS1.

SEQ ID NOs: 7267-7268 show the DNA sequences of AAVS1 target sites.

MG73-1 TRAC Targeting

SEQ ID NO: 7269 shows the nucleotide sequence of an sgRNA engineered to function with an MG73-1 nuclease in order to target TRAC.

SEQ ID NO: 7270 shows the DNA sequence of a TRAC target site.

MG89-2 TRAC Targeting

SEQ ID NOs: 7271-7277 show the nucleotide sequences of sgRNAs engineered to function with an MG89-2 nuclease in order to target TRAC.

SEQ ID NOs: 7278-7284 show the DNA sequences of TRAC target sites.

MG99-1 TRAC Targeting

SEQ ID NOs: 11514-11515 show the nucleotide sequences of sgRNAs engineered to function with an MG99-1 nuclease in order to target TRAC.

SEQ ID NOs: 11516-11517 show the DNA sequences of TRAC target sites.

MG3-6 Human HAO-1 Targeting

SEQ ID NOs: 11352-11372 show the nucleotide sequences of sgRNAs engineered to function with an MG3-6 nuclease in order to target human HAO-1.

MG3-6 human GPR146 Targeting

SEQ ID NOs: 11374-11405 show the nucleotide sequences of sgRNAs engineered to function with an MG3-6 nuclease in order to target human GPR146.

SEQ ID NOs: 11406-11437 show the DNA sequences of human GPR146 target sites.

MG3-6 mouse GPR146 Targeting

SEQ ID NOs: 11438-11472 show the nucleotide sequences of sgRNAs engineered to function with an MG3-6 nuclease in order to target mouse GPR146.

SEQ ID NOs: 11473-11507 show the DNA sequences of mouse GPR146 target sites.

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The practice of some methods disclosed herein employ, unless otherwise indicated, techniques of immunology, biochemistry, chemistry, molecular biology, microbiology, cell biology, genomics and recombinant DNA. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)) (which is entirely incorporated by reference herein).

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within one or more than one standard deviation, per the practice in the art. Alternatively, "about" can mean a range of up to 20%, up to 15%, up to 10%, up to 5%, or up to 1% of a given value.

As used herein, a "cell" generally refers to a biological cell. A cell may be the basic structural, functional or biological unit of a living organism. A cell may originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, *Cannabis*, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens* C. Agardh, and the like), seaweeds (e.g., kelp), a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), and etcetera. Sometimes a cell is not originating from a natural organism (e.g., a cell can be a synthetically made, sometimes termed an artificial cell).

The term "nucleotide," as used herein, generally refers to a base-sugar-phosphate combination. A nucleotide may comprise a synthetic nucleotide. A nucleotide may comprise a synthetic nucleotide analog. Nucleotides may be monomeric units of a nucleic acid sequence (e.g., deoxyribonucleic acid (DNA) and ribonucleic acid (RNA)). The term nucleotide may include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives may include, for example, [αS]dATP, 7-deaza-dGTP and 7-deaza-dATP, and nucleotide derivatives that confer nuclease resistance on the nucleic acid molecule containing them. The term nucleotide as used herein may refer to dideoxyribonucleoside triphosphates (ddNTPs) and their derivatives. Illustrative examples of dideoxyribonucleoside triphosphates may include, but are not limited to, ddATP, ddCTP, ddGTP, ddITP, and ddTTP. A nucleotide may be unlabeled or detectably labeled, such as using moieties comprising optically detectable moieties (e.g., fluorophores). Labeling may also be carried out with quantum dots. Detectable labels may include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl) aminonaphthalene-1-sulfonic acid (EDANS). Specific examples of fluorescently labeled nucleotides can include [R6G]dUTP, [TAMRA]dUTP, [RI 10]dCTP, [R6G]dCTP, [TAMRA]dCTP, [JOE]ddATP, [R6G]ddATP, [FAM]ddCTP, [R110]ddCTP, [TAMRA]ddGTP, [ROX]ddTTP, [dR6G] ddATP, [dR110]ddCTP, [dTAMRA]ddGTP, and [dROX] ddTTP available from Perkin Elmer, Foster City, Calif; FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides can also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-dCTP, biotin-14-dCTP), and biotin-dUTP (e.g., biotin-11-dUTP, biotin-16-dUTP, biotin-20-dUTP).

The terms "polynucleotide," "oligonucleotide," and "nucleic acid" are used interchangeably to generally refer to a polymeric form of nucleotides of any length, either deoxyribonucleotides or ribonucleotides, or analogs thereof, either in single-, double-, or multi-stranded form. A polynucleotide may be exogenous or endogenous to a cell. A polynucleotide may exist in a cell-free environment. A polynucleotide may be a gene or fragment thereof. A polynucleotide may be DNA. A polynucleotide may be RNA. A polynucleotide may have any three-dimensional structure and may perform any function. A polynucleotide may comprise one or more analogs (e.g., altered backbone, sugar, or nucleobase). If present, modifications to the nucleotide structure may be imparted before or after assembly of the polymer. Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g., rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes, and primers. The sequence of nucleotides may be interrupted by non-nucleotide components.

The terms "transfection" or "transfected" generally refer to introduction of a nucleic acid into a cell by non-viral or viral-based methods. The nucleic acid molecules may be gene sequences encoding complete proteins or functional portions thereof. See, e.g., Sambrook et al., 1989, Molecular Cloning: A Laboratory Manual, 18.1-18.88.

The terms "peptide," "polypeptide," and "protein" are used interchangeably herein to generally refer to a polymer of at least two amino acid residues joined by peptide bond(s). This term does not connote a specific length of polymer, nor is it intended to imply or distinguish whether the peptide is produced using recombinant techniques, chemical or enzymatic synthesis, or is naturally occurring. The terms apply to naturally occurring amino acid polymers as well as amino acid polymers comprising at least one modified amino acid. In some cases, the polymer may be interrupted by non-amino acids. The terms include amino acid chains of any length, including full length proteins, and proteins with or without secondary or tertiary structure (e.g., domains). The terms also encompass an amino acid polymer that has been modified, for example, by disulfide bond formation, glycosylation, lipidation, acetylation, phosphorylation, oxidation, and any other manipulation such as conjugation with a labeling component. The terms "amino acid" and "amino acids," as used herein, generally refer to natural and non-natural amino acids, including, but not limited to, modified amino acids and amino acid analogues. Modified amino acids may include natural amino acids and non-natural amino acids, which have been chemically modified to include a group or a chemical moiety not naturally present on the amino acid. Amino acid analogues may refer to amino acid derivatives. The term "amino acid" includes both D-amino acids and L-amino acids.

As used herein, the "non-native" can generally refer to a nucleic acid or polypeptide sequence that is not found in a native nucleic acid or protein. Non-native may refer to affinity tags. Non-native may refer to fusions. Non-native may refer to a naturally occurring nucleic acid or polypeptide sequence that comprises mutations, insertions or deletions. A non-native sequence may exhibit or encode for an activity (e.g., enzymatic activity, methyltransferase activity, acetyltransferase activity, kinase activity, ubiquitinating activity, etc.) that may also be exhibited by the nucleic acid or polypeptide sequence to which the non-native sequence is fused. A non-native nucleic acid or polypeptide sequence may be linked to a naturally-occurring nucleic acid or polypeptide sequence (or a variant thereof) by genetic engineering to generate a chimeric nucleic acid or polypeptide sequence encoding a chimeric nucleic acid or polypeptide.

The term "promoter", as used herein, generally refers to the regulatory DNA region which controls transcription or expression of a gene, and which may be located adjacent to or overlapping a nucleotide or region of nucleotides at which RNA transcription is initiated. A promoter may contain specific DNA sequences which bind protein factors, often referred to as transcription factors, which facilitate binding of RNA polymerase to the DNA leading to gene transcription. A 'basal promoter', also referred to as a 'core promoter', may generally refer to a promoter that contains all the basic elements to promote transcriptional expression of an operably linked polynucleotide. Eukaryotic basal promoters often contain a TATA-box or a CAAT box.

The term "expression", as used herein, generally refers to the process by which a nucleic acid sequence or a polynucleotide is transcribed from a DNA template (such as into mRNA or other RNA transcript) or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As used herein, "operably linked", "operable linkage", "operatively linked", or grammatical equivalents thereof generally refer to juxtaposition of genetic elements, e.g., a promoter, an enhancer, a polyadenylation sequence, etc., wherein the elements are in a relationship permitting them to operate in the expected manner. For instance, a regulatory element, which may comprise promoter or enhancer sequences, is operatively linked to a coding region if the regulatory element helps initiate transcription of the coding sequence. There may be intervening residues between the regulatory element and coding region so long as this functional relationship is maintained.

A "vector" as used herein, generally refers to a macromolecule or association of macromolecules that comprises or associates with a polynucleotide and which may be used to mediate delivery of the polynucleotide to a cell. Examples of vectors include plasmids, viral vectors, liposomes, and other gene delivery vehicles. The vector generally comprises genetic elements, e.g., regulatory elements, operatively linked to a gene to facilitate expression of the gene in a target.

As used herein, "an expression cassette" and "a nucleic acid cassette" are used interchangeably generally to refer to a combination of nucleic acid sequences or elements that are expressed together or are operably linked for expression. In some cases, an expression cassette refers to the combination of regulatory elements and a gene or genes to which they are operably linked for expression.

A "functional fragment" of a DNA or protein sequence generally refers to a fragment that retains a biological activity (either functional or structural) that is substantially similar to a biological activity of the full-length DNA or protein sequence. A biological activity of a DNA sequence may be its ability to influence expression in a manner attributed to the full-length sequence.

As used herein, an "engineered" object generally indicates that the object has been modified by human intervention. According to non-limiting examples: a nucleic acid may be modified by changing its sequence to a sequence that does not occur in nature; a nucleic acid may be modified by ligating it to a nucleic acid that it does not associate with in nature such that the ligated product possesses a function not present in the original nucleic acid; an engineered nucleic acid may synthesized in vitro with a sequence that does not exist in nature; a protein may be modified by changing its amino acid sequence to a sequence that does not exist in nature; an engineered protein may acquire a new function or property. An "engineered" system comprises at least one engineered component.

As used herein, "synthetic" and "artificial" are used interchangeably to refer to a protein or a domain thereof that has low sequence identity (e.g., less than 50% sequence identity, less than 25% sequence identity, less than 10% sequence identity, less than 5% sequence identity, less than 1% sequence identity) to a naturally occurring human protein. For example, VPR and VP64 domains are synthetic transactivation domains.

The term "tracrRNA" or "tracr sequence", as used herein, can generally refer to a nucleic acid with at least about 5%, 10%, 20%, 30%, 40%, 50%, 60%, 70%, 80%, 90%, 95%, or 100% sequence identity or sequence similarity to a wild type exemplary tracrRNA sequence (e.g., a tracrRNA from *S. pyogenes S. aureus*, etc or SEQ ID NOs: 5476-5511). tracrRNA can refer to a nucleic acid with at most about 5%, 10%, 20%, 30%, 40%, 50%, 60%, 70%, 80%, 90%, or 100% sequence identity or sequence similarity to a wild type exemplary tracrRNA sequence (e.g., a tracrRNA from *S. pyogenes S. aureus*, etc). tracrRNA may refer to a modified form of a tracrRNA that can comprise a nucleotide change such as a deletion, insertion, or substitution, variant, mutation, or chimera. A tracrRNA may refer to a nucleic acid that can be at least about 60% identical to a wild type exemplary tracrRNA (e.g., a tracrRNA from *S. pyogenes S. aureus*, etc) sequence over a stretch of at least 6 contiguous nucleotides. For example, a tracrRNA sequence can be at least about 60% identical, at least about 65% identical, at least about 70% identical, at least about 75% identical, at least about 80% identical, at least about 85% identical, at least about 90% identical, at least about 95% identical, at least about 98% identical, at least about 99% identical, or 100% identical to a wild type exemplary tracrRNA (e.g., a tracrRNA from *S. pyogenes S. aureus*, etc) sequence over a stretch of at least 6 contiguous nucleotides. Type II tracrRNA sequences can be predicted on a genome sequence by identifying regions with complementarity to part of the repeat sequence in an adjacent CRISPR array.

As used herein, a "guide nucleic acid" can generally refer to a nucleic acid that may hybridize to another nucleic acid. A guide nucleic acid may be RNA. A guide nucleic acid may be DNA. The guide nucleic acid may be programmed to bind to a sequence of nucleic acid site-specifically. The nucleic acid to be targeted, or the target nucleic acid, may comprise nucleotides. The guide nucleic acid may comprise nucleotides. A portion of the target nucleic acid may be complementary to a portion of the guide nucleic acid. The strand of a double-stranded target polynucleotide that is complementary to and hybridizes with the guide nucleic acid may be called the complementary strand. The strand of the double-stranded target polynucleotide that is complementary to the complementary strand, and therefore may not be complementary to the guide nucleic acid may be called noncomplementary strand. A guide nucleic acid may comprise a polynucleotide chain and can be called a "single guide nucleic acid." A guide nucleic acid may comprise two polynucleotide chains and may be called a "double guide nucleic acid." If not otherwise specified, the term "guide nucleic acid" may be inclusive, referring to both single guide nucleic acids and double guide nucleic acids. A guide nucleic acid may comprise a segment that can be referred to as a "nucleic acid-targeting segment" or a "nucleic acid-targeting sequence." A nucleic acid-targeting segment may comprise a sub-segment that may be referred to as a "protein binding segment" or "protein binding sequence" or "Cas protein binding segment".

The term "sequence identity" or "percent identity" in the context of two or more nucleic acids or polypeptide sequences, generally refers to two (e.g., in a pairwise alignment) or more (e.g., in a multiple sequence alignment) sequences that are the same or have a specified percentage of amino acid residues or nucleotides that are the same, when compared and aligned for maximum correspondence over a local or global comparison window, as measured using a sequence comparison algorithm. Suitable sequence comparison algorithms for polypeptide sequences include, e.g., BLASTP using parameters of a wordlength (W) of 3, an expectation I of 10, and the BLOSUM62 scoring matrix setting gap costs at existence of 11, extension of 1, and using a conditional compositional score matrix adjustment for polypeptide sequences longer than 30 residues; BLASTP using parameters of a wordlength (W) of 2, an expectation (E) of 1000000, and the PAM30 scoring matrix setting gap costs at 9 to open gaps and 1 to extend gaps for sequences of less than 30 residues (these are the default parameters for BLASTP in the BLAST suite available at https://blast.ncbi.nlm.nih.gov); CLUSTALW with parameters of; the Smith-Waterman homology search algorithm with parameters of a match of 2, a mismatch of −1, and a gap of −1; MUSCLE with default parameters; MAFFT with parameters retree of 2 and maxiterations of 1000; Novafold with default parameters; HMMER hmmalign with default parameters.

Included in the current disclosure are variants of any of the enzymes described herein with one or more conservative amino acid substitutions. Such conservative substitutions can be made in the amino acid sequence of a polypeptide without disrupting the three-dimensional structure or function of the polypeptide. Conservative substitutions can be accomplished by substituting amino acids with similar hydrophobicity, polarity, and R chain length for one another. Additionally or alternatively, by comparing aligned sequences of homologous proteins from different species, conservative substitutions can be identified by locating amino acid residues that have been mutated between species (e.g. non-conserved residues) without altering the basic functions of the encoded proteins. Such conservatively substituted variants may include variants with at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% identity to any one of the endonuclease protein sequences described herein (e.g. MG1, MG2, MG3, MG3a, MG3b, MG4, MG5, MG6, MG7, MG14, MG15, MG16, MG17, MG18, MG21, MG22, MG23, MG24, MG25, MG38, MG40, MG41, MG42, MG43, MG44, MG46, MG47, MG48, MG49, MG50, MG51, MG52, MG71, MG72, MG73, MG74, MG86, MG87, MG88, MG89, MG94, MG95, MG96, MG97, MG98, MG99, MG100, MG111, MG112, MG116, MG123, MG124, MG125, or MG150 family endonucleases described herein). In some embodiments, such conservatively substituted variants are functional variants. Such functional variants can encompass sequences with substitutions such that the activity of critical active site residues of the endonuclease are not disrupted. In some embodiments, a functional variant of any of the proteins described herein lacks substitution of at least one conserved or functional residue.

Conservative substitution tables providing functionally similar amino acids are available from a variety of references (see, for e.g., Creighton, Proteins: Structures and Molecular Properties (W H Freeman & Co.; 2nd edition (December 1993)). The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

Also included in the current disclosure are variants of any of the nucleic acid sequences described herein with one or more substitutions. Such variants may include variants with at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identity to any one of the nucleic acid sequences described herein.

As used herein, the term "RuvC_III domain" generally refers to a third discontinuous segment of a RuvC endonuclease domain (the RuvC nuclease domain being comprised of three discontiguous segments, RuvC_I, RuvC_II, and RuvC_III). A RuvC domain or segments thereof can generally be identified by alignment to documented domain sequences, structural alignment to proteins with annotated domains, or by comparison to Hidden Markov Models (HMMs) built based on documented domain sequences (e.g., Pfam HMM PF18541 for RuvC_III).

As used herein, the term "HNH domain" generally refers to an endonuclease domain having characteristic histidine and asparagine residues. An HNH domain can generally be identified by alignment to documented domain sequences, structural alignment to proteins with annotated domains, or by comparison to Hidden Markov Models (HMMs) built based on documented domain sequences (e.g., Pfam HMM PF01844 for domain HNH).

Overview

The discovery of new Cas enzymes with unique functionality and structure may offer the potential to further disrupt deoxyribonucleic acid (DNA) editing technologies, improving speed, specificity, functionality, and ease of use. Relative to the predicted prevalence of Clustered Regularly Interspaced Short Palindromic Repeats (CRISPR) systems in microbes and the sheer diversity of microbial species, relatively few functionally characterized CRISPR/Cas enzymes exist in the literature. This is partly because a huge number of microbial species may not be readily cultivated in laboratory conditions. Metagenomic sequencing from natural environmental niches that represent large numbers of microbial species may offer the potential to drastically increase the number of new CRISPR/Cas systems documented and speed the discovery of new oligonucleotide editing functionalities. A recent example of the fruitfulness of such an approach is demonstrated by the 2016 discovery of CasX/CasY CRISPR systems from metagenomic analysis of natural microbial communities.

CRISPR/Cas systems are RNA-directed nuclease complexes that have been described to function as an adaptive immune system in microbes. In their natural context, CRISPR/Cas systems occur in CRISPR (clustered regularly interspaced short palindromic repeats) operons or loci, which generally comprise two parts: (i) an array of short repetitive sequences (30-40 bp) separated by equally short spacer sequences, which encode the RNA-based targeting element; and (ii) ORFs encoding the Cas encoding the nuclease polypeptide directed by the RNA-based targeting element alongside accessory proteins/enzymes. Efficient nuclease targeting of a particular target nucleic acid sequence generally requires both (i) complementary hybridization between the first 6-8 nucleic acids of the target (the target seed) and the crRNA guide; and (ii) the presence of a protospacer-adjacent motif (PAM) sequence within a defined vicinity of the target seed (the PAM usually being a sequence not commonly represented within the host genome). Depending on the exact function and organization of the system, CRISPR-Cas systems are commonly organized into 2 classes, 5 types and 16 subtypes based on shared functional characteristics and evolutionary similarity.

Class I CRISPR-Cas systems have large, multisubunit effector complexes, and comprise Types I, III, and IV.

Type I CRISPR-Cas systems are considered of moderate complexity in terms of components. In Type I CRISPR-Cas systems, the array of RNA-targeting elements is transcribed as a long precursor crRNA (pre-crRNA) that is processed at repeat elements to liberate short, mature crRNAs that direct the nuclease complex to nucleic acid targets when they are followed by a suitable short consensus sequence called a protospacer-adjacent motif (PAM). This processing occurs via an endoribonuclease subunit (Cas6) of a large endonuclease complex called Cascade, which also comprises a nuclease (Cas3) protein component of the crRNA-directed nuclease complex. Cas I nucleases function primarily as DNA nucleases.

Type III CRISPR systems may be characterized by the presence of a central nuclease, known as Cas10, alongside a repeat-associated mysterious protein (RAMP) that comprises Csm or Cmr protein subunits. Like in Type I systems, the mature crRNA is processed from a pre-crRNA using a Cas6-like enzyme. Unlike type I and II systems, type III systems appear to target and cleave DNA-RNA duplexes (such as DNA strands being used as templates for an RNA polymerase).

Type IV CRISPR-Cas systems possess an effector complex that consists of a highly reduced large subunit nuclease (csf1), two genes for RAMP proteins of the Cas5 (csf3) and Cas7 (csf2) groups, and, in some cases, a gene for a predicted small subunit; such systems are commonly found on endogenous plasmids.

Class II CRISPR-Cas systems generally have single-polypeptide multidomain nuclease effectors, and comprise Types II, V and VI.

Type II CRISPR-Cas systems are considered the simplest in terms of components. In Type II CRISPR-Cas systems, the processing of the CRISPR array into mature crRNAs does not require the presence of a special endonuclease subunit, but rather a small trans-encoded crRNA (tracrRNA) with a region complementary to the array repeat sequence; the tracrRNA interacts with both its corresponding effector nuclease (e.g. Cas9) and the repeat sequence to form a precursor dsRNA structure, which is cleaved by endogenous RNAse III to generate a mature effector enzyme loaded with both tracrRNA and crRNA. Cas II nucleases are known as DNA nucleases. Type 2 effectors generally exhibit a structure consisting of a RuvC-like endonuclease domain that adopts the RNase H fold with an unrelated HNH nuclease domain inserted within the folds of the RuvC-like nuclease domain. The RuvC-like domain is responsible for the cleavage of the target (e.g., crRNA complementary) DNA strand, while the HNH domain is responsible for cleavage of the displaced DNA strand.

Type V CRISPR-Cas systems are characterized by a nuclease effector (e.g. Cas12) structure similar to that of Type II effectors, comprising a RuvC-like domain. Similar to Type II, most (but not all) Type V CRISPR systems use a tracrRNA to process pre-crRNAs into mature crRNAs; however, unlike Type II systems which requires RNAse III to cleave the pre-crRNA into multiple crRNAs, type V systems are capable of using the effector nuclease itself to cleave pre-crRNAs. Like Type-II CRISPR-Cas systems, Type V CRISPR-Cas systems are again known as DNA nucleases. Unlike Type II CRISPR-Cas systems, some Type V enzymes (e.g., Cas12a) appear to have a robust single-stranded nonspecific deoxyribonuclease activity that is activated by the first crRNA directed cleavage of a double-stranded target sequence.

Type VI CRIPSR-Cas systems have RNA-guided RNA endonucleases. Instead of RuvC-like domains, the single polypeptide effector of Type VI systems (e.g. Cas13) comprises two HEPN ribonuclease domains. Differing from both Type II and V systems, Type VI systems also appear to not require a tracrRNA for processing of pre-crRNA into crRNA. Similar to type V systems, however, some Type VI systems (e.g., C2C2) appear to possess robust single-stranded nonspecific nuclease (ribonuclease) activity activated by the first crRNA directed cleavage of a target RNA.

Because of their simpler architecture, Class II CRISPR-Cas have been most widely adopted for engineering and development as designer nuclease/genome editing applications.

One of the early adaptations of such a system for in vitro use can be found in Jinek et al. (Science. 2012 Aug. 17; 337(6096):816-21, which is entirely incorporated herein by reference). The Jinek study first described a system that involved (i) recombinantly-expressed, purified full-length Cas9 (e.g., a Class II, Type II Cas enzyme) isolated from *S. pyogenes* SF370, (ii) purified mature ~42 nt crRNA bearing a ~20 nt 5' sequence complementary to the target DNA sequence desired to be cleaved followed by a 3' tracr-binding sequence (the whole crRNA being in vitro transcribed from a synthetic DNA template carrying a T7 promoter sequence); (iii) purified tracrRNA in vitro transcribed from a synthetic DNA template carrying a T7 promoter sequence, and (iv) Mg2+. Jinek later described an improved, engineered system wherein the crRNA of (ii) is joined to the 5' end of (iii) by a linker (e.g., GAAA) to form a single fused synthetic guide RNA (sgRNA) capable of directing Cas9 to a target by itself.

Mali et al. (Science. 2013 Feb. 15; 339(6121): 823-826.), which is entirely incorporated herein by reference, later adapted this system for use in mammalian cells by providing DNA vectors encoding (i) an ORF encoding codon-optimized Cas9 (e.g., a Class II, Type II Cas enzyme) under a suitable mammalian promoter with a C-terminal nuclear localization sequence (e.g., SV40 NLS) and a suitable polyadenylation signal (e.g., TK pA signal); and (ii) an ORF encoding an sgRNA (having a 5' sequence beginning with G followed by 20 nt of a complementary targeting nucleic acid sequence joined to a 3' tracr-binding sequence, a linker, and the tracrRNA sequence) under a suitable Polymerase III promoter (e.g., the U6 promoter).

MG Enzymes

In one aspect, the present disclosure provides for an engineered nuclease system discovered through metagenomic sequencing. In some cases, the metagenomic sequencing is conducted on samples. In some cases, the samples may be collected by a variety of environments. Such environments may be a human microbiome, an animal microbiome, environments with high temperatures, environments with low temperatures. Such environments may include sediment.

MG3 Enzymes

In one aspect, the present disclosure provides for an engineered nuclease system comprising (a) an endonuclease. In some cases, the endonuclease is a Cas endonuclease. In some cases, the endonuclease is a Type II, Class II Cas endonuclease. The endonuclease may comprise a RuvC_III domain, wherein said RuvC_III domain has at least about 70% sequence identity to any one of SEQ ID NOs: 2242-2251. In some cases, the endonuclease may comprise a RuvC_III domain, wherein the RuvC_III domain has at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% identity to any one of SEQ ID NOs: 2242-2251. In some cases, the endonuclease may comprise a RuvC_III domain, wherein the substantially identical to any one of SEQ ID NOs: 2242-2251. The endonuclease may comprise a RuvC_III domain having at least about 70% sequence identity to any one of SEQ ID NOs: 2242-2244. In some cases, the endonuclease may comprise a RuvC_III domain having at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% identity to any one of SEQ ID NOs: 2242-2244. In some cases, the endonuclease may comprise a RuvC_III domain substantially identical to any one of SEQ ID NOs: 2242-2244.

The endonuclease may comprise an HNH domain having at least about 70% identity to any one of SEQ ID NOs: 4056-4066. In some cases, the endonuclease may comprise an HNH domain having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to any one of SEQ ID NOs: 4056-4066. The endonuclease may comprise an HNH domain substantially identical to any one of SEQ ID NOs: 4056-4066. The endonuclease may comprise an HNH domain having at least about 70% identity to any one of SEQ ID NOs: 4056-4058. In some cases, the endonuclease may comprise an HNH domain having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to any one of SEQ ID NOs: 4056-4058. The endonuclease may comprise an HNH domain substantially identical to any one of SEQ ID NOs: 4056-4058.

In some cases, the endonuclease may comprise a variant having at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identity to any one of SEQ ID NOs: 421-431. In some cases, the endonuclease may be substantially identical to any one of SEQ ID NOs: 421-431. In some cases, the endonuclease may comprise a variant having at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identity to any one of SEQ ID NOs:421-423. In some cases, the endonuclease may be substantially identical to any one of SEQ ID NOs: 421-423.

In some cases, the endonuclease may comprise a variant having one or more nuclear localization sequences (NLSs). The NLS may be proximal to the N- or C-terminus of said endonuclease. The NLS may be appended N-terminal or C-terminal to any one of SEQ ID NOs: 421-431, or to a variant having at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identity to any one of SEQ ID NOs: 421-431. The NLS may be an SV40 large T antigen NLS. The NLS may be a c-myc NLS. The NLS can comprise a sequence with at least about 80%, at least about 85%, at least about 90%, at least about 95%, at least about 99% identity to any one of SEQ ID NOs: 5593-5608. The NLS can comprise a sequence substantially identical to any one of SEQ ID NOs: 5593-5608.

In some cases, sequence identity may be determined by the BLASTP, CLUSTALW, MUSCLE, MAFFT, Novafold, or CLUSTALW with the parameters of the Smith-Waterman homology search algorithm. The sequence identity may be determined by the BLASTP algorithm using parameters of a wordlength (W) of 3, an expectation (E) of 10, and using a BLOSUM62 scoring matrix setting gap costs at existence of 11, extension of 1, and using a conditional compositional score matrix adjustment.

In some cases, the system above may comprise (b) at least one engineered synthetic guide ribonucleic acid (sgRNA) capable of forming a complex with the endonuclease bearing a 5' targeting region complementary to a desired cleavage sequence. In some cases, the 5' targeting region may comprises a PAM sequence compatible with the endonuclease. In some cases, the 5' most nucleotide of the targeting region may be G. In some cases, the 5' targeting region may be 15-23 nucleotides in length. The guide sequence and the tracr sequence may be supplied as separate ribonucleic acids (RNAs) or a single ribonucleic acid (RNA). The guide RNA may comprise a crRNA tracrRNA binding sequence 3' to the targeting region. The guide RNA may comprise a tracrRNA sequence preceded by a 4-nucleotide linker 3' to the crRNA tracrRNA binding region. The sgRNA may comprise, from 5' to 3': a non-natural guide nucleic acid sequence capable of hybridizing to a target sequence in a cell; and a tracr sequence. In some cases, the non-natural guide nucleic acid sequence and the tracr sequence are covalently linked.

In some cases, the tracr sequence may have a particular sequence. The tracr sequence may have at least about 80% to at least about 60-100 (e.g., at least about 60, at least about 65, at least about 70, at least about 75, at least about 80, at least about 85, or at least about 90) consecutive nucleotides of a natural tracrRNA sequence. The tracr sequence may have at least about 80% sequence identity to at least about 60-100 (e.g., at least about 60, at least about 65, at least about 70, at least about 75, at least about 80, at least about 85, or at least about 90) consecutive nucleotides of any one of SEQ ID NOs: 5495-5502. In some cases, the tracrRNA may have at least about 80%, at least about 85%, at least about 90%, at least about 91%, at least about 92%, at least about 93%, at least about 94%, at least about 95%, at least about 96%, at least about 97%, at least about 98%, or at least about 99% identity to at least about 60-90 (e.g., at least about 60, at least about 65, at least about 70, at least about 75, at least about 80, at least about 85, or at least about 90) consecutive nucleotides of any one of SEQ ID NOs: 5495-5502. In some cases, the tracrRNA may be substantially identical to at least about 60-100 (e.g., at least about 60, at least about 65, at least about 70, at least about 75, at least about 80, at least about 85, or at least about 90) consecutive nucleotides of any one of SEQ ID NOs: 5495-5502. The tracrRNA may comprise any of SEQ ID NOs: 5495-5502.

In some cases, the at least one engineered synthetic guide ribonucleic acid (sgRNA) capable of forming a complex with the endonuclease may comprise a sequence having at least about 80% identity to any one of SEQ ID NOs: 5466-5467. The sgRNA may comprise a sequence having at least about 80%, at least about 85%, at least about 90%, at least about 91%, at least about 92%, at least about 93%, at least about 94%, at least about 95%, at least about 96%, at least about 97%, at least about 98%, or at least about 99% identity to any one of SEQ ID NOs: 5466-5467. The sgRNA may comprise a sequence substantially identical to any one of SEQ ID NOs: 5466-5467.

In some cases, the system above may comprise two different sgRNAs targeting a first region and a second region for cleavage in a target DNA locus, wherein the second region is 3' to the first region. In some cases, the system above may comprise a single- or double-stranded DNA repair template comprising from 5' to 3': a first homology arm comprising a sequence of at least about 20 (e.g., at least about 40, 80, 120, 150, 200, 300, 500, or 1 kb) nucleotides 5' to the first region, a synthetic DNA sequence of at least about 10 nucleotides, and a second homology arm comprising a sequence of at least about 20 (e.g., at least about 40, 80, 120, 150, 200, 300, 500, or 1 kb) nucleotides 3' to the second region.

In another aspect, the present disclosure provides a method for modifying a target nucleic acid locus of interest. The method may comprise delivering to the target nucleic acid locus any of the non-natural systems disclosed herein, including an enzyme and at least one synthetic guide RNA (sgRNA) disclosed herein. The enzyme may form a complex with the at least one sgRNA, and upon binding of the complex to the target nucleic acid locus of interest, may modify the target nucleic acid locus of interest. Delivering the enzyme to said locus may comprise transfecting a cell with the system or nucleic acids encoding the system. Delivering the nuclease to said locus may comprise electroporating a cell with the system or nucleic acids encoding the system. Delivering the nuclease to said locus may comprise incubating the system in a buffer with a nucleic acid comprising the locus of interest. In some cases, the target nucleic acid locus comprises deoxyribonucleic acid (DNA) or ribonucleic acid (RNA). The target nucleic acid locus may comprise genomic DNA, viral DNA, viral RNA, or bacterial DNA. The target nucleic acid locus may be within a cell. The target nucleic acid locus may be in vitro. The target nucleic acid locus may be within a eukaryotic cell or a prokaryotic cell. The cell may be an animal cell, a human cell, bacterial cell, archaeal cell, or a plant cell. The enzyme may induce a single or double-stranded break at or proximal to the target locus of interest.

In cases where the target nucleic acid locus may be within a cell, the enzyme may be supplied as a nucleic acid containing an open reading frame encoding the enzyme having a RuvC_III domain having at least about 75% (e.g., at least about 90%, at least about 91%, at least about 92%, at least about 93%, at least about 94%, at least about 95%, at least about 96%, at least about 97%, at least about 98%, at least about 99%) identity to any one of SEQ ID NOs: 2242-2251. The deoxyribonucleic acid (DNA) containing an open reading frame encoding said endonuclease may comprise a sequence substantially identical to any of SEQ ID NOs: 5578-5580 or at variant having at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identity to any one of SEQ ID NOs: 5578-5580. In some cases, the nucleic acid comprises a promoter to which the open reading frame encoding the endonuclease is operably linked. The promoter may be a CMV, EF1a, SV40, PGK1, Ubc, human beta actin, CAG, TRE, or CaMKIIa promoter. The endonuclease may be supplied as a capped mRNA containing said open reading frame encoding said endonuclease. The endonuclease may be supplied as a translated polypeptide. The at least one engineered sgRNA may be supplied as deoxyribonucleic acid (DNA) containing a gene sequence encoding said at least one engineered sgRNA operably linked to a ribonucleic acid (RNA) pol III promoter. In some cases, the organism may be eukaryotic. In some cases, the organism may be fungal. In some cases, the organism may be human.

Systems of the present disclosure may be used for various applications, such as, for example, nucleic acid editing (e.g., gene editing), binding to a nucleic acid molecule (e.g., sequence-specific binding). Such systems may be used, for example, for addressing (e.g., removing or replacing) a genetically inherited mutation that may cause a disease in a subject, inactivating a gene in order to ascertain its function in a cell, as a diagnostic tool to detect disease-causing genetic elements (e.g. via cleavage of reverse-transcribed viral RNA or an amplified DNA sequence encoding a disease-causing mutation), as deactivated enzymes in combination with a probe to target and detect a specific nucleotide sequence (e.g. sequence encoding antibiotic resistance int bacteria), to render viruses inactive or incapable of infecting host cells by targeting viral genomes, to add genes or amend metabolic pathways to engineer organisms to produce valuable small molecules, macromolecules, or secondary metabolites, to establish a gene drive element for evolutionary selection, to detect cell perturbations by foreign small molecules and nucleotides as a biosensor.

EXAMPLES

Example 1—Metagenomic Analysis for New Proteins

Metagenomic samples were collected from sediment, soil and animal. Deoxyribonucleic acid (DNA) was extracted with a Zymobiomics DNA mini-prep kit and sequenced on an Illumina HiSeq® 2500. Samples were collected with consent of property owners. Additional raw sequence data from public sources included animal microbiomes, sediment, soil, hot springs, hydrothermal vents, marine, peat bogs, permafrost, and sewage sequences. Metagenomic sequence data was searched using Hidden Markov Models generated based on documented Cas protein sequences including type II Cas effector proteins to identify new Cas effectors. Novel effector proteins identified by the search were aligned to documented proteins to identify potential active sites. This metagenomic workflow resulted in delineation of the families of class II, type II CRISPR endonucleases described herein.

Example 2—(General Protocol) PAM Sequence Identification/Confirmation for the Endonucleases Described Herein PAM sequences were determined by sequencing plasmids containing randomly-generated PAM sequences that can be cleaved by putative endonucleases expressed in an *E. coli* lysate-based expression system (myTXTL, Arbor Biosciences). In this system, an *E. coli* codon optimized nucleotide sequence was transcribed and translated from a PCR fragment under control of a T7 promoter. A second PCR fragment with a tracr sequence under a T7 promoter and a minimal CRISPR array composed of a T7 promoter followed by a repeat-spacer-repeat sequence was transcribed in the same reaction. Successful expression of the endonuclease and tracr sequence in the TXTL system followed by CRISPR array processing provided active in vitro CRISPR nuclease complexes.

A library of target plasmids containing a spacer sequence matching that in the minimal array followed by 8N mixed bases (putative PAM sequences) was incubated with the output of the TXTL reaction. After 1-3 hr, the reaction was stopped and the DNA was recovered via a DNA clean-up kit, e.g., Zymo DCC, AMPure XP beads, QiaQuick etc. Adapter sequences were blunt-end ligated to DNA with active PAM sequences that had been cleaved by the endonuclease, whereas DNA that had not been cleaved was inaccessible for ligation. DNA segments comprising active PAM sequences were then amplified by PCR with primers specific to the library and the adapter sequence. The PCR amplification products were resolved on a gel to identify amplicons that corresponded to cleavage events. The amplified segments of the cleavage reaction were also used as template for preparation of an NGS library. Sequencing this resulting library, which was a subset of the starting 8N library, revealed the sequences which contain the correct PAM for the active CRISPR complex. For PAM testing with a single RNA construct, the same procedure was repeated except that an in vitro transcribed RNA was added along with the plasmid library and the tracr/minimal CRISPR array template was omitted. For endonucleases where NGS libraries were prepared, seqLogo (see e.g., Huber et al. Nat Methods. 2015 February; 12(2):115-21) representations were constructed. The seqLogo module used to construct these representations takes the position weight matrix of a DNA sequence motif (e.g. a PAM sequence) and plots the corresponding sequence logo as introduced by Schneider and Stephens (see e.g. Schneider et al. Nucleic Acids Res. 1990 Oct. 25; 18(20): 6097-100. The characters representing the sequence in the seqLogo representations have been stacked on top of each other for each position in the aligned sequences (e.g. PAM sequences). The height of each letter is proportional to its frequency, and the letters have been sorted so the most common one is on top.

Example 3—(General Protocol) RNA Folding of tracrRNA and sgRNA Structures

Folded structures of guide RNA sequences at 37° C. were computed using the method of Andronescu et al. Bioinformatics. 2007 Jul. 1; 23(13):i19-28, which is incorporated by reference herein in its entirety.

Example 4—(General Protocol) In Vitro Cleavage Efficiency of MG CRISPR Complexes Endonucleases were expressed as His-tagged fusion proteins from an inducible T7 promoter in a protease deficient *E. coli* B strain. Cells expressing the His-tagged proteins were lysed by sonication and the His-tagged proteins were purified by Ni-NTA affinity chromatography on a HisTrap FF column (GE Lifescience) on an AKTA Avant FPLC (GE Lifescience). The eluate was resolved by SDS-PAGE on acrylamide gels (Bio-Rad) and stained with InstantBlue Ultrafast coomassie (Sigma-Aldrich). Purity was determined using densitometry of the protein band with ImageLab software (Bio-Rad). Purified endonucleases were dialyzed into a storage buffer composed of 50 mM Tris-HCl, 300 mM NaCl, 1 mM TCEP, 5% glycerol; pH 7.5 and stored at −80° C.

Target DNAs containing spacer sequences and PAM sequences (determined e.g., as in Example 2) were constructed by DNA synthesis. A single representative PAM was chosen for testing when the PAM had degenerate bases. The target DNAs comprised 2200 bp of linear DNA derived from a plasmid via PCR amplification with a PAM and spacer located 700 bp from one end. Successful cleavage resulted in fragments of 700 and 1500 bp. The target DNA, in vitro transcribed single RNA, and purified recombinant protein were combined in cleavage buffer (10 mM Tris, 100 mM NaCl, 10 mM $MgCl_2$) with an excess of protein and RNA and incubated for 5 minutes to 3 hours, usually 1 hr. The reaction was stopped via addition of RNAse A and incubation at 60 minutes. The reaction was then resolved on a 1.2% TAE agarose gel and the fraction of cleaved target DNA is quantified in ImageLab software.

Example 5—(General Protocol) Testing of Genome Cleavage Activity of MG CRISPR Complexes in *E. coli*

*E. coli* lacks the capacity to efficiently repair double-stranded DNA breaks. Thus, cleavage of genomic DNA can be a lethal event. Exploiting this phenomenon, endonuclease activity was tested in *E. coli* by recombinantly expressing an endonuclease and a tracrRNA in a target strain with spacer/target and PAM sequences integrated into its genomic DNA.

In this assay, the PAM sequence is specific for the endonuclease being tested as determined by the methods described in Example 2. sgRNA sequences were determined based upon the sequence and predicted structure of the tracrRNA. Repeat-anti-repeat pairings of 8-12 bp (generally 10 bp) were chosen, starting from the 5' end of the repeat. The remaining 3' end of the repeat and 5' end of the tracrRNA were replaced with a tetraloop. Generally, the tetraloop was GAAA, but other tetraloops can be used, particularly if the GAAA sequence is predicted to interfere with folding. In these cases, a TTCG tetraloop was used.

Engineered strains with PAM sequences integrated into their genomic DNA were transformed with DNA encoding the endonuclease. Transformants were then made chemocompetent and transformed with 50 ng of single guide RNAs either specific to the target sequence (“on target”), or non-specific to the target (“non target”). After heat shock, transformations were recovered in SOC for 2 hrs at 37° C. Nuclease efficiency was then determined by a 5-fold dilution series grown on induction media. Colonies were quantified from the dilution series in triplicate.

Example 6a—(General Protocol) Testing of Genome Cleavage Activity of MG CRISPR Complexes in Mammalian Cells To show targeting and cleavage activity in mammalian cells, the MG Cas effector protein sequences were tested in two mammalian expression vectors: (a) one with a C-terminal SV40 NLS and a 2A-GFP tag, and (b) one with no GFP tag and two SV40 NLS sequences, one on the N-terminus and one on the C-terminus. In some instances, nucleotide sequences encoding the endonucleases were codon-optimized for expression in mammalian cells.

The corresponding single guide RNA sequence (sgRNA) with targeting sequence attached is cloned into a second mammalian expression vector. The two plasmids are cotransfected into HEK293T cells. 72 hr after co-transfection of the expression plasmid and a sgRNA targeting plasmid into HEK293T cells, the DNA is extracted and used for the preparation of an NGS-library. Percent NHEJ is measured via indels in the sequencing of the target site to demonstrate the targeting efficiency of the enzyme in mammalian cells. At least 10 different target sites were chosen to test each protein's activity.

Example 6b—(General Protocol) Testing of Genome Cleavage Activity of MG CRISPR Complexes in Mammalian Cells To show targeting and cleavage activity in mammalian cells, the MG Cas effector protein sequences were cloned into two mammalian expression vector: (a) one with flanking N and C-terminal SV40 NLS sequences, a C-terminal His tag, and a 2A-GFP tag at the C terminus after the His tag (Backbone 1), and (b) one with flanking NLS sequences and C-terminal His tag but no T2A GFP tag (Backbone 2). In some instances, nucleotide sequences encoding the endonucleases were the native sequence, codon-optimized for expression in *E. coli*, or codon-optimized for expression in mammalian cells.

The corresponding single guide RNA sequence (sgRNA) with targeting sequence attached was cloned into a second mammalian expression vector. The two plasmids were cotransfected into HEK293T cells. 72 hr after co-transfection of the expression plasmid and a sgRNA targeting plasmid into HEK293T cells, the DNA was extracted and used for the preparation of an NGS-library. Percent NHEJ was measured via indels in the sequencing of the target site to demonstrate the targeting efficiency of the enzyme in mammalian cells. About 7-12 different target sites were chosen for testing each protein's activity. An arbitrary threshold of 5% indels was used to identify active candidates.

Example 7—Gene Editing Outcomes at the DNA Level for B2M

Primary T cells were purified from PBMCs using a negative selection kit (Miltenyi) according to the manufacturer's recommendations. Nucleofection of MG3-6 RNPs (106 pmol protein/160 pmol guide) (SEQ ID NOs: 6305-6386) was performed into T cells (200,000) using the Lonza 4D electroporator. Cells were harvested and genomic DNA prepared five days post-transfection. PCR primers appropriate for use in NGS-based DNA sequencing were generated, optimized, and used to amplify the individual target sequences for each guide RNA (SEQ ID NOs: 6387-6468). The amplicons were sequenced on an Illumina MiSeq machine and analyzed with a proprietary Python script to measure gene editing (FIG. 1).

TABLE 1A

Guide sequences used in Example 7

| SEQ ID NO: | Entity Name | Sequence |
|---|---|---|
| 6305 | MG3-6-B2M-sgRNA-A1 | mC*mG*mC*rUrArCrUrCrUrCrUrCrUrUrUrCrUrGrGrCrCrUr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6306 | MG3-6-B2M-sgRNA-B1 | mA*mG*mA*rGrArCrUrCrArCrGrCrUrGrGrArUrArGrCrCrUr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6307 | MG3-6-B2M-sgRNA-C1 | mG*mA*mG*rArGrArGrUrArGrCrGrCrGrArGrCrArCrArGrCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6308 | MG3-6-B2M-sgRNA-D1 | mC*mC*mC*rGrArUrArUrUrCrCrUrCrArGrGrUrArCrUrCrCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6309 | MG3-6-B2M-sgRNA-E1 | mA*mU*mU*rCrCrUrCrArGrGrUrArCrUrCrCrArArArGrArUr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |

TABLE 1A-continued

Guide sequences used in Example 7

| SEQ ID NO: | Entity Name | Sequence |
|---|---|---|
| 6310 | MG3-6-B2M-sgRNA-F1 | mA*mA*mU*rUrUrCrCrUrGrArArUrUrGrCrUrArUrGrUrGrUr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6311 | MG3-6-B2M-sgRNA-G1 | mG*mA*mG*rArArUrUrGrArArArArArGrUrGrGrArGrCrArUr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6312 | MG3-6-B2M-sgRNA-H1 | mG*mC*mA*rUrUrCrArGrArCrUrUrGrUrCrUrUrUrCrArGrCr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6313 | MG3-6-B2M-sgRNA-A2 | mA*mG*mA*rCrUrUrArCrCrCrCrArCrUrUrArArCrUrArUrCr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6314 | MG3-6-B2M-sgRNA-B2 | mU*mU*mC*rArGrUrGrUrArGrUrArCrArArGrArGrArUrArGr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6315 | MG3-6-B2M-sgRNA-C2 | mA*mG*mU*rUrCrUrCrCrUrUrGrGrUrGrGrCrCrCrGrCrCrGr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6316 | MG3-6-B2M-sgRNA-D2 | mG*mU*mG*rGrCrCrCrGrCrCrGrUrGrGrGrGrCrUrArGrUrCr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6317 | MG3-6-B2M-sgRNA-E2 | mC*mC*mG*rCrCrGrUrGrGrGrGrCrUrArGrUrCrCrArGrGrGr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrUxmU*mU*mU |
| 6318 | MG3-6-B2M-sgRNA-F2 | mG*mC*mC*rCrCrUrUrUrCrGrGrCrGrGrGrGrArGrCrArGrGr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6319 | MG3-6-B2M-sgRNA-G2 | mG*mA*mC*rCrUrUrUrGrGrCrCrUrArCrGrGrCrGrArCrGrGr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6320 | MG3-6-B2M-sgRNA-H2 | mG*mC*mG*rUrCrGrArUrArArGrCrGrUrCrArGrArGrCrGrCr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6321 | MG3-6-B2M-sgRNA-A3 | mC*mG*mU*rCrArGrArGrCrGrCrCrGrArGrGrUrUrGrGrGrGr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |

TABLE 1A-continued

Guide sequences used in Example 7

| SEQ ID NO: | Entity Name | Sequence |
|---|---|---|
| 6322 | MG3-6-B2M-sgRNA-B3 | mG*mG*mG*rUrUrUrCrUrCrUrUrCrCrGrCrUrCrUrUrUrCrGr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6323 | MG3-6-B2M-sgRNA-C3 | mG*mC*mG*rCrArGrCrUrGrGrArGrUrGrGrGrGrArCrGrGr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6324 | MG3-6-B2M-sgRNA-D3 | mG*mC*mU*rCrGrUrCrCrCrArArArGrGrCrGrCrGrGrCrGrCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6325 | MG3-6-B2M-sgRNA-E3 | mU*mG*mU*rGrArArCrGrCrGrUrGrGrArGrGrGrGrCrGrCrUr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6326 | MG3-6-B2M-sgRNA-F3 | mG*mU*mC*rUrGrCrUrGrCrGrGrCrUrCrUrGrCrUrUrCrCrCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6327 | MG3-6-B2M-sgRNA-G3 | mG*mC*mU*rUrCrCrCrUrUrArGrArCrUrGrGrArGrArGrCrUr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6328 | MG3-6-B2M-sgRNA-H3 | mA*mA*mG*rUrUrCrGrCrArUrGrUrCrCrUrArGrCrArCrCrUr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6329 | MG3-6-B2M-sgRNA-A4 | mU*mC*mC*rUrArGrCrArCrCrUrCrUrGrGrGrUrCrUrArUrGr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6330 | MG3-6-B2M-sgRNA-B4 | mC*mC*mU*rCrCrCrCrArCrGrGrUrGrUrGrGrCrCrCrCrArCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6331 | MG3-6-B2M-sgRNA-C4 | mA*mA*mG*rGrGrArArGrCrArGrArGrCrCrGrCrArGrCrArGr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrUxmU*mU*mU |
| 6332 | MG3-6-B2M-sgRNA-D4 | mG*mC*mU*rUrArCrCrCrGrGrGrCrGrArCrGrCrCrUrCrCrCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrUmU*mU*mU |
| 6333 | MG3-6-B2M-sgRNA-E4 | mC*mU*mC*rCrArGrCrUrGrCrGrCrUrGrGrGrGrArGrCrCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |

TABLE 1A-continued

Guide sequences used in Example 7

| SEQ ID NO: | Entity Name | Sequence |
|---|---|---|
| 6334 | MG3-6-B2M-sgRNA-F4 | mU*mU*mG*rUrCrCrCrGrArCrCrCrUrCrCrCrGrUrCrGrCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6335 | MG3-6-B2M-sgRNA-G4 | mG*mA*mC*rCrCrUrCrCrCrGrUrCrGrCrCrGrUrArGrGrCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6336 | MG3-6-B2M-sgRNA-H4 | mG*mU*mG*rCrGrCrArCrCrCrCrCrUrUrCrCrCrCrArCrUrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6337 | MG3-6-B2M-sgRNA-A5 | mC*mC*mA*rGrGrCrCrArCrCrCrCrGrCrCrGrCrUrUrCrCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6338 | MG3-6-B2M-sgRNA-B5 | mG*mC*mC*rGrCrUrUrCrCrCrCrGrArGrArUrCrCrArGrCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6339 | MG3-6-B2M-sgRNA-C5 | mC*mC*mA*rGrCrCrCrUrGrGrArCrUrArGrCrCrCrCrArCrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6340 | MG3-6-B2M-sgRNA-D5 | mU*mC*mA*rCrGrGrArGrCrGrArGrArGrArGrCrArCrArGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6341 | MG3-6-B2M-sgRNA-E5 | mA*mG*mA*rGrGrGrUrGrCrArGrArGrCrGrGrGrArGrArGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6342 | MG3-6-B2M-sgRNA-F5 | mA*mG*mG*rArCrCrArGrArGrCrGrGrGrArGrGrGrUrArGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6343 | MG3-6-B2M-sgRNA-G5 | mC*mG*mA*rGrArUrUrGrArArGrUrCrArArGrCrCrUrArArCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6344 | MG3-6-B2M-sgRNA-H5 | mA*mG*mA*rArArArArCrGrCrCrUrGrCrCrUrUrCrUrGrCrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6345 | MG3-6-B2M-sgRNA-A6 | mU*mC*mU*rCrCrArGrArGrCrArArArCrUrGrGrGrCrGrGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |

TABLE 1A-continued

Guide sequences used in Example 7

| SEQ ID NO: | Entity Name | Sequence |
|---|---|---|
| 6346 | MG3-6-B2M-sgRNA-B6 | mG*mG*mC*rCrCrUrGrUrGrGrUrCrUrUrUrUrCrGrUrArCrAr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6347 | MG3-6-B2M-sgRNA-C6 | mA*mC*mU*rUrUrCrGrGrUrUrUrUrGrArArArArCrArUrGrAr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6348 | MG3-6-B2M-sgRNA-D6 | mA*mA*mA*rGrArGrGrArArGrCrCrCrUrCrUrGrUrArCrGrAr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6349 | MG3-6-B2M-sgRNA-E6 | mA*mG*mC*rCrCrUrCrUrGrUrArCrGrArArArArGrArCrCrAr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6350 | MG3-6-B2M-sgRNA-F6 | mU*mG*mC*rGrCrUrCrCrCrGrCrArArArArGrCrCrCrUrGrGr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6351 | MG3-6-B2M-sgRNA-G6 | mA*mA*mA*rArGrArArArArGrArArArGrArArArGrArArGrUr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6352 | MG3-6-B2M-sgRNA-H6 | mA*mA*mA*rGrArUrArArUrCrCrArArGrArUrGrGrUrUrArCr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6353 | MG3-6-B2M-sgRNA-A7 | mU*mA*mC*rCrArArGrArCrUrGrUrUrGrArGrGrArCrGrCrCr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6354 | MG3-6-B2M-sgRNA-B7 | mU*mC*mC*rArArArGrUrArArUrArCrArUrGrCrCrArUrGrCr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrUmU*mU*mU |
| 6355 | MG3-6-B2M-sgRNA-C7 | mA*mU*mU*rArCrUrUrUrGrGrArArArUrUrUrUrCrArArArAr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6356 | MG3-6-B2M-sgRNA-D7 | mA*mA*mA*rUrArArGrArUrUrUrUrUrUrUrUrArArArUrAr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |
| 6357 | MG3-6-B2M-sgRNA-E7 | mU*mG*mC*rCrArGrGrUrArCrUrUrArGrArArArGrUrGrCrUr<br>GrUrUrGrArGrArArUrCrGrArArArGrArUrUrCrUrUrArArUrAr<br>ArGrGrCrArUrCrCrUrUrCrCrGrArUrGrCrUrGrArCrUrUrCrUr<br>CrArCrCrGrUrCrCrGrUrUrUrUrCrCrArArUrArGrGrArGrCrGr<br>GrGrCrGrGrUrArUrGrU*mU*mU*mU |

TABLE 1A-continued

Guide sequences used in Example 7

| SEQ ID NO: | Entity Name | Sequence |
|---|---|---|
| 6358 | MG3-6-B2M-sgRNA-F7 | mC*mU*mC*rArArCrArGrUrCrUrUrGrGrUrArArCrCrArUrCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6359 | MG3-6-B2M-sgRNA-G7 | mU*mG*mA*rUrArCrUrUrGrUrCrCrUrCrUrUrCrUrUrArGrAr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6360 | MG3-6-B2M-sgRNA-H7 | mG*mC*mU*rUrUrUrArArUrGrUrUrArUrGrArArArArArArAr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6361 | MG3-6-B2M-sgRNA-A8 | mU*mA*mU*rGrArArArArArArArUrCrArGrGrUrCrUrUrCrAr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6362 | MG3-6-B2M-sgRNA-B8 | mG*mA*mU*rUrCrCrCrCrArArUrCrCrArCrCrUrCrUrUrGrAr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6363 | MG3-6-B2M-sgRNA-C8 | mG*mG*mC*rArGrCrUrArCrUrCrCrUrCrCrUrUrGrUrCrUrGr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrUxmU*mU*mU |
| 6364 | MG3-6-B2M-sgRNA-D8 | mG*mC*mU*rGrUrGrGrGrGrArGrArArGrGrArGrGrArGrUrAr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6365 | MG3-6-B2M-sgRNA-E8 | mU*mA*mG*rArArArCrArCrCrCrUrArUrCrArUrUrArArGrGr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrUxmU*mU*mU |
| 6366 | MG3-6-B2M-sgRNA-F8 | mA*mG*mG*rCrUrArCrUrArGrCrCrCrCrArUrCrArArGrArGr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6367 | MG3-6-B2M-sgRNA-G8 | mG*mA*mG*rGrUrGrGrArUrUrGrGrGrGrArArUrCrUrArArUr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6368 | MG3-6-B2M-sgRNA-H8 | mA*mU*mA*rArGrArArCrArUrArUrUrArArArUrGrCrCrUrCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 6369 | MG3-6-B2M-sgRNA-A9 | mU*mA*mA*rArUrGrCrCrUrCrArGrGrGrArUrCrArGrArGrCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrUxmU*mU*mU |

TABLE 1A-continued

Guide sequences used in Example 7

| SEQ ID NO: | Entity Name | Sequence |
|---|---|---|
| 6370 | MG3-6-B2M-sgRNA-B9 | mC*mU*mC*rUrCrUrGrUrUrGrArGrGrArArGrGrCrGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrUxmU*mU*mU |
| 6371 | MG3-6-B2M-sgRNA-C9 | mC*mU*mA*rArGrArArGrArGrGrArCrArArGrUrArUrCrArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6372 | MG3-6-B2M-sgRNA-D9 | mC*mA*mC*rCrUrArUrCrCrCrUrGrUrUrGrUrArUrUrUrUrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6373 | MG3-6-B2M-sgRNA-E9 | mA*mU*mU*rUrGrCrCrArGrCrUrCrUrGrUrArUrGrCrArUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6374 | MG3-6-B2M-sgRNA-F9 | mG*mA*mA*rArUrUrArGrGrUrArCrArArArGrUrCrArGrArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6375 | MG3-6-B2M-sgRNA-G9 | mU*mA*mU*rArArArArCrCrUrCrArGrCrArGrArArArUrArArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6376 | MG3-6-B2M-sgRNA-H9 | mU*mG*mU*rUrGrUrUrUrGrGrUrArArGrArArCrArUrArCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6377 | MG3-6-B2M-sgRNA-A10 | mA*mA*mC*rArArArArCrCrUrCrUrUrUrArUrUrUrCrUrGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6378 | MG3-6-B2M-sgRNA-B10 | mA*mU*mU*rUrCrUrGrCrUrGrArGrGrUrUrUrUrArUrArUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6379 | MG3-6-B2M-sgRNA-C10 | mG*mC*mA*rArArUrArCrCrUrUrArArArUrGrGrUrUrGrArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6380 | MG3-6-B2M-sgRNA-D10 | mA*mU*mA*rArArArUrArCrArArCrArGrGrGrArUrArGrGrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6381 | MG3-6-B2M-sgRNA-E10 | mA*mA*mU*rGrGrArGrUrArArUrGrCrArUrGrUrGrArCrArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6382 | MG3-6-B2M-sgRNA-F10 | mA*mC*mA*rGrGrUrGrArUrUrGrCrUrGrUrArArArCrUrArGrGrUrUrGrArGrArArUrCrGrArArArGrArUrUrCrUrUrArArUrAr |

TABLE 1A-continued

| Guide sequences used in Example 7 | | |
|---|---|---|
| SEQ ID NO: | Entity Name | Sequence |
| | | ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |
| 6383 | MG3-6-B2M-sgRNA-G10 | mC*mU*mU*rUrCrCrArArArArUrGrArGrArGrGrCrArUrGrAr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |
| 6384 | MG3-6-B2M-sgRNA-H10 | mA*mA*mU*rArUrUrGrCrCrArGrGrGrUrArUrUrUrCrArCrUr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |
| 6385 | MG3-6-B2M-sgRNA-A11 | mU*mG*mC*rCrUrUrUrUrUrGrUrUrUrUrUrUrUrCrUrAr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |
| 6386 | MG3-6-B2M-sgRNA-B11 | mU*mC*mU*rArGrCrArGrUrArUrCrUrUrCrUrGrUrCrArCrUr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |

Notations for chemical modifications: m = 2'O-methyl ribonucleotide (e.g mC = cytosine ribonucleotide with 2'-O Methyl in place of 2' hydroxyl); f = 2'-fluoro ribonucleotide (e.g fC = cytosine ribonucleotide with 2' fluorine in place of 2' hydroxyl); * = phosphorothioate bond; r: native RNA linkage comprising the sugar ribose (for example the ribose or RNA form of the A base is written rA), d: deoxyribose sugar (DNA) linkage (for example a deoxyribose form of the A base is written dA)

TABLE 1B

| Sites targeted in Example 7 | | |
|---|---|---|
| SEQ ID NO: | Entity Name | Sequence |
| 6387 | MG3-6-B2M-target site-A1 | CGCTACTCTCT CTTTCTGGCCT |
| 6388 | MG3-6-B2M-target site-B1 | AGAGACTCACG CTGGATAGCCT |
| 6389 | MG3-6-B2M-target site-C1 | GAGAGAGTAGC GCGAGCACAGC |
| 6390 | MG3-6-B2M-target site-D1 | CCCGATATTCC TCAGGTACTCC |
| 6391 | MG3-6-B2M-target site-E1 | ATTCCTCAGGT ACTCCAAAGAT |
| 6392 | MG3-6-B2M-target site-F1 | AATTTCCTGAA TTGCTATGTGT |
| 6393 | MG3-6-B2M-target site-G1 | GAGAATTGAAA AAGTGGAGCAT |
| 6394 | MG3-6-B2M-target site-H1 | GCATTCAGACT TGTCTTTCAGC |
| 6395 | MG3-6-B2M-target site-A2 | AGACTTACCCC ACTTAACTATC |
| 6396 | MG3-6-B2M-target site-B2 | TTCAGTGTAGT ACAAGAGATAG |
| 6397 | MG3-6-B2M-target site-C2 | AGTTCTCCTTG GTGGCCCGCCG |

TABLE 1B-continued

| Sites targeted in Example 7 | | |
|---|---|---|
| SEQ ID NO: | Entity Name | Sequence |
| 6398 | MG3-6-B2M-target site-D2 | GTGGCCCGCCG TGGGGCTAGTC |
| 6399 | MG3-6-B2M-target site-E2 | CCGCCGTGGGG CTAGTCCAGGG |
| 6400 | MG3-6-B2M-target site-F2 | GCCCCTTTCGG CGGGGAGCAGG |
| 6401 | MG3-6-B2M-target site-G2 | GACCTTTGGCC TACGGCGACGG |
| 6402 | MG3-6-B2M-target site-H2 | GCGTCGATAAG CGTCAGAGCGC |
| 6403 | MG3-6-B2M-target site-A3 | CGTCAGAGCGC CGAGGTTGGGG |
| 6404 | MG3-6-B2M-target site-B3 | GGGTTTCTCTT CCGCTCTTTCG |
| 6405 | MG3-6-B2M-target site-C3 | GCGCAGCTGGA GTGGGGGACGG |
| 6406 | MG3-6-B2M-target site-D3 | GCTCGTCCCAA AGGCGCGGCGC |
| 6407 | MG3-6-B2M-target site-E3 | TGTGAACGCGT GGAGGGGCGCT |

TABLE 1B-continued

Sites targeted in Example 7

| SEQ ID NO: | Entity Name | Sequence |
|---|---|---|
| 6408 | MG3-6-B2M-target site-F3 | GTCTGCTGCGG CTCTGCTTCCC |
| 6409 | MG3-6-B2M-target site-G3 | GCTTCCCTTAG ACTGGAGAGCT |
| 6410 | MG3-6-B2M-target site-H3 | AAGTTCGCATG TCCTAGCACCT |
| 6411 | MG3-6-B2M-target site-A4 | TCCTAGCACCT CTGGGTCTATG |
| 6412 | MG3-6-B2M-target site-B4 | CCTCCCCACGG TGTGGCCCCAC |
| 6413 | MG3-6-B2M-target site-C4 | AAGGGAAGCAG AGCCGCAGCAG |
| 6414 | MG3-6-B2M-target site-D4 | GCTTACCCGGG CGACGCCTCCC |
| 6415 | MG3-6-B2M-target site-E4 | CTCCAGCTGCG CTGGGGGAGCC |
| 6416 | MG3-6-B2M-target site-F4 | TTGTCCCGACC CTCCCGTCGCC |
| 6417 | MG3-6-B2M-target site-G4 | GACCCTCCCGT CGCCGTAGGCC |
| 6418 | MG3-6-B2M-target site-H4 | GTGCGCACCCC CTTCCCCACTC |
| 6419 | MG3-6-B2M-target site-A5 | CCAGGCCACCC CGCCGCTTCCC |
| 6420 | MG3-6-B2M-target site-B5 | GCCGCTTCCCC GAGATCCAGCC |
| 6421 | MG3-6-B2M-target site-C5 | CCAGCCCTGGA CTAGCCCCACG |
| 6422 | MG3-6-B2M-target site-D5 | TCACGGAGCGA GAGAGCACAGC |
| 6423 | MG3-6-B2M-target site-E5 | AGAGGGTGCAG AGCGGGAGAGG |
| 6424 | MG3-6-B2M-target site-F5 | AGGACCAGAGC GGGAGGGTAGG |
| 6425 | MG3-6-B2M-target site-G5 | CGAGATTGAAG TCAAGCCTAAC |
| 6426 | MG3-6-B2M-target site-H5 | AGAAAAACGCC TGCCTTCTGCG |
| 6427 | MG3-6-B2M-target site-A6 | TCTCCAGAGCA AACTGGGCGGC |
| 6428 | MG3-6-B2M-target site-B6 | GGCCCTGTGGT CTTTTCGTACA |
| 6429 | MG3-6-B2M-target site-C6 | ACTTTCGGTTT TGAAAACATGA |
| 6430 | MG3-6-B2M-target site-D6 | AAAGAGGAAGC CCTCTGTACGA |
| 6431 | MG3-6-B2M-target site-E6 | AGCCCTCTGTA CGAAAAGACCA |
| 6432 | MG3-6-B2M-target site-F6 | TGCGCTCCCGC AAAAGCCCTGG |

TABLE 1B-continued

Sites targeted in Example 7

| SEQ ID NO: | Entity Name | Sequence |
|---|---|---|
| 6433 | MG3-6-B2M-target site-G6 | AAAAGAAAAGA AAGAAAGAAGT |
| 6434 | MG3-6-B2M-target site-H6 | AAAGATAATCC AAGATGGTTAC |
| 6435 | MG3-6-B2M-target site-A7 | TACCAAGACTG TTGAGGACGCC |
| 6436 | MG3-6-B2M-target site-B7 | TCCAAAGTAAT ACATGCCATGC |
| 6437 | MG3-6-B2M-target site-C7 | ATTACTTTGGA AATTTTCAAAA |
| 6438 | MG3-6-B2M-target site-D7 | AAATAAGATTT TTTTTTAAATA |
| 6439 | MG3-6-B2M-target site-E7 | TGCCAGGTACT TAGAAAGTGCT |
| 6440 | MG3-6-B2M-target site-F7 | CTCAACAGTCT TGGTAACCATC |
| 6441 | MG3-6-B2M-target site-G7 | TGATACTTGTC CTCTTCTTAGA |
| 6442 | MG3-6-B2M-target site-H7 | GCTTTTAATGT TATGAAAAAAA |
| 6443 | MG3-6-B2M-target site-A8 | TATGAAAAAAA TCAGGTCTTCA |
| 6444 | MG3-6-B2M-target site-B8 | GATTCCCCAAT CCACCTCTTGA |
| 6445 | MG3-6-B2M-target site-C8 | GGCAGCTACTC CTCCTTGTCTG |
| 6446 | MG3-6-B2M-target site-D8 | GCTGTGGGGAG AAGGAGGAGTA |
| 6447 | MG3-6-B2M-target site-E8 | TAGAAACACCC TATCATTAAGG |
| 6448 | MG3-6-B2M-target site-F8 | AGGCTACTAGC CCCATCAAGAG |
| 6449 | MG3-6-B2M-target site-G8 | GAGGTGGATTG GGGAATCTAAT |
| 6450 | MG3-6-B2M-target site-H8 | ATAAGAACATA TTAAATGCCTC |
| 6451 | MG3-6-B2M-target site-A9 | TAAATGCCTCA GGGATCAGAGC |
| 6452 | MG3-6-B2M-target site-B9 | CTCTCTGTTTG AGGGAAGGCGG |
| 6453 | MG3-6-B2M-target site-C9 | CTAAGAAGAGG ACAAGTATCAG |
| 6454 | MG3-6-B2M-target site-D9 | CACCTATCCCT GTTGTATTTTA |
| 6455 | MG3-6-B2M-target site-E9 | ATTTGCCAGCT CTTGTATGCAT |
| 6456 | MG3-6-B2M-target site-F9 | GAAATTAGGTA CAAAGTCAGAG |

TABLE 1B-continued

Sites targeted in Example 7

| SEQ ID NO: | Entity Name | Sequence |
|---|---|---|
| 6457 | MG3-6-B2M-target site-G9 | TATAAAACCTC AGCAGAAATAA |
| 6458 | MG3-6-B2M-target site-H9 | TGTTGTTTGGT AAGAACATACC |
| 6459 | MG3-6-B2M-target site-A10 | AACAAAACCTC TTTATTTCTGC |
| 6460 | MG3-6-B2M-target site-B10 | ATTTCTGCTGA GGTTTTATATG |
| 6461 | MG3-6-B2M-target site-C10 | GCAAATACCTT AAATGGTTGAG |
| 6462 | MG3-6-B2M-target site-D10 | ATAAAATACAA CAGGGATAGGT |
| 6463 | MG3-6-B2M-target site-E10 | AATGGAGTAAT GCATGTGACAG |
| 6464 | MG3-6-B2M-target site-F10 | ACAGGTGATTG CTGTAAACTAG |
| 6465 | MG3-6-B2M-target site-G10 | CTTTCCAAAAT GAGAGGCATGA |
| 6466 | MG3-6-B2M-target site-H10 | AATATTGCCAG GGTATTTCACT |
| 6467 | MG3-6-B2M-target site-A11 | TGCCTTTTTTG TTTTTTTTCTA |
| 6468 | MG3-6-B2M-target site-B11 | TCTAGCAGTAT CTTCTGTCACT |

Example 8—Gene Editing Outcomes at the DNA Level for Mouse TRAC

Figure 2A:
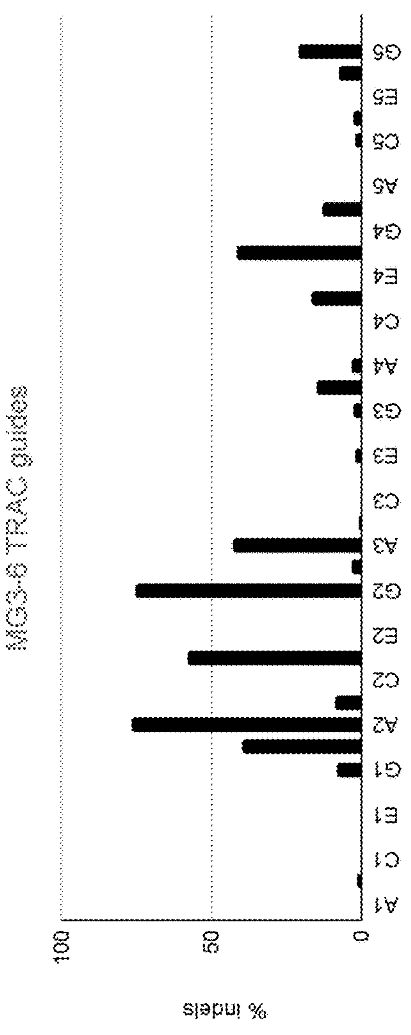
FIG. 2A and FIG. 2B depicts the gene editing outcomes at the DNA level for mouse TRAC.
Figure 2B:
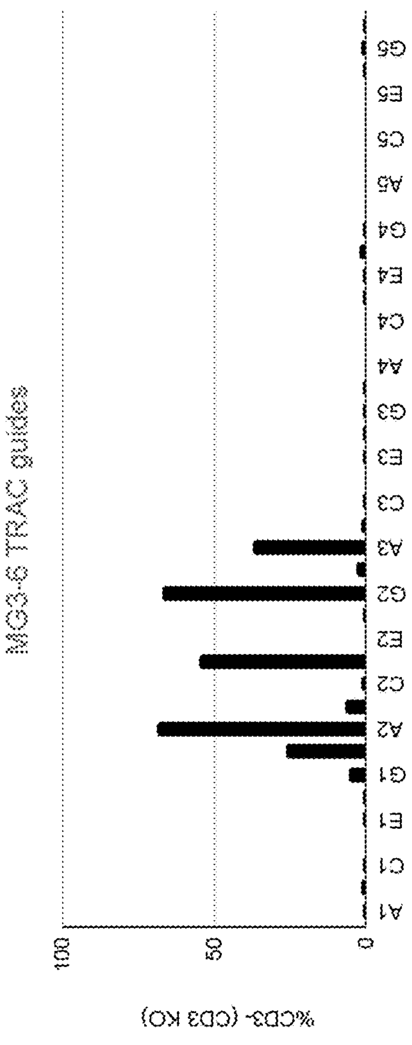

Primary T cells were purified from C57BL/6 mouse spleens. Nucleofection of MG3-6 RNPs (126 pmol protein/160 pmol guide) (SEQ ID NOs: 6469-6508) was performed into T cells (200,000) using the Lonza 4D electroporator and 100 pmol transfection enhancer (IDT). Cells were harvested and genomic DNA prepared five days post-transfection. PCR primers appropriate for use in NGS-based DNA sequencing were generated, optimized, and used to amplify the individual target sequences for each guide RNA (SEQ ID NOs: 6509-6548). The amplicons were sequenced on an Illumina MiSeq machine and analyzed with a proprietary Python script to measure gene editing (FIG. 2). For analysis by flow cytometry, 3 days post-nucleofection, 100,000 mouse T cells were stained with anti-mouse CD3 antibody (Clone 17A2, Invitrogen 11-0032-82) for 30 minutes at 4° C. and analyzed on an Attune Nxt flow cytometer.

TABLE 2A

Guide sequences used in Example 8

| SEQ ID NO: | Entity Name | Sequence |
|---|---|---|
| 6469 | MG3-6-mTRAC-sgRNA-A1 | mA*mG*mA*rArCrCrUrGrCrUrGrUrGrUrArCrCrArGrUrUrArGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6470 | MG3-6-mTRAC-sgRNA-B1 | mA*mA*mC*rUrGrUrGrCrUrGrGrArCrArUrGrArArArGrCrUrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6471 | MG3-6-m TRAC-sgRNA-C1 | mA*mA*mG*rCrUrArUrGrGrArUrUrCrCrArArGrArGrCrArArGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6472 | MG3-6-m TRAC-sgRNA-D1 | mUmC*mA*rCrCrUrGrCrCrArArGrArUrArUrCrUrUrCrArArGrU rUrGrArGrArArUrCrGrArArArGrArUrUrCrUrUrArArUrArArGrG rCrArUrCrCrUrUrCrCrGrArUrGrCrUrGrArCrUrUrCrUrCrArCrC rGrUrCrCrGrUrUrUrUrCrCrArArUrArGrGrArGrCrGrGrGrCrGr GrUrArUrGrU*mU*mU*mU |
| 6473 | MG3-6-mTRAC-sgRNA-E1 | mA*mG*mU*rUrUrUrGrUrCrArGrUrGrArUrGrArArCrGrUrUrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6474 | MG3-6-mTRAC-sgRNA-F1 | mG*mA*mA*rCrArGrGrCrArGrArGrGrGrUrGrCrUrGrUrCrCrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr |

TABLE 2A-continued

| Guide sequences used in Example 8 | | |
|---|---|---|
| SEQ ID NO: | Entity Name | Sequence |
| | | CrGrUrCrCrGrUrUrUrUrCrCrArArUrArGrGrArGrCrGrGrGrCrGr<br>GrUrArUrGrU*mU*mU*mU |
| 6475 | MG3-6-mTRAC-sgRNA-G1 | mC*mA*mG*rArGrGrGrUrGrCrUrGrUrCrCrUrGrArGrArCrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6476 | MG3-6-mTRAC-sgRNA-H1 | mA*mG*mG*rArUrCrUrUrUrUrArArCrUrGrGrUrArCrArCrArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6477 | MG3-6-mTRAC-sgRNA-A2 | mUmU*mU*rArArCrUrGrGrUrArCrArCrArGrCrArGrGrUrUrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6478 | MG3-6-mTRAC-sgRNA-B2 | mA*mG*mG*rUrUrCrUrGrGrGrUrUrCrUrGrGrArUrGrUrCrUrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6479 | MG3-6-mTRAC-sgRNA-C2 | mA*mA*mC*rUrUrUrCrArArArArCrCrUrGrUrCrArGrUrUrArGrU<br>rUrGrArGrArArUrCrGrArArArGrArUrUrCrUrUrArArUrArArGrG<br>rCrArUrCrCrUrUrCrCrGrArUrGrCrUrGrArCrUrUrCrUrCrArCrC<br>rGrUrCrCrGrUrUrUrUrCrCrArArUrArGrGrArGrCrGrGrGrCrGr<br>GrUrArUrGrU*mU*mU*mU |
| 6480 | MG3-6-mTRAC-sgRNA-D2 | mC*mG*mA*rArUrCrCrUrCrCrUrGrCrUrGrArArArGrUrArGrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6481 | MG3-6-mTRAC-sgRNA-E2 | mG*mG*mA*rUrUrUrArArCrCrUrGrCrUrCrArUrGrArCrGrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6482 | MG3-6-mTRAC-sgRNA-F2 | mC*mU*mU*rUrCrArUrGrCrCrUrUrCrUrUrArCrCrUrCrArArGrU<br>rUrGrArGrArArUrCrGrArArArGrArUrUrCrUrUrArArUrArArGrG<br>rCrArUrCrCrUrUrCrCrGrArUrGrCrUrGrArCrUrUrCrUrCrArCrC<br>rGrUrCrCrGrUrUrUrUrCrCrArArUrArGrGrArGrCrGrGrGrCrGr<br>GrUrArUrGrU*mU*mU*mU |
| 6483 | MG3-6-mTRAC-sgRNA-G2 | mG*mA*mC*rCrArCrArGrCrCrUrCrArGrCrGrUrCrArUrGrArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6484 | MG3-6-m TRAC-sgRNA-H2 | mU*mA*mA*rArUrCrCrGrGrCrUrArCrUrUrUrCrArGrCrArGrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6485 | MG3-6-mTRAC-sgRNA-A3 | mA*mG*mG*rArUrUrCrGrGrArGrUrCrCrCrArUrArArCrUrGrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6486 | MG3-6-mTRAC-sgRNA-B3 | mA*mU*mA*rArCrUrGrArCrArGrGrUrUrUrUrGrArArArGrUrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |

TABLE 2A-continued

Guide sequences used in Example 8

| SEQ ID NO: | Entity Name | Sequence |
|---|---|---|
| 6487 | MG3-6-m TRAC-sgRNA-C3 | mG*mU*mA*rCrUrUrCrCrUrCrArCrUrCrCrArGrGrUrCrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6488 | MG3-6-mTRAC-sgRNA-D3 | mC*mC*mA*rCrCrUrCrGrUrCrArArGrArCrGrGrCrUrGrUrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6489 | MG3-6-mTRAC-sgRNA-E3 | mU*mG*mG*rCrCrCrUrGrArUrUrCrArCrArArUrCrCrCrArCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6490 | MG3-6-mTRAC-sgRNA-F3 | mU*mU*mC*rArCrArArUrCrCrCrArCrCrUrGrGrArUrCrUrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6491 | MG3-6-mTRAC-sgRNA-G3 | mC*mU*mG*rGrArUrCrUrCrCrCrArGrArUrUrUrGrUrGrArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrUmU*mU*mU |
| 6492 | MG3-6-mTRAC-sgRNA-H3 | mC*mA*mU*rUrCrArCrArArArArArArCrGrGrCrArGrGrGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6493 | MG3-6-m TRAC-sgRNA-A4 | mA*mA*mC*rGrGrCrArGrGrGrGrCrGrGrGrGrCrUrUrCrUrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6494 | MG3-6-mTRAC-sgRNA-B4 | mG*mG*mG*rCrGrGrGrGrCrUrUrCrUrCrCrUrGrGrArUrCrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6495 | MG3-6-mTRAC-sgRNA-C4 | mA*mU*mC*rUrGrArArGrArCrCrCrCrUrCrCrCrCrCrArUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6496 | MG3-6-mTRAC-sgRNA-D4 | mG*mU*mU*rUrUrUrUrGrUrUrUrUrUrUrUrUrUrUrUrUrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6497 | MG3-6-mTRAC-sgRNA-E4 | mG*mG*mU*rGrUrArGrArArArUrUrArUrCrUrCrArUrUrGrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 6498 | MG3-6-mTRAC-sgRNA-F4 | mG*mG*mC*rUrCrArArUrArCrArCrArCrArGrUrArGrCrArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |

TABLE 2A-continued

| Guide sequences used in Example 8 | | |
|---|---|---|
| SEQ ID NO: | Entity Name | Sequence |
| 6499 | MG3-6-mTRAC-sgRNA-G4 | mA*mU*mU*rUrUrUrUrUrUrArCrArArCrArUrUrCrUrCrCrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6500 | MG3-6-m TRAC-sgRNA-H4 | mA*mC*mA*rGrGrGrGrArGrUrCrUrGrCrCrArUrGrGrGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6501 | MG3-6-m TRAC-sgRNA-A5 | mG*mU*mC*rUrGrCrCrArUrGrGrGrGrArGrGrGrUrCrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrUxmU*mU*mU |
| 6502 | MG3-6-mTRAC-sgRNA-B5 | mA*mG*mC*rArArCrCrUrUrCrCrUrCrArCrArArArUrCrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6503 | MG3-6-mTRAC-sgRNA-C5 | mU*mC*mA*rCrArArArUrCrUrGrGrGrArGrArUrCrCrArGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6504 | MG3-6-mTRAC-sgRNA-D5 | mA*mG*mA*rUrCrCrArGrGrUrGrGrGrArUrUrGrUrGrArArUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6505 | MG3-6-mTRAC-sgRNA-E5 | mU*mG*mG*rGrArUrUrGrUrGrArArUrCrArGrGrGrCrCrArArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6506 | MG3-6-mTRAC-sgRNA-F5 | mG*mA*mC*rArGrCrCrGrUrCrUrUrGrArCrGrArGrGrUrGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6507 | MG3-6-mTRAC-sgRNA-G5 | mU*mG*mA*rGrGrArGrGrArUrGrGrArGrCrUrUrGrGrGrArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6508 | MG3-6-mTRAC-sgRNA-H5 | mG*mG*mA*rGrUrCrArGrGrCrUrCrUrGrUrCrArGrUrCrUrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |

Notations for chemical modifications: m = 2'O-methyl ribonucleotide (e.g mC = cytosine ribonucleotide with 2'-O Methyl in place of 2' hydroxyl); f = 2'-fluoro ribonucleotide (e.g fC = cytosine ribonucleotide with 2' fluorine in place of 2' hydroxyl); * = phosphorothioate bond; r: native RNA linkage comprising the sugar ribose (for example the ribose or RNA form of the A base is written rA), d: deoxyribose sugar (DNA) linkage (for example a deoxyribose form of the A base is written dA)

TABLE 2B

List of sites targeted in Example 8

| SEQ ID NO: | Entity Name | Sequence |
|---|---|---|
| 6509 | MG3-6-mTRAC-target site-A1 | AGAACCTGCTGTGTACCAGTTA |
| 6510 | MG3-6-mTRAC-target site-B1 | AACTGTGCTGGACATGAAAGCT |
| 6511 | MG3-6-mTRAC-target site-C1 | AAGCTATGGATTCCAAGAGCAA |
| 6512 | MG3-6-mTRAC-target site-D1 | TCACCTGCCAAGATATCTTCAA |
| 6513 | MG3-6-mTRAC-target site-E1 | AGTTTTGTCAGTGATGAACGTT |
| 6514 | MG3-6-mTRAC-target site-F1 | GAACAGGCAGAGGGTGCTGTCC |
| 6515 | MG3-6-mTRAC-target site-G1 | CAGAGGGTGCTGTCCTGAGACC |
| 6516 | MG3-6-mTRAC-target site-H1 | AGGATCTTTTAACTGGTACACA |
| 6517 | MG3-6-mTRAC-target site-A2 | TTTAACTGGTACACAGCAGGTT |
| 6518 | MG3-6-mTRAC-target site-B2 | AGGTTCTGGGTTCTGGATGTCT |
| 6519 | MG3-6-mTRAC-target site-C2 | AACTTTCAAAACCTGTCAGTTA |
| 6520 | MG3-6-mTRAC-target site-D2 | CGAATCCTCCTGCTGAAAGTAG |
| 6521 | MG3-6-mTRAC-target site-E2 | GGATTTAACCTGCTCATGACGC |
| 6522 | MG3-6-mTRAC-target site-F2 | CTTTCATGCCTTCTTACCTCAA |
| 6523 | MG3-6-mTRAC-target site-G2 | GACCACAGCCTCAGCGTCATGA |
| 6524 | MG3-6-mTRAC-target site-H2 | TAAATCCGGCTACTTTCAGCAG |
| 6525 | MG3-6-mTRAC-target site-A3 | AGGATTCGGAGTCCCATAACTG |
| 6526 | MG3-6-mTRAC-target site-B3 | ATAACTGACAGGTTTTGAAAGT |
| 6527 | MG3-6-mTRAC-target site-C3 | GTACTTCCTCACTCCAGGTCTG |
| 6528 | MG3-6-mTRAC-target site-D3 | CCACCTCGTCAAGACGGCTGTC |
| 6529 | MG3-6-mTRAC-target site-E3 | TGGCCCTGATTCACAATCCCAC |
| 6530 | MG3-6-mTRAC-target site-F3 | TTCACAATCCCACCTGGATCTC |
| 6531 | MG3-6-mTRAC-target site-G3 | CTGGATCTCCCAGATTTGTGAG |
| 6532 | MG3-6-mTRAC-target site-H3 | CATTCACAAAAAACGGCAGGGG |
| 6533 | MG3-6-mTRAC-target site-A4 | AACGGCAGGGGCGGGGCTTCTC |

TABLE 2B-continued

| List of sites targeted in Example 8 | | |
|---|---|---|
| SEQ ID NO: | Entity Name | Sequence |
| 6534 | MG3-6-mTRAC-target site-B4 | GGGCGGGGCTTCTCCTGGATCT |
| 6535 | MG3-6-mTRAC-target site-C4 | ATCTGAAGACCCCTCCCCCATG |
| 6536 | MG3-6-mTRAC-target site-D4 | GTTTTTTGTTTTTTTTTTTTTT |
| 6537 | MG3-6-mTRAC-target site-E4 | GGTGTAGAAATTATCTCATTGT |
| 6538 | MG3-6-mTRAC-target site-F4 | GGCTCAATACACACAGTAGCAG |
| 6539 | MG3-6-mTRAC-target site-G4 | ATTTTTTTTACAACATTCTCCA |
| 6540 | MG3-6-mTRAC-target site-H4 | ACAGGGGAGTCTGCCATGGGGG |
| 6541 | MG3-6-mTRAC-target site-A5 | GTCTGCCATGGGGGAGGGGTCT |
| 6542 | MG3-6-mTRAC-target site-B5 | AGCAACCTTCCTCACAAATCTG |
| 6543 | MG3-6-mTRAC-target site-C5 | TCACAAATCTGGGAGATCCAGG |
| 6544 | MG3-6-mTRAC-target site-D5 | AGATCCAGGTGGGATTGTGAAT |
| 6545 | MG3-6-mTRAC-target site-E5 | TGGGATTGTGAATCAGGGCCAA |
| 6546 | MG3-6-mTRAC-target site-F5 | GACAGCCGTCTTGACGAGGTGG |
| 6547 | MG3-6-mTRAC-target site-G5 | TGAGGAGGATGGAGCTTGGGAG |
| 6548 | MG3-6-mTRAC-target site-H5 | GGAGTCAGGCTCTGTCAGTCTT |

Example 9—Gene Editing Outcomes at the DNA Level for HPRT

Figure 3:
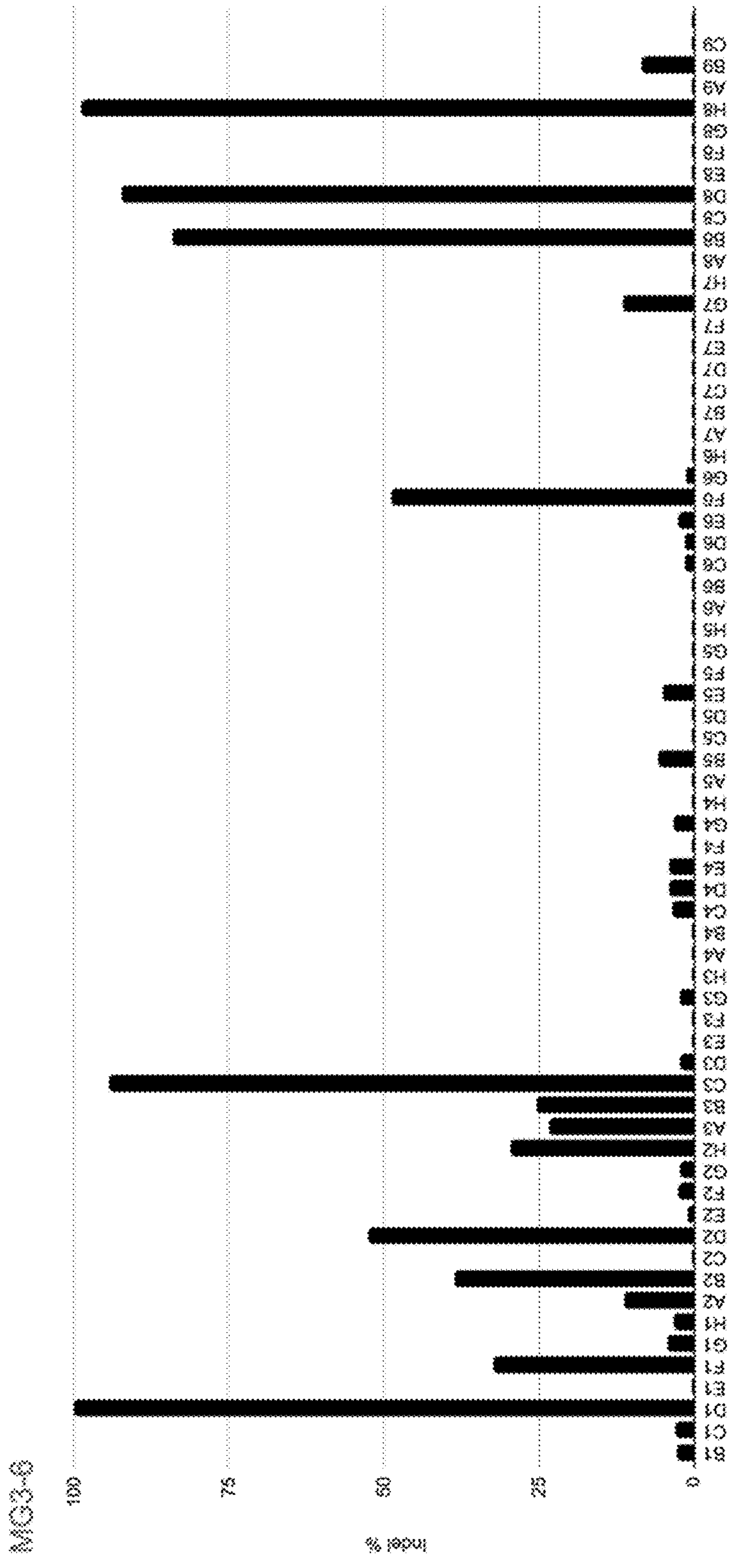
FIG. 3 depicts the gene editing outcomes at the DNA level for HPRT.

Primary T cells were purified from PBMCs using a negative selection kit (Miltenyi) according to the manufacturer's recommendations. Nucleofection of MG3-6 RNPs (126 pmol protein/160 pmol guide) (SEQ ID NOs: 6549-6615) was performed into T cells (200,000) using the Lonza 4D electroporator. Cells were harvested and genomic DNA prepared five days post-transfection. PCR primers appropriate for use in NGS-based DNA sequencing were generated, optimized, and used to amplify the individual target sequences for each guide RNA (SEQ ID NOs: 6616-6682). The amplicons were sequenced on an Illumina MiSeq machine and analyzed with a proprietary Python script to measure gene editing (FIG. 3).

TABLE 3A

| Guide sequences used in Example 9 | | |
|---|---|---|
| SEQ ID NO: | Entity Name | Sequence |
| 6549 | MG3-6-HPRT-sgRNA-A1 | mU*mU*mC*rCrUrCrUrGrCrArUrCrArGrUrUrUrArArUrGrGr UrUrGrArGrArArUrCrGrArArArGrArUrUrCrUrArArUrArArGr GrCrArUrCrCrUrUrCrCrGrArUrGrCrUrGrArCrUrUrCrUrCrArCr CrGrUrCrCrGrUrUrUrCrCrArArUrArGrGrArGrCrGrGrGrCrGr GrUrArUrGrU*mU*mU*mU |

TABLE 3A-continued

| SEQ ID NO: | Entity Name | Sequence |
|---|---|---|
| | Guide sequences used in Example 9 | |
| 6550 | MG3-6-HPRT-sgRNA-B1 | mG*mU*mG*rGrGrCrUrUrGrUrGrUrUrCrUrArArArGrGrArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrUxmU*mU*mU |
| 6551 | MG3-6-HPRT-sgRNA-C1 | mA*mG*mG*rArGrUrGrArGrArUrUrGrGrUrUrUrUrUrUrGrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6552 | MG3-6-HPRT-sgRNA-D1 | mU*mA*mA*rArArArArUrArArUrArUrUrUrArUrArArUrUrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6553 | MG3-6-HPRT-sgRNA-E1 | mG*mA*mG*rUrArUrUrUrUrUrArUrUrGrArArArArGrCrArUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6554 | MG3-6-HPRT-sgRNA-F1 | mA*mA*mA*rArArUrArUrUrUrUrCrCrCrUrArArCrArArArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6555 | MG3-6-HPRT-sgRNA-G1 | mA*mU*mC*rUrCrArGrCrUrArUrUrUrArGrUrCrArArArArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6556 | MG3-6-HPRT-sgRNA-H1 | mG*mUmC*rCrUrArCrUrUrUrUrGrArCrUrArArArUrArGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6557 | MG3-6-HPRT-sgRNA-A2 | mA*mA*mC*rUrCrUrCrCrArArUrArUrArGrGrUrGrGrCrUrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6558 | MG3-6-HPRT-sgRNA-B2 | mA*mU*mU*rUrUrUrCrCrCrArUrArArArUrUrCrArArGrArUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6559 | MG3-6-HPRT-sgRNA-C2 | mC*mC*mA*rGrGrArCrUrGrGrArUrUrUrUrGrUrArGrGrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6560 | MG3-6-HPRT-sgRNA-D2 | mU*mG*mC*rArCrCrUrArCrArArArArUrCrCrArGrUrCrCrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrUxmU*mU*mU |
| 6561 | MG3-6-HPRT-sgRNA-E2 | mG*mU*mA*rArGrArArUrGrCrCrArGrCrCrCrCrCrArGrGrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrUxmU*mU*mU |

TABLE 3A-continued

Guide sequences used in Example 9

| SEQ ID NO: | Entity Name | Sequence |
|---|---|---|
| 6562 | MG3-6-HPRT-sgRNA-F2 | mA*mA*mG*rCrArGrUrArArGrArArUrGrCrCrArGrCrCrCrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6563 | MG3-6-HPRT-sgRNA-G2 | mG*mC*mU*rGrGrCrArUrUrCrUrUrArCrUrGrCrUrUrGrCrUrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6564 | MG3-6-HPRT-sgRNA-H2 | mU*mG*mC*rUrUrGrCrUrGrArGrGrGrCrCrArGrArUrGrArUrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6565 | MG3-6-HPRT-sgRNA-A3 | mA*mU*mA*rGrArUrUrCrCrArGrArArUrArUrCrUrCrCrArUrGrU<br>rUrGrArGrArArUrCrGrArArArGrArUrUrCrUrUrArArUrArArGrG<br>rCrArUrCrCrUrUrCrCrGrArUrGrCrUrGrArCrUrUrCrUrCrArCrC<br>rGrUrCrCrGrUrUrUrUrCrCrArArUrArGrGrArGrCrGrGrGrCrGr<br>GrUrArUrGrU*mU*mU*mU |
| 6566 | MG3-6-HPRT-sgRNA-B3 | mU*mG*mA*rCrArGrUrArUrUrGrCrArGrUrUrArUrArCrArUrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6567 | MG3-6-HPRT-sgRNA-C3 | mC*mG*mA*rArArArGrUrArArUrGrUrArArUrCrUrCrArUrArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6568 | MG3-6-HPRT-sgRNA-D3 | mG*mG*mA*rUrUrArUrArUrCrUrUrArArGrUrCrUrUrArUrArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6569 | MG3-6-HPRT-sgRNA-E3 | mA*mA*mC*rArCrArUrGrArCrArArArArUrUrArUrUrUrArArGrU<br>rUrGrArGrArArUrCrGrArArArGrArUrUrCrUrUrArArUrArArGrG<br>rCrArUrCrCrUrUrCrCrGrArUrGrCrUrGrArCrUrUrCrUrCrArCrC<br>rGrUrCrCrGrUrUrUrUrCrCrArArUrArGrGrArGrCrGrGrGrCrGr<br>GrUrArUrGrU*mU*mU*mU |
| 6570 | MG3-6-HPRT-sgRNA-F3 | mG*mU*mU*rUrGrUrCrCrUrGrArArUrArGrCrArUrGrGrCrArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6571 | MG3-6-HPRT-sgRNA-G3 | mC*mUmG*rArArUrArGrCrArUrGrGrCrArGrArGrGrArUrUrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6572 | MG3-6-HPRT-sgRNA-H3 | mA*mU*mC*rCrUrUrArUrUrCrUrUrArArUrUrUrUrGrCrArArGrU<br>rUrGrArGrArArUrCrGrArArArGrArUrUrCrUrUrArArUrArArGrG<br>rCrArUrCrCrUrUrCrCrGrArUrGrCrUrGrArCrUrUrCrUrCrArCrC<br>rGrUrCrCrGrUrUrUrUrCrCrArArUrArGrGrArGrCrGrGrGrCrGr<br>GrUrArUrGrU*mU*mU*mU |
| 6573 | MG3-6-HPRT-sgRNA-A4 | mG*mC*mC*rCrCrCrUrUrGrCrArArArArUrUrArArGrArArUrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6574 | MG3-6-HPRT-sgRNA-B4 | mG*mG*mU*rGrArGrGrArArGrUrGrArUrArGrGrArArGrGrGrGr<br>UrUrGrArGrArArUrCrGrArArArGrArUrUrCrUrUrArArUrArArGr |

TABLE 3A-continued

Guide sequences used in Example 9

| SEQ ID NO: | Entity Name | Sequence |
|---|---|---|
| | | GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6575 | MG3-6-HPRT-sgRNA-C4 | mG*mU*mG*rArUrArGrGrArArGrGrGrGrUrGrGrGrCrCrCrUrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6576 | MG3-6-HPRT-sgRNA-D4 | mG*mG*mA*rArGrGrGrGrUrGrGrGrCrCrCrUrGrArArGrArUrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6577 | MG3-6-HPRT-sgRNA-E4 | mA*mA*mU*rUrCrCrArGrGrArGrGrUrCrCrArGrArUrCrUrUrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6578 | MG3-6-HPRT-sgRNA-F4 | mU*mC*mA*rUrCrArCrUrCrArArUrUrCrCrArGrGrArGrGrUrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6579 | MG3-6-HPRT-sgRNA-G4 | mC*mA*mG*rCrArUrUrCrArUrCrArCrUrCrArArUrUrCrCrArGrU rUrGrArGrArArUrCrGrArArArGrArUrUrCrUrUrArArUrArArGrG rCrArUrCrCrUrUrCrCrGrArUrGrCrUrGrArCrUrUrCrUrCrArCrC rGrUrCrCrGrUrUrUrUrCrCrArArUrArGrGrArGrCrGrGrGrCrGr GrUrArUrGrU*mU*mU*mU |
| 6580 | MG3-6-HPRT-sgRNA-H4 | mC*mA*mG*rCrArUrArGrGrUrArArGrGrUrGrArGrGrArGrGrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6581 | MG3-6-HPRT-sgRNA-A5 | mA*mC*mA*rUrArArArArArCrUrGrCrArGrArCrUrGrArUrCrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6582 | MG3-6-HPRT-sgRNA-B5 | mA*mC*mC*rUrGrArCrCrCrCrUrArCrArUrArArArArArCrUrGrU rUrGrArGrArArUrCrGrArArArGrArUrUrCrUrUrArArUrArArGrG rCrArUrCrCrUrUrCrCrGrArUrGrCrUrGrArCrUrUrCrUrCrArCrC rGrUrCrCrGrUrUrUrUrCrCrArArUrArGrGrArGrCrGrGrGrCrGr GrUrArUrGrU*mU*mU*mU |
| 6583 | MG3-6-HPRT-sgRNA-C5 | mG*mA*mU*rCrArGrUrCrUrGrCrArGrUrUrUrUrUrArUrGrUrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrUxmU*mUmU |
| 6584 | MG3-6-HPRT-sgRNA-D5 | mU*mC*mU*rGrCrUrUrUrUrUrCrCrUrArArGrUrGrArUrUrArGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6585 | MG3-6-HPRT-sgRNA-E5 | mA*mC*mA*rGrArUrArCrCrGrUrGrArUrUrUrUrUrUrCrArArGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |

TABLE 3A-continued

| Guide sequences used in Example 9 | | |
|---|---|---|
| SEQ ID NO: | Entity Name | Sequence |
| 6586 | MG3-6-HPRT-sgRNA-F5 | mA*mC*mU*rGrCrUrGrArCrArUrArUrGrArCrUrCrArCrUrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrUxmU*mU*mU |
| 6587 | MG3-6-HPRT-sgRNA-G5 | mC*mA*mU*rArUrGrUrCrArGrCrArGrUrUrUrGrArCrUrGrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6588 | MG3-6-HPRT-sgRNA-H5 | mU*mA*mU*rCrArGrUrGrArGrUrUrUrUrCrUrUrUrArArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6589 | MG3-6-HPRT-sgRNA-A6 | mG*mC*mU*rUrArUrUrUrUrCrUrArCrArUrGrCrUrCrUrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6590 | MG3-6-HPRT-sgRNA-B6 | mU*mU*mA*rArArUrGrUrCrArArCrCrUrArCrUrGrUrGrGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mUxmU*mU |
| 6591 | MG3-6-HPRT-sgRNA-C6 | mG*mA*mG*rGrArUrUrArArArGrUrCrUrArUrGrCrCrArCrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6592 | MG3-6-HPRT-sgRNA-D6 | mA*mA*mG*rArArCrArArCrArArArArGrArArUrArCrCrCrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6593 | MG3-6-HPRT-sgRNA-E6 | mU*mG*mG*rUrArUrArUrGrCrUrGrUrGrGrArArUrUrGrArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6594 | MG3-6-HPRT-sgRNA-F6 | mG*mA*mG*rArUrArGrArCrUrGrGrUrUrCrGrUrGrArGrCrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrUxmU*mU*mU |
| 6595 | MG3-6-HPRT-sgRNA-G6 | mG*mU*mA*rGrGrArCrArUrGrCrUrCrArArArCrArArUrArCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6596 | MG3-6-HPRT-sgRNA-H6 | mA*mU*mU*rArArGrCrArGrCrUrGrCrUrCrArCrUrArCrArArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6597 | MG3-6-HPRT-sgRNA-A7 | mG*mA*mG*rArUrGrGrArGrCrUrUrUrArUrUrArArArCrArUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6598 | MG3-6-HPRT-sgRNA-B7 | mG*mA*mA*rCrUrCrArGrCrArCrUrUrCrArUrArUrGrCrCrUrGrUrUrGrArGrArArUrCrGrArArArGrArUrUrCrUrUrArArUrArArGr |

TABLE 3A-continued

| Guide sequences used in Example 9 | | |
|---|---|---|
| SEQ ID NO: | Entity Name | Sequence |
| | | GrCrArUrCrCrUrUrCrCrGrArUrGrCrUrGrArCrUrUrCrUrCrArCr CrGrUrCrCrGrUrUrUrCrCrArArUrArGrGrArGrCrGrGrGrCrGr GrUrArUrGrU*mU*mU*mU |
| 6599 | MG3-6-HPRT-sgRNA-C7 | mU*mG*mA*rGrUrUrCrUrCrUrUrGrArArCrUrCrCrUrArArUrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrCrCrArArUrArGrGrArGrCrGrGrGrCrGr GrUrArUrGrU*mU*mU*mU |
| 6600 | MG3-6-HPRT-sgRNA-D7 | mA*mU*mU*rCrCrUrGrArGrUrUrCrArGrGrUrArGrGrGrArGrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrCrCrArArUrArGrGrArGrCrGrGrGrCrGr GrUrArUrGrU*mU*mU*mU |
| 6601 | MG3-6-HPRT-sgRNA-E7 | mU*mA*mU*rArUrArUrGrUrUrUrArArArGrArGrCrUrGrGrArGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrCrCrArArUrArGrGrArGrCrGrGrGrCrGr GrUrArUrGrU*mU*mU*mU |
| 6602 | MG3-6-HPRT-sgRNA-F7 | mG*mG*mU*rArUrGrArArArGrCrArUrArArGrUrUrUrCrUrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrCrCrArArUrArGrGrArGrCrGrGrGrCrGr GrUrArUrGrU*mU*mU*mU |
| 6603 | MG3-6-HPRT-sgRNA-G7 | mU*mG*mA*rGrArCrUrGrCrCrUrUrUrArArCrArUrCrUrGrUrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrCrCrArArUrArGrGrArGrCrGrGrGrCrGr GrUrArUrGrU*mU*mU*mU |
| 6604 | MG3-6-HPRT-sgRNA-H7 | mA*mA*mU*rArUrUrUrUrUrCrArArCrArGrGrCrArGrCrArUrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrCrCrArArUrArGrGrArGrCrGrGrGrCrGr GrUrArUrGrU*mU*mU*mU |
| 6605 | MG3-6-HPRT-sgRNA-A8 | mC*mU*mC*rCrCrArCrArCrCrCrUrUrUrArUrArGrUrUrUrGrU rUrGrArGrArArUrCrGrArArArGrArUrUrCrUrUrArArUrArArGrG rCrArUrCrCrUrUrCrCrGrArUrGrCrUrGrArCrUrUrCrUrCrArCrC rGrUrCrCrGrUrUrUrCrCrArArUrArGrGrArGrCrGrGrGrCrGr GrUrArUrGrU*mU*mU*mU |
| 6606 | MG3-6-HPRT-sgRNA-B8 | mU*mA*mU*rArGrUrUrUrArGrGrGrArUrUrGrUrArUrUrUrCrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrCrCrArArUrArGrGrArGrCrGrGrGrCrGr GrUrArUrGrU*mU*mU*mU |
| 6607 | MG3-6-HPRT-sgRNA-C8 | mA*mG*mG*rGrArUrUrGrUrArUrUrUrCrCrArArGrGrUrUrUrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrCrCrArArUrArGrGrArGrCrGrGrGrCrGr GrUrArUrGrU*mU*mU*mU |
| 6608 | MG3-6-HPRT-sgRNA-D8 | mA*mG*mU*rGrUrCrArArUrGrArGrCrArArArGrArUrGrArArGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrCrCrArArUrArGrGrArGrCrGrGrGrCrGr GrUrArUrGrU*mU*mU*mU |
| 6609 | MG3-6-HPRT-sgRNA-E8 | mC*mC*mA*rUrUrGrArArGrGrGrGrArGrCrUrArArUrArArGrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrCrCrArArUrArGrGrArGrCrGrGrGrCrGr GrUrArUrGrU*mU*mU*mU |

TABLE 3A-continued

Guide sequences used in Example 9

| SEQ ID NO: | Entity Name | Sequence |
|---|---|---|
| 6610 | MG3-6-HPRT-sgRNA-F8 | mU*mG*mG*rArCrArCrArUrGrGrGrUrArGrUrCrArGrGrGrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6611 | MG3-6-HPRT-sgRNA-G8 | mC*mC*mU*rGrGrArArCrCrUrGrArArGrGrArCrArGrUrUrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6612 | MG3-6-HPRT-sgRNA-H8 | mG*mU*mG*rCrArGrGrUrCrUrCrArGrArArCrUrGrUrCrCrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6613 | MG3-6-HPRT-sgRNA-A9 | mA*mU*mG*rArArArUrGrGrArGrArGrCrUrArArArUrUrArUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6614 | MG3-6-HPRT-sgRNA-B9 | mG*mU*mC*rArCrUrUrUrUrArArCrArCrArCrCrCrArArGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6615 | MG3-6-HPRT-sgRNA-C9 | mU*mA*mG*rArGrArGrGrCrArCrArUrUrUrGrCrCrArGrUrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |

Notations for chemical modifications: m = 2'O-methyl ribonucleotide (e.g mC = cytosine ribonucleotide with 2'-O Methyl in place of 2' hydroxyl); f = 2'-fluoro ribonucleotide (e.g fC = cytosine ribonucleotide with 2' fluorine in place of 2' hydroxyl); * = phosphorothioate bond; r: native RNA linkage comprising the sugar ribose (for example the ribose or RNA form of the A base is written rA), d: deoxyribose sugar (DNA) linkage (for example a deoxyribose form of the A base is written dA)

TABLE 3B

Sites targeted in Example 9

| SEQ ID NO: | Entity Name | Sequence |
|---|---|---|
| 6616 | MG3-6-HPRT-target site-A1 | TTCCTCTGCATCAGTTTTAATG |
| 6617 | MG3-6-HPRT-target site-B1 | GTGGGCTTGTGTTCTAAAGGAG |
| 6618 | MG3-6-HPRT-target site-C1 | AGGAGTGAGATTGGTTTTTTGT |
| 6619 | MG3-6-HPRT-target site-D1 | TAAAAAATAATATTTATAATTT |
| 6620 | MG3-6-HPRT-target site-E1 | GAGTATTTTTATTGAAAAGCAT |
| 6621 | MG3-6-HPRT-target site-F1 | AAAAATATTTTCCCTAACAAAG |
| 6622 | MG3-6-HPRT-target site-G1 | ATCTCAGCTATTTAGTCAAAAG |
| 6623 | MG3-6-HPRT-target site-H1 | GTCCTACTTTTGACTAAATAGC |

TABLE 3B-continued

Sites targeted in Example 9

| SEQ ID NO: | Entity Name | Sequence |
|---|---|---|
| 6624 | MG3-6-HPRT-target site-A2 | AACTCTCCAATATAGGTGGCTA |
| 6625 | MG3-6-HPRT-target site-B2 | ATTTTTCCCATAAATTCAAGAT |
| 6626 | MG3-6-HPRT-target site-C2 | CCAGGACTGGATTTTGTAGGTG |
| 6627 | MG3-6-HPRT-target site-D2 | TGCACCTACAAAATCCAGTCCT |
| 6628 | MG3-6-HPRT-target site-E2 | GTAAGAATGCCAGCCCCCAGGA |
| 6629 | MG3-6-HPRT-target site-F2 | AAGCAGTAAGAATGCCAGCCCC |
| 6630 | MG3-6-HPRT-target site-G2 | GCTGGCATTCTTACTGCTTGCT |
| 6631 | MG3-6-HPRT-target site-H2 | TGCTTGCTGAGGGCCAGATGAT |

TABLE 3B-continued

| SEQ ID NO: | Entity Name | Sequence |
|---|---|---|
| Sites targeted in Example 9 | | |
| 6632 | MG3-6-HPRT-target site-A3 | ATAGATTCCAG AATATCTCCAT |
| 6633 | MG3-6-HPRT-target site-B3 | TGACAGTATTG CAGTTATACAT |
| 6634 | MG3-6-HPRT-target site-C3 | CGAAAAGTAAT GTAATCTCATA |
| 6635 | MG3-6-HPRT-target site-D3 | GGATTATATCT TAAGTCTTATA |
| 6636 | MG3-6-HPRT-target site-E3 | AACACATGACA AAATTATTTAA |
| 6637 | MG3-6-HPRT-target site-F3 | GTTTGTCCTGA ATAGCATGGCA |
| 6638 | MG3-6-HPRT-target site-G3 | CTGAATAGCAT GGCAGAGGATT |
| 6639 | MG3-6-HPRT-target site-H3 | ATCCTTATTCT TAATTTTGCAA |
| 6640 | MG3-6-HPRT-target site-A4 | GCCCCCTTGCA AAATTAAGAAT |
| 6641 | MG3-6-HPRT-target site-B4 | GGTGAGGAAGT GATAGGAAGGG |
| 6642 | MG3-6-HPRT-target site-C4 | GTGATAGGAAG GGGTGGGCCCT |
| 6643 | MG3-6-HPRT-target site-D4 | GGAAGGGGTGG GCCCTGAAGAT |
| 6644 | MG3-6-HPRT-target site-E4 | AATTCCAGGAG GTCCAGATCTT |
| 6645 | MG3-6-HPRT-target site-F4 | TCATCACTCAA TTCCAGGAGGT |
| 6646 | MG3-6-HPRT-target site-G4 | CAGCATTCATC ACTCAATTCCA |
| 6647 | MG3-6-HPRT-target site-H4 | CAGCATAGGTA AGGTGAGGAGG |
| 6648 | MG3-6-HPRT-target site-A5 | ACATAAAAACT GCAGACTGATC |
| 6649 | MG3-6-HPRT-target site-B5 | ACCTGACCCCT ACATAAAAACT |
| 6650 | MG3-6-HPRT-target site-C5 | GATCAGTCTGC AGTTTTTATGT |
| 6651 | MG3-6-HPRT-target site-D5 | TCTGCTTTTTC CTAAGTGATTA |
| 6652 | MG3-6-HPRT-target site-E5 | ACAGATACCGT GATTTTTTCAA |
| 6653 | MG3-6-HPRT-target site-F5 | ACTGCTGACAT ATGACTCACTA |
| 6654 | MG3-6-HPRT-target site-G5 | CATATGTCAGC AGTTTGACTGT |
| 6655 | MG3-6-HPRT-target site-H5 | TATCAGTGAGT TTTTCTTTTAA |
| 6656 | MG3-6-HPRT-target site-A6 | GCTTATTTTTC TACATGCTCTT |
| 6657 | MG3-6-HPRT-target site-B6 | TTAAATGTCAA CCTACTGTGGC |
| 6658 | MG3-6-HPRT-target site-C6 | GAGGATTAAAG TCTATGCCACA |
| 6659 | MG3-6-HPRT-target site-D6 | AAGAACAACAA AAGAATACCCA |
| 6660 | MG3-6-HPRT-target site-E6 | TGGTATATGCT GTGGAATTGAG |
| 6661 | MG3-6-HPRT-target site-F6 | GAGATAGACTG GTTCGTGAGCG |
| 6662 | MG3-6-HPRT-target site-G6 | GTAGGACATGC TCAAACAATAC |
| 6663 | MG3-6-HPRT-target site-H6 | ATTAAGCAGCT GCTCACTACAA |
| 6664 | MG3-6-HPRT-target site-A7 | GAGATGGAGCT TTATTAAACAT |
| 6665 | MG3-6-HPRT-target site-B7 | GAACTCAGCAC TTCATATGCCT |
| 6666 | MG3-6-HPRT-target site-C7 | TGAGTTCTCTT GAACTCCTAAT |
| 6667 | MG3-6-HPRT-target site-D7 | ATTCCTGAGTT CAGGTAGGGAG |
| 6668 | MG3-6-HPRT-target site-E7 | TATATATGTTT AAAGAGCTGGA |
| 6669 | MG3-6-HPRT-target site-F7 | GGTATGAAAGC ATAAGTTTTCT |
| 6670 | MG3-6-HPRT-target site-G7 | TGAGACTGCCT TTAACATCTGT |
| 6671 | MG3-6-HPRT-target site-H7 | AATATTTTTCA ACAGGCAGCAT |
| 6672 | MG3-6-HPRT-target site-A8 | CTCCCACACCC TTTTATAGTTT |
| 6673 | MG3-6-HPRT-target site-B8 | TATAGTTTAGG GATTGTATTTC |
| 6674 | MG3-6-HPRT-target site-C8 | AGGGATTGTAT TTCCAAGGTTT |
| 6675 | MG3-6-HPRT-target site-D8 | AGTGTCAATGA GCAAAGATGAA |
| 6676 | MG3-6-HPRT-target site-E8 | CCATTGAAGGG GAGCTAATAAG |
| 6677 | MG3-6-HPRT-target site-F8 | TGGACACATGG GTAGTCAGGGT |
| 6678 | MG3-6-HPRT-target site-G8 | CCTGGAACCTG AAGGACAGTTC |
| 6679 | MG3-6-HPRT-target site-H8 | GTGCAGGTCTC AGAACTGTCCT |
| 6680 | MG3-6-HPRT-target site-A9 | ATGAAATGGAG AGCTAAATTAT |

TABLE 3B-continued

| Sites targeted in Example 9 | | |
|---|---|---|
| SEQ ID NO: | Entity Name | Sequence |
| 6681 | MG3-6-HPRT-target site-B9 | GTCACTTTTAA CACACCCAAGG |
| 6682 | MG3-6-HPRT-target site-C9 | TAGAGAGGCAC ATTTGCCAGTA |

Example 10—Gene Editing Outcomes at the DNA Level for Human TRBC1/2

Figure 4:
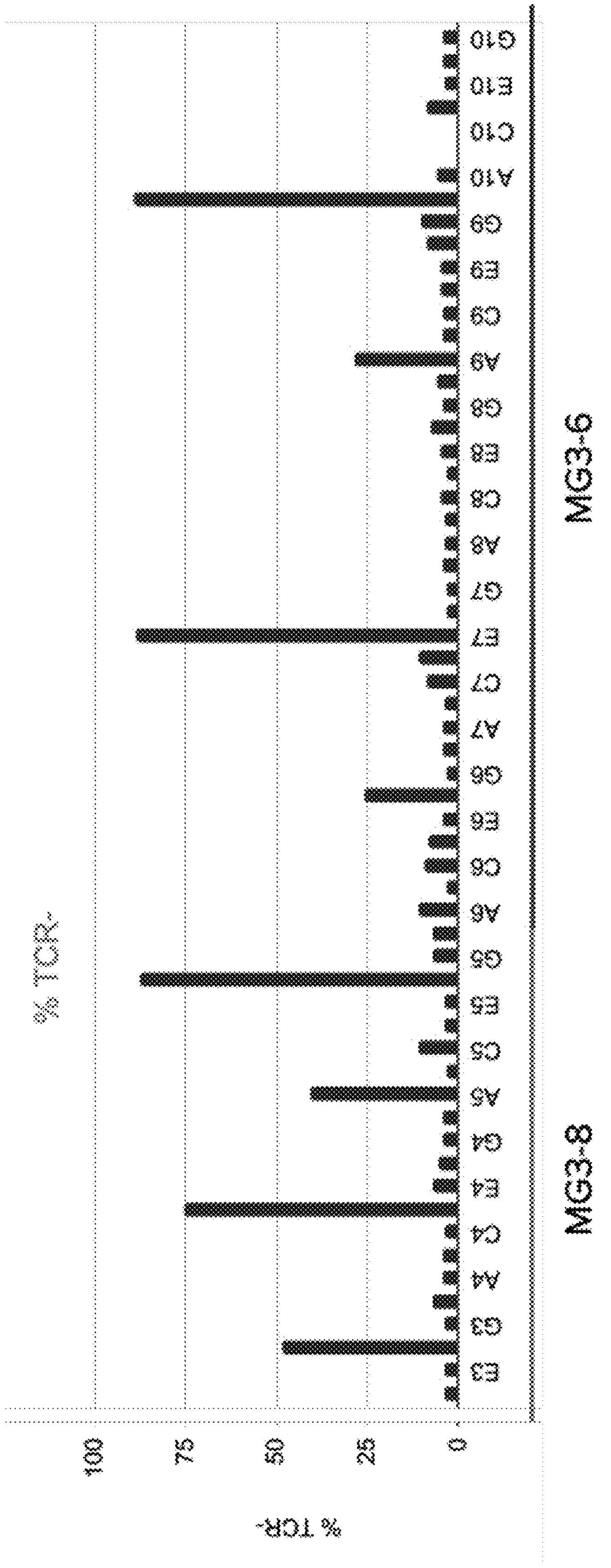
FIG. 4 depicts the flow cytometry results for gene editing of human TRBC1/2.

Primary T cells were purified from PBMCs using a negative selection kit (Miltenyi) according to the manufacturer's recommendations. Nucleofection of MG3-6 or MG3-8 RNPs (106 pmol protein/160 pmol guide) (MG3-6: SEQ ID NOs: 6683-6721; MG3-8: SEQ ID NOs: 6761-6781) was performed into T cells (200,000) using the Lonza 4D electroporator. For analysis by flow cytometry, 3 days post-nucleofection, 100,000 T cells were stained with anti-CD3 antibody for 30 minutes at 4° C. and analyzed on an Attune Nxt flow cytometer (FIG. 4).

TABLE 4A

| Guide sequences used in Example 10 | | |
|---|---|---|
| SEQ ID NO: | Entity Name | Sequence |
| 6683 | MG3-6-TRBC1/2-sgRNA-A6 | mA*mG*mG*rUrCrCrUrCrUrGrGrArArArGrGrGrArArGrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6684 | MG3-6-TRBC1/2-sgRNA-B6 | mC*mA*mG*rGrUrCrCrUrCrUrGrGrArArArGrGrGrArArGrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6685 | MG3-6-TRBC1/2-sgRNA-C6 | mC*mC*mA*rCrArCrUrGrGrUrGrUrGrCrCrUrGrGrCrCrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6686 | MG3-6-TRBC1/2-sgRNA-D6 | mG*mA*mA*rUrGrGrGrArArGrGrArGrGrUrGrCrArCrArGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6687 | MG3-6-TRBC1/2-sgRNA-E6 | mU*mG*mA*rGrGrGrCrGrGrGrCrUrGrCrUrCrCrUrUrGrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6688 | MG3-6-TRBC1/2-sgRNA-F6 | mA*mG*mU*rArUrCrUrGrGrArGrUrCrArUrUrGrArGrGrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6689 | MG3-6-TRBC1/2-sgRNA-G6 | mA*mU*mA*rCrUrGrCrCrUrGrArGrCrArGrCrCrGrCrCrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6690 | MG3-6-TRBC1/2-sgRNA-H6 | mU*mU*mG*rArCrArGrCrGrGrArArGrUrGrGrUrUrGrCrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6691 | MG3-6-TRBC1/2-sgRNA-A7 | mC*mU*mU*rGrArCrArGrCrGrGrArArGrUrGrGrUrUrGrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6692 | MG3-6-TRBC1/2-sgRNA-B7 | mC*mC*mG*rCrUrGrUrCrArArGrUrCrCrArGrUrUrCrUrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr |

TABLE 4A-continued

| Guide sequences used in Example 10 | | |
|---|---|---|
| SEQ ID NO: | Entity Name | Sequence |
| | | UrCrCrGrUrUrUrCrCrArArUrArGrGrArGrCrGrGrGrCrGrGrUr ArUrGrU*mU*mU*mU |
| 6693 | MG3-6-TRBC1/2-sgRNA-C7 | mU*mC*mG*rGrArGrArArUrGrArCrGrArGrUrGrGrArCrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6694 | MG3-6-TRBC1/2-sgRNA-D7 | mC*mA*mG*rArUrCrGrUrCrArGrCrGrCrCrGrArGrGrCrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6695 | MG3-6-TRBC1/2-sgRNA-E7 | mC*mG*mG*rCrGrCrUrGrArCrGrArUrCrUrGrGrGrUrGrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6696 | MG3-6-TRBC1/2-sgRNA-F7 | mG*mC*mC*rArArCrArGrUrGrUrCrCrUrArCrCrArGrCrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6697 | MG3-6-TRBC1/2-sgRNA-G7 | mC*mU*mU*rCrCrCrUrArGrCrArGrGrArUrCrUrCrArUrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6698 | MG3-6-TRBC1/2-sgRNA-H7 | mA*mU*mA*rCrArGrGrGrUrGrGrCrCrUrUrCrCrCrUrArGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6699 | MG3-6-TRBC1/2-sgRNA-A8 | mG*mG*mC*rGrCrUrGrArCrCrArGrCrArCrArGrCrArUrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6700 | MG3-6-TRBC1/2-sgRNA-B8 | mU*mC*mU*rCrUrUrCrUrGrCrArGrGrUrCrArArGrArGrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6701 | MG3-6-TRBC1/2-sgRNA-C8 | mC*mC*mU*rGrCrArGrArArGrArGrArArArGrUrUrUrUrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6702 | MG3-6-TRBC1/2-sgRNA-D8 | mA*mC*mC*rUrGrCrArGrArArGrArGrArArArGrUrUrUrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6703 | MG3-6-TRBC1/2-sgRNA-E8 | mC*mC*mA*rCrArCrUrGrGrUrGrUrGrCrCrUrGrGrCrCrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |
| 6704 | MG3-6-TRBC1/2-sgRNA-F8 | mA*mC*mC*rArGrCrUrCrArGrCrUrCrCrArCrGrUrGrGrUrUr GrArGrArArUrCrGrArArArGrArUrUrCrUrUrArArUrArArGrGrCr ArUrCrCrUrUrCrCrGrArUrGrCrUrGrArCrUrUrCrUrCrArCrCrGr UrCrCrGrUrUrUrUrCrCrArArUrArGrGrArGrCrGrGrGrCrGrGrUr ArUrGrU*mU*mU*mU |

TABLE 4A-continued

| Guide sequences used in Example 10 | | |
|---|---|---|
| SEQ ID NO: | Entity Name | Sequence |
| 6705 | MG3-6-TRBC1/2-sgRNA-G8 | mG*mA*mA*rUrGrGrGrArArGrGrArGrGrUrGrCrArCrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6706 | MG3-6-TRBC1/2-sgRNA-H8 | mU*mG*mA*rGrGrGrCrGrGrGrCrUrGrCrUrCrCrUrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6707 | MG3-6-TRBC1/2-sgRNA-A9 | mA*mG*mU*rArUrCrUrGrGrArGrUrCrArUrUrGrArGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6708 | MG3-6-TRBC1/2-sgRNA-B9 | mA*mU*mA*rCrUrGrCrCrUrGrArGrCrArGrCrCrGrCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6709 | MG3-6-TRBC1/2-sgRNA-C9 | mU*mU*mG*rArCrArGrCrGrGrArArGrUrGrGrUrUrGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6710 | MG3-6-TRBC1/2-sgRNA-D9 | mC*mU*mU*rGrArCrArGrCrGrGrArArGrUrGrGrUrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6711 | MG3-6-TRBC1/2-sgRNA-E9 | mC*mC*mG*rCrUrGrUrCrArArGrUrCrCrArGrUrUrCrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6712 | MG3-6-TRBC1/2-sgRNA-F9 | mU*mC*mG*rGrArGrArArUrGrArCrGrArGrUrGrGrArCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6713 | MG3-6-TRBC1/2-sgRNA-G9 | mC*mA*mG*rArUrCrGrUrCrArGrCrGrCrCrGrArGrGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6714 | MG3-6-TRBC1/2-sgRNA-H9 | mC*mG*mG*rCrGrCrUrGrArCrGrArUrCrUrGrGrGrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6715 | MG3-6-TRBC1/2-sgRNA-A10 | mG*mU*mC*rArArCrArGrArGrUrCrUrUrArCrCrArGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6716 | MG3-6-TRBC1/2-sgRNA-B10 | mC*mU*mU*rCrCrCrUrArGrCrArArGrArUrCrUrCrArUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |

TABLE 4A-continued

Guide sequences used in Example 10

| SEQ ID NO: | Entity Name | Sequence |
|---|---|---|
| 6717 | MG3-6-TRBC1/2-sgRNA-C10 | mG*mC*mU*rGrArUrGrGrCrCrArUrGrGrUrArArGrGrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6718 | MG3-6-TRBC1/2-sgRNA-D10 | mU*mG*mU*rGrGrArArGrArGrArGrArArCrArUrUrUrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6719 | MG3-6-TRBC1/2-sgRNA-E10 | mC*mU*mG*rUrGrGrArArGrArGrArGrArArCrArUrUrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6720 | MG3-6-TRBC1/2-sgRNA-F10 | mU*mC*mU*rCrUrUrCrCrArCrArGrGrUrCrArArGrArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6721 | MG3-6-TRBC1/2-sgRNA-G10 | mA*mG*mG*rUrCrArArGrArGrArArArGrGrArUrUrCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6761 | MG3-8-TRBC1/2-sgRNA-D3 | mA*mG*mG*rUrCrCrUrCrUrGrGrArArArGrGrGrArArGrGrUrUrGrArGrArArUrCrUrUrUrCrGrArArArGrArArArGrArUrUrCrUrUrArArUrArArGrGrCrArUrCrCrUrUrCrCrGrArUrGrCrUrGrArCrUrUrCrUrCrArCrCrGrUrCrCrGrGrCrUrCrCrUrCrUrUrArGrGrArArCrGrGrGrCrGrGrUrArUrGrU*mU*mU*mU |
| 6762 | MG3-8-TRBC1/2-sgRNA-E3 | mC*mU*mG*rArArCrArArGrGrUrGrUrUrCrCrCrArCrCrGrUrUrGrArGrArArUrCrUrUrUrCrGrArArArGrArArArGrArUrUrCrUrUrArArUrArArGrGrCrArUrCrCrUrUrCrCrGrArUrGrCrUrGrArCrUrUrCrUrCrArCrCrGrUrCrCrGrGrCrUrCrCrUrCrUrUrArGrGrArArCrGrGrGrCrGrGrUrArUrGrU*mU*mU*mU |
| 6763 | MG3-8-TRBC1/2-sgRNA-F3 | mC*mU*mC*rGrGrGrUrGrGrGrArArCrArCrCrUrUrGrUrGrUrUrGrArGrArArUrCrUrUrUrCrGrArArArGrArArArGrArUrUrCrUrUrArArUrArArGrGrCrArUrCrCrUrUrCrCrGrArUrGrCrUrGrArCrUrUrCrUrCrArCrCrGrUrCrCrGrGrCrUrCrCrUrCrUrUrArGrGrArArCrGrGrGrCrGrGrUrArUrGrU*mU*mU*mU |
| 6764 | MG3-8-TRBC1/2-sgRNA-G3 | mA*mA*mU*rGrGrGrArArGrGrArGrGrUrGrCrArCrArGrGrUrUrGrArGrArArUrCrUrUrUrCrGrArArArGrArArArGrArUrUrCrUrUrArArUrArArGrGrCrArUrCrCrUrUrCrCrGrArUrGrCrUrGrArCrUrUrCrUrCrArCrCrGrUrCrCrGrGrCrUrCrCrUrCrUrUrArGrGrArArCrGrGrGrCrGrGrUrArUrGrU*mU*mU*mU |
| 6765 | MG3-8-TRBC1/2-sgRNA-H3 | mG*mG*mG*rCrUrGrCrUrCrCrUrUrGrArGrGrGrGrCrUrGrUrUrGrArGrArArUrCrUrUrUrCrGrArArArGrArArArGrArUrUrCrUrUrArArUrArArGrGrCrArUrCrCrUrUrCrCrGrArUrGrCrUrGrArCrUrUrCrUrCrArCrCrGrUrCrCrGrGrCrUrCrCrUrCrUrUrArGrGrArArCrGrGrGrCrGrGrUrArUrGrU*mU*mU*mU |
| 6766 | MG3-8-TRBC1/2-sgRNA-A4 | mU*mA*mC*rUrGrCrCrUrGrArGrCrArGrCrCrGrCrCrUrGrUrUrGrArGrArArUrCrUrUrUrCrGrArArArGrArArArGrArUrUrCrUrUrArArUrArArGrGrCrArUrCrCrUrUrCrCrGrArUrGrCrUrGrArCrUrUrCrUrCrArCrCrGrUrCrCrGrGrCrUrCrCrUrCrUrUrArGrGrArArCrGrGrGrCrGrGrUrArUrGrU*mU*mU*mU |
| 6767 | MG3-8-TRBC1/2-sgRNA-B4 | mU*mU*mG*rArCrArGrCrGrGrArArGrUrGrGrUrUrGrCrGrUrUrGrArGrArArUrCrUrUrUrCrGrArArArGrArArArGrArUrUrCrUrUrArArUrArArGrGrCrArUrCrCrUrUrCrCrGrArUrGrCrUrGrArCrUrUrCrUrCrArCrCrGrUrCrCrGrGrCrUrCrCrUrCrUrUrArGrGrArArCrGrGrGrCrGrGrUrArUrGrUxmU*mU*mU |

TABLE 4A-continued

Guide sequences used in Example 10

| SEQ ID NO: | Entity Name | Sequence |
|---|---|---|
| 6768 | MG3-8-TRBC1/2-sgRNA-C4 | mG*mU*mG*rArCrGrGrGrUrUrUrGrGrCrCrCrUrArUrCrGrUrUr<br>GrArGrArArUrCrUrUrUrCrGrArArArGrArArArGrArUrUrCrUrUr<br>ArArUrArArGrGrCrArUrCrCrUrUrCrCrGrArUrGrCrUrGrArCrUr<br>UrCrUrCrArCrCrGrUrCrCrGrGrCrUrCrCrUrCrUrUrArGrGrArAr<br>CrGrGrGrCrGrGrUrArUrGrU*mU*mU*mU |
| 6769 | MG3-8-TRBC1/2-sgRNA-D4 | mC*mG*mG*rCrGrCrUrGrArCrGrArUrCrUrGrGrGrUrGrGrUrUr<br>GrArGrArArUrCrUrUrUrCrGrArArArGrArArArGrArUrUrCrUrUr<br>ArArUrArArGrGrCrArUrCrCrUrUrCrCrGrArUrGrCrUrGrArCrUr<br>UrCrUrCrArCrCrGrUrCrCrGrGrCrUrCrCrUrCrUrUrArGrGrArAr<br>CrGrGrGrCrGrGrUrArUrGrU*mU*mU*mU |
| 6770 | MG3-8-TRBC1/2-sgRNA-E4 | mC*mC*mA*rArCrArGrUrGrUrCrCrUrArCrCrArGrCrArGrUrUr<br>GrArGrArArUrCrUrUrUrCrGrArArArGrArArArGrArUrUrCrUrUr<br>ArArUrArArGrGrCrArUrCrCrUrUrCrCrGrArUrGrCrUrGrArCrUr<br>UrCrUrCrArCrCrGrUrCrCrGrGrCrUrCrCrUrCrUrUrArGrGrArAr<br>CrGrGrGrCrGrGrUrArUrGrU*mU*mU*mU |
| 6771 | MG3-8-TRBC1/2-sgRNA-F4 | mC*mC*mU*rGrCrArGrArArGrArGrArArArGrUrUrUrUrGrUrUr<br>GrArGrArArUrCrUrUrUrCrGrArArArGrArArArGrArUrUrCrUrUr<br>ArArUrArArGrGrCrArUrCrCrUrUrCrCrGrArUrGrCrUrGrArCrUr<br>UrCrUrCrArCrCrGrUrCrCrGrGrCrUrCrCrUrCrUrUrArGrGrArAr<br>CrGrGrGrCrGrGrUrArUrGrU*mU*mU*mU |
| 6772 | MG3-8-TRBC1/2-sgRNA-G4 | mC*mU*mG*rArArArArArCrGrUrGrUrUrCrCrCrArCrCrGrUrUr<br>GrArGrArArUrCrUrUrUrCrGrArArArGrArArArGrArUrUrCrUrUr<br>ArArUrArArGrGrCrArUrCrCrUrUrCrCrGrArUrGrCrUrGrArCrUr<br>UrCrUrCrArCrCrGrUrCrCrGrGrCrUrCrCrUrCrUrUrArGrGrArAr<br>CrGrGrGrCrGrGrUrArUrGrU*mU*mU*mU |
| 6773 | MG3-8-TRBC1/2-sgRNA-H4 | mC*mU*mU*rGrGrGrUrGrGrGrArArCrArCrGrUrUrUrUrGrUrUr<br>GrArGrArArUrCrUrUrUrCrGrArArArGrArArArGrArUrUrCrUrUr<br>ArArUrArArGrGrCrArUrCrCrUrUrCrCrGrArUrGrCrUrGrArCrUr<br>UrCrUrCrArCrCrGrUrCrCrGrGrCrUrCrCrUrCrUrUrArGrGrArAr<br>CrGrGrGrCrGrGrUrArUrGrU*mU*mU*mU |
| 6774 | MG3-8-TRBC1/2-sgRNA-A5 | mA*mA*mU*rGrGrGrArArGrGrArGrGrUrGrCrArCrArGrGrUrUr<br>GrArGrArArUrCrUrUrUrCrGrArArArGrArArArGrArUrUrCrUrUr<br>ArArUrArArGrGrCrArUrCrCrUrUrCrCrGrArUrGrCrUrGrArCrUr<br>UrCrUrCrArCrCrGrUrCrCrGrGrCrUrCrCrUrCrUrUrArGrGrArAr<br>CrGrGrGrCrGrGrUrArUrGrU*mU*mU*mU |
| 6775 | MG3-8-TRBC1/2-sgRNA-B5 | mG*mG*mG*rCrUrGrCrUrCrCrUrUrGrArGrGrGrGrCrUrGrUrUr<br>GrArGrArArUrCrUrUrUrCrGrArArArGrArArArGrArUrUrCrUrUr<br>ArArUrArArGrGrCrArUrCrCrUrUrCrCrGrArUrGrCrUrGrArCrUr<br>UrCrUrCrArCrCrGrUrCrCrGrGrCrUrCrCrUrCrUrUrArGrGrArAr<br>CrGrGrGrCrGrGrUrArUrGrUxmU*mU*mU |
| 6776 | MG3-8-TRBC1/2-sgRNA-C5 | mU*mA*mC*rUrGrCrCrUrGrArGrCrArGrCrCrGrCrCrUrGrUrUr<br>GrArGrArArUrCrUrUrUrCrGrArArArGrArArArGrArUrUrCrUrUr<br>ArArUrArArGrGrCrArUrCrCrUrUrCrCrGrArUrGrCrUrGrArCrUr<br>UrCrUrCrArCrCrGrUrCrCrGrGrCrUrCrCrUrCrUrUrArGrGrArAr<br>CrGrGrGrCrGrGrUrArUrGrU*mU*mU*mU |
| 6777 | MG3-8-TRBC1/2-sgRNA-D5 | mU*mU*mG*rArCrArGrCrGrGrArArGrUrGrGrUrUrGrCrGrUrUr<br>GrArGrArArUrCrUrUrUrCrGrArArArGrArArArGrArUrUrCrUrUr<br>ArArUrArArGrGrCrArUrCrCrUrUrCrCrGrArUrGrCrUrGrArCrUr<br>UrCrUrCrArCrCrGrUrCrCrGrGrCrUrCrCrUrCrUrUrArGrGrArAr<br>CrGrGrGrCrGrGrUrArUrGrU*mU*mU*mU |
| 6778 | MG3-8-TRBC1/2-sgRNA-E5 | mG*mU*mG*rArCrArGrGrUrUrUrGrGrCrCrCrUrArUrCrGrUrUr<br>GrArGrArArUrCrUrUrUrCrGrArArArGrArArArGrArUrUrCrUrUr<br>ArArUrArArGrGrCrArUrCrCrUrUrCrCrGrArUrGrCrUrGrArCrUr<br>UrCrUrCrArCrCrGrUrCrCrGrGrCrUrCrCrUrCrUrUrArGrGrArAr<br>CrGrGrGrCrGrGrUrArUrGrU*mU*mU*mU |
| 6779 | MG3-8-TRBC1/2-sgRNA-F5 | mC*mG*mG*rCrGrCrUrGrArCrGrArUrCrUrGrGrGrUrGrGrUrUr<br>GrArGrArArUrCrUrUrUrCrGrArArArGrArArArGrArUrUrCrUrUr<br>ArArUrArArGrGrCrArUrCrCrUrUrCrCrGrArUrGrCrUrGrArCrUr<br>UrCrUrCrArCrCrGrUrCrCrGrGrCrUrCrCrUrCrUrUrArGrGrArAr<br>CrGrGrGrCrGrGrUrArUrGrU*mU*mU*mU |
| 6780 | MG3-8-TRBC1/2-sgRNA-G5 | mU*mC*mA*rArCrArGrArGrUrCrUrUrArCrCrArGrCrArGrUrUr<br>GrArGrArArUrCrUrUrUrCrGrArArArGrArArArGrArUrUrCrUrUr |

TABLE 4A-continued

Guide sequences used in Example 10

| SEQ ID NO: | Entity Name | Sequence |
|---|---|---|
| | | ArArUrArArGrGrCrArUrCrCrUrUrCrCrGrArUrGrCrUrGrArCrUr UrCrUrCrArCrCrGrUrCrCrGrGrCrUrCrCrUrCrUrUrArGrGrArAr CrGrGrGrCrGrGrUrArUrGrU*mU*mU*mU |
| 6781 | MG3-8-TRBC1/2-sgRNA-H5 | mU*mG*mU*rGrGrArArGrArGrArGrArArCrArUrUrUrUrGrUrUr GrArGrArArUrCrUrUrUrCrGrArArArGrArArArGrArUrUrCrUrUr ArArUrArArGrGrCrArUrCrCrUrUrCrCrGrArUrGrCrUrGrArCrUr UrCrUrCrArCrCrGrUrCrCrGrGrCrUrCrCrUrCrUrUrArGrGrArAr CrGrGrGrCrGrGrUrArUrGrUxmU*mU*mU |

Notations for chemical modifications: m = 2'O-methyl ribonucleotide (e.g mC = cytosine ribonucleotide with 2'-O Methyl in place of 2' hydroxyl); f = 2'-fluoro ribonucleotide (e.g fC = cytosine ribonucleotide with 2' fluorine in place of 2' hydroxyl); * = phosphorothioate bond; r: native RNA linkage comprising the sugar ribose (for example the ribose or RNA form of the A base is written rA), d: deoxyribose sugar (DNA) linkage (for example a deoxyribose form of the A base is written dA)

TABLE 4B

Sites targeted in Example 10

| SEQ ID NO: | Entity Name | Sequence |
|---|---|---|
| 6722 | MG3-6-TRBC1/2-target site-A6 | AGGTCCTCTGGAAAGGGAAG |
| 6723 | MG3-6-TRBC1/2-target site-B6 | CAGGTCCTCTGGAAAGGGAA |
| 6724 | MG3-6-TRBC1/2-target site-C6 | CCACACTGGTGTGCCTGGCC |
| 6725 | MG3-6-TRBC1/2-target site-D6 | GAATGGGAAGGAGGTGCACA |
| 6726 | MG3-6-TRBC1/2-target site-E6 | TGAGGGCGGGCTGCTCCTTG |
| 6727 | MG3-6-TRBC1/2-target site-F6 | AGTATCTGGAGTCATTGAGG |
| 6728 | MG3-6-TRBC1/2-target site-G6 | ATACTGCCTGAGCAGCCGCC |
| 6729 | MG3-6-TRBC1/2-target site-H6 | TTGACAGCGGAAGTGGTTGC |
| 6730 | MG3-6-TRBC1/2-target site-A7 | CTTGACAGCGGAAGTGGTTG |
| 6731 | MG3-6-TRBC1/2-target site-B7 | CCGCTGTCAAGTCCAGTTCT |
| 6732 | MG3-6-TRBC1/2-target site-C7 | TCGGAGAATGACGAGTGGAC |
| 6733 | MG3-6-TRBC1/2-target site-D7 | CAGATCGTCAGCGCCGAGGC |
| 6734 | MG3-6-TRBC1/2-target site-E7 | CGGCGCTGACGATCTGGGTG |
| 5735 | MG3-6-TRBC1/2-target site-F7 | GCCAACAGTGTCCTACCAGC |
| 6736 | MG3-6-TRBC1/2-target site-G7 | CTTCCCTAGCAGGATCTCAT |
| 6737 | MG3-6-TRBC1/2-target site-H7 | ATACAGGGTGGCCTTCCCTA |
| 6738 | MG3-6-TRBC1/2-target site-A8 | GGCGCTGACCAGCACAGCAT |

TABLE 4B-continued

Sites targeted in Example 10

| SEQ ID NO: | Entity Name | Sequence |
|---|---|---|
| 6739 | MG3-6-TRBC1/2-target site-B8 | TCTCTTCTGCAGGTCAAGAG |
| 6740 | MG3-6-TRBC1/2-target site-C8 | CCTGCAGAAGAGAAAGTTTT |
| 6741 | MG3-6-TRBC1/2-target site-D8 | ACCTGCAGAAGAGAAAGTTT |
| 6742 | MG3-6-TRBC1/2-target site-E8 | CCACACTGGTGTGCCTGGCC |
| 6743 | MG3-6-TRBC1/2-target site-F8 | ACCAGCTCAGCTCCACGTGG |
| 6744 | MG3-6-TRBC1/2-target site-G8 | GAATGGGAAGGAGGTGCACA |
| 6745 | MG3-6-TRBC1/2-target site-H8 | TGAGGGCGGGCTGCTCCTTG |
| 6746 | MG3-6-TRBC1/2-target site-A9 | AGTATCTGGAGTCATTGAGG |
| 6747 | MG3-6-TRBC1/2-target site-B9 | ATACTGCCTGAGCAGCCGCC |
| 6748 | MG3-6-TRBC1/2-target site-C9 | TTGACAGCGGAAGTGGTTGC |
| 6749 | MG3-6-TRBC1/2-target site-D9 | CTTGACAGCGGAAGTGGTTG |
| 6750 | MG3-6-TRBC1/2-target site-E9 | CCGCTGTCAAGTCCAGTTCT |
| 6751 | MG3-6-TRBC1/2-target site-F9 | TCGGAGAATGACGAGTGGAC |
| 6752 | MG3-6-TRBC1/2-target site-G9 | CAGATCGTCAGCGCCGAGGC |
| 6753 | MG3-6-TRBC1/2-target site-H9 | CGGCGCTGACGATCTGGGTG |

TABLE 4B-continued

| Sites targeted in Example 10 | | |
|---|---|---|
| SEQ ID NO: | Entity Name | Sequence |
| 6754 | MG3-6-TRBC1/2-target site-A10 | GTCAACAGAGTCTTACCAGC |
| 6755 | MG3-6-TRBC1/2-target site-B10 | CTTCCCTAGCAAGATCTCAT |
| 6756 | MG3-6-TRBC1/2-target site-C10 | GCTGATGGCCATGGTAAGGA |
| 6757 | MG3-6-TRBC1/2-target site-D10 | TGTGGAAGAGAGAACATTTT |
| 6758 | MG3-6-TRBC1/2-target site-E10 | CTGTGGAAGAGAGAACATTT |
| 6759 | MG3-6-TRBC1/2-target site-F10 | TCTCTTCCACAGGTCAAGAG |
| 6760 | MG3-6-TRBC1/2-target site-G10 | AGGTCAAGAGAAAGGATTCC |
| 6782 | MG3-8-TRBC1/2-target site-D3 | AGGTCCTCTGGAAAGGGAAG |
| 6783 | MG3-8-TRBC1/2-target site-E3 | CTGAACAAGGTGTTCCCACC |
| 6784 | MG3-8-TRBC1/2-target site-F3 | CTCGGGTGGGAACACCTTGT |
| 6785 | MG3-8-TRBC1/2-target site-G3 | AATGGGAAGGAGGTGCACAG |
| 6786 | MG3-8-TRBC1/2-target site-H3 | GGGCTGCTCCTTGAGGGGCT |
| 6787 | MG3-8-TRBC1/2-target site-A4 | TACTGCCTGAGCAGCCGCCT |
| 6788 | MG3-8-TRBC1/2-target site-B4 | TTGACAGCGGAAGTGGTTGC |
| 6789 | MG3-8-TRBC1/2-target site-C4 | GTGACGGGTTTGGCCCTATC |
| 6790 | MG3-8-TRBC1/2-target site-D4 | CGGCGCTGACGATCTGGGTG |
| 6791 | MG3-8-TRBC1/2-target site-E4 | CCAACAGTGTCCTACCAGCA |
| 6792 | MG3-8-TRBC1/2-target site-F4 | CCTGCAGAAGAGAAAGTTTT |
| 6793 | MG3-8-TRBC1/2-target site-G4 | CTGAAAAACGTGTTCCCACC |
| 6794 | MG3-8-TRBC1/2-target site-H4 | CTTGGGTGGGAACACGTTTT |
| 6795 | MG3-8-TRBC1/2-target site-A5 | AATGGGAAGGAGGTGCACAG |
| 6796 | MG3-8-TRBC1/2-target site-B5 | GGGCTGCTCCTTGAGGGGCT |
| 6797 | MG3-8-TRBC1/2-target site-C5 | TACTGCCTGAGCAGCCGCCT |

TABLE 4B-continued

| Sites targeted in Example 10 | | |
|---|---|---|
| SEQ ID NO: | Entity Name | Sequence |
| 6798 | MG3-8-TRBC1/2-target site-D5 | TTGACAGCGGAAGTGGTTGC |
| 6799 | MG3-8-TRBC1/2-target site-E5 | GTGACAGGTTTGGCCCTATC |
| 6800 | MG3-8-TRBC1/2-target site-F5 | CGGCGCTGACGATCTGGGTG |
| 6801 | MG3-8-TRBC1/2-target site-G5 | TCAACAGAGTCTTACCAGCA |
| 6802 | MG3-8-TRBC1/2-target site-H5 | TGTGGAAGAGAGAACATTTT |

Example 11—MG3-6 Guide Screen for Mouse HAO-1 Gene Using mRNA Transfection

Figure 5:
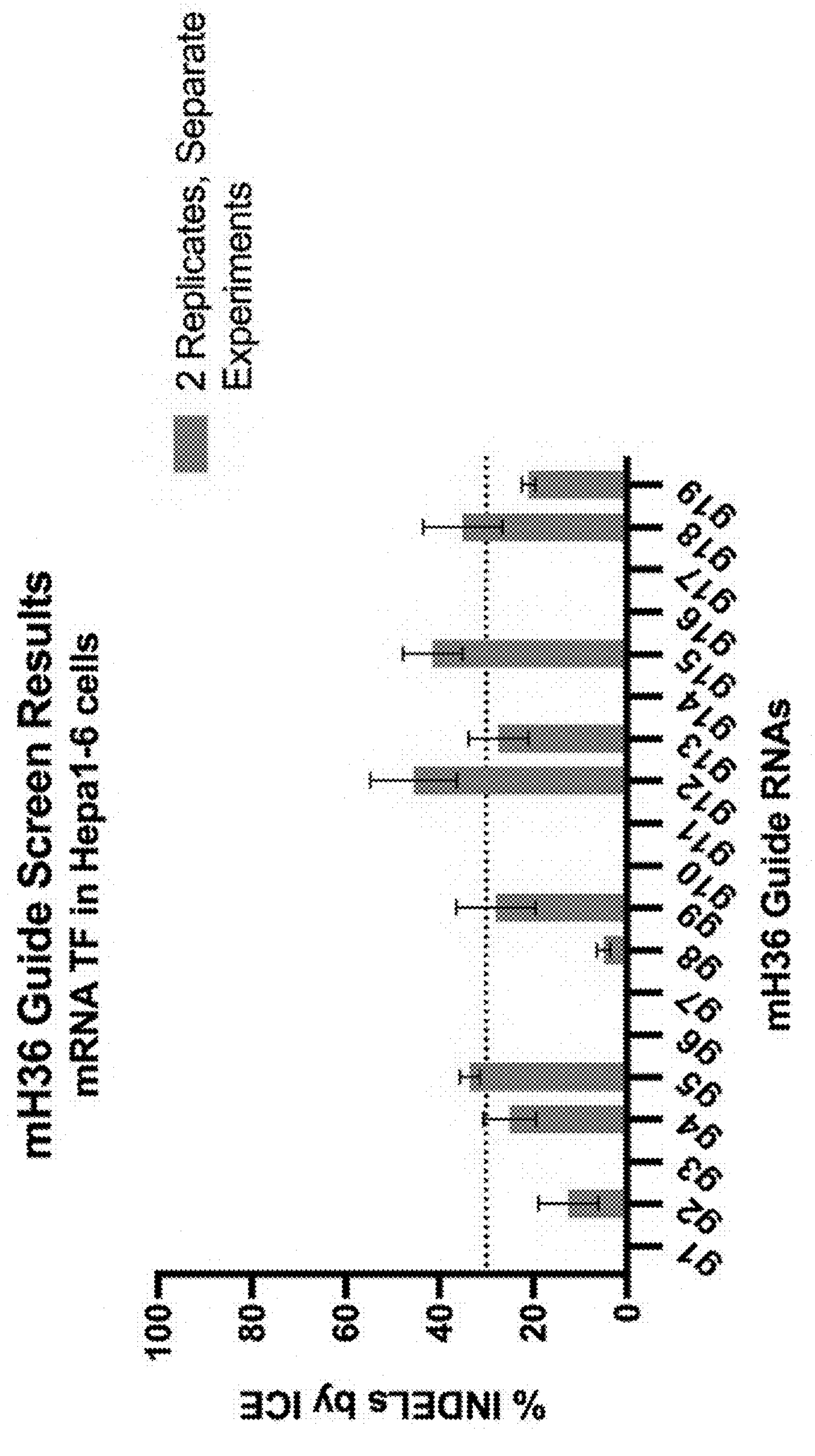
FIG. 5 depicts the results of a guide screen in Hepa1-6 cells; guides were delivered as mRNA and gRNA using lipofectamine Messenger Max.

Guides for MG3-6 were identified in exons 1, 2, 3, and 4 of the human HAO1 gene using a guide-finding algorithm that searches for the appropriate PAM sequence. A total of 19 guides were selected for evaluation in mammalian cells. 300 ng mRNA and 120 ng single guide RNA were transfected into Hepa1-6 cells as follows. One day prior to transfection, Hepa1-6 cells that had been cultured for less than 10 days in DMEM, 10% FBS, 1×NEAA media, without Pen/Step, were seeded into a TC-treated 24 well plate. Cells were counted, and the equivalent volume to 60,000 viable cells were added to each well. Additional pre-equilibrated media was added to each well to bring the total volume to 500 μL. On the day of transfection, 25 μL of OptiMEM media and 1.25 μL of Lipofectamine Messenger Max Solution (Thermo Fisher) were mixed in a mastermix solution, vortexed, and allowed to sit for at least 5 minutes at room temperature. In separate tubes, 300 ng of the MG3-6 mRNA and 120 ng of the sgRNA were mixed together with 25 μL of OptiMEM media and vortexed briefly. The appropriate volume of MessengerMax solution was added to each RNA solution, mixed by flicking the tube, and briefly spun down at a low speed. The complete editing reagent solutions were allowed to incubate for 10 minutes at room temperature, then added directly to the Hepa1-6 cells. Two days post transfection, the media was aspirated off of each well of Hepa1-6 cells and genomic DNA was purified by automated magnetic bead purification, via the KingFisher Flex with the MagMAX™ DNA Multi-Sample Ultra 2.0 Kit. The activity of the guides is summarized in Table 5A and FIG. 5, while the primers used are summarized in Table 5B.

TABLE 5A

Average Activity of MG3-6 guides at mouse HAO1 delivered by mRNA Transfection

| Guide Name | PAM | SEQ ID NO. | Spacer Sequence | Editing Activity (Average % INDELs) |
|---|---|---|---|---|
| mH36-1 | GCAGACC | 11802 | CATGCTGTTCATAATCACTGAT | 0 |
| mH36-2 | ACAGGTC | 11803 | CAGAAGTCAGTGTATGACTATT | 12.5 |
| mH36-3 | CCAGACC | 11804 | TAACGTCTCCTGATCATTTGCC | 0 |
| mH36-4 | ACAGATC | 11805 | CTCTGTCCTAAAACAGAAGTTG | 25 |
| mH36-5 | TGGGGCT | 11806 | GAGTCAGCATGCCAATATGTGT | 33.5 |
| mH36-6 | TCAGACC | 11807 | TTCTCCATTTCATTACAGCCTG | 0 |
| mH36-7 | ACAGGCT | 11808 | TCATGCCAGTTCCCATGGTCTG | 0 |
| mH36-8 | TTGGGCT | 11809 | GAACTGGCATGATGCTGAGTTC | 5 |
| mH36-9 | CTGGGCC | 11810 | AGTTGCATCCAGCGAAGTGCCT | 28 |
| mH36-10 | AAAGACC | 11811 | CTGGATGCAACTGTACATCTAC | 0 |
| mH36-11 | TGAGATC | 11812 | AACTGTACATCTACAAAGACCG | 0 |
| mH36-12 | CAGGGTT | 11813 | GATAGTGAAGCGAGCTGAGAAG | 45.5 |
| mH36-13 | CAAGGCC | 11814 | AGCGAGCTGAGAAGCAGGGTTA | 27.5 |
| mH36-14 | ACAGGTT | 11815 | AACCGCATTGATGACGTGCGGA | 0 |
| mH36-15 | TCAGGTC | 11816 | AGGTTCAAGCTGCCACCACAAC | 41.5 |
| mH36-16 | GTGGACT | 11817 | AAGGGAAATTTTGGAGACAACA | 0 |
| mH36-17 | ATAGACC | 11818 | TGCTGAATATGTGGCACAAGCT | 0 |
| mH36-18 | ATGGGTC | 11819 | GTAATATCATCCCAGCTGAGAG | 35 |
| mH36-19 | AGAGGTT | 11820 | TATTGTTGTAAAGGGCATTTTG | 21 |

TABLE 5B

Primers designed for the mouse HAO1 gene, used for PCR at each of the first four exons, and for sanger sequencing

| Target Exon | Use | Primer Name | SEQ ID NO. | Primer Sequence |
|---|---|---|---|---|
| Mouse | Fwd PCR | PCR mHE1_F_+233 | 11821 | GTGACCAACCCTACCCGTTT |
| HAO1 | Rev PCR | PCR mHE1_R_-553 | 11822 | GCAAGCACCTACTGTCTCGT |
| Exon 1 | Sequencing | Seq_mHE1_F_+139 | 11823 | GTCTAGGCATACAATGTTTGCTCA |
| Mouse | Fwd PCR | HAO1_E2_F5721 | 11824 | CAACGAAGGTTCCCTCCAGG |
| HAO1 | Rev PCR | HAO1_E2_R6271 | 11825 | GGAAGGGTGTTCGAGAAGGA |
| Exon 2 | Sequencing | 5938F_Seq_HAO1_E2 | 11826 | CTATGCAAGGAAAAGATTTGGCC |
| Mouse | Fwd PCR | HAO1_E3_F23198 | 11827 | TGCCCTAGACAAGCTGACAC |
| HAO1 | Rev PCR | HAO1_E3_R23879 | 11828 | CAGATTCTGGAAGTGGCCCA |
| Exon 3 | Sequencing | HAO1_E3_F23198 | 11827 | Same as Fwd PCR Primer |
| Mouse | Fwd PCR | PCR_mHE4_F_+300 | 11829 | GGCTGGCTGAAAATAGCATCC |
| HAO1 | Rev PCR | HAO1_E4_R31650 | 11830 | AGGTTTGGTTCCCCTCACCT |
| Exon 4 | Sequencing | PCR_mHE4_R_-149 | 11831 | TCTGCCATGAAGGCATATGGAC |

Example 12—Guide Chemistry Optimization for the MG3-6 Type II Nuclease (Prophetic)

Various chemically modified guides are designed and tested for activity. The most active guide in a guide screen in mouse hepatocytes (Hepa1-6 cells)—targeting albumin intron 1 is chosen as the spacer sequence model to insert various chemical modifications. The gRNA comprises the spacer located in the 5' followed by the CRISPR repeat and the trans-activating CRISPR RNA (tracr). The CRISPR repeat and the tracr are identical to MG3-6. The CRISPR repeat and tracr form a structured RNA comprising 3 stem loops. Different areas of the stem loops are modified by replacing the 2' hydroxyl in the ribose by 2'-O-methyl groups or replacing the phosphodiester backbone by a phosphorothioate (PS) bond. Moreover, the spacer in the 5' of the guide is modified by adding 2'-O-methyls, PS bonds, and 2'-fluoros. The editing activity of guides with the exact same base sequence but different chemical modifications is evaluated in Hepa1-6 cells by co-transfection of mRNA encoding MG3-6 and the guide. A guide with the same base sequence and a commercially available chemical modification called AltR1/AltR2 is used as a control. The spacer sequence in these guides targets a 22 nucleotide region in albumin intron1 of the mouse genome.

In order to test the stability of the chemically modified guides compared to the guide with no chemical modification (native RNA), a stability assay using crude cell extracts is used. Crude cell extracts from mammalian cells are selected because they contain the mixture of nucleases that a guide RNA will be exposed to when delivered to mammalian cells in vitro or in vivo. Hepa 1-6 cells are collected by adding 3 ml of cold PBS per 15 cm dish of confluent cells and releasing the cells from the surface of the dish using a cell scraper. The cells are pelleted at 200 g for 10 min and frozen at −80° C. for future use. For the stability assays, cells are resuspended in 4 volumes of cold PBS (e.g., for a 100 mg pellet cells are resuspended in 400 μL of cold PBS). Triton X-100 is added to a concentration of 0.2% (v/v), cells are vortexed for 10 seconds, put on ice for 10 minutes, and vortexed again for 10 seconds. Triton X-100 is a mild non-ionic detergent that disrupts cell membranes but does not inactivate or denature proteins at the concentration used. Stability reactions are set up on ice and comprise 20 μL of cell crude extract with 2 pmoles of each guide (1 μL of a 2 μM stock). Six reactions are set up per guide comprising: input, 0.5 hour, 1 hour, 4 hours, 9 hours, and in some cases 21 hours (The time in hours referring to the length of time each sample is incubated). Samples are incubated at 37° C. from 0.5 hours up to 21 hours while the input control is left on ice for 5 minutes. After each incubation period, the reaction is stopped by adding 300 μL of a mixture of phenol and guanidine thiocyanate (Tri reagent, Zymo Research) which immediately denatures all proteins and efficiently inhibits ribonucleases and facilitates the subsequent recovery of RNA. After adding Tri Reagent, the samples are vortexed for 15 seconds and stored at −20° C. RNA is extracted from the samples using Direct-zol RNA miniprep kit (Zymo Research) and eluted in 100 μL of nuclease-free water. Detection of the modified guide is performed using Tagman RT—qPCR using the Taqman miRNA Assay technology (Thermo Fisher). Data is plotted as a function of percentage of sgRNA remaining in relation to the input sample.

Example 13—Efficiency of mRNA Electroporation in T Cells

Figure 6:
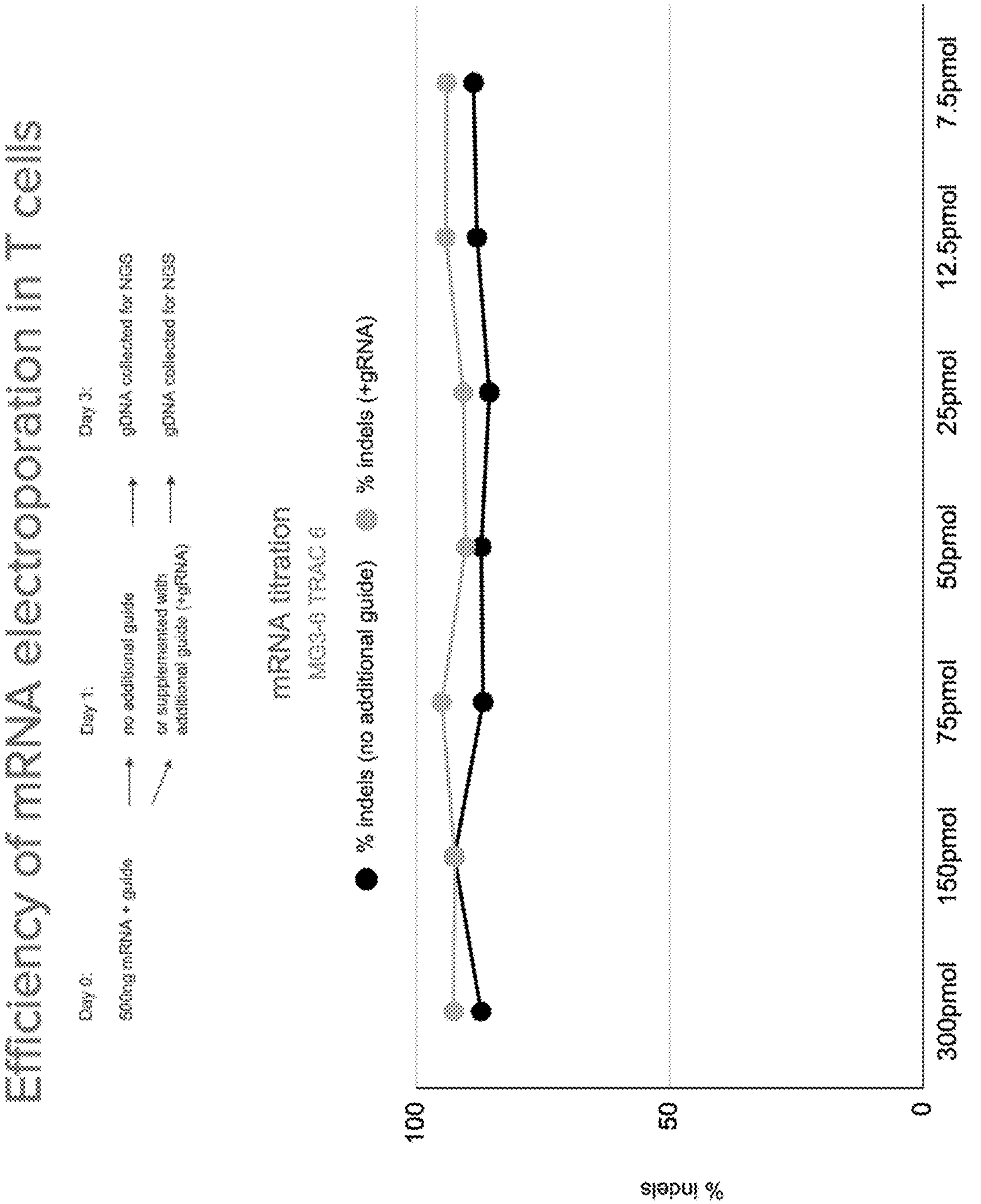
FIG. 6 depicts analysis of gene-editing outcomes by NGS for mRNA electroporation in T cells.

Primary T cells were purified from PBMCs using a negative selection kit (Miltenyi) according to the manufacturer's recommendations. Nucleofection of mRNA was performed as follow: 200,000 cells were co-transfected with 500 ng of mRNA and the indicated amount of guide RNA using a Lonza 4D electroporator (DS-120). Cells were harvested and genomic DNA prepared three days post initial transfection. For conditions labeled "+gRNA": 15 h post initial transfection, cells were nucleofected with indicated amount of additional guide. PCR primers appropriate for use in NGS-based DNA sequencing were generated, optimized, and used to amplify the individual target sequences for each guide RNA. The amplicons were sequenced on an Illumina MiSeq machine and analyzed with a proprietary Python script to measure gene editing (FIG. 6).

Example 14—ELISA Assay to Assess Pre-Existing Antibody Response

MG3-6 and MG3-8 were expressed in and purified from human HEK293 cells using the Expi293™ Expression System Kit (ThermoFisher Scientific). Briefly, 293 cells were lipofected with plasmids encoding the nucleases driven by a strong viral promoter. Cells were grown in suspension culture with agitation and harvested two days post-transfection. The nuclease proteins were fused to a Six-His affinity tag and purified by metal-affinity chromatography to between 50-60% purity. Parallel lysates were made from mock-transfected cells and were subjected to an identical metal-affinity chromatography process. Cas9 was purchased from IDT and was >95% pure.

Figure 7:
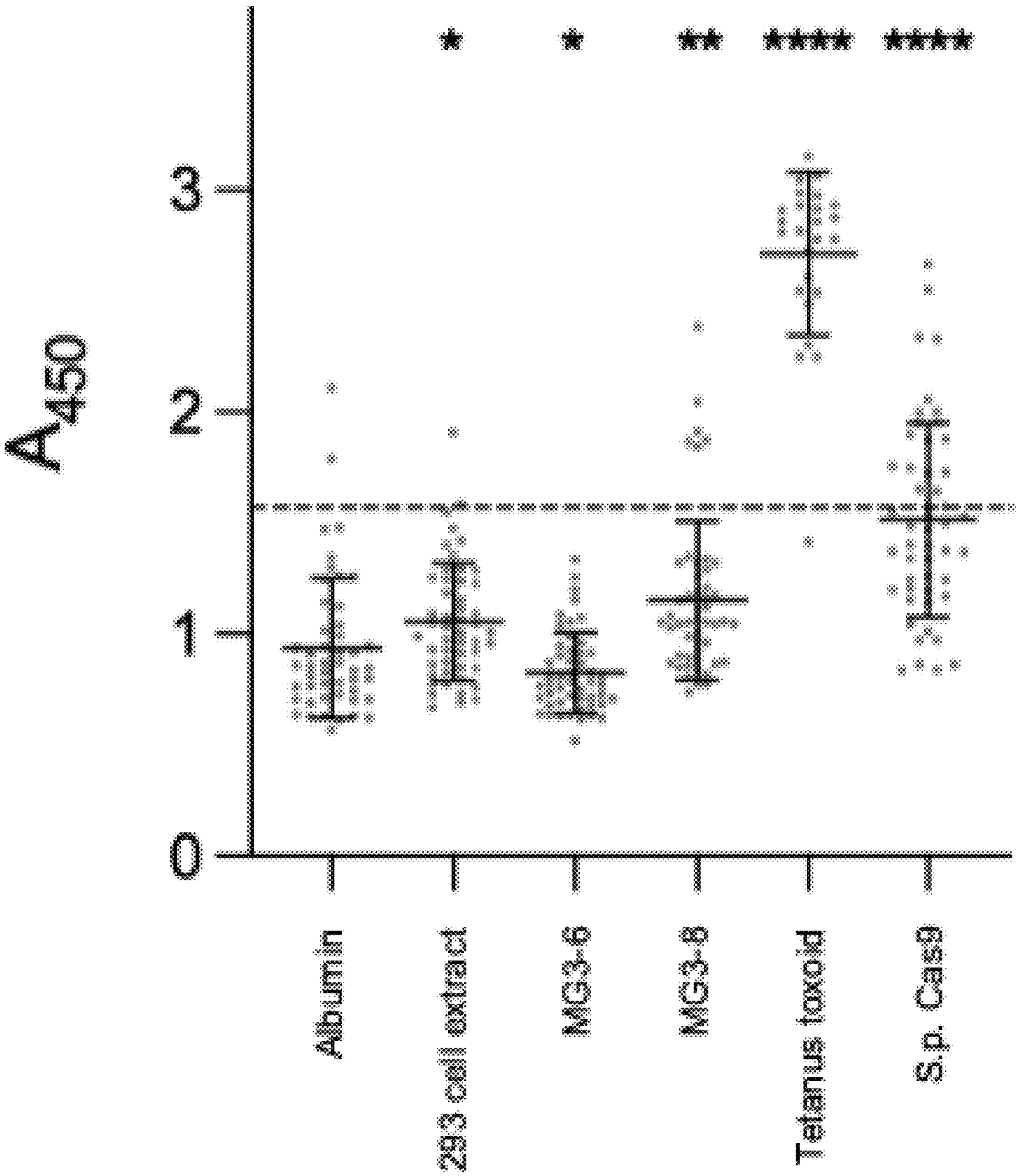
FIG. 7 depicts ELISA results from a screen performed at a serum dilution of 1:50 to detect antibodies against MG-3-6 and MG3-8 (n=50). Tetanus toxoid was used as the positive control due to wide-spread vaccination against this antigen. Serum samples above the dashed line were considered antibody-positive; the line represents the mean absorbance of the negative control (human albumin) plus two standard deviations from the mean. *P<0.05, P<0.01, **P<0.0001 as determined by an unpaired Student's t-test; ns, not significant.

MaxiSorp® ELISA plates (Thermo Scientific) were coated with 0.5 μg of nucleases or control proteins diluted in 1× phosphate buffered saline (PBS) and incubated overnight at room temperature. Plates were then washed and incubated with a 1% (w/v) bovine serum albumin (BSA) (Sigma-Aldrich)/1×PBS solution (1% BSA-PBS) for an hour at room temperature. After another washing step, wells were incubated for 1 h at room temperature with more than 50 separate serum samples taken from randomly selected donors (1:50 dilution in 1% BSA-PBS). Plates were then washed and incubated for an hour at room temperature with a peroxidase-labeled goat anti-human (Fcγ fragment-specific) secondary antibody (Jackson Immuno Research), diluted 1:50,000 in 1% BSA-PBS. The assay was developed using a 3,3',5,5'-Tetramethylbenzidine (TMB) Liquid Substrate System kit (Sigma-Aldrich), according to the manufacturer's specifications. Antibody titers are reported as absorbance values measured at 450 nm (FIG. 7). Tetanus toxoid was used as the positive control due to wide-spread vaccination against this antigen and was purchased from Sigma Aldrich.

Figure 8:
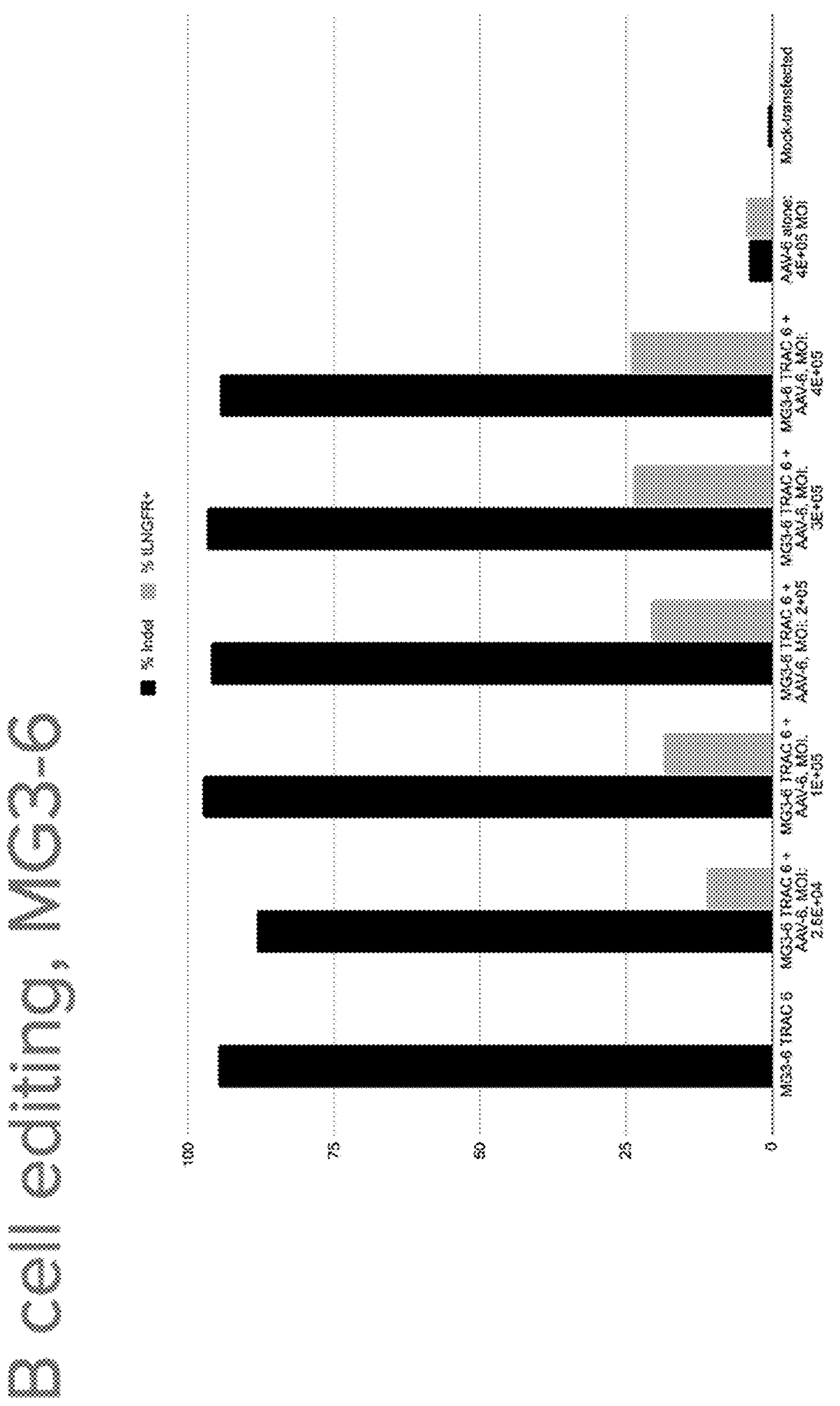
FIG. 8 depicts the gene editing outcomes at the DNA and cell-surface protein level for TRAC in human peripheral blood B cells.

Example 15—Gene Editing Outcomes at the DNA and Cell-Surface Protein Level for TRAC in Human Peripheral Blood B Cells Human Peripheral Blood B cells were purchased from STEMCELL Technologies and expanded using ImmunoCult™ Human B Cell Expansion Kit for 2 days prior to nucleofection. Nucleofection of MG3-6 RNPs (106 pmol protein/160 pmol guide) was performed into B cells (200,000) using the Lonza 4D electroporator. Post-nucleofection cells were immediately recovered into media containing AAV-6 sourced from Virovek. Cells were harvested and genomic DNA prepared five days post-transfection. For NGS analysis, PCR primers appropriate for use in NGS-based DNA sequencing were used to amplify the target sequence for the TRAC 6 guide RNA (SEQ ID NO: 6804). The amplicon was sequenced on an Illumina MiSeq machine and analyzed with a proprietary Python script to measure gene editing. For analysis by flow cytometry, 100,000 cells were stained for viability, expression of B cell surface marker CD19 (CD19 Monoclonal Antibody (HIB19), APC, eBioscience™) and for transgene (SEQ ID NO: 6810) insertion as measured by expression of tLNGFR (CD271 (LNGFR) Antibody, anti-human, REAfinity™). Cells were stained for 30 min at 4° C. and data was acquired on an Attune Nxt flow cytometer. Cells expressing tLNGFR were gated on single, live, CD19+ cells (FIG. 8).

TABLE 6

| SEQ ID NO: | Entity Name | Sequence |
|---|---|---|
| | | Guide sequences used in Example 15 |
| 6804 | MG3-6-TRAC-sgRNA-6 | mC*mG*mA*rArUrCrCrUrCrCrUrCrCrUrGrArArArGrUrGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |

Example 16—Gene Editing Outcomes at the DNA Level for TRAC and AAVS1 in Hematopoietic Stem Cells (HSCs)

Figure 9:
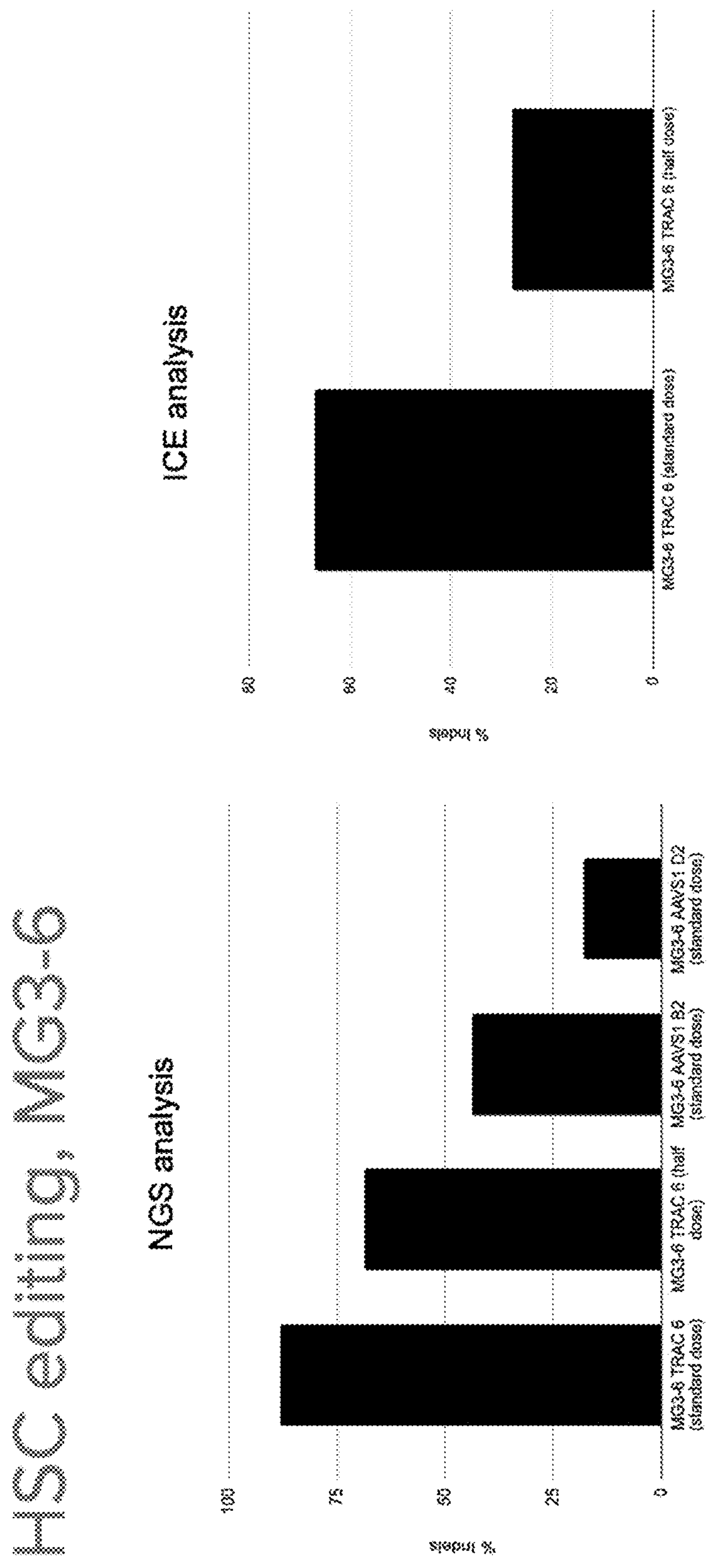
FIG. 9 depicts the gene editing outcomes at the DNA level for TRAC in hematopoietic stem cells.

Mobilized peripheral blood CD34+ cells were acquired from AllCells and cultured in STEMCELL StemSpan™ SFEM II media supplemented with StemSpan™ CC110 cytokine cocktail for 48 hours prior to nucleofection. Nucleofection of MG3-6 RNPs (106 pmol protein/120 pmol guide for standard dose, 52 pmol protein/60 pmol guide for half dose) was performed into HSCs (200,000) using the Lonza 4D electroporator. Cells were harvested and genomic DNA prepared three days post-transfection. PCR primers appropriate for use in Sanger and NGS-based DNA sequencing were generated, optimized, and used to amplify the individual target sequences for each guide RNA (SEQ ID NOs: 6804, 6806, and 6808). The NGS amplicons were sequenced on an Illumina MiSeq machine and analyzed with a proprietary Python script to measure gene editing. The ICE amplicons were sent to Elim Biopharmaceuticals Inc. for Sanger sequencing and analyzed with a proprietary Python script to measure gene editing (FIG. 9).

Example 17—Gene Editing Outcomes at the DNA and Cell-Surface Protein Level for TRAC in Induced Pluripotent Stem Cells (iPSCs) for MG3-6 Delivered as Ribonucleoprotein ATCC-BXS0116 Human [Non-Hispanic Caucasian Female] Induced Pluripotent Stem (IPS) Cells are cultured on Corning Matrigel-coated plasticware in mTESR Plus media (STEMCELL Technologies) containing 10 μM ROCK inhibitor Y-27632 for 24 hr prior to nucleofection. Nucleofection of MG3-6 RNPs (106 pmol protein/120 pmol guide) was performed into iPSCs (200,000) using the Lonza 4D electroporator. Cells were harvested with Accutase for flow cytometry and genomic DNA extraction five days post-transfection. PCR primers appropriate for use in NGS-based DNA sequencing were used to amplify the individual target sequences for the TRAC 6 gRNA (SEQ ID NO: 6804). The amplicons were sequenced on an Illumina MiSeq machine and analyzed with a proprietary Python script to measure gene editing. For analysis by flow cytometry, 5 days post-nucleofection 100,000 iPSCs per sample were stained with LIVE/DEAD™ Fixable Near-IR Dead Cell Stain Kit and CD271 (LNGFR) Antibody, anti-human, REAfinity™ to measure viability and transgene (SEQ ID NO: 6810) insertion, respectively. Cells were fixed and permeabilized

TABLE 7

| SEQ ID NO: | Entity Name | Sequence |
|---|---|---|
| | | Guide sequences used in Example 16 |
| 6804 | MG3-6-TRAC-sgRNA-6 | mC*mG*mA*rArUrCrCrUrCrCrUrCrCrUrGrArArArGrUrGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6806 | MG3-6-AAVS1-sgRNA-B2 | mA*mG*mG*rArArUrCrUrGrCrCrUrArArCrArGrGrArGrGrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6808 | MG3-6-AAVS1-sgRNA-D2 | mU*mA*mG*rGrArArGrGrArGrGrArGrGrCrCrUrArArGrGrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |

Figure 10:
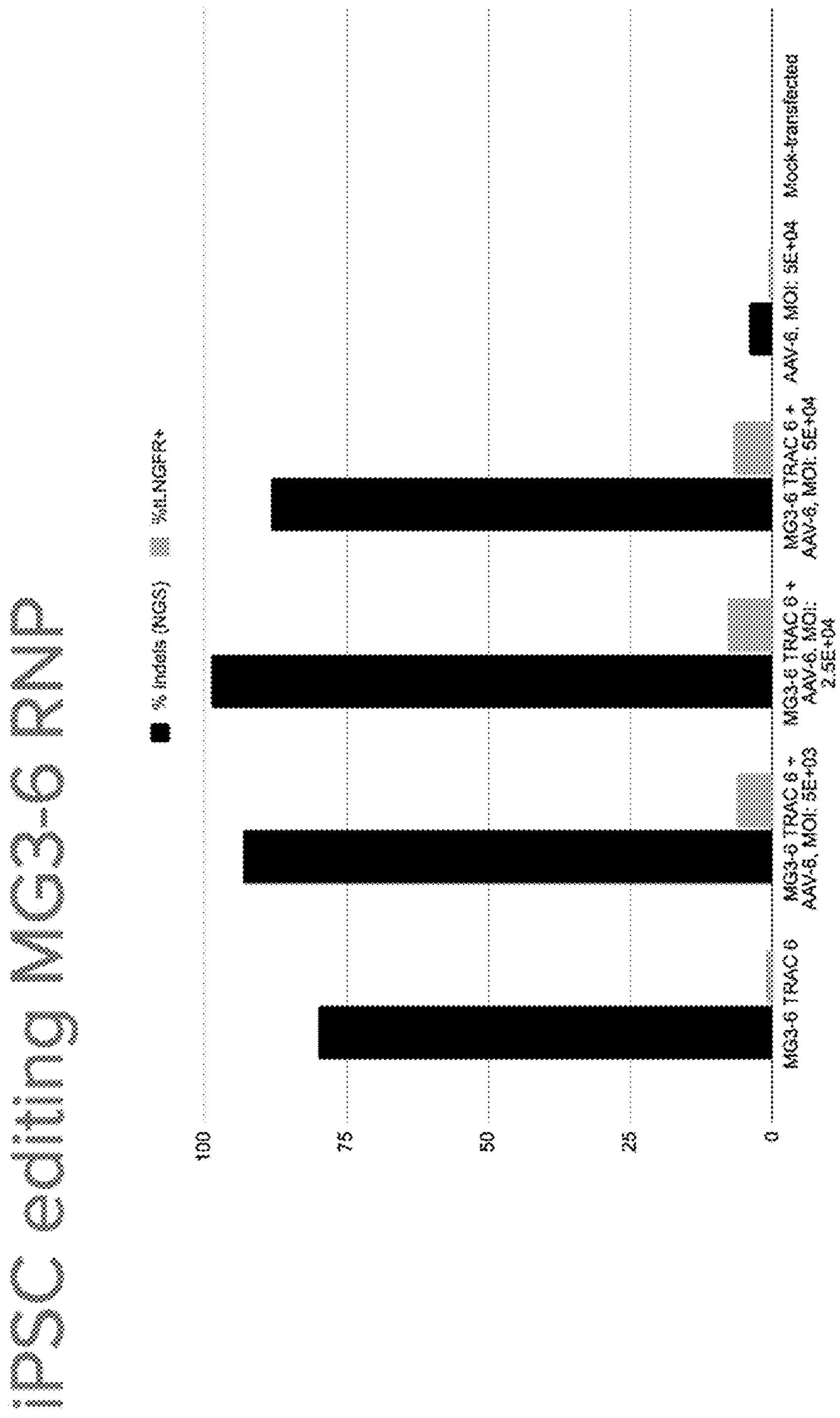
FIG. 10 depicts the gene editing outcomes at the DNA and cell-surface protein level for TRAC in induced pluripotent stem cells (iPSCs) for MG3-6 delivered as a ribonucleoprotein.

(Inside Stain Kit, Miltenyi) and further stained for pluripotency transcription factors Oct4 and Sox2 (Anti-Oct3/4 Isoform A-APC, human and mouse REA338 1: Anti-Sox2-FITC, human and mouse REA320. Cells were acquired on an Attune NxT flow cytometer, and analyzed for tLNGFR expression based on gating on single, live Oct4+Sox2+ cells (FIG. 10)

TABLE 8

Guide sequences used in Example 17

| SEQ ID NO: | Entity Name | Sequence |
|---|---|---|
| 6804 | MG3-6-TRAC-sgRNA-6 | mC*mG*mA*rArUrCrCrUrCrCrUrCrCrUrGrArArArGrUrGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |

Figure 11:
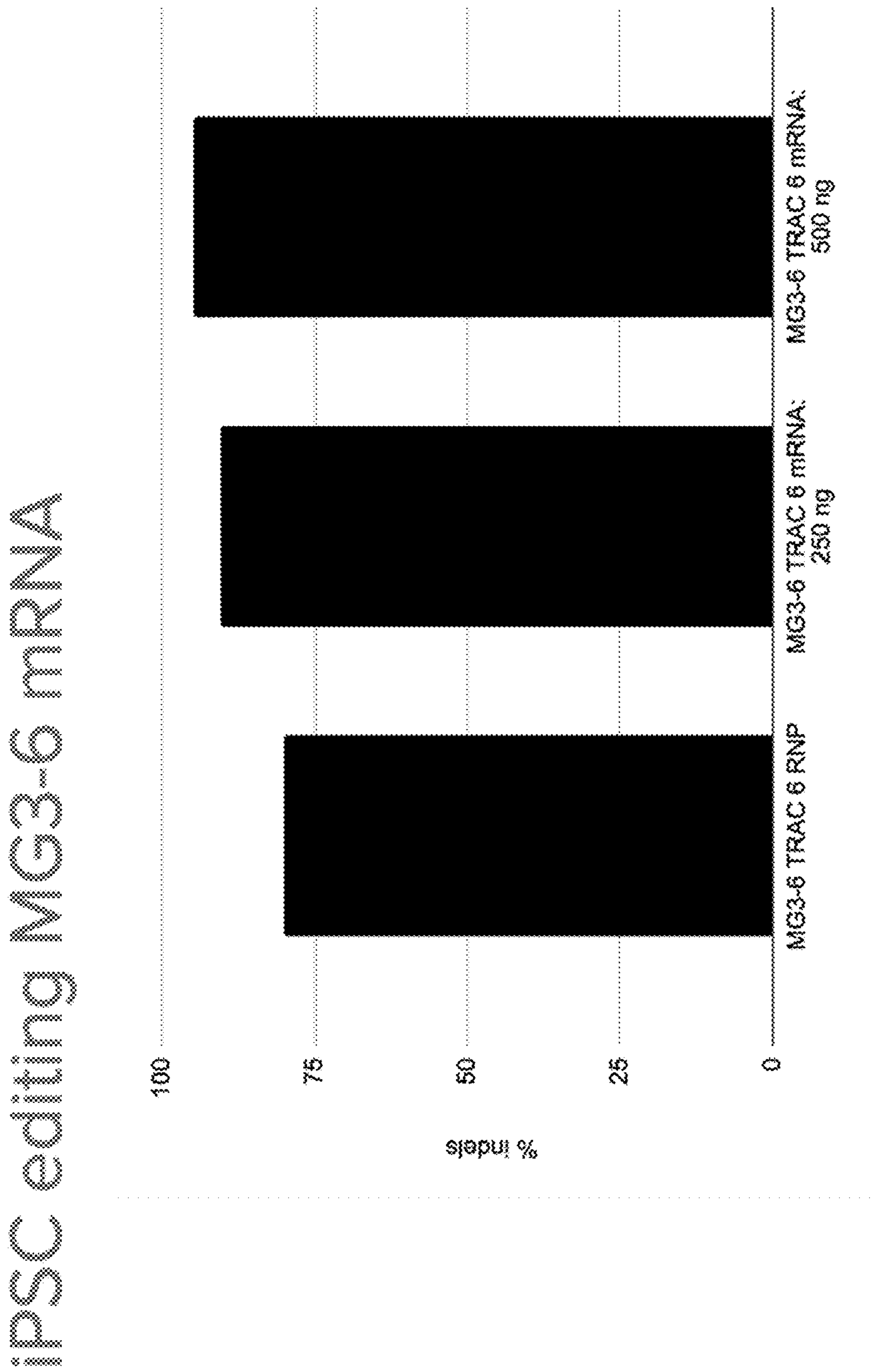
FIG. 11 depicts the gene editing outcomes at the DNA level for TRAC in induced pluripotent stem cells (iPSCs) for MG3-6 delivered as mRNA.

Example 18—Gene Editing Outcomes at the DNA Protein Level for TRAC in Induced Pluripotent Stem Cells (iPSCs) for MG3-6 Delivered as mRNA ATCC-BXS0116 Human [Non-Hispanic Caucasian Female] Induced Pluripotent Stem (IPS) Cells are cultured on Corning Matrigel-coated plasticware in mTESR Plus (STEMCELL Technologies) containing 10 μM ROCK inhibitor Y-27632 for 24 hr prior to nucleofection. Nucleofection of MG3-6 RNPs (106 pmol protein/120 pmol guide) or mRNA (250 or 500 ng mRNA/12 pmol guide) was performed into iPSCs (200,000) using the Lonza 4D electroporator. Cells were harvested with Accutase for genomic DNA extraction five days post-transfection. PCR primers appropriate for use in NGS-based DNA sequencing were used to amplify the individual target sequences for the TRAC 6 gRNA (SEQ ID NO: 6804). The amplicons were sequenced on an Illumina MiSeq machine and analyzed with a proprietary Python script to measure gene editing (FIG. 11).

TABLE 9

Guide sequences used in Example 18

| SEQ ID NO: | Entity Name | Sequence |
|---|---|---|
| 6804 | MG3-6-TRAC-sgRNA-6 | mC*mG*mA*rArUrCrCrUrCrCrUrCrCrUrGrArArArGrUrGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |

Example 19—Gene Editing Outcomes at the DNA Level for CD2

Figure 12:
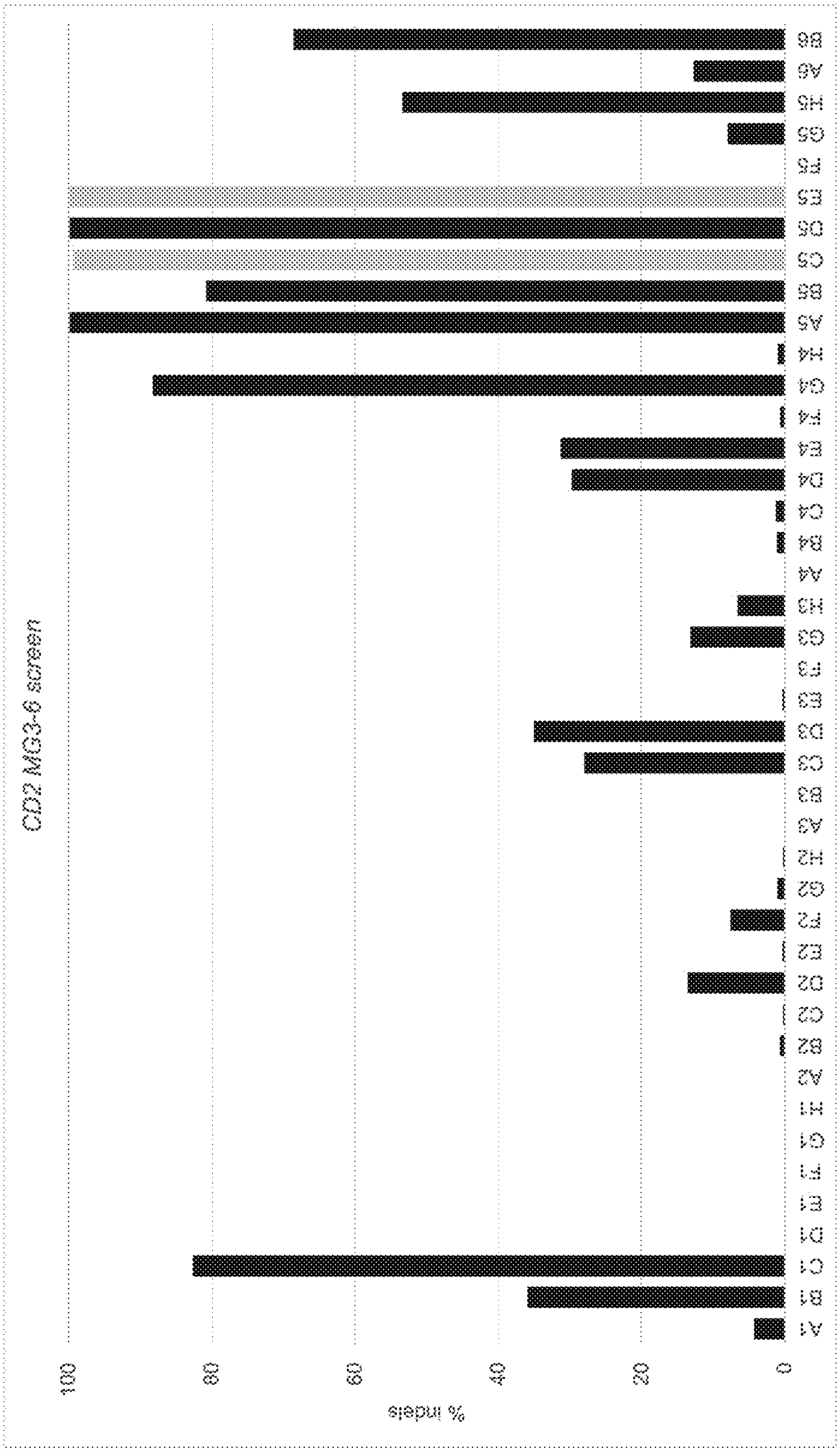
FIG. 12 depicts the gene editing outcomes at the DNA level for CD2 in primary T cells.

Primary T cells were purified from PBMCs using a negative selection kit (Miltenyi) according to the manufacturer's recommendations. Nucleofection of MG3-6 RNPs (106 pmol protein/160 pmol guide) was performed into T cells (200,000) using the Lonza 4D electroporator. Cells were harvested and genomic DNA prepared five days post-transfection. PCR primers appropriate for use in NGS-based DNA sequencing were generated, optimized, and used to amplify the individual target sequences for each guide RNA. The amplicons were sequenced on an Illumina MiSeq machine and analyzed with a proprietary Python script to measure gene editing (FIG. 12).

TABLE 10A

Guide sequences used in Example 19

| SEQ ID NO: | Entity Name | Sequence |
| --- | --- | --- |
| 6811 | MG3-6-CD2-sgRNA-A1 | mA*mU*mU*rUrArCrArUrGrGrArArArGrCrUrCrArUrCrUrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6812 | MG3-6-CD2-sgRNA-B1 | mU*mU*mU*rUrUrArUrArGrGrUrGrCrArGrUrCrUrCrCrArArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6813 | MG3-6-CD2-sgRNA-C1 | mU*mG*mC*rCrUrUrGrGrArArArCrCrUrGrGrGrGrUrGrCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6814 | MG3-6-CD2-sgRNA-D1 | mG*mG*mG*rArArArArArArCrUrUrCrArGrArCrArArGrArArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6815 | MG3-6-CD2-sgRNA-E1 | mU*mU*mG*rCrArCrArArUrUrCrArGrArArArArGrArGrArArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6816 | MG3-6-CD2-sgRNA-F1 | mG*mA*mA*rCrUrCrUrGrArArArArUrUrArArGrCrArUrCrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6817 | MG3-6-CD2-sgRNA-G1 | mU*mG*mU*rUrGrGrArArArArArArUrArUrUrUrGrArUrUrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6818 | MG3-6-CD2-sgRNA-H1 | mU*mG*mA*rUrGrUrCrCrUrGrArCrCrCrArArGrGrCrArCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6819 | MG3-6-CD2-sgRNA-A2 | mC*mC*mA*rArGrGrCrArUrUrCrGrUrArArUrCrUrCrUrUrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6820 | MG3-6-CD2-sgRNA-B2 | mU*mU*mU*rUrArGrArGrArGrGrGrUrCrUrCrArArArArCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6821 | MG3-6-CD2-sgRNA-C2 | mG*mG*mG*rUrCrUrCrArArArArCrCrArArArGrArUrCrUrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6822 | MG3-6-CD2-sgRNA-D2 | mG*mG*mA*rArArCrArUrCrUrArArArArCrUrUrUrCrUrCrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6823 | MG3-6-CD2-sgRNA-E2 | mC*mU*mC*rArGrArGrGrGrUrCrArUrCrArCrArCrArCrArArGrUrUrGrArGrArArUrCrGrArArArGrArUrUrCrUrUrArArUrArArGr |

TABLE 10A-continued

Guide sequences used in Example 19

| SEQ ID NO: | Entity Name | Sequence |
|---|---|---|
| | | GrCrArUrCrCrUrUrCrCrGrArUrGrCrUrGrArCrUrUrCrUrCrArCr<br>CrGrUrCrCrGrUrUrUrCrCrArArUrArGrGrArGrCrGrGrGrCrGr<br>GrUrArUrGrU*mU*mU*mU |
| 6824 | MG3-6-CD2-sgRNA-F2 | mC*mC*mG*rCrCrArCrGrCrArCrCrUrGrGrArCrArGrCrUrGrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrCrCrArArUrArGrGrArGrCrGrGrGrCrGr<br>GrUrArUrGrU*mU*mU*mU |
| 6825 | MG3-6-CD2-sgRNA-G2 | mU*mG*mG*rArCrArGrCrUrGrArCrArGrGrCrUrCrGrArCrArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrCrCrArArUrArGrGrArGrCrGrGrGrCrGr<br>GrUrArUrGrU*mU*mU*mU |
| 6826 | MG3-6-CD2-sgRNA-H2 | mG*mC*mU*rGrUrGrCrArCrUrUrGrArArUrUrUrUrGrCrArCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrCrCrArArUrArGrGrArGrCrGrGrGrCrGr<br>GrUrArUrGrU*mU*mU*mU |
| 6827 | MG3-6-CD2-sgRNA-A3 | mU*mU*mU*rArGrArUrGrUrUrCrCrCrArUrCrUrUrGrArUrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrCrCrArArUrArGrGrArGrCrGrGrGrCrGr<br>GrUrArUrGrU*mU*mU*mU |
| 6828 | MG3-6-CD2-sgRNA-B3 | mC*mC*mA*rUrCrUrUrGrArUrArCrArGrGrUrUrArArUrUrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrCrCrArArUrArGrGrArGrCrGrGrGrCrGr<br>GrUrArUrGrU*mU*mU*mU |
| 6829 | MG3-6-CD2-sgRNA-C3 | mG*mG*mU*rCrArGrUrUrCrCrArUrCrArUrUrArCrCrUrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrCrCrArArUrArGrGrArGrCrGrGrGrCrGr<br>GrUrArUrGrU*mU*mU*mU |
| 6830 | MG3-6-CD2-sgRNA-D3 | mU*mU*mC*rCrArUrUrCrArUrUrArCrCrUrCrArCrArGrGrUrGrU<br>rUrGrArGrArArUrCrGrArArArGrArUrUrCrUrUrArArUrArArGrG<br>rCrArUrCrCrUrUrCrCrGrArUrGrCrUrGrArCrUrUrCrUrCrArCrC<br>rGrUrCrCrGrUrUrUrCrCrArArUrArGrGrArGrCrGrGrGrCrGr<br>GrUrArUrGrU*mU*mU*mU |
| 6831 | MG3-6-CD2-sgRNA-E3 | mG*mG*mG*rUrUrGrUrGrUrUrGrArUrArCrArArGrUrCrCrArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrCrCrArArUrArGrGrArGrCrGrGrGrCrGr<br>GrUrArUrGrU*mU*mU*mU |
| 6832 | MG3-6-CD2-sgRNA-F3 | mA*mA*mG*rUrCrCrArGrGrArGrArUrCrUrUrUrGrGrUrUrUrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrCrCrArArUrArGrGrArGrCrGrGrGrCrGr<br>GrUrArUrGrU*mU*mU*mU |
| 6833 | MG3-6-CD2-sgRNA-G3 | mG*mG*mC*rArGrCrArUrCrCrUrUrGrGrCrCrArGrArGrUrArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrCrCrArArUrArGrGrArGrCrGrGrGrCrGr<br>GrUrArUrGrU*mU*mU*mU |
| 6834 | MG3-6-CD2-sgRNA-H3 | mG*mC*mC*rArGrArGrUrArArUrGrGrGrCrUrCrUrCrUrGrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrCrCrArArUrArGrGrArGrCrGrGrGrCrGr<br>GrUrArUrGrU*mU*mU*mU |

TABLE 10A-continued

Guide sequences used in Example 19

| SEQ ID NO: | Entity Name | Sequence |
|---|---|---|
| 6835 | MG3-6-CD2-sgRNA-A4 | mC*mA*mC*rUrUrCrUrCrUrUrCrCrUrUrUrUrGrCrArGrArGrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6836 | MG3-6-CD2-sgRNA-B4 | mU*mA*mU*rArGrArArArArCrGrArGrCrArGrUrGrCrCrArCrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6837 | MG3-6-CD2-sgRNA-C4 | mA*mG*mC*rArGrUrGrCrCrArCrArArArGrArCrCrArUrCrArGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6838 | MG3-6-CD2-sgRNA-D4 | mA*mU*mG*rCrCrArArUrGrArUrGrArGrArUrArGrArUrGrUrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrUmU*mU*mU |
| 6839 | MG3-6-CD2-sgRNA-E4 | mG*mA*mA*rGrArGrArArGrUrGrGrGrArUrGrGrCrUrGrGrGrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6840 | MG3-6-CD2-sgRNA-F4 | mC*mC*mA*rCrArGrArGrUrArGrCrUrArCrUrGrArArGrArArGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6841 | MG3-6-CD2-sgRNA-G4 | mC*mG*mU*rGrUrUrCrArGrCrArCrCrArGrCrCrUrCrArGrArGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6842 | MG3-6-CD2-sgRNA-H4 | mG*mG*mG*rCrArCrArCrArArGrUrUrCrArCrCrArGrCrArGrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6843 | MG3-6-CD2-sgRNA-A5 | mC*mA*mG*rCrArGrArArArGrGrCrCrCrGrCrCrCrCrUrCrCrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6844 | MG3-6-CD2-sgRNA-B5 | mU*mG*mA*rGrUrUrUrUrCrUrGrCrUrGrCrCrCrCrArUrGrGrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6845 | MG3-6-CD2-sgRNA-C5 | mA*mU*mG*rGrGrGrArGrGrUrUrUrUrGrGrCrUrGrArArCrUrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6846 | MG3-6-CD2-sgRNA-D5 | mU*mG*mA*rArCrUrCrGrArGrGrUrCrUrGrGrGrGrArGrGrGrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6847 | MG3-6-CD2-sgRNA-E5 | mA*mA*mC*rUrUrGrUrGrUrGrCrCrCrGrArCrGrGrArGrCrArGr UrUrGrArGrArArUrCrGrArArArGrArUrUrCrUrUrArArUrArArGr |

TABLE 10A-continued

Guide sequences used in Example 19

| SEQ ID NO: | Entity Name | Sequence |
|---|---|---|
| | | GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mUxmU*mU |
| 6848 | MG3-6-CD2-sgRNA-F5 | mC*mG*mA*rCrGrGrArGrCrArGrGrArGrGrCrCrUrCrUrUrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6849 | MG3-6-CD2-sgRNA-G5 | mG*mG*mA*rGrGrArGrGrArUrGrUrUrGrGrGrArArGrUrUrGrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6850 | MG3-6-CD2-sgRNA-H5 | mG*mU*mU*rGrGrGrArArGrUrUrGrCrUrGrGrArUrUrCrUrGrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6851 | MG3-6-CD2-sgRNA-A6 | mA*mG*mG*rGrGrUrUrGrArArGrCrUrGrGrArArUrUrUrGrGrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6852 | MG3-6-CD2-sgRNA-B6 | mC*mC*mC*rUrUrUrCrUrUrCrArGrUrArGrCrUrArCrUrCrUrGrU<br>rUrGrArGrArArUrCrGrArArArGrArUrUrCrUrUrArArUrArArGrG<br>rCrArUrCrCrUrUrCrCrGrArUrGrCrUrGrArCrUrUrCrUrCrArCrC<br>rGrUrCrCrGrUrUrUrUrCrCrArArUrArGrGrArGrCrGrGrGrCrGr<br>GrUrArUrGrU*mU*mU*mU |

Notations for chemical modifications: m = 2'O-methyl ribonucleotide (e.g mC = cytosine ribonucleotide with 2'-O Methyl in place of 2' hydroxyl); f = 2'-fluoro ribonucleotide (e.g fC = cytosine ribonucleotide with 2' fluorine in place of 2' hydroxyl); * = phosphorothioate bond; r: native RNA linkage comprising the sugar ribose (for example the ribose or RNA form of the A base is written rA), d: deoxyribose sugar (DNA) linkage (for example a deoxyribose form of the A base is written dA)

TABLE 10B

Sites Targeted in Example 19

| SEQ ID NO: | Entity Name | Sequence |
|---|---|---|
| 6853 | MG3-6-CD2-target site-A1 | ATTTACATGGAAAGCTCATCTT |
| 6854 | MG3-6-CD2-target site-B1 | TTTTTATAGGTGCAGTCTCCAA |
| 6855 | MG3-6-CD2-target site-C1 | TGCCTTGGAAACCTGGGGTGCC |
| 6856 | MG3-6-CD2-target site-D1 | GGGAAAAAACTTCAGACAAGAA |
| 6857 | MG3-6-CD2-target site-E1 | TTGCACAATTCAGAAAAGAGAA |
| 6858 | MG3-6-CD2-target site-F1 | GAACTCTGAAAATTAAGCATCT |
| 6859 | MG3-6-CD2-target site-G1 | TGTTGGAAAAAATATTTGATTT |
| 6860 | MG3-6-CD2-target site-H1 | TGATGTCCTGACCCAAGGCACC |
| 6861 | MG3-6-CD2-target site-A2 | CCAAGGCATTCGTAATCTCTTT |
| 6862 | MG3-6-CD2-target site-B2 | TTTTAGAGAGGGTCTCAAAACC |
| 6863 | MG3-6-CD2-target site-C2 | GGGTCTCAAAACCAAAGATCTC |

TABLE 10B-continued

| SEQ ID NO: | Entity Name | Sequence |
|---|---|---|
| | Sites Targeted in Example 19 | |
| 6864 | MG3-6-CD2-target site-D2 | GGAAACATCTAAAACTTTCTCA |
| 6865 | MG3-6-CD2-target site-E2 | CTCAGAGGGTCATCACACACAA |
| 6866 | MG3-6-CD2-target site-F2 | CCGCCACGCACCTGGACAGCTG |
| 6867 | MG3-6-CD2-target site-G2 | TGGACAGCTGACAGGCTCGACA |
| 6868 | MG3-6-CD2-target site-H2 | GCTGTGCACTTGAATTTTGCAC |
| 6869 | MG3-6-CD2-target site-A3 | TTTAGATGTTTCCCATCTTGAT |
| 6870 | MG3-6-CD2-target site-B3 | CCATCTTGATACAGGTTTAATT |
| 6871 | MG3-6-CD2-target site-C3 | GGTCAGTTCCATTCATTACCTC |
| 6872 | MG3-6-CD2-target site-D3 | TTCCATTCATTACCTCACAGGT |
| 6873 | MG3-6-CD2-target site-E3 | GGGTTGTGTTGATACAAGTCCA |
| 6874 | MG3-6-CD2-target site-F3 | AAGTCCAGGAGATCTTTGGTTT |
| 6875 | MG3-6-CD2-target site-G3 | GGCAGCATCCTTGGCCAGAGTA |
| 6876 | MG3-6-CD2-target site-H3 | GCCAGAGTAATGGGCTCTCTGC |
| 6877 | MG3-6-CD2-target site-A4 | CACTTCTCTTCCTTTTGCAGAG |
| 6878 | MG3-6-CD2-target site-B4 | TATAGAAAACGAGCAGTGCCAC |
| 6879 | MG3-6-CD2-target site-C4 | AGCAGTGCCACAAAGACCATCA |
| 6880 | MG3-6-CD2-target site-D4 | ATGCCAATGATGAGATAGATGT |
| 6881 | MG3-6-CD2-target site-E4 | GAAGAGAAGTGGGATGGCTGGG |
| 6882 | MG3-6-CD2-target site-F4 | CCACAGAGTAGCTACTGAAGAA |
| 6883 | MG3-6-CD2-target site-G4 | CGTGTTCAGCACCAGCCTCAGA |
| 6884 | MG3-6-CD2-target site-H4 | GGGCACACAAGTTCACCAGCAG |
| 6885 | MG3-6-CD2-target site-A5 | CAGCAGAAAGGCCCGCCCCTCC |
| 6886 | MG3-6-CD2-target site-B5 | TGAGTTTTCTGCTGCCCCATGG |
| 6887 | MG3-6-CD2-target site-C5 | ATGGGGAGGTTTTGGCTGAACT |
| 6888 | MG3-6-CD2-target site-D5 | TGAACTCGAGGTCTGGGGAGGG |
| 6889 | MG3-6-CD2-target site-E5 | AACTTGTGTGCCCGACGGAGCA |
| 6890 | MG3-6-CD2-target site-F5 | CGACGGAGCAGGAGGCCTCTTC |
| 6891 | MG3-6-CD2-target site-G5 | GGAGGAGGATGTTGGGAAGTTG |
| 6892 | MG3-6-CD2-target site-H5 | GTTGGGAAGTTGCTGGATTCTG |
| 6893 | MG3-6-CD2-target site-A6 | AGGGGTTGAAGCTGGAATTTGG |
| 6894 | MG3-6-CD2-target site-B6 | CCCTTTCTTCAGTAGCTACTCT |

Example 20—Gene Editing Outcomes at the DNA Level for CD5

Figure 13:
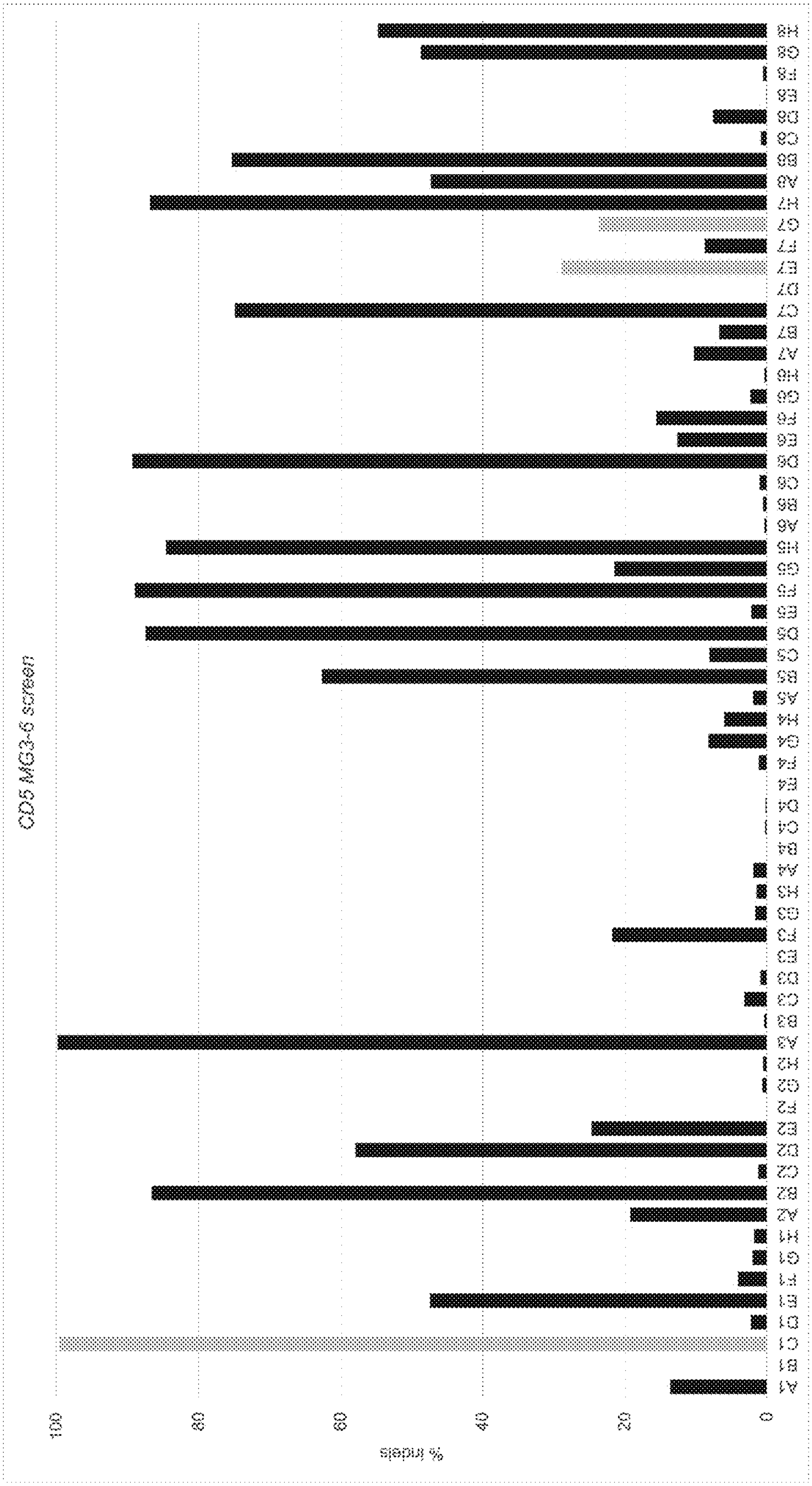
FIG. 13 depicts the gene editing outcomes at the DNA level for CD5 in primary T cells.

Primary T cells were purified from PBMCs using a negative selection kit (Miltenyi) according to the manufacturer's recommendations. Nucleofection of MG3-6 RNPs (106 pmol protein/160 pmol guide) was performed into T cells (200,000) using the Lonza 4D electroporator. Cells were harvested and genomic DNA prepared five days post-transfection. PCR primers appropriate for use in NGS-based DNA sequencing were generated, optimized, and used to amplify the individual target sequences for each guide RNA. The amplicons were sequenced on an Illumina MiSeq machine and analyzed with a proprietary Python script to measure gene editing (FIG. 13).

TABLE 11A

Guide sequences used in Example 20

| SEQ ID NO: | Entity Name | Sequence |
|---|---|---|
| 6895 | MG3-6-CD5-sgRNA-A1 | mA*mG*mA*rArGrGrCrCrArGrArArArCrCrArUrGrCrCrCrArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6896 | MG3-6-CD5-sgRNA-B1 | mG*mU*mA*rCrArArGrGrUrGrGrCrCrArGrCrGrGrUrUrGrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrUxmU*mU*mU |
| 6897 | MG3-6-CD5-sgRNA-C1 | mU*mU*mC*rUrGrArCrCrCrCrCrArGrArUrUrUrCrCrArGrGrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6898 | MG3-6-CD5-sgRNA-D1 | mC*mA*mC*rCrCrGrUrUrCrCrArArCrUrCrGrArArGrUrGrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6899 | MG3-6-CD5-sgRNA-E1 | mA*mC*mU*rCrGrArArGrUrGrCrCrArGrGrGrCrCrArGrCrUrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6900 | MG3-6-CD5-sgRNA-F1 | mG*mC*mA*rCrArUrGrGrUrUrUrGrCrArGrCrCrArGrArGrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6901 | MG3-6-CD5-sgRNA-G1 | mG*mG*mG*rCrCrGrGrArGrCrUrCrCrArArGrCrArGrUrGrGrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6902 | MG3-6-CD5-sgRNA-H1 | mC*mU*mC*rArArUrCrArUrCrUrGrCrUrArCrGrGrArCrArArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6903 | MG3-6-CD5-sgRNA-A2 | mC*mA*mG*rArArArUrGrArCrArUrGrUrGrUrCrArCrUrCrUrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6904 | MG3-6-CD5-sgRNA-B2 | mG*mG*mC*rUrGrGrCrUrArGrUrUrArCrCrCrArCrCrUrArArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6905 | MG3-6-CD5-sgRNA-C2 | mG*mC*mU*rArGrUrUrArCrCrCrArCrCrUrArArGrCrArGrGrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6906 | MG3-6-CD5-sgRNA-D2 | mU*mG*mA*rGrGrUrGrUrGrUrArGrGrUrGrArCrArArGrGrArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6907 | MG3-6-CD5-sgRNA-E2 | mG*mU*mG*rUrArGrGrUrGrArCrArArGrGrArArGrGrGrGrCrGr<br>UrUrGrArGrArArUrCrGrArArArGrArUrUrCrUrUrArArUrArArGr |

TABLE 11A-continued

Guide sequences used in Example 20

| SEQ ID NO: | Entity Name | Sequence |
|---|---|---|
| | | GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6908 | MG3-6-CD5-sgRNA-F2 | mG*mC*mA*rCrCrCrCrArCrArGrUrUrCrArGrCrCrGrCrUrGrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6909 | MG3-6-CD5-sgRNA-G2 | mU*mG*mG*rCrArGrArCrUrUrUrUrGrArCrGrCrUrUrGrArCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6910 | MG3-6-CD5-sgRNA-H2 | mC*mC*mA*rUrGrUrGrCrCrArUrCrCrGrUrCrCrUrUrGrArGrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6911 | MG3-6-CD5-sgRNA-A3 | mG*mG*mU*rGrArGrCrCrUrUrGrCrCrUrGrGrArArArUrCrUrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6912 | MG3-6-CD5-sgRNA-B3 | mC*mA*mG*rArArGrArCrArArCrArCrCrUrCrCrArArCrGrArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6913 | MG3-6-CD5-sgRNA-C3 | mC*mA*mA*rCrUrCrCrArGrArGrCrCrCrArCrArGrGrUrArArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6914 | MG3-6-CD5-sgRNA-D3 | mG*mG*mG*rCrUrCrUrGrGrArGrUrUrGrUrGrGrUrGrGrGrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6915 | MG3-6-CD5-sgRNA-E3 | mU*mG*mU*rCrGrUrUrGrGrArGrGrUrGrUrUrGrUrCrUrUrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6916 | MG3-6-CD5-sgRNA-F3 | mC*mU*mC*rUrCrUrCrCrUrCrUrCrCrUrArGrCrUrCrCrUrCrGrU<br>rUrGrArGrArArUrCrGrArArArGrArUrUrCrUrUrArArUrArArGrG<br>rCrArUrCrCrUrUrCrCrGrArUrGrCrUrGrArCrUrUrCrUrCrArCrC<br>rGrUrCrCrGrUrUrUrUrCrCrArArUrArGrGrArGrCrGrGrGrCrGr<br>GrUrArUrGrUxmU*mU*mU |
| 6917 | MG3-6-CD5-sgRNA-G3 | mG*mC*mC*rUrGrGrGrGrGrUrArCrCrArUrCrArGrCrUrArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6918 | MG3-6-CD5-sgRNA-H3 | mC*mC*mA*rUrCrArGrCrUrArUrGrArGrGrCrCrCrArGrGrArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |

TABLE 11A-continued

Guide sequences used in Example 20

| SEQ ID NO: | Entity Name | Sequence |
|---|---|---|
| 6919 | MG3-6-CD5-sgRNA-A4 | mC*mU*mA*rUrGrArGrGrCrCrCrArGrGrArCrArArGrArCrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6920 | MG3-6-CD5-sgRNA-B4 | mG*mC*mU*rCrCrUrUrCrUrUrGrArArGrCrArUrCrUrGrCrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6921 | MG3-6-CD5-sgRNA-C4 | mA*mG*mA*rGrArCrUrGrArGrGrCrArGrGrCrArGrArGrCrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6922 | MG3-6-CD5-sgRNA-D4 | mA*mC*mC*rArGrCrCrCrUrUrGrCrCrArArUrCrCrArArUrGrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6923 | MG3-6-CD5-sgRNA-E4 | mU*mG*mC*rCrCrUrCrCrUrUrUrGrCrUrCrArGrGrUrArArGrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6924 | MG3-6-CD5-sgRNA-F4 | mG*mG*mC*rArArGrArArCrUrCrGrGrCrCrArCrUrUrUrUrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6925 | MG3-6-CD5-sgRNA-G4 | mC*mC*mA*rGrGrGrArGrGrUrArCrArGrCrUrUrGrArGrUrUrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6926 | MG3-6-CD5-sgRNA-H4 | mA*mG*mC*rUrUrGrArGrUrUrCrUrGrGrArUrCrUrUrCrCrArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6927 | MG3-6-CD5-sgRNA-A5 | mC*mU*mG*rGrArUrCrUrUrCrCrArUrUrGrGrArUrUrGrGrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6928 | MG3-6-CD5-sgRNA-B5 | mG*mG*mC*rUrGrGrUrGrUrUrCrCrCrGrUrGrGrCrUrCrCrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrUxmU*mU*mU |
| 6929 | MG3-6-CD5-sgRNA-C5 | mG*mU*mU*rCrCrCrGrUrGrGrCrUrCrCrCrCrUrGrGrGrUrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6930 | MG3-6-CD5-sgRNA-D5 | mU*mG*mC*rUrUrCrArArGrArArGrGrArGrCrCrArCrArCrUrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6931 | MG3-6-CD5-sgRNA-E5 | mA*mG*mG*rUrUrGrUrUrGrCrArGrArGrGrArArGrUrUrCrUrGr<br>UrUrGrArGrArArUrCrGrArArArGrArUrUrCrUrUrArArUrArArGr |

TABLE 11A-continued

Guide sequences used in Example 20

| SEQ ID NO: | Entity Name | Sequence |
|---|---|---|
| | | GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6932 | MG3-6-CD5-sgRNA-F5 | mU*mG*mC*rArGrArGrGrArArGrUrUrCrUrCrCrArGrGrUrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrUxmU*mU*mU |
| 6933 | MG3-6-CD5-sgRNA-G5 | mU*mC*mU*rCrCrArGrGrUrCrCrUrGrGrGrUrCrUrUrGrUrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6934 | MG3-6-CD5-sgRNA-H5 | mG*mC*mC*rUrCrArUrArGrCrUrGrArUrGrGrUrArCrCrCrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6935 | MG3-6-CD5-sgRNA-A6 | mC*mA*mC*rGrCrCrGrGrCrArCrArGrUrGrCrUrGrGrCrCrGrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6936 | MG3-6-CD5-sgRNA-B6 | mA*mA*mG*rGrCrArCrCrGrUrGrGrArGrGrUrGrCrGrCrCrArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6937 | MG3-6-CD5-sgRNA-C6 | mG*mA*mC*rGrCrUrGrGrUrGrArCrCrCrArArCrArUrCrCrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6938 | MG3-6-CD5-sgRNA-D6 | mG*mG*mA*rCrArGrArArGrArGrCrCrCrCrCrGrGrGrArUrGrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6939 | MG3-6-CD5-sgRNA-E6 | mU*mC*mC*rUrGrGrCrUrGrArArGrArGrCrUrGrUrCrArCrArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6940 | MG3-6-CD5-sgRNA-F6 | mC*mC*mC*rCrArCrCrArGrArCrGrGrCrUrCrUrGrCrArCrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6941 | MG3-6-CD5-sgRNA-G6 | mC*mC*mC*rArGrGrCrCrArGrGrArUrCrCrArArArCrCrCrCrGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |
| 6942 | MG3-6-CD5-sgRNA-H6 | mU*mU*mC*rArCrUrArGrCrUrUrCrUrUrGrUrArGrGrCrArArGr<br>UrUrGrArGrArArUrCrGrArArArGrArUrUrCrUrUrArArUrArArGr<br>GrCrArUrCrCrUrUrCrCrGrArUrGrCrUrGrArCrUrUrCrUrCrArCr<br>CrGrUrCrCrGrUrUrUrUrCrCrArArUrArGrGrArGrCrGrGrGrCrGr<br>GrUrArUrGrU*mU*mU*mU |

TABLE 11A-continued

Guide sequences used in Example 20

| SEQ ID NO: | Entity Name | Sequence |
|---|---|---|
| 6943 | MG3-6-CD5-sgRNA-A7 | mC*mC*mA*rGrCrArGrCrArCrCrArCrCrArGrGrArGrCrArCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6944 | MG3-6-CD5-sgRNA-B7 | mA*mU*mG*rCrUrUrGrCrCrArCrCrGrUrGrCrCrUrGrCrGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6945 | MG3-6-CD5-sgRNA-C7 | mA*mC*mC*rGrUrGrCrCrUrGrCrGrGrCrCrArGrGrCrCrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6946 | MG3-6-CD5-sgRNA-D7 | mC*mC*mU*rGrCrGrGrCrCrArGrGrCrCrUrGrCrGrGrGrGrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6947 | MG3-6-CD5-sgRNA-E7 | mU*mC*mC*rGrCrCrArGrArArGrArArGrCrArGrCrGrCrCrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrUmU*mU*mU |
| 6948 | MG3-6-CD5-sgRNA-F7 | mU*mU*mA*rCrUrGrUrUrUrGrGrUrUrCrArUrUrCrCrCrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6949 | MG3-6-CD5-sgRNA-G7 | mU*mC*mC*rArCrUrGrGrCrGrCrUrGrCrUrUrCrUrUrCrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6950 | MG3-6-CD5-sgRNA-H7 | mA*mG*mC*rUrGrArCrArGrGrUrGrGrGrArGrUrUrCrCrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6951 | MG3-6-CD5-sgRNA-A8 | mG*mG*mC*rUrGrUrArUrUrCrGrUrUrArUrCrCrArCrGrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6952 | MG3-6-CD5-sgRNA-B8 | mUmC*mG*rUrUrArUrCrCrArCrGrUrGrGrGrArGrGrCrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6953 | MG3-6-CD5-sgRNA-C8 | mG*mG*mA*rGrGrCrUrGrUrGrGrGrGrUrUrCrUrCrArGrCrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6954 | MG3-6-CD5-sgRNA-D8 | mC*mC*mU*rUrUrCrUrUrUrCrCrCrCrArGrCrUrCrUrGrGrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 6955 | MG3-6-CD5-sgRNA-E8 | mC*mC*mG*rArCrArGrUrGrArCrUrArUrGrArUrCrUrGrCrArGrUrUrGrArGrArArUrCrGrArArArGrArUrUrCrUrUrArArUrArArGr |

TABLE 11A-continued

| Guide sequences used in Example 20 | | |
|---|---|---|
| SEQ ID NO: | Entity Name | Sequence |
| | | GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrUmUxmU*mU |
| 6956 | MG3-6-CD5-sgRNA-F8 | mG*mA*mC*rUrArUrGrArUrCrUrGrCrArUrGrGrGrGrCrUrCrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6957 | MG3-6-CD5-sgRNA-G8 | mC*mU*mU*rUrArCrArGrCrCrUrCrUrGrArGrCrCrCrCrArUrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |
| 6958 | MG3-6-CD5-sgRNA-H8 | mA*mU*mA*rGrUrCrArCrUrGrUrCrGrGrArGrGrArGrUrUrGrGr UrUrGrArGrArArUrCrGrArArArGrArUrUrCrUrUrArArUrArArGr GrCrArUrCrCrUrUrCrCrGrArUrGrCrUrGrArCrUrUrCrUrCrArCr CrGrUrCrCrGrUrUrUrUrCrCrArArUrArGrGrArGrCrGrGrGrCrGr GrUrArUrGrU*mU*mU*mU |

Notations for chemical modifications: m = 2'O-methyl ribonucleotide (e.g mC = cytosine ribonucleotide with 2'-O Methyl in place of 2' hydroxyl); f = 2'-fluoro ribonucleotide (e.g fC = cytosine ribonucleotide with 2' fluorine in place of 2' hydroxyl); * = phosphorothioate bond; r: native RNA linkage comprising the sugar ribose (for example the ribose or RNA form of the A base is written rA), d: deoxyribose sugar (DNA) linkage (for example a deoxyribose form of the A base is written dA)

TABLE 11B

| Sites Targeted in Example 20 | | |
|---|---|---|
| SEQ ID NO: | Entity Name | Sequence |
| 6959 | MG3-6-CD5-target site-A1 | AGAAGGCCAGAAACCATGCCCA |
| 6960 | MG3-6-CD5-target site-B1 | GTACAAGGTGGCCAGCGGTTGC |
| 6961 | MG3-6-CD5-target site-C1 | TTCTGACCCCCAGATTTCCAGG |
| 6962 | MG3-6-CD5-target site-D1 | CACCCGTTCCAACTCGAAGTGC |
| 6963 | MG3-6-CD5-target site-E1 | ACTCGAAGTGCCAGGGCCAGCT |
| 6964 | MG3-6-CD5-target site-F1 | GCACATGGTTTGCAGCCAGAGC |
| 6965 | MG3-6-CD5-target site-G1 | GGGCCGGAGCTCCAAGCAGTGG |
| 6966 | MG3-6-CD5-target site-H1 | CTCAATCATCTGCTACGGACAA |
| 6967 | MG3-6-CD5-target site-A2 | CAGAAATGACATGTGTCACTCT |
| 6968 | MG3-6-CD5-target site-B2 | GGCTGGCTAGTTACCCACCTAA |
| 6969 | MG3-6-CD5-target site-C2 | GCTAGTTACCCACCTAAGCAGG |
| 6970 | MG3-6-CD5-target site-D2 | TGAGGTGTGTAGGTGACAAGGA |
| 6971 | MG3-6-CD5-target site-E2 | GTGTAGGTGACAAGGAAGGGGC |
| 6972 | MG3-6-CD5-target site-F2 | GCACCCCACAGTTCAGCCGCTG |
| 6973 | MG3-6-CD5-target site-G2 | TGGCAGACTTTTGACGCTTGAC |
| 6974 | MG3-6-CD5-target site-H2 | CCATGTGCCATCCGTCCTTGAG |
| 6975 | MG3-6-CD5-target site-A3 | GGTGAGCCTTGCCTGGAAATCT |
| 6976 | MG3-6-CD5-target site-B3 | CAGAAGACAACACCTCCAACGA |
| 6977 | MG3-6-CD5-target site-C3 | CAACTCCAGAGCCCACAGGTAA |

TABLE 11B-continued

Sites Targeted in Example 20

| SEQ ID NO: | Entity Name | Sequence |
|---|---|---|
| 6978 | MG3-6-CD5-target site-D3 | GGGCTCTGGAGTTGTGGTGGGC |
| 6979 | MG3-6-CD5-target site-E3 | TGTCGTTGGAGGTGTTGTCTTC |
| 6980 | MG3-6-CD5-target site-F3 | CTCTCTCCTCTCCTAGCTCCTC |
| 6981 | MG3-6-CD5-target site-G3 | GCCTGGGGGGTACCATCAGCTA |
| 6982 | MG3-6-CD5-target site-H3 | CCATCAGCTATGAGGCCCAGGA |
| 6983 | MG3-6-CD5-target site-A4 | CTATGAGGCCCAGGACAAGACC |
| 6984 | MG3-6-CD5-target site-B4 | GCTCCTTCTTGAAGCATCTGCC |
| 6985 | MG3-6-CD5-target site-C4 | AGAGACTGAGGCAGGCAGAGCC |
| 6986 | MG3-6-CD5-target site-D4 | ACCAGCCCTTGCCAATCCAATG |
| 6987 | MG3-6-CD5-target site-E4 | TGCCCTCCTTTGCTCAGGTAAG |
| 6988 | MG3-6-CD5-target site-F4 | GGCAAGAACTCGGCCACTTTTC |
| 6989 | MG3-6-CD5-target site-G4 | CCAGGGAGGTACAGCTTGAGTT |
| 6990 | MG3-6-CD5-target site-H4 | AGCTTGAGTTCTGGATCTTCCA |
| 6991 | MG3-6-CD5-target site-A5 | CTGGATCTTCCATTGGATTGGC |
| 6992 | MG3-6-CD5-target site-B5 | GGCTGGTGTTCCCGTGGCTCCC |
| 6993 | MG3-6-CD5-target site-C5 | GTTCCCGTGGCTCCCCTGGGTC |
| 6994 | MG3-6-CD5-target site-D5 | TGCTTCAAGAAGGAGCCACACT |
| 6995 | MG3-6-CD5-target site-E5 | AGGTTGTTGCAGAGGAAGTTCT |
| 6996 | MG3-6-CD5-target site-F5 | TGCAGAGGAAGTTCTCCAGGTC |
| 6997 | MG3-6-CD5-target site-G5 | TCTCCAGGTCCTGGGTCTTGTC |
| 6998 | MG3-6-CD5-target site-H5 | GCCTCATAGCTGATGGTACCCC |
| 6999 | MG3-6-CD5-target site-A6 | CACGCCGGCACAGTGCTGGCCG |
| 7000 | MG3-6-CD5-target site-B6 | AAGGCACCGTGGAGGTGCGCCA |
| 7001 | MG3-6-CD5-target site-C6 | GACGCTGGTGACCCAACATCCC |
| 7002 | MG3-6-CD5-target site-D6 | GGACAGAAGAGCCCCCGGGATG |
| 7003 | MG3-6-CD5-target site-E6 | TCCTGGCTGAAGAGCTGTCACA |
| 7004 | MG3-6-CD5-target site-F6 | CCCCACCAGACGGCTCTGCACC |
| 7005 | MG3-6-CD5-target site-G6 | CCCAGGCCAGGATCCAAACCCC |
| 7006 | MG3-6-CD5-target site-H6 | TTCACTAGCTTCTTGTAGGCAA |
| 7007 | MG3-6-CD5-target site-A7 | CCAGCAGCACCACCAGGAGCAC |
| 7008 | MG3-6-CD5-target site-B7 | ATGCTTGCCACCGTGCCTGCGG |
| 7009 | MG3-6-CD5-target site-C7 | ACCGTGCCTGCGGCCAGGCCTG |
| 7010 | MG3-6-CD5-target site-D7 | CCTGCGGCCAGGCCTGCGGGGT |
| 7011 | MG3-6-CD5-target site-E7 | TCCGCCAGAAGAAGCAGCGCCA |
| 7012 | MG3-6-CD5-target site-F7 | TTACTGTTTTGGTTCATTCCCG |
| 7013 | MG3-6-CD5-target site-G7 | TCCACTGGCGCTGCTTCTTCTG |
| 7014 | MG3-6-CD5-target site-H7 | AGCTGACAGGTGGGAGTTCCTG |

TABLE 11B-continued

| Sites Targeted in Example 20 | | |
|---|---|---|
| SEQ ID NO: | Entity Name | Sequence |
| 7015 | MG3-6-CD5-target site-A8 | GGCTGTATTCGTTATCCACGTG |
| 7016 | MG3-6-CD5-target site-B8 | TCGTTATCCACGTGGGAGGCTG |
| 7017 | MG3-6-CD5-target site-C8 | GGAGGCTGTGGGGTTCTCAGCA |
| 7018 | MG3-6-CD5-target site-D8 | CCTTTCTTTCCCCAGCTCTGGA |
| 7019 | MG3-6-CD5-target site-E8 | CCGACAGTGACTATGATCTGCA |
| 7020 | MG3-6-CD5-target site-F8 | GACTATGATCTGCATGGGGCTC |
| 7021 | MG3-6-CD5-target site-G8 | CTTTACAGCCTCTGAGCCCCAT |
| 7022 | MG3-6-CD5-target site-H8 | ATAGTCACTGTCGGAGGAGTTG |

Example 21—Targeted RNA Cleavage by MG3-6 and MG3-8

Figure 14:
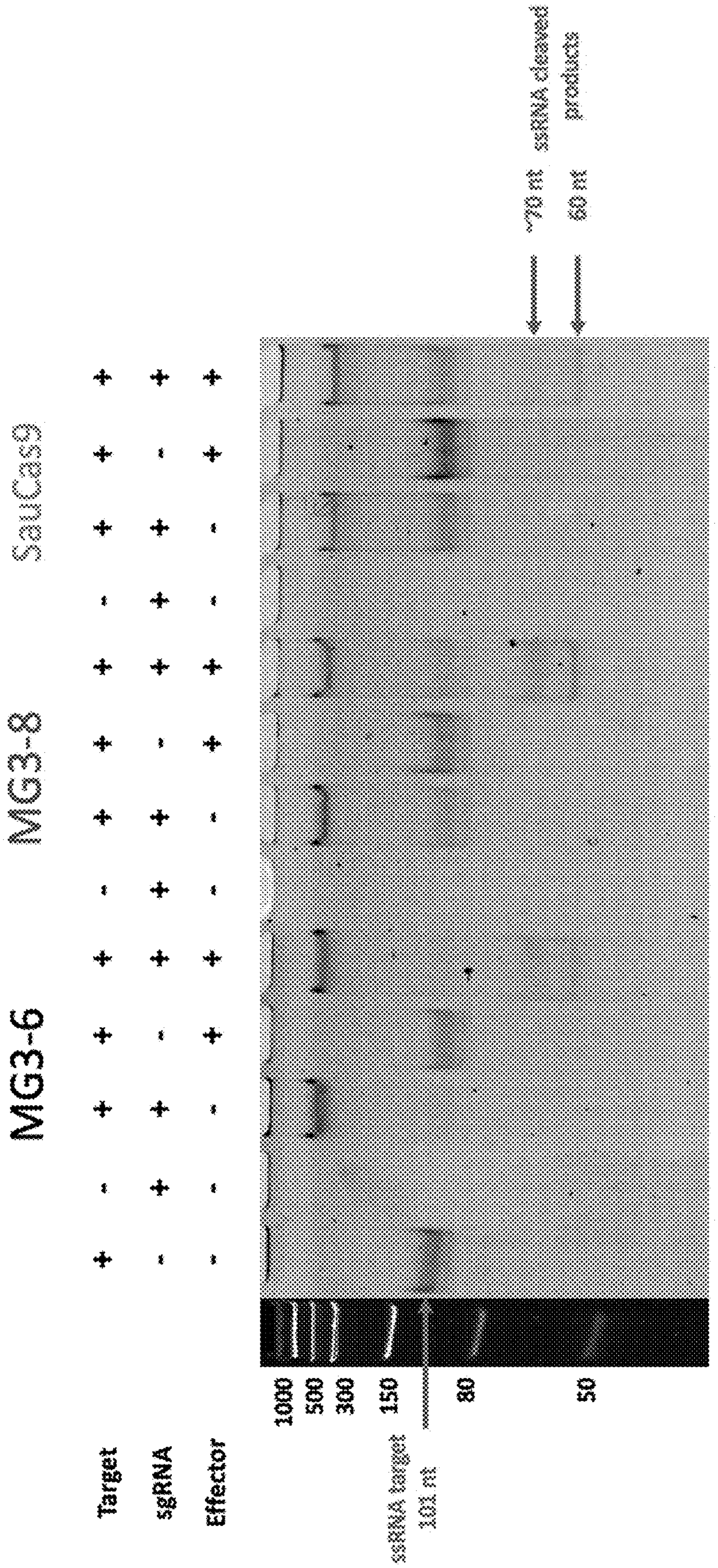
FIG. 14 depicts targeted RNA cleavage by MG3-6 and MG3-8.

A 101 ft RNA containing the spacer (GGUCAGGGCGC-GUCAGCGGGUGUUGGCGGGUGUCGGGGCUGGC-UUAAAUUUUG GACCAGUCGAGGC-UUGCGACGUGGUGGCUUUUCCAGUCGGGAA-ACCUG) with 5' adjacent sequence UUGGACCA were prepared via transcription of a T7 promoter-containing PCR product using the T7 Megascript kit (NEB) according to manufacturer instructions. The resulting RNA was purified using a Monarch RNA prep spin column (NEB) and then labeled with the 5' EndTag kit (Vector labs) using a FAM-maleimide dye per recommended instructions. The resulting RNA has one 5' label and an expected band size of 60 nt if cleaved at a single position in the spacer. For testing RNA cleavage, 2 pmol of protein and sgRNA were pre-incubated for 15 minutes before adding ssRNA target. The RNP complex was added to the labeled RNA at a 10:1 ratio (200 nM RNA: 2 μM RNP) in cleavage buffer (10 mM Tris, 100 mM NaCl, and 10 mM $MgCl_2$) and incubated at 37° C. for 1 hr. Reactions were quenched with proteinase K and resolved on a 1500 TBE Urea-PAGE gel (Bio-rad). The gel shows site-directed RNA cleavage by MG3-6 and MG3-8 as well as commercial positive control SauCas9 (NEB) (FIG. 14). The results indicated that MG3-6 and MG3-8 are capable of targeted RNA cleavage and are comparable in terms of RNA cleavage to SauCas9.

Example 22—Gene Editing Outcomes at the DNA Level for FAS

Figure 15:
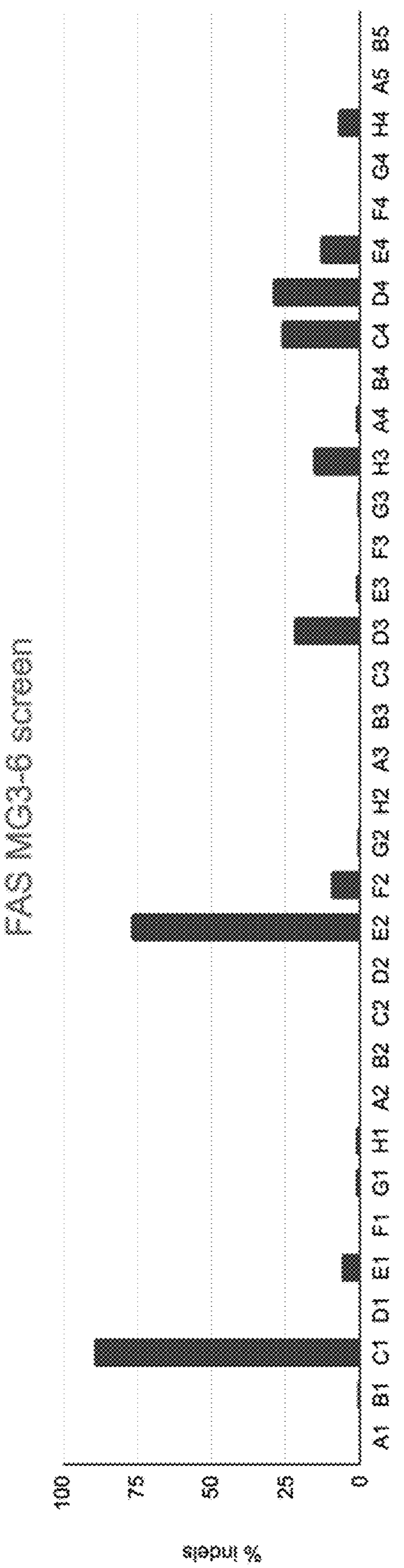
FIG. 15 depicts the gene editing outcomes at the DNA level for FAS in T cells.

Primary T cells were purified from PBMCs using a negative selection kit (Miltenyi) according to the manufacturer's recommendations. Nucleofection of MG3-6 RNPs (104 pmol protein/120 pmol guide) (SEQ ID NOs: 7023-7056) was performed into T cells (200,000) using the Lonza 4D electroporator. Cells were harvested and genomic DNA prepared three days post-transfection. PCR primers appropriate for use in NGS-based DNA sequencing were generated, optimized, and used to amplify the individual target sequences for each guide RNA (SEQ ID NOs: 7057-7090). The amplicons were sequenced on an Illumina MiSeq machine and analyzed with a proprietary Python script to measure gene editing (FIG. 15).

TABLE 12

| Guide RNAs and Sequences Targeted for Example 22 | | |
|---|---|---|
| SEQ ID NO: | NAME | SEQUENCE |
| 7023 | MG3-6-FAS-sgRNA-A1 | mC*mU*mG*rArUrGrArGrUrGrGrUrUrUrCrCrCrUrGrArGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrUxmU*mU*mU |
| 7024 | MG3-6-FAS-sgRNA-B1 | mU*mU*mA*rGrArUrGrCrUrCrArGrArGrUrGrUrGrUrGrCrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7025 | MG3-6-FAS-sgRNA-C1 | mG*mU*mG*rUrGrCrArCrArArGrGrCrUrGrGrCrArCrGrCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |

TABLE 12-continued

Guide RNAs and Sequences Targeted for Example 22

| SEQ ID NO: | NAME | SEQUENCE |
|---|---|---|
| 7026 | MG3-6-FAS-sgRNA-D1 | mG*mA*mG*rArCrArArGrCrCrUrArUrCrArArCrArCrCrUrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7027 | MG3-6-FAS-sgRNA-E1 | mA*mC*mC*rArCrCrArGrUrCrUrUrGrUrArGrGrUrGrUrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7028 | MG3-6-FAS-sgRNA-F1 | mC*mU*mU*rGrUrCrUrCrUrGrUrUrCrCrArCrCrUrUrUrCrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7029 | MG3-6-FAS-sgRNA-G1 | mA*mG*mU*rArGrArCrUrGrUrUrArGrUrGrCrCrArUrGrArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mUxmU*mU |
| 7030 | MG3-6-FAS-sgRNA-H1 | mU*mU*mA*rCrArGrGrUrUrCrUrUrArCrGrUrCrUrGrUrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7031 | MG3-6-FAS-sgRNA-A2 | mC*mA*mA*rGrUrGrArCrUrGrArCrArUrCrArArCrUrCrCrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrUxmU*mU*mU |
| 7032 | MG3-6-FAS-sgRNA-B2 | mA*mC*mU*rCrCrArArGrGrGrArUrUrGrGrArArUrUrGrArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7033 | MG3-6-FAS-sgRNA-C2 | mU*mG*mA*rGrGrArArGrArCrUrGrUrUrArCrUrArCrArGrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7034 | MG3-6-FAS-sgRNA-D2 | mU*mA*mC*rArGrUrUrGrArGrArCrUrCrArGrArArCrUrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrUmU*mU*mU |
| 7035 | MG3-6-FAS-sgRNA-E2 | mU*mU*mU*rGrUrGrUrArArCrArUrArCrCrUrGrGrArGrGrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7036 | MG3-6-FAS-sgRNA-F2 | mU*mG*mG*rCrArGrArArUrUrGrGrCrCrArUrCrArUrGrArUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7037 | MG3-6-FAS-sgRNA-G2 | mU*mU*mG*rGrGrCrArGrGrUrGrArArArGrGrArArArGrCrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7038 | MG3-6-FAS-sgRNA-H2 | mC*mU*mG*rCrArCrArGrUrCrArArUrGrGrGrGrArUrGrArArGrUrUrGrArGrArArUrCrGrArArArGrArUrUrCrUrUrArArUrArAr |

TABLE 12-continued

| Guide RNAs and Sequences Targeted for Example 22 | | |
|---|---|---|
| SEQ ID NO: | NAME | SEQUENCE |
| | | GrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7039 | MG3-6-FAS-sgRNA-A3 | mU*mU*mU*rUrCrUrUrCrCrArArArUrGrCrArGrArArGrArUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7040 | MG3-6-FAS-sgRNA-B3 | mA*mU*mC*rUrUrCrUrGrCrArUrUrGrGrArArGrArArArArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7041 | MG3-6-FAS-sgRNA-C3 | mU*mA*mG*rArArGrUrGrGrArArArUrArArArCrUrGrCrArCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7042 | MG3-6-FAS-sgRNA-D3 | mA*mA*mG*rArCrUrArArArCrUrUrArCrUrUrGrGrUrGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrUxmU*mU*mU |
| 7043 | MG3-6-FAS-sgRNA-E3 | mG*mU*mU*rUrArCrArUrCrUrGrCrArCrUrUrGrGrUrArUrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7044 | MG3-6-FAS-sgRNA-F3 | mA*mA*mG*rArArGrArCrArArArGrCrCrArCrCrCrCrArArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7045 | MG3-6-FAS-sgRNA-G3 | mA*mC*mA*rArArGrCrCrArCrCrCrCrArArGrUrUrArGrArUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7046 | MG3-6-FAS-sgRNA-H3 | mC*mC*mC*rCrArArGrUrUrArGrArUrCrUrGrGrArUrCrCrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7047 | MG3-6-FAS-sgRNA-A4 | mC*mA*mG*rArArArGrCrArCrArGrArArArGrGrArArArArCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7048 | MG3-6-FAS-sgRNA-B4 | mA*mA*mU*rArCrCrUrArCrArGrGrArUrUrUrArArArGrUrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7049 | MG3-6-FAS-sgRNA-C4 | mC*mA*mG*rUrGrGrCrArArUrArArArUrUrUrArUrCrUrGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |

TABLE 12-continued

Guide RNAs and Sequences Targeted for Example 22

| SEQ ID NO: | NAME | SEQUENCE |
|---|---|---|
| 7050 | MG3-6-FAS-sgRNA-D4 | mA*mG*mU*rCrArUrGrArCrArCrUrArArGrUrCrArArGrUrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrUmUmU*mU |
| 7051 | MG3-6-FAS-sgRNA-E4 | mG*mU*mG*rUrCrArArUrGrArArGrCrCrArArArArUrArGrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7052 | MG3-6-FAS-sgRNA-F4 | mA*mG*mA*rArGrCrGrUrArUrGrArCrArCrArUrUrGrArUrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mUxmU*mU |
| 7053 | MG3-6-FAS-sgRNA-G4 | mU*mU*mU*rGrUrArCrUrCrUrUrGrCrArGrArGrArArArArUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7054 | MG3-6-FAS-sgRNA-H4 | mG*mU*mU*rUrUrUrCrArCrUrCrUrArGrArCrCrArArGrCrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7055 | MG3-6-FAS-sgRNA-A5 | mU*mG*mA*rArUrUrUrUrCrUrCrUrGrCrArArGrArGrUrArCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7056 | MG3-6-FAS-sgRNA-B5 | mA*mG*mA*rGrUrArCrArArArGrArUrUrGrGrCrUrUrUrUrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrUxmU*mU*mU |
| 7057 | MG3-6-FAS-target site-A1 | CTGATGAGTGGTTTCCCTGAGC |
| 7058 | MG3-6-FAS-target site-B1 | TTAGATGCTCAGAGTGTGTGCA |
| 7059 | MG3-6-FAS-target site-C1 | GTGTGCACAAGGCTGGCACGCC |
| 7060 | MG3-6-FAS-target site-D1 | GAGACAAGCCTATCAACACCTA |
| 7061 | MG3-6-FAS-target site-E1 | ACCACCAGTCTTGTAGGTGTTG |
| 7062 | MG3-6-FAS-target site-F1 | CTTGTCTCTGTTCCACCTTTCA |
| 7063 | MG3-6-FAS-target site-G1 | AGTAGACTGTTAGTGCCATGAG |
| 7064 | MG3-6-FAS-target site-H1 | TTACAGGTTCTTACGTCTGTTG |
| 7065 | MG3-6-FAS-target site-A2 | CAAGTGACTGACATCAACTCCA |
| 7066 | MG3-6-FAS-target site-B2 | ACTCCAAGGGATTGGAATTGAG |
| 7067 | MG3-6-FAS-target site-C2 | TGAGGAAGACTGTTACTACAGT |

TABLE 12-continued

| Guide RNAs and Sequences Targeted for Example 22 | | |
|---|---|---|
| SEQ ID NO: | NAME | SEQUENCE |
| 7068 | MG3-6-FAS-target site-D2 | TACAGTTGAGACTCAGAACTTG |
| 7069 | MG3-6-FAS-target site-E2 | TTTGTGTAACATACCTGGAGGA |
| 7070 | MG3-6-FAS-target site-F2 | TGGCAGAATTGGCCATCATGAT |
| 7071 | MG3-6-FAS-target site-G2 | TTGGGCAGGTGAAAGGAAAGCT |
| 7072 | MG3-6-FAS-target site-H2 | CTGCACAGTCAATGGGGATGAA |
| 7073 | MG3-6-FAS-target site-A3 | TTTTCTTCCAAATGCAGAAGAT |
| 7074 | MG3-6-FAS-target site-B3 | ATCTTCTGCATTTGGAAGAAAA |
| 7075 | MG3-6-FAS-target site-C3 | TAGAAGTGGAAATAAACTGCAC |
| 7076 | MG3-6-FAS-target site-D3 | AAGACTAAAACTTACTTGGTGC |
| 7077 | MG3-6-FAS-target site-E3 | GTTTACATCTGCACTTGGTATT |
| 7078 | MG3-6-FAS-target site-F3 | AAGAAGACAAAGCCACCCCAAG |
| 7079 | MG3-6-FAS-target site-G3 | ACAAAGCCACCCCAAGTTAGAT |
| 7080 | MG3-6-FAS-target site-H3 | CCCCAAGTTAGATCTGGATCCT |
| 7081 | MG3-6-FAS-target site-A4 | CAGAAAGCACAGAAAGGAAAAC |
| 7082 | MG3-6-FAS-target site-B4 | AATACCTACAGGATTTAAAGTT |
| 7083 | MG3-6-FAS-target site-C4 | CAGTGGCAATAAATTTATCTGG |
| 7084 | MG3-6-FAS-target site-D4 | AGTCATGACACTAAGTCAAGTT |
| 7085 | MG3-6-FAS-target site-E4 | GTGTCAATGAAGCCAAAATAGA |
| 7086 | MG3-6-FAS-target site-F4 | AGAAGCGTATGACACATTGATT |
| 7087 | MG3-6-FAS-target site-G4 | TTTGTACTCTTGCAGAGAAAAT |
| 7088 | MG3-6-FAS-target site-H4 | GTTTTTCACTCTAGACCAAGCT |
| 7089 | MG3-6-FAS-target site-A5 | TGAATTTTCTCTGCAAGAGTAC |
| 7090 | MG3-6-FAS-target site-B5 | AGAGTACAAAGATTGGCTTTTT |

r = native ribose base, m = 2'-O methyl modified base, F = 2' Fluro modified base, * = phosphorothioate bond

Example 23—Gene Editing Outcomes at the DNA Level for PD-1

Figure 16:
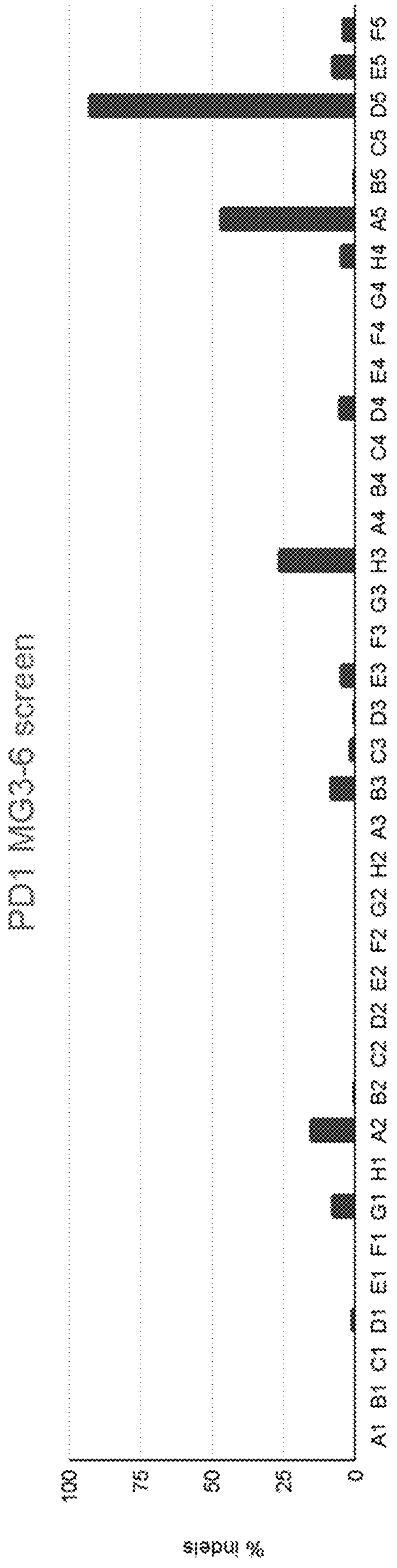
FIG. 16 depicts the gene editing outcomes at the DNA level for PD-1 in T cells.

Primary T cells were purified from PBMCs using a negative selection kit (Miltenyi) according to the manufacturer's recommendations. Nucleofection of MG3-6 RNPs (104 pmol protein/120 pmol guide) (SEQ ID NOs: 7091-7128) was performed into T cells (200,000) using the Lonza 4D electroporator. Cells were harvested and genomic DNA prepared three days post-transfection. PCR primers appropriate for use in NGS-based DNA sequencing were generated, optimized, and used to amplify the individual target sequences for each guide RNA (SEQ ID NOs: 7129-7166). The amplicons were sequenced on an Illumina MiSeq machine and analyzed with a proprietary Python script to measure gene editing (FIG. 16).

TABLE 13

Guide RNAs and Sequences Targeted for Example 23

| SEQ ID NO: | NAME | SEQUENCE |
|---|---|---|
| 7091 | MG3-6-PD-1-sgRNA-A1 | mG*mG*mU*rGrGrCrCrArArGrGrArArGrCrCrGrGrUrCrArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7092 | MG3-6-PD-1-sgRNA-B1 | mG*mG*mG*rCrCrArArGrArGrCrArGrUrGrUrCrCrArUrCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrUxmU*mU*mU |
| 7093 | MG3-6-PD-1-sgRNA-C1 | mG*mG*mC*rCrCrUrCrGrGrArGrUrGrCrCrCrArGrCrCrArCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7094 | MG3-6-PD-1-sgRNA-D1 | mG*mG*mC*rCrUrCrArGrUrGrGrCrUrGrGrGrCrArCrUrCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7095 | MG3-6-PD-1-sgRNA-E1 | mG*mG*mG*rCrArCrCrUrCrArUrCrCrCrCrCrGrCrCrCrGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7096 | MG3-6-PD-1-sgRNA-F1 | mC*mU*mG*rCrUrCrArGrGrGrArCrArCrArGrGrGrCrArCrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7097 | MG3-6-PD-1-sgRNA-G1 | mG*mG*mA*rCrArCrArGrGrGrCrArCrGrGrGrGrGrGrCrUrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7098 | MG3-6-PD-1-sgRNA-H1 | mA*mG*mC*rUrGrGrArUrUrUrCrCrArGrUrGrGrCrGrArGrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7099 | MG3-6-PD-1-sgRNA-A2 | mG*mU*mU*rCrUrCrUrGrUrGrGrArCrUrArUrGrGrGrGrArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7100 | MG3-6-PD-1-sgRNA-B2 | mC*mU*mC*rArGrCrCrGrUrGrCrCrUrGrUrGrUrUrCrUrCrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7101 | MG3-6-PD-1-sgRNA-C2 | mA*mC*mA*rGrArGrArArCrArCrArGrGrCrArCrGrGrCrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrA |

TABLE 13-continued

| Guide RNAs and Sequences Targeted for Example 23 | | |
|---|---|---|
| SEQ ID NO: | NAME | SEQUENCE |
| | | rCrCrGrUrCrCrGrUrUrUrCrCrArArUrArGrGrArGrCrGrGrGr<br>CrGrGrUrArUrGrU*mU*mU*mU |
| 7102 | MG3-6-PD-1-sgRNA-D2 | mG*mG*mG*rUrCrCrUrGrGrCrCrGrUrCrArUrCrUrGrCrUrCrG<br>rUrUrGrArGrArArUrCrGrArArArGrArUrUrCrUrUrArArUrArAr<br>GrGrCrArUrCrCrUrUrCrCrGrArUrGrCrUrGrArCrUrUrCrUrCrA<br>rCrCrGrUrCrCrGrUrUrUrCrCrArArUrArGrGrArGrCrGrGrGr<br>CrGrGrUrArUrGrU*mU*mU*mU |
| 7103 | MG3-6-PD-1-sgRNA-E2 | mC*mG*mG*rCrCrCrGrGrGrArGrCrArGrArUrGrArCrGrGrCrG<br>rUrUrGrArGrArArUrCrGrArArArGrArUrUrCrUrUrArArUrArAr<br>GrGrCrArUrCrCrUrUrCrCrGrArUrGrCrUrGrArCrUrUrCrUrCrA<br>rCrCrGrUrCrCrGrUrUrUrCrCrArArUrArGrGrArGrCrGrGrGr<br>CrGrGrUrArUrGrU*mU*mUxmU |
| 7104 | MG3-6-PD-1-sgRNA-F2 | mG*mG*mG*rArGrCrArGrArUrGrArCrGrGrCrCrArGrGrArCrG<br>rUrUrGrArGrArArUrCrGrArArArGrArUrUrCrUrUrArArUrArAr<br>GrGrCrArUrCrCrUrUrCrCrGrArUrGrCrUrGrArCrUrUrCrUrCrA<br>rCrCrGrUrCrCrGrUrUrUrCrCrArArUrArGrGrArGrCrGrGrGr<br>CrGrGrUrArUrGrU*mU*mU*mU |
| 7105 | MG3-6-PD-1-sgRNA-G2 | mU*mG*mG*rGrCrArGrCrCrUrGrGrUrGrCrUrGrCrUrArGrUrG<br>rUrUrGrArGrArArUrCrGrArArArGrArUrUrCrUrUrArArUrArAr<br>GrGrCrArUrCrCrUrUrCrCrGrArUrGrCrUrGrArCrUrUrCrUrCrA<br>rCrCrGrUrCrCrGrUrUrUrCrCrArArUrArGrGrArGrCrGrGrGr<br>CrGrGrUrArUrGrU*mU*mU*mU |
| 7106 | MG3-6-PD-1-sgRNA-H2 | mG*mC*mC*rArGrGrArCrCrCrArGrArCrUrArGrCrArGrCrArG<br>rUrUrGrArGrArArUrCrGrArArArGrArUrUrCrUrUrArArUrArAr<br>GrGrCrArUrCrCrUrUrCrCrGrArUrGrCrUrGrArCrUrUrCrUrCrA<br>rCrCrGrUrCrCrGrUrUrUrCrCrArArUrArGrGrArGrCrGrGrGr<br>CrGrGrUrArUrGrU*mU*mU*mU |
| 7107 | MG3-6-PD-1-sgRNA-A3 | mA*mC*mU*rArGrCrArGrCrArCrCrArGrGrCrUrGrCrCrCrArGr<br>UrUrGrArGrArArUrCrGrArArArGrArUrUrCrUrUrArArUrArArG<br>rGrCrArUrCrCrUrUrCrCrGrArUrGrCrUrGrArCrUrUrCrUrCrAr<br>CrCrGrUrCrCrGrUrUrUrCrCrArArUrArGrGrArGrCrGrGrGr<br>CrGrGrUrArUrGrU*mU*mU*mU |
| 7108 | MG3-6-PD-1-sgRNA-B3 | mG*mG*mC*rCrGrCrCrCrArCrGrArCrArCrCrArArCrCrArCrGr<br>UrUrGrArGrArArUrCrGrArArArGrArUrUrCrUrUrArArUrArArG<br>rGrCrArUrCrCrUrUrCrCrGrArUrGrCrUrGrArCrUrUrCrUrCrAr<br>CrCrGrUrCrCrGrUrUrUrCrCrArArUrArGrGrArGrCrGrGrGr<br>CrGrGrUrArUrGrU*mU*mU*mU |
| 7109 | MG3-6-PD-1-sgRNA-C3 | mA*mA*mC*rUrGrGrCrCrGrGrCrUrGrGrCrCrUrGrGrGrUrGrG<br>rUrUrGrArGrArArUrCrGrArArArGrArUrUrCrUrUrArArUrArAr<br>GrGrCrArUrCrCrUrUrCrCrGrArUrGrCrUrGrArCrUrUrCrUrCrA<br>rCrCrGrUrCrCrGrUrUrUrCrCrArArUrArGrGrArGrCrGrGrGr<br>CrGrGrUrArUrGrU*mU*mU*mU |
| 7110 | MG3-6-PD-1-sgRNA-D3 | mA*mC*mA*rGrCrCrCrArCrCrCrCrArGrCrCrCrCrUrCrArCrGr<br>UrUrGrArGrArArUrCrGrArArArGrArUrUrCrUrUrArArUrArArG<br>rGrCrArUrCrCrUrUrCrCrGrArUrGrCrUrGrArCrUrUrCrUrCrAr<br>CrCrGrUrCrCrGrUrUrUrCrCrArArUrArGrGrArGrCrGrGrGr<br>CrGrGrUrArUrGrU*mU*mU*mU |
| 7111 | MG3-6-PD-1-sgRNA-E3 | mC*mU*mG*rGrCrCrUrGrGrGrUrGrArGrGrGrGrCrUrGrGrGrG<br>rUrUrGrArGrArArUrCrGrArArArGrArUrUrCrUrUrArArUrArAr<br>GrGrCrArUrCrCrUrUrCrCrGrArUrGrCrUrGrArCrUrUrCrUrCrA<br>rCrCrGrUrCrCrGrUrUrUrCrCrArArUrArGrGrArGrCrGrGrGr<br>CrGrGrUrArUrGrU*mU*mU*mU |
| 7112 | MG3-6-PD-1-sgRNA-F3 | mC*mC*mU*rGrUrCrArCrCrCrUrGrArGrCrUrCrUrGrCrCrCrGr<br>UrUrGrArGrArArUrCrGrArArArGrArUrUrCrUrUrArArUrArArG<br>rGrCrArUrCrCrUrUrCrCrGrArUrGrCrUrGrArCrUrUrCrUrCrAr<br>CrCrGrUrCrCrGrUrUrUrCrCrArArUrArGrGrArGrCrGrGrGr<br>CrGrGrUrArUrGrU*mU*mU*mU |
| 7113 | MG3-6-PD-1-sgRNA-G3 | mG*mG*mC*rUrCrUrCrUrUrUrGrArUrCrUrGrCrGrCrCrUrUrGr<br>UrUrGrArGrArArUrCrGrArArArGrArUrUrCrUrUrArArUrArArG<br>rGrCrArUrCrCrUrUrCrCrGrArUrGrCrUrGrArCrUrUrCrUrCrAr<br>CrCrGrUrCrCrGrUrUrUrCrCrArArUrArGrGrArGrCrGrGrGr<br>CrGrGrUrArUrGrU*mU*mU*mU |

TABLE 13-continued

Guide RNAs and Sequences Targeted for Example 23

| SEQ ID NO: | NAME | SEQUENCE |
|---|---|---|
| 7114 | MG3-6-PD-1-sgRNA-H3 | mC*mC*mA*rUrCrUrCrCrCrUrGrGrCrCrCrCrCrArArGrGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7115 | MG3-6-PD-1-sgRNA-A4 | mA*mU*mG*rArCrArGrCrGrGrCrArCrCrUrArCrCrUrCrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mUxmU*mU |
| 7116 | MG3-6-PD-1-sgRNA-B4 | mG*mG*mU*rArGrGrUrGrCrCrGrCrUrGrUrCrArUrUrGrCrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7117 | MG3-6-PD-1-sgRNA-C4 | mG*mU*mG*rArCrUrUrCrCrArCrArUrGrArGrCrGrUrGrGrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7118 | MG3-6-PD-1-sgRNA-D4 | mG*mA*mC*rArCrGrGrArArGrCrGrGrCrArGrUrCrCrUrGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrUmU*mU*mU |
| 7119 | MG3-6-PD-1-sgRNA-E4 | mC*mG*mA*rGrGrArCrCrGrCrArGrCrCrArGrCrCrCrGrGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7120 | MG3-6-PD-1-sgRNA-F4 | mG*mG*mA*rCrArArGrCrUrGrGrCrCrGrCrCrUrUrCrCrCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7121 | MG3-6-PD-1-sgRNA-G4 | mG*mC*mC*rArGrCrUrUrGrUrCrCrGrUrCrUrGrGrUrUrGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7122 | MG3-6-PD-1-sgRNA-H4 | mU*mG*mU*rCrCrCrCrUrUrCrGrGrUrCrArCrCrArCrGrArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7123 | MG3-6-PD-1-sgRNA-A5 | mA*mG*mC*rArGrGrGrCrUrGrGrGrGrArGrArArGrGrUrGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7124 | MG3-6-PD-1-sgRNA-B5 | mU*mG*mG*rGrGrArGrArArGrGrUrGrGrGrGrGrGrUrUrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 7125 | MG3-6-PD-1-sgRNA-C5 | mC*mU*mC*rCrArUrCrUrCrUrCrArGrArCrUrCrCrCrCrArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |

TABLE 13-continued

Guide RNAs and Sequences Targeted for Example 23

| SEQ ID NO: | NAME | SEQUENCE |
|---|---|---|
| 7126 | MG3-6-PD-1-sgRNA-D5 | mG*mC*mC*rArGrGrArUrGrGrUrUrCrUrUrArGrGrUrArGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7127 | MG3-6-PD-1-sgRNA-E5 | mA*mG*mU*rCrGrUrCrUrGrGrGrCrGrGrUrGrCrUrArCrArArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7128 | MG3-6-PD-1-sgRNA-F5 | mA*mG*mA*rCrGrArCrUrGrGrCrCrArGrGrGrCrGrCrCrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7129 | MG3-6-PD-1-target site-A1 | GGTGGCCAAGGAAGCCGGTCAG |
| 7130 | MG3-6-PD-1-target site-B1 | GGGCCAAGAGCAGTGTCCATCC |
| 7131 | MG3-6-PD-1-target site-C1 | GGCCCTCGGAGTGCCCAGCCAC |
| 7132 | MG3-6-PD-1-target site-D1 | GGCCTCAGTGGCTGGGCACTCC |
| 7133 | MG3-6-PD-1-target site-E1 | GGGCACCTCATCCCCCGCCCGC |
| 7134 | MG3-6-PD-1-target site-F1 | GGACACAGGGCACGGGGGGCTC |
| 7135 | MG3-6-PD-1-target site-G1 | GGACACAGGGCACGGGGGGCTC |
| 7136 | MG3-6-PD-1-target site-H1 | AGCTGGATTTCCAGTGGCGAGA |
| 7137 | MG3-6-PD-1-target site-A2 | GTTCTCTGTGGACTATGGGGAG |
| 7138 | MG3-6-PD-1-target site-B2 | CTCAGCCGTGCCTGTGTTCTCT |
| 7139 | MG3-6-PD-1-target site-C2 | ACAGAGAACACAGGCACGGCTG |
| 7140 | MG3-6-PD-1-target site-D2 | GGGTCCTGGCCGTCATCTGCTC |
| 7141 | MG3-6-PD-1-target site-E2 | CGGCCCGGGAGCAGATGACGGC |
| 7142 | MG3-6-PD-1-target site-F2 | GGGAGCAGATGACGGCCAGGAC |
| 7143 | MG3-6-PD-1-target site-G2 | TGGGCAGCCTGGTGCTGCTAGT |
| 7144 | MG3-6-PD-1-target site-H2 | GCCAGGACCCAGACTAGCAGCA |
| 7145 | MG3-6-PD-1-target site-A3 | ACTAGCAGCACCAGGCTGCCCA |
| 7146 | MG3-6-PD-1-target site-B3 | GGCCGCCCACGACACCAACCAC |
| 7147 | MG3-6-PD-1-target site-C3 | AACTGGCCGGCTGGCCTGGGTG |

TABLE 13-continued

Guide RNAs and Sequences Targeted for Example 23

| SEQ ID NO: | NAME | SEQUENCE |
|---|---|---|
| 7148 | MG3-6-PD-1-target site-D3 | ACAGCCCACCCCAGCCCCTCAC |
| 7149 | MG3-6-PD-1-target site-E3 | CTGGCCTGGGTGAGGGGCTGGG |
| 7150 | MG3-6-PD-1-target site-F3 | CCTGTCACCCTGAGCTCTGCCC |
| 7151 | MG3-6-PD-1-target site-G3 | GGCTCTCTTTGATCTGCGCCTT |
| 7152 | MG3-6-PD-1-target site-H3 | CCATCTCCCTGGCCCCCAAGGC |
| 7153 | MG3-6-PD-1-target site-A4 | ATGACAGCGGCACCTACCTCTG |
| 7154 | MG3-6-PD-1-target site-B4 | GGTAGGTGCCGCTGTCATTGCG |
| 7155 | MG3-6-PD-1-target site-C4 | GTGACTTCCACATGAGCGTGGT |
| 7156 | MG3-6-PD-1-target site-D4 | GACACGGAAGCGGCAGTCCTGG |
| 7157 | MG3-6-PD-1-target site-E4 | CGAGGACCGCAGCCAGCCCGGC |
| 7158 | MG3-6-PD-1-target site-F4 | GGACAAGCTGGCCGCCTTCCCC |
| 7159 | MG3-6-PD-1-target site-G4 | GCCAGCTTGTCCGTCTGGTTGC |
| 7160 | MG3-6-PD-1-target site-H4 | TGTCCCCTTCGGTCACCACGAG |
| 7161 | MG3-6-PD-1-target site-A5 | AGCAGGGCTGGGGAGAAGGTGG |
| 7162 | MG3-6-PD-1-target site-B5 | TGGGGAGAAGGTGGGGGGGTTC |
| 7163 | MG3-6-PD-1-target site-C5 | CTCCATCTCTCAGACTCCCCAG |
| 7164 | MG3-6-PD-1-target site-D5 | GCCAGGATGGTTCTTAGGTAGG |
| 7165 | MG3-6-PD-1-target site-E5 | AGTCGTCTGGGCGGTGCTACAA |
| 7166 | MG3-6-PD-1-target site-F5 | AGACGACTGGCCAGGGCGCCTG |

r = native ribose base, m = 2'-O methyl modified base, F = 2' Fluro modified base, * = phosphorothioate bond

Example 24—Gene Editing Outcomes at the DNA Level for hRosa26

Figure 17:
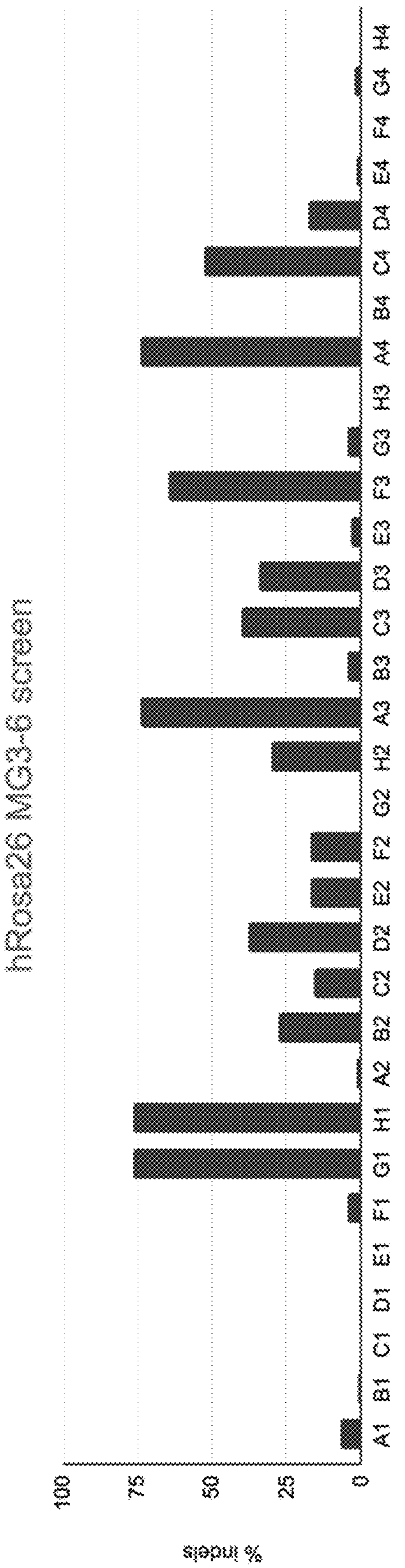
FIG. 17 depicts the gene editing outcomes at the DNA level for hRosa26 in T cells.

Primary T cells were purified from PBMCs using a negative selection kit (Miltenyi) according to the manufacturer's recommendations. Nucleofection of MG3-6 RNPs (104 pmol protein/120 pmol guide) (SEQ ID NOs: 7167-7198) was performed into T cells (200,000) using the Lonza 4D electroporator. Cells were harvested and genomic DNA prepared three days post-transfection. PCR primers appropriate for use in NGS-based DNA sequencing were generated, optimized, and used to amplify the individual target sequences for each guide RNA (SEQ ID NOs: 7199-7230). The amplicons were sequenced on an Illumina MiSeq machine and analyzed with a proprietary Python script to measure gene editing (FIG. 17).

TABLE 14

Guide RNAs and Sequences Targeted for Example 24

| SEQ ID NO: | NAME | SEQUENCE |
|---|---|---|
| 7167 | MG3-6-hRosa26-sgRNA-A1 | mA*mU*mC*rUrGrUrCrUrGrGrUrUrUrCrGrCrGrArGrArCrArG<br>rUrUrGrArGrArArUrCrGrArArArGrArUrUrCrUrUrArArUrArAr<br>GrGrCrArUrCrCrUrUrCrCrGrArUrGrCrUrGrArCrUrUrCrUrCrA<br>rCrCrGrUrCrCrGrUrUrUrUrCrCrArArUrArGrGrArGrCrGrGrGr<br>CrGrGrUrArUrGrU*mU*mU*mU |
| 7168 | MG3-6-hRosa26-sgRNA-B1 | mU*mU*mU*rCrGrCrGrArGrArCrArCrCrArGrGrCrUrArCrCrGr<br>UrUrGrArGrArArUrCrGrArArArGrArUrUrCrUrUrArArUrArArG<br>rGrCrArUrCrCrUrUrCrCrGrArUrGrCrUrGrArCrUrUrCrUrCrAr<br>CrCrGrUrCrCrGrUrUrUrUrCrCrArArUrArGrGrArGrCrGrGrGr<br>CrGrGrUrArUrGrU*mU*mU*mU |
| 7169 | MG3-6-hRosa26-sgRNA-C1 | mA*mG*mC*rArArGrUrArCrArArCrArArArUrGrGrArArArArGr<br>UrUrGrArGrArArUrCrGrArArArGrArUrUrCrUrUrArArUrArArG<br>rGrCrArUrCrCrUrUrCrCrGrArUrGrCrUrGrArCrUrUrCrUrCrAr<br>CrCrGrUrCrCrGrUrUrUrUrCrCrArArUrArGrGrArGrCrGrGrGr<br>CrGrGrUrArUrGrU*mU*mU*mU |
| 7170 | MG3-6-hRosa26-sgRNA-D1 | mG*mC*mA*rArArArGrCrUrArArArArUrUrUrUrUrCrUrArUrGr<br>UrUrGrArGrArArUrCrGrArArArGrArUrUrCrUrUrArArUrArArG<br>rGrCrArUrCrCrUrUrCrCrGrArUrGrCrUrGrArCrUrUrCrUrCrAr<br>CrCrGrUrCrCrGrUrUrUrUrCrCrArArUrArGrGrArGrCrGrGrGr<br>CrGrGrUrArUrGrU*mU*mU*mU |
| 7171 | MG3-6-hRosa26-sgRNA-E1 | mU*mG*mC*rUrArCrArCrUrUrUrGrGrUrGrGrUrGrCrArGrCrG<br>rUrUrGrArGrArArUrCrGrArArArGrArUrUrCrUrUrArArUrArAr<br>GrGrCrArUrCrCrUrUrCrCrGrArUrGrCrUrGrArCrUrUrCrUrCrA<br>rCrCrGrUrCrCrGrUrUrUrUrCrCrArArUrArGrGrArGrCrGrGrGr<br>CrGrGrUrArUrGrU*mU*mU*mU |
| 7172 | MG3-6-hRosa26-sgRNA-F1 | mA*mC*mU*rCrCrCrCrUrGrCrArGrGrGrCrArArCrGrCrCrCrGr<br>UrUrGrArGrArArUrCrGrArArArGrArUrUrCrUrUrArArUrArArG<br>rGrCrArUrCrCrUrUrCrCrGrArUrGrCrUrGrArCrUrUrCrUrCrAr<br>CrCrGrUrCrCrGrUrUrUrUrCrCrArArUrArGrGrArGrCrGrGrGr<br>CrGrGrUrArUrGrU*mU*mU*mU |
| 7173 | MG3-6-hRosa26-sgRNA-G1 | mC*mG*mA*rCrUrCrGrArCrArUrGrGrArGrGrCrGrArUrGrArG<br>rUrUrGrArGrArArUrCrGrArArArGrArUrUrCrUrUrArArUrArAr<br>GrGrCrArUrCrCrUrUrCrCrGrArUrGrCrUrGrArCrUrUrCrUrCrA<br>rCrCrGrUrCrCrGrUrUrUrUrCrCrArArUrArGrGrArGrCrGrGrGr<br>CrGrGrUrArUrGrU*mU*mU*mU |
| 7174 | MG3-6-hRosa26-sgRNA-H1 | mA*mU*mC*rArCrGrCrGrArGrGrArGrGrArArArGrGrArGrGrG<br>rUrUrGrArGrArArUrCrGrArArArGrArUrUrCrUrUrArArUrArAr<br>GrGrCrArUrCrCrUrUrCrCrGrArUrGrCrUrGrArCrUrUrCrUrCrA<br>rCrCrGrUrCrCrGrUrUrUrUrCrCrArArUrArGrGrArGrCrGrGrGr<br>CrGrGrUrArUrGrU*mU*mU*mU |
| 7175 | MG3-6-hRosa26-sgRNA-A2 | mA*mG*mG*rArArArGrGrArGrGrGrArGrGrGrCrUrUrCrUrUrG<br>rUrUrGrArGrArArUrCrGrArArArGrArUrUrCrUrUrArArUrArAr<br>GrGrCrArUrCrCrUrUrCrCrGrArUrGrCrUrGrArCrUrUrCrUrCrA<br>rCrCrGrUrCrCrGrUrUrUrUrCrCrArArUrArGrGrArGrCrGrGrGr<br>CrGrGrUrArUrGrU*mU*mU*mU |
| 7176 | MG3-6-hRosa26-sgRNA-B2 | mA*mC*mC*rUrCrCrUrCrCrArCrCrGrCrArGrCrUrCrCrCrUrGr<br>UrUrGrArGrArArUrCrGrArArArGrArUrUrCrUrUrArArUrArArG<br>rGrCrArUrCrCrUrUrCrCrGrArUrGrCrUrGrArCrUrUrCrUrCrAr<br>CrCrGrUrCrCrGrUrUrUrUrCrCrArArUrArGrGrArGrCrGrGrGr<br>CrGrGrUrArUrGrUmUmU*mU |
| 7177 | MG3-6-hRosa26-sgRNA-C2 | mG*mC*mG*rCrCrUrCrCrCrArCrCrCrArCrArArArCrCrArGrGr<br>UrUrGrArGrArArUrCrGrArArArGrArUrUrCrUrUrArArUrArArG<br>rGrCrArUrCrCrUrUrCrCrGrArUrGrCrUrGrArCrUrUrCrUrCrAr |

TABLE 14-continued

| Guide RNAs and Sequences Targeted for Example 24 | | |
|---|---|---|
| SEQ ID NO: | NAME | SEQUENCE |
| | | CrCrGrUrCrCrGrUrUrUrCrCrArArUrArGrGrArGrCrGrGrCrGrGrUrArUrGrUxmU*mU*mU |
| 7178 | MG3-6-hRosa26-sgRNA-D2 | mC*mC*mC*rArCrCrCrCrArCrGrArGrUrGrCrCrUrGrUrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7179 | MG3-6-hRosa26-sgRNA-E2 | mC*mU*mC*rGrUrGrGrGrGrUrGrGrGrGrArGrGrArGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7180 | MG3-6-hRosa26-sgRNA-F2 | mG*mC*mU*rGrCrGrGrUrGrGrArGrGrArGrGrUrGrGrArGrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7181 | MG3-6-hRosa26-sgRNA-G2 | mU*mC*mU*rCrUrGrCrUrGrCrCrUrCrCrCrGrUrCrUrUrGrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7182 | MG3-6-hRosa26-sgRNA-H2 | mC*mU*mC*rCrCrGrUrCrUrUrGrUrArArGrGrArCrCrGrCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7183 | MG3-6-hRosa26-sgRNA-A3 | mC*mG*mA*rGrUrCrGrCrUrUrCrUrCrGrArUrUrArUrGrGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7184 | MG3-6-hRosa26-sgRNA-B3 | mA*mU*mU*rArUrGrGrGrCrGrGrGrArUrUrCrUrUrUrUrGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mUxmU*mU |
| 7185 | MG3-6-hRosa26-sgRNA-C3 | mG*mG*mG*rArUrUrCrUrUrUrUrGrCrCrUrArGrGrCrUrUrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrUxmUxmU*mU |
| 7186 | MG3-6-hRosa26-sgRNA-D3 | mC*mC*mU*rGrCrArGrGrGrArGrUrGrArGrCrArGrCrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7187 | MG3-6-hRosa26-sgRNA-E3 | mA*mC*mU*rCrCrGrArUrUrArGrUrUrUrArUrCrUrUrCrCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7188 | MG3-6-hRosa26-sgRNA-F3 | mU*mC*mC*rCrArCrGrGrArCrUrArGrArGrUrUrGrGrUrGrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 7189 | MG3-6-hRosa26-sgRNA-G3 | mA*mA*mA*rUrGrGrArGrCrUrUrArGrUrCrArUrUrCrArCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |

TABLE 14-continued

| Guide RNAs and Sequences Targeted for Example 24 | | |
|---|---|---|
| SEQ ID NO: | NAME | SEQUENCE |
| 7190 | MG3-6-hRosa26-sgRNA-H3 | mA*mC*mC*rUrGrGrGrCrUrGrArUrUrUrArUrGrCrArArG rUrUrGrArGrArArUrCrGrArArArGrArUrUrCrUrUrArArUrArAr GrGrCrArUrCrCrUrUrCrCrGrArUrGrCrUrGrArCrUrUrCrUrCrA rCrCrGrUrCrCrGrUrUrUrCrCrArArUrArGrGrArGrCrGrGrGr CrGrGrUrArUrGrU*mU*mU*mU |
| 7191 | MG3-6-hRosa26-sgRNA-A4 | mG*mC*mU*rGrArUrUrUrArUrGrCrArArCrGrArGrArCrUrGr UrUrGrArGrArArUrCrGrArArArGrArUrUrCrUrUrArArUrArArG rGrCrArUrCrCrUrUrCrCrGrArUrGrCrUrGrArCrUrUrCrUrCrAr CrCrGrUrCrCrGrUrUrUrCrCrArArUrArGrGrArGrCrGrGrGr CrGrGrUrArUrGrU*mU*mU*mU |
| 7192 | MG3-6-hRosa26-sgRNA-B4 | mA*mU*mC*rArCrCrUrGrArGrUrUrUrArUrArCrCrArUrUrGr UrUrGrArGrArArUrCrGrArArArGrArUrUrCrUrUrArArUrArArG rGrCrArUrCrCrUrUrCrCrGrArUrGrCrUrGrArCrUrUrCrUrCrAr CrCrGrUrCrCrGrUrUrUrCrCrArArUrArGrGrArGrCrGrGrGr CrGrGrUrArUrGrU*mU*mU*mU |
| 7193 | MG3-6-hRosa26-sgRNA-C4 | mG*mC*mU*rGrCrArCrCrArCrCrArArArGrUrGrUrArGrCrArGr UrUrGrArGrArArUrCrGrArArArGrArUrUrCrUrUrArArUrArArG rGrCrArUrCrCrUrUrCrCrGrArUrGrCrUrGrArCrUrUrCrUrCrAr CrCrGrUrCrCrGrUrUrUrCrCrArArUrArGrGrArGrCrGrGrGr CrGrGrUrArUrGrU*mU*mU*mU |
| 7194 | MG3-6-hRosa26-sgRNA-D4 | mU*mU*mC*rCrCrUrCrCrCrUrCrArCrCrCrUrCrUrCrUrCrCrGr UrUrGrArGrArArUrCrGrArArArGrArUrUrCrUrUrArArUrArArG rGrCrArUrCrCrUrUrCrCrGrArUrGrCrUrGrArCrUrUrCrUrCrAr CrCrGrUrCrCrGrUrUrUrCrCrArArUrArGrGrArGrCrGrGrGr CrGrGrUrArUrGrU*mU*mU*mU |
| 7195 | MG3-6-hRosa26-sgRNA-E4 | mG*mC*mC*rUrGrGrUrGrUrCrUrCrGrCrGrArArArCrCrArGrG rUrUrGrArGrArArUrCrGrArArArGrArUrUrCrUrUrArArUrArAr GrGrCrArUrCrCrUrUrCrCrGrArUrGrCrUrGrArCrUrUrCrUrCrA rCrCrGrUrCrCrGrUrUrUrCrCrArArUrArGrGrArGrCrGrGrGr CrGrGrUrArUrGrU*mU*mU*mU |
| 7196 | MG3-6-hRosa26-sgRNA-F4 | mA*mC*mA*rGrArUrUrGrGrUrUrCrCrArCrCrArCrArArArUrGr UrUrGrArGrArArUrCrGrArArArGrArUrUrCrUrUrArArUrArArG rGrCrArUrCrCrUrUrCrCrGrArUrGrCrUrGrArCrUrUrCrUrCrAr CrCrGrUrCrCrGrUrUrUrCrCrArArUrArGrGrArGrCrGrGrGr CrGrGrUrArUrGrU*mU*mU*mU |
| 7197 | MG3-6-hRosa26-sgRNA-G4 | mC*mA*mC*rCrArCrArArArUrUrArArGrGrCrUrUrGrArGrCrGr UrUrGrArGrArArUrCrGrArArArGrArUrUrCrUrUrArArUrArArG rGrCrArUrCrCrUrUrCrCrGrArUrGrCrUrGrArCrUrUrCrUrCrAr CrCrGrUrCrCrGrUrUrUrCrCrArArUrArGrGrArGrCrGrGrGr CrGrGrUrArUrGrU*mU*mU*mU |
| 7198 | MG3-6-hRosa26-sgRNA-H4 | mC*mA*mU*rUrUrUrArUrCrCrUrUrUrUrUrCrCrUrUrArGrCrGr UrUrGrArGrArArUrCrGrArArArGrArUrUrCrUrUrArArUrArArG rGrCrArUrCrCrUrUrCrCrGrArUrGrCrUrGrArCrUrUrCrUrCrAr CrCrGrUrCrCrGrUrUrUrCrCrArArUrArGrGrArGrCrGrGrGr CrGrGrUrArUrGrU*mU*mU*mU |
| 7199 | MG3-6-hRosa26-target site-A1 | ATCTGTCTGGTTTCGCGAGACA |
| 7200 | MG3-6-hRosa26-target site-B1 | TTTCGCGAGACACCAGGCTACC |
| 7201 | MG3-6-hRosa26-target site-C1 | AGCAAGTACAACAAATGGAAAA |
| 7202 | MG3-6-hRosa26-target site-D1 | GCAAAAGCTAAAATTTTTCTAT |
| 7203 | MG3-6-hRosa26-target site-E1 | TGCTACACTTTGGTGGTGCAGC |

TABLE 14-continued

Guide RNAs and Sequences Targeted for Example 24

| SEQ ID NO: | NAME | SEQUENCE |
|---|---|---|
| 7204 | MG3-6-hRosa26-target site-F1 | ACTCCCCTGCAGGGCAACGCCC |
| 7205 | MG3-6-hRosa26-target site-G1 | CGACTCGACATGGAGGCGATGA |
| 7206 | MG3-6-hRosa26-target site-H1 | ATCACGCGAGGAGGAAAGGAGG |
| 7207 | MG3-6-hRosa26-target site-A2 | AGGAAAGGAGGGAGGGCTTCTT |
| 7208 | MG3-6-hRosa26-target site-B2 | ACCTCCTCCACCGCAGCTCCCT |
| 7209 | MG3-6-hRosa26-target site-C2 | GCGCCTCCCACCCACAAACCAG |
| 7210 | MG3-6-hRosa26-target site-D2 | CCCACCCCCACGAGTGCCTGTA |
| 7211 | MG3-6-hRosa26-target site-E2 | CTCGTGGGGGTGGGGGAGGAGC |
| 7212 | MG3-6-hRosa26-target site-F2 | GCTGCGGTGGAGGAGGTGGAGA |
| 7213 | MG3-6-hRosa26-target site-G2 | TCTCTGCTGCCTCCCGTCTTGT |
| 7214 | MG3-6-hRosa26-target site-H2 | CTCCCGTCTTGTAAGGACCGCC |
| 7215 | MG3-6-hRosa26-target site-A3 | CGAGTCGCTTCTCGATTATGGG |
| 7216 | MG3-6-hRosa26-target site-B3 | ATTATGGGGGGATTCTTTTGC |
| 7217 | MG3-6-hRosa26-target site-C3 | GGGATTCTTTTGCCTAGGCTTA |
| 7218 | MG3-6-hRosa26-target site-D3 | CCTGCAGGGGAGTGAGCAGCTG |
| 7219 | MG3-6-hRosa26-target site-E3 | ACTCCGATTAGTTTATCTTCCC |
| 7220 | MG3-6-hRosa26-target site-F3 | TCCCACGGACTAGAGTTGGTGT |
| 7221 | MG3-6-hRosa26-target site-G3 | AAATGGAGCTTAGTCATTCACC |
| 7222 | MG3-6-hRosa26-target site-H3 | ACCTGGGGCTGATTTTATGCAA |
| 7223 | MG3-6-hRosa26-target site-A4 | GCTGATTTTATGCAACGAGACT |
| 7224 | MG3-6-hRosa26-target site-B4 | ATCACCTGAGTTTTATACCATT |
| 7225 | MG3-6-hRosa26-target site-C4 | GCTGCACCACCAAAGTGTAGCA |
| 7226 | MG3-6-hRosa26-target site-D4 | TTCCCTCCCTCACCCTCTCTCC |
| 7227 | MG3-6-hRosa26-target site-E4 | GCCTGGTGTCTCGCGAAACCAG |
| 7228 | MG3-6-hRosa26-target site-F4 | ACAGATTGGTTCCACCACAAAT |

TABLE 14-continued

Guide RNAs and Sequences Targeted for Example 24

| SEQ ID NO: | NAME | SEQUENCE |
|---|---|---|
| 7229 | MG3-6-hRosa26-target site-G4 | CACCACAAATTAAGGCTTGAGC |
| 7230 | MG3-6-hRosa26-target site-H4 | CATTTTATCCTTTTTCCTTAGC |

r = native ribose base, m = 2'-O methyl modified base, F = 2' Fluro modified base, * = phosphorothioate bond

Figure 18:
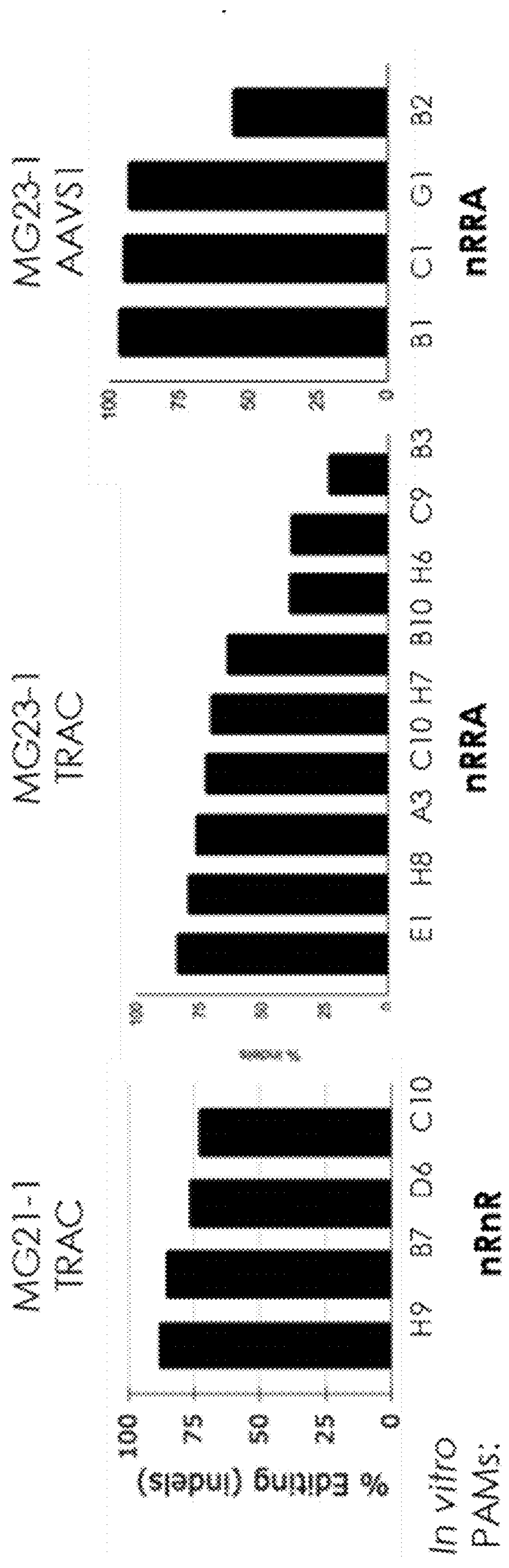
FIG. 18 depicts the gene editing outcomes at the DNA level for TRAC and AAVS1 in K562 cells.
Figure 18:
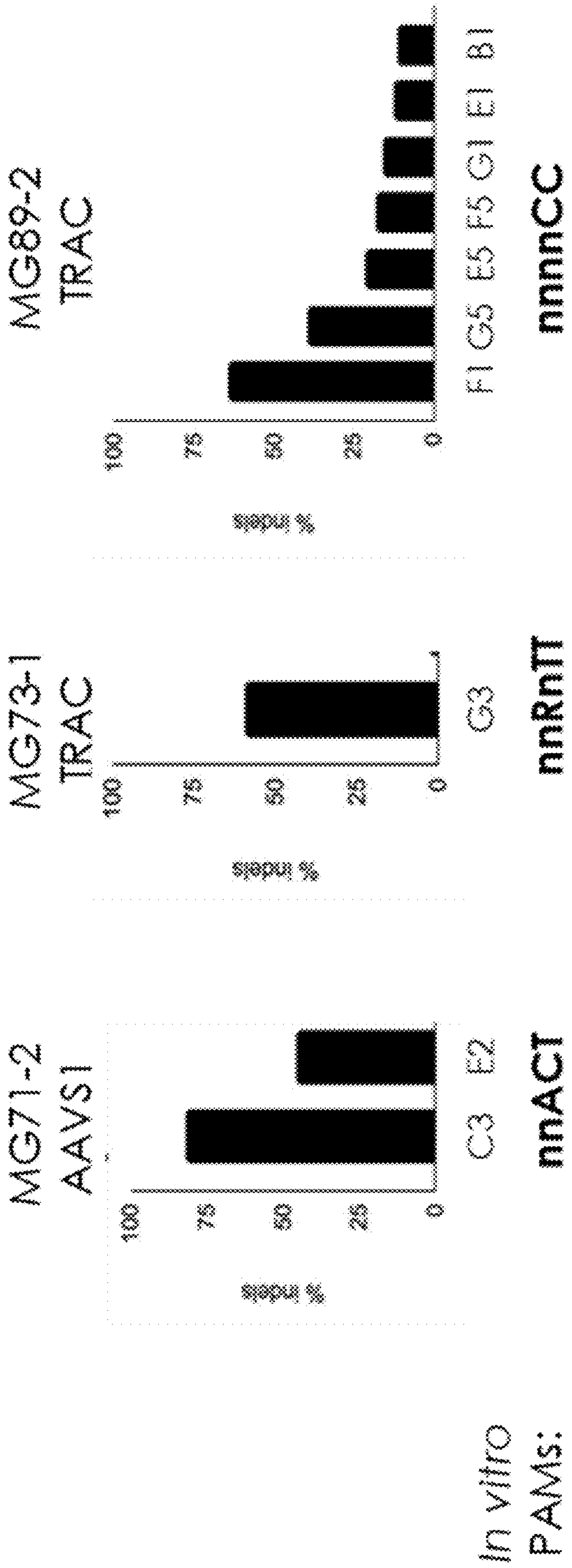

Example 25—Gene Editing Outcomes at the DNA Level for TRAC and AAVS1 in K562 Cells Nucleofection of MG21-1, MG23-1, MG73-1, MG89-2, and MG71-2 mRNA along with the matching guide RNA (500 ng mRNA/150 pmol guide) was performed into K562 cells (200,000) using the Lonza 4D electroporator. Cells were harvested and genomic DNA prepared three days post-transfection. PCR primers appropriate for use in NGS-based DNA sequencing were generated, optimized, and used to amplify the individual target sequences for each guide RNA. The amplicons were sequenced on an Illumina MiSeq machine and analyzed with a proprietary Python script to measure gene editing (FIG. 18).

TABLE 15

Guide RNAs and Sequences Targeted for Example 25 When Targeting TRAC

| SEQ ID NO: | NAME | SEQUENCE |
|---|---|---|
| 7231 | MG21-1-TRAC-sgRNA-H9 | mC*mA*mC*rCrUrUrCrUrUrCrCrCrCrArGrCrCrCrArGrGrUrGrUrUrGrUrArGrUrUrCrCrCrCrUrUrUrUrGrArArArArArArArGrUrGrUrGrUrUrArCrUrGrCrArArUrArArGrGrUrArArArArCrArCrCrArCrGrArArGrCrUrCrUrGrCrCrCrUrArArCrUrGrCrCrUrUrArGrCrArGrUrUrArGrGrGrCrArUrC*mU*mU*mU |
| 7232 | MG21-1-TRAC-sgRNA-B7 | mC*mA*mA*rGrArGrCrArArCrArGrUrGrCrUrGrUrGrGrCrCrGrUrUrGrUrArGrUrUrCrCrCrCrUrUrUrUrGrArArArArArArArGrUrGrUrGrUrUrArCrUrGrCrArArUrArArGrGrUrArArArArCrArCrCrArCrGrArArGrCrUrCrUrGrCrCrCrUrArArCrUrGrCrCrUrUrArGrCrArGrUrUrArGrGrGrCrArUrC*mU*mU*mU |
| 7233 | MG21-1-TRAC-sgRNA-D6 | mA*mG*mA*rCrArUrGrArGrGrUrCrUrArUrGrGrArCrUrUrCrGrUrUrGrUrArGrUrUrCrCrCrCrUrUrUrUrGrArArArArArArArGrUrGrUrGrUrUrArCrUrGrCrArArUrArArGrGrUrArArArArCrArCrCrArCrGrArArGrCrUrCrUrGrCrCrCrUrArArCrUrGrCrCrUrUrArGrCrArGrUrUrArGrGrGrCrArUrC*mU*mU*mU |
| 7234 | MG21-1-TRAC-sgRNA-C10 | mC*mC*mA*rArArGrCrUrGrCrCrCrUrUrArCrCrUrGrGrGrCrGrUrUrGrUrArGrUrUrCrCrCrCrUrUrUrUrGrArArArArArArArGrUrGrUrGrUrUrArCrUrGrCrArArUrArArGrGrUrArArArArCrArCrCrArCrGrArArGrCrUrCrUrGrCrCrCrUrArArCrUrGrCrCrUrUrArGrCrArGrUrUrArGrGrGrCrArUrC*mU*mU*mU |
| 7235 | MG21-1-TRAC-target site-H9 | CACCTTCTTCCCCAGCCCAGGT |
| 7236 | MG21-1-TRAC-target site-B7 | CAAGAGCAACAGTGCTGTGGCC |
| 7237 | MG21-1-TRAC-target site-D6 | AGACATGAGGTCTATGGACTTC |
| 7238 | MG21-1-TRAC-target site-C10 | CCAAAGCTGCCCTTACCTGGGC |
| 7239 | MG23-1-TRAC-sgRNA-E1 | mC*mC*mG*rUrGrUrArCrCrArGrCrUrGrArGrArGrArCrUrCrGrUrUrUrGrArGrArArCrCrUrGrArArArArGrGrUrGrArGrUrGrCrArArArUrArArGrGrUrUrUrArArCrCrGrArArArUrUrGrUrUrUrArCrCrUrGrCrArUrUrGrUrGrCrArGrUrArUrArArGrArArArGrArCrCrGrCrGrArGrGrUrCrU*mU*mU*mU |

TABLE 15-continued

| Guide RNAs and Sequences Targeted for Example 25 When Targeting TRAC | | |
|---|---|---|
| SEQ ID NO: | NAME | SEQUENCE |
| 7240 | MG23-1-TRAC-sgRNA-H8 | mU*mU*mG*rGrGrUrUrCrCrGrArArUrCrCrUrCrCrUrCrCrUrGrUrUrUrGrArGrArArCrCrUrGrArArArArGrGrUrGrArGrUrGrCrArArArUrArArGrGrUrUrUrArArCrCrGrArArArUrUrGrUrUrUrArCrCrUrGrCrArUrUrGrUrGrCrArGrUrArUrArArGrArArArGrArCrCrGrCrGrArGrGrUrCrU*mU*mU*mU |
| 7241 | MG23-1-TRAC-sgRNA-A3 | mA*mC*mA*rGrUrGrCrUrGrUrGrGrCrCrUrGrGrArGrCrArArGrUrUrUrGrArGrArArCrCrUrGrArArArArGrGrUrGrArGrUrGrCrArArArUrArArGrGrUrUrUrArArCrCrGrArArArUrUrGrUrUrUrArCrCrUrGrCrArUrUrGrUrGrCrArGrUrArUrArArGrArArArGrArCrCrGrCrGrArGrGrUrCrU*mU*mU*mU |
| 7242 | MG23-1-TRAC-sgRNA-C10 | mU*mG*mA*rArArGrUrUrUrArGrGrUrUrCrGrUrArUrCrUrGrGrUrUrUrGrArGrArArCrCrUrGrArArArArGrGrUrGrArGrUrGrCrArArArUrArArGrGrUrUrUrArArCrCrGrArArArUrUrGrUrUrUrArCrCrUrGrCrArUrUrGrUrGrCrArGrUrArUrArArGrArArArGrArCrCrGrCrGrArGrGrUrCrU*mU*mU*mU |
| 7243 | MG23-1-TRAC-sgRNA-H7 | mG*mC*mU*rUrGrArCrArUrCrArCrArGrGrArArCrUrUrUrCrGrUrUrUrGrArGrArArCrCrUrGrArArArArGrGrUrGrArGrUrGrCrArArArUrArArGrGrUrUrUrArArCrCrGrArArArUrUrGrUrUrUrArCrCrUrGrCrArUrUrGrUrGrCrArGrUrArUrArArGrArArArGrArCrCrGrCrGrArGrGrUrCrU*mU*mU*mU |
| 7244 | MG23-1-TRAC-sgRNA-B10 | mA*mA*mC*rCrCrArArUrCrArCrUrGrArCrArGrGrUrUrUrUrGrUrUrUrGrArGrArArCrCrUrGrArArArArGrGrUrGrArGrUrGrCrArArArUrArArGrGrUrUrUrArArCrCrGrArArArUrUrGrUrUrUrArCrCrUrGrCrArUrUrGrUrGrCrArGrUrArUrArArGrArArArGrArCrCrGrCrGrArGrGrUrCrU*mU*mU*mU |
| 7245 | MG23-1-TRAC-sgRNA-H6 | mC*mC*mU*rGrUrGrArUrGrUrCrArArGrCrUrGrGrUrCrGrArGrUrUrUrGrArGrArArCrCrUrGrArArArArGrGrUrGrArGrUrGrCrArArArUrArArGrGrUrUrUrArArCrCrGrArArArUrUrGrUrUrUrArCrCrUrGrCrArUrUrGrUrGrCrArGrUrArUrArArGrArArArGrArCrCrGrCrGrArGrGrUrCrUxmU*mU*mU |
| 7246 | MG23-1-TRAC-sgRNA-E7 | mU*mA*mG*rArCrCrCrCrUrGrUrCrUrUrArCrCrUrGrUrUrUrGrUrUrUrGrArGrArArCrCrUrGrArArArArGrGrUrGrArGrUrGrCrArArArUrArArGrGrUrUrUrArArCrCrGrArArArUrUrGrUrUrUrArCrCrUrGrCrArUrUrGrUrGrCrArGrUrArUrArArGrArArArGrArCrCrGrCrGrArGrGrUrCrU*mU*mU*mU |
| 7247 | MG23-1-TRAC-sgRNA-C9 | mA*mG*mC*rCrGrCrArGrCrGrUrCrArUrGrArGrCrArGrArUrGrUrUrUrGrArGrArArCrCrUrGrArArArArGrGrUrGrArGrUrGrCrArArArUrArArGrGrUrUrUrArArCrCrGrArArArUrUrGrUrUrUrArCrCrUrGrCrArUrUrGrUrGrCrArGrUrArUrArArGrArArArGrArCrCrGrCrGrArGrGrUrCrU*mU*mU*mU |
| 7248 | MG23-1-TRAC-target site-E1 | CCGTGTACCAGCTGAGAGACTC |
| 7249 | MG23-1-TRAC-target site-H8 | TTGGGTTCCGAATCCTCCTCCT |
| 7250 | MG23-1-TRAC-target site-A3 | ACAGTGCTGTGGCCTGGAGCAA |
| 7251 | MG23-1-TRAC-target site-C10 | TGAAAGTTTAGGTTCGTATCTG |
| 7252 | MG23-1-TRAC-target site-H7 | GCTTGACATCACAGGAACTTTC |
| 7253 | MG23-1-TRAC-target site-B10 | AACCCAATCACTGACAGGTTTT |
| 7254 | MG23-1-TRAC-target site-H6 | CCTGTGATGTCAAGCTGGTCGA |
| 7255 | MG23-1-TRAC-target site-E7 | TAGACCCCTGTCTTACCTGTTT |
| 7256 | MG23-1-TRAC-target site-C9 | AGCCGCAGCGTCATGAGCAGAT |

TABLE 15-continued

Guide RNAs and Sequences Targeted for Example 25 When Targeting TRAC

| SEQ ID NO: | NAME | SEQUENCE |
|---|---|---|
| 7269 | MG73-1-TRAC-sgRNA-G3 | mU*mC*mU*rUrGrGrUrUrUrUrArCrArGrArUrArCrGrArArCrCrUrGrUrUrArUrArGrUrGrGrGrArArArUrCrArCrUrArUrArArUrArArGrUrGrArArArUrCrGrCrArArGrGrCrUrCrUrGrUrUrCrUrUrGrArArCrArUrCrCrUrUrUrArUrUrArUrArArArArCrUrCrCrUrGrCrCrArArUrCrGrGrUrUrGrGrArGrU*mU*mU*mU |
| 7270 | MG73-1-TRAC-target site-G3 | TCTTGGTTTTACAGATACGAACCT |
| 7271 | MG89-2-TRAC-sgRNA-F1 | mA*mU*mA*rUrCrCrArGrArArCrCrCrUrGrArCrCrCrUrGrCrCrGrGrUrUrGrUrArGrCrUrUrCrCrUrUrGrArArGrArArArUrUrCrArArCrGrUrUrGrUrUrArCrArArUrArArGrGrUrUrUrUrCrGrArArArGrArUrUrArCrCrGrArArCrCrCrGrCrCrCrUrCrArCrUrUrArGrGrUrGrArGrGrGrCrU*mU*mU*mU |
| 7272 | MG89-2-TRAC-sgRNA-G5 | mG*mG*mC*rCrArCrUrUrUrCrArGrGrArGrGrArGrGrArUrUrCrGrGrUrUrGrUrArGrCrUrUrCrCrUrUrGrArArGrArArArUrUrCrArArCrGrUrUrGrUrUrArCrArArUrArArGrGrUrUrUrUrCrGrArArArGrArUrUrArCrCrGrArArCrCrCrGrCrCrCrUrCrArCrUrUrArGrGrUrGrArGrGrGrCrU*mU*mU*mU |
| 7273 | MG89-2-TRAC-sgRNA-E5 | mC*mG*mC*rArGrCrGrUrCrArUrGrArGrCrArGrArUrUrArArArCrGrUrUrGrUrArGrCrUrUrCrCrUrUrGrArArGrArArArUrUrCrArArCrGrUrUrGrUrUrArCrArArUrArArGrGrUrUrUrUrCrGrArArArGrArUrUrArCrCrGrArArCrCrCrGrCrCrCrUrCrArCrUrUrArGrGrUrGrArGrGrGrCrU*mU*mU*mU |
| 7274 | MG89-2-TRAC-sgRNA-F5 | mC*mG*mG*rCrCrArCrUrUrUrCrArGrGrArGrGrArGrGrArUrUrCrGrUrUrGrUrArGrCrUrUrCrCrUrUrGrArArGrArArArUrUrCrArArCrGrUrUrGrUrUrArCrArArUrArArGrGrUrUrUrUrCrGrArArArGrArUrUrArCrCrGrArArCrCrCrGrCrCrCrUrCrArCrUrUrArGrGrUrGrArGrGrGrCrU*mU*mU*mU |
| 7275 | MG89-2-TRAC-sgRNA-G1 | mG*mC*mC*rGrUrGrUrArCrCrArGrCrUrGrArGrArGrArCrUrCrUrGrUrUrGrUrArGrCrUrUrCrCrUrUrGrArArGrArArArUrUrCrArArCrGrUrUrGrUrUrArCrArArUrArArGrGrUrUrUrUrCrGrArArArGrArUrUrArCrCrGrArArCrCrCrGrCrCrCrUrCrArCrUrUrArGrGrUrGrArGrGrGrCrU*mU*mU*mU |
| 7276 | MG89-2-TRAC-sgRNA-E1 | mC*mC*mC*rArCrArGrArUrArUrCrCrArGrArArCrCrCrUrGrArCrGrUrUrGrUrArGrCrUrUrCrCrUrUrGrArArGrArArArUrUrCrArArCrGrUrUrGrUrUrArCrArArUrArArGrGrUrUrUrUrCrGrArArArGrArUrUrArCrCrGrArArCrCrCrGrCrCrCrUrCrArCrUrUrArGrGrUrGrArGrGrGrCrU*mU*mU*mU |
| 7277 | MG89-2-TRAC-sgRNA-B1 | mA*mU*mC*rCrUrCrUrUrGrUrCrCrCrArCrArGrArUrArUrCrCrArGrUrUrGrUrArGrCrUrUrCrCrUrUrGrArArGrArArArUrUrCrArArCrGrUrUrGrUrUrArCrArArUrArArGrGrUrUrUrUrCrGrArArArGrArUrUrArCrCrGrArArCrCrCrGrCrCrCrUrCrArCrUrUrArGrGrUrGrArGrGrGrCrUxmU*mU*mU |
| 7278 | MG89-2-TRAC-target site-F1 | ATATCCAGAACCCTGACCCTGCCG |
| 7279 | MG89-2-TRAC-target site-G5 | GGCCACTTTCAGGAGGAGGATTCG |
| 7280 | MG89-2-TRAC-target site-E5 | CGCAGCGTCATGAGCAGATTAAAC |
| 7281 | MG89-2-TRAC-target site-F5 | CGGCCACTTTCAGGAGGAGGATTC |
| 7282 | MG89-2-TRAC-target site-G1 | GCCGTGTACCAGCTGAGAGACTCT |

TABLE 15-continued

| Guide RNAs and Sequences Targeted for Example 25 When Targeting TRAC | | |
|---|---|---|
| SEQ ID NO: | NAME | SEQUENCE |
| 7283 | MG89-2-TRAC-target site-E1 | CCCACAGATATCCAGAACCCTGAC |
| 7284 | MG89-2-TRAC-target site-B1 | ATCCTCTTGTCCCACAGATATCCA |

r = native ribose base, m = 2'-O methyl modified base, F = 2' Fluro modified base, * = phosphorothioate bond

TABLE 16

| Guide RNAs and Sequences Targeted for Example 25 When Targeting AAVS1 | | |
|---|---|---|
| SEQ ID NO: | NAME | SEQUENCE |
| 7257 | MG23-1-AAVS1-sgRNA-B1 | mG*mC*mU*rArCrUrGrGrCrCrUrUrArUrCrUrCrArCrArGrGrGrUrUrUrGrArGrArArCrCrUrGrArArArArGrGrUrGrArGrUrGrCrArArArUrArArGrGrUrUrUrArArCrCrGrArArArUrUrGrUrUrUrArCrCrUrGrCrArUrUrGrUrGrCrArGrUrArUrArArGrArArArGrArCrCrGrCrGrArGrGrUrCrU*mU*mU*mU |
| 7258 | MG23-1-AAVS1-sgRNA-C1 | mC*mU*mA*rCrUrGrGrCrCrUrUrArUrCrUrCrArCrArGrGrUrGrUrUrUrGrArGrArArCrCrUrGrArArArArGrGrUrGrArGrUrGrCrArArArUrArArGrGrUrUrUrArArCrCrGrArArArUrUrGrUrUrUrArCrCrUrGrCrArUrUrGrUrGrCrArGrUrArUrArArGrArArArGrArCrCrGrCrGrArGrGrUrCrU*mU*mU*mU |
| 7259 | MG23-1-AAVS1-sgRNA-G1 | mA*mC*mU*rGrArCrGrCrArCrGrGrArGrGrArArCrArArUrArGrUrUrUrGrArGrArArCrCrUrGrArArArArGrGrUrGrArGrUrGrCrArArArUrArArGrGrUrUrUrArArCrCrGrArArArUrUrGrUrUrUrArCrCrUrGrCrArUrUrGrUrGrCrArGrUrArUrArArGrArArArGrArCrCrGrCrGrArGrGrUrCrU*mU*mU*mU |
| 7260 | MG23-1-AAVS1-sgRNA-B2 | mG*mG*mA*rArCrArArUrArUrArArArUrUrGrGrGrGrArCrUrGrUrUrUrGrArGrArArCrCrUrGrArArArArGrGrUrGrArGrUrGrCrArArArUrArArGrGrUrUrUrArArCrCrGrArArArUrUrGrUrUrUrArCrCrUrGrCrArUrUrGrUrGrCrArGrUrArUrArArGrArArArGrArCrCrGrCrGrArGrGrUrCrU*mU*mU*mU |
| 7261 | MG23-1-AAVS1-target site-B1 | GCTACTGGCCTTATCTCACAGG |
| 7262 | MG23-1-AAVS1-target site-C1 | CTACTGGCCTTATCTCACAGGT |
| 7263 | MG23-1-AAVS1-target site-G1 | ACTGACGCACGGAGGAACAATA |
| 7264 | MG23-1-AAVS1-target site-B2 | GGAACAATATAAATTGGGGACT |
| 7265 | MG71-2-AAVS1-sgRNA-C3 | mG*mG*mA*rGrArGrGrGrUrArGrCrGrCrArGrGrGrUrGrGrUrUrUrGrArGrArGrUrGrArGrArArArUrCrArCrGrArGrUrUrCrArArArArArArCrArUrGrArUrUrUrArUrUrCrArArArCrCrGrUrCrUrUrCrUrUrCrGrGrArArGrGrCrCrCrCrArCrArGrUrGrUrGrUrGrGrArCrArGrUrArArArGrCrUrUrGrCrUrUrCrGrGrCrArArGrCrU*mU*mU*mU |
| 7266 | MG71-2-AAVS1-sgRNA-E2 | mG*mC*mC*rCrUrGrCrCrArGrGrArCrGrGrGrGrCrUrGrGrUrUrUrGrArGrArGrUrGrArGrArArArUrCrArCrGrArGrUrUrCrArArArArArArCrArUrGrArUrUrUrArUrUrCrArArArCrCrGrUrCrUrUrCrUrUrCrGrGrArArGrGrCrCrCrCrArCrArGrUrGrUrGrUrGrGrArCrArGrUrArArArGrCrUrUrGrCrUrUrCrGrGrCrArArGrCrU*mU*mU*mU |

TABLE 16-continued

| Guide RNAs and Sequences Targeted for Example 25 When Targeting AAVS1 | | |
|---|---|---|
| SEQ ID NO: | NAME | SEQUENCE |
| 7267 | MG71-2-AAVS1-target site-C3 | GGAGAGGGTAGCGCAGGGTG |
| 7268 | MG71-2-AAVS1-target site-E2 | GCCCTGCCAGGACGGGGCTG |

r = native ribose base, m = 2'-O methyl modified base, F = 2' Fluro modified base, * = phosphorothioate bond

Example 26—MG3-6 Nuclease Guide Screen for Human HAO-1 Gene Using mRNA Transfection of Hep3B Cells Guide RNAs for the MG3-6 nuclease targeting exons 1 to 4 of the human HAO-1 gene (encodes glycolate oxidase) were identified in silico by searching for the PAM sequence 5' NNRGRYY 3'. A total of 21 guides with the fewest predicted off-target sites in the human genome were chemically synthesized as single guide RNAs with AltR1/AltR2 end-modifications (IDT). The full sequences of the sgRNA are SEQ ID NOs: 11352-11372.

TABLE 17

| Guide sequences used in Example 26 | | |
|---|---|---|
| SEQ ID NO: | Entity Name | Sequence |
| 11352 | hH36-1 | AAUUAGCCGGGGGAGCAUUUUCGUUGAGAAUCGAAAGAUUCUUAAUAAGGCAUCCUUCCGAUGCUGACUUCUCACCGUCCGUUUUCCAAUAGGAGCGGGCGGUAUGUUUU |
| 11353 | hH36-2 | CCCAGACCUGUAAUAGUCAUAUGUUGAGAAUCGAAAGAUUCUUAAUAAGGCAUCCUUCCGAUGCUGACUUCUCACCGUCCGUUUUCCAAUAGGAGCGGGCGGUAUGUUUU |
| 11354 | hH36-3 | CCAAAGUCUAUAUAUGACUAUUGUUGAGAAUCGAAAGAUUCUUAAUAAGGCAUCCUUCCGAUGCUGACUUCUCACCGUCCGUUUUCCAAUAGGAGCGGGCGGUAUGUUUU |
| 11355 | hH36-4 | CAAAGUUUCUUCAUCAUUUGCCGUUGAGAAUCGAAAGAUUCUUAAUAAGGCAUCCUUCCGAUGCUGACUUCUCACCGUCCGUUUUCCAAUAGGAGCGGGCGGUAUGUUUU |
| 11356 | hH36-5 | GAUGCUCCGGAAUGUUGCUGAAGUUGAGAAUCGAAAGAUUCUUAAUAAGGCAUCCUUCCGAUGCUGACUUCUCACCGUCCGUUUUCCAAUAGGAGCGGGCGGUAUGUUUU |
| 11357 | hH36-6 | CUCUGUCCUAAAACAGAAGUCGGUUGAGAAUCGAAAGAUUCUUAAUAAGGCAUCCUUCCGAUGCUGACUUCUCACCGUCCGUUUUCCAAUAGGAGCGGGCGGUAUGUUUU |
| 11358 | hH36-7 | UGUCGACUUCUGUUUUAGGACAGUUGAGAAUCGAAAGAUUCUUAAUAAGGCAUCCUUCCGAUGCUGACUUCUCACCGUCCGUUUUCCAAUAGGAGCGGGCGGUAUGUUUU |
| 11359 | hH36-8 | GGGUCAGCAUGCCAAUAUGUGUGUUGAGAAUCGAAAGAUUCUUAAUAAGGCAUCCUUCCGAUGCUGACUUCUCACCGUCCGUUUUCCAAUAGGAGCGGGCGGUAUGUUUU |
| 11360 | hH36-9 | UCAUGCCCGUUCCCAGGGACUGGUUGAGAAUCGAAAGAUUCUUAAUAAGGCAUCCUUCCGAUGCUGACUUCUCACCGUCCGUUUUCCAAUAGGAGCGGGCGGUAUGUUUU |
| 11361 | hH36-10 | ACUCAACAUCAUGCCCGUUCCCGUUGAGAAUCGAAAGAUUCUUAAUAAGGCAUCCUUCCGAUGCUGACUUCUCACCGUCCGUUUUCCAAUAGGAGCGGGCGGUAUGUUUU |
| 11362 | hH36-11 | GAACGGGCAUGAUGUUGAGUUCGUUGAGAAUCGAAAGAUUCUUAAUAAGGCAUCCUUCCGAUGCUGACUUCUCACCGUCCGUUUUCCAAUAGGAGCGGGCGGUAUGUUUU |
| 11363 | hH36-12 | AGUUGCAGCCAACGAAGUGCCUGUUGAGAAUCGAAAGAUUCUUAAUAAGGCAUCCUUCCGAUGCUGACUUCUCACCGUCCGUUUUCCAAUAGGAGCGGGCGGUAUGUUUU |

TABLE 17-continued

Guide sequences used in Example 26

| SEQ ID NO: | Entity Name | Sequence |
|---|---|---|
| 11364 | hH36-13 | UUGGCUGCAACUGUAUAUCUACGUUGAGAAUCGAAAGAUUCUUAAUAAGGCAUCCUUCCGAUGCUGACUUCUCACCGUCCGUUUUCCAAUAGGAGCGGGCGGUAUGUUUU |
| 11365 | hH36-14 | GCUAGUGCGGCAGGCAGAGAAGGUUGAGAAUCGAAAGAUUCUUAAUAAGGCAUCCUUCCGAUGCUGACUUCUCACCGUCCGUUUUCCAAUAGGAGCGGGCGGUAUGUUUU |
| 11366 | hH36-15 | GGCAGGCAGAGAAGAUGGGCUAGUUGAGAAUCGAAAGAUUCUUAAUAAGGCAUCCUUCCGAUGCUGACUUCUCACCGUCCGUUUUCCAAUAGGAGCGGGCGGUAUGUUUU |
| 11367 | hH36-16 | AACCGUCUGGAUGAUGUGCGUAGUUGAGAAUCGAAAGAUUCUUAAUAAGGCAUCCUUCCGAUGCUGACUUCUCACCGUCCGUUUUCCAAUAGGAGCGGGCGGUAUGUUUU |
| 11368 | hH36-17 | GAGGAAAAUUUUGGAGACGACAGUUGAGAAUCGAAAGAUUCUUAAUAAGGCAUCCUUCCGAUGCUGACUUCUCACCGUCCGUUUUCCAAUAGGAGCGGGCGGUAUGUUUU |
| 11369 | hH36-18 | UGCUGCAUAUGUGGCUAAAGCAGUUGAGAAUCGAAAGAUUCUUAAUAAGGCAUCCUUCCGAUGCUGACUUCUCACCGUCCGUUUUCCAAUAGGAGCGGGCGGUAUGUUUU |
| 11370 | hH36-19 | UUGAUAUCUUCCCAGCUGAUAGGUUGAGAAUCGAAAGAUUCUUAAUAAGGCAUCCUUCCGAUGCUGACUUCUCACCGUCCGUUUUCCAAUAGGAGCGGGCGGUAUGUUUU |
| 11371 | hH36-20 | UGGGAAGAUAUCAAAUGGCUGAGUUGAGAAUCGAAAGAUUCUUAAUAAGGCAUCCUUCCGAUGCUGACUUCUCACCGUCCGUUUUCCAAUAGGAGCGGGCGGUAUGUUUU |
| 11372 | hH36-21 | AAUUGUUGCAAAGGGCAUUUUGGUUGAGAAUCGAAAGAUUCUUAAUAAGGCAUCCUUCCGAUGCUGACUUCUCACCGUCCGUUUUCCAAUAGGAGCGGGCGGUAUGUUUU |

Hep3B Transfection Protocol

The mRNA encoding MG3-6 was generated by T7 polymerase in vitro transcription of a plasmid in which the coding sequence of MG3-6 had been cloned. The MG3-6 coding sequence was codon optimized using human codon usage tables and flanked by nuclear localization signals derived from SV40 (at the N-terminus) and from Nucleoplasmin (at the C-terminus). In addition, a 5' untranslated region (5' UTR) was included at the 5' end of the coding sequence to improve translation. A 3' UTR followed by an approximately 90 to 110 nucleotide poly A tract was included in the mRNA (encoded in the plasmid) at the 3' end of the coding sequence to improve mRNA stability in vivo. The DNA sequence that encodes the MG3-6 mRNA without the polyA tail is shown in SEQ ID 22. The in vitro transcription reaction included the Clean Cap® capping reagent (Trilink BioTechnologies) and the resulting RNA was purified using the MEGAClear™ Transcription Clean-Up kit (Invitrogen) and purity was evaluated using the TapeStation (Agilent) and found to be composed of >90% full length RNA.

300 ng of MG3-6 mRNA and 120 ng of each single guide RNA were transfected into Hep3B cells as follows. One day prior to transfection, Hep3B cells that had been cultured for less than 10 days in EMEM-10% FBS-2 mM glutamine-1% NEAA media, without Pen/Step, were seeded into a TC-treated 24 well plate. Cells were counted, and the equivalent volume to 60,000 viable cells were added to each well. Additional pre-equilibrated media was added to each well to bring the total volume to 500 μL. On the day of transfection, 25 μL of OptiMEM media and 1.25 μL of Lipofectamine Messenger Max Solution (Thermo Fisher) were mixed in a master mix solution, vortexed, and allowed to sit for at least 5 minutes at room temperature. In separate tubes, 300 ng of the MG3-6/3-4 mRNA and 120 ng of the sgRNA were mixed with 25 μL of OptiMEM media and vortexed briefly. The appropriate volume of MessengerMax solution was added to each RNA solution, mixed by flicking the tube, and briefly spun down at a low speed. The complete editing reagent solutions were allowed to incubate for 10 minutes at room temperature, then added directly to the Hep3B cells. Two days post transfection, the media was aspirated from each well of Hep3B cells and genomic DNA was purified by automated magnetic bead purification on the KingFisher Flex robot with the MagMAX™ DNA Multi-Sample Ultra 2.0 Kit.

PCR Amplification and Editing Analysis by Sanger Sequencing

HAO-1 gene sequences targeted by the different sgRNA were amplified by PCR from purified genomic DNA using the exon-specific primers of Table 18 and Phusion Flash High-Fidelity PCR Master Mix (Thermo Fisher).

TABLE 18

Primers designed for the human HAO1 gene, used for PCR at each of the first four exons, and for Sanger sequencing.

| Target Exon | Use | Primer Name | Primer Sequence |
|---|---|---|---|
| Human | Fwd PCR | PCR_hHe1_F_+490 | TTTCATGGATGCCCCGTTCA |
| HAO1 | Rev PCR | PCR_hHe1_R_-412 | ACGAAAAGCCAGCAGGAAGA |
| Exon 1 | Sequencing | Seq_hHe1_R_-121 | AGCCCCAAGAACTTTTCCCT |
| Human | Fwd PCR | PCR_hHe2_F_+391 | TGCATCAGTGGTTGTCAGGG |
| HAO1 | Rev PCR | PCR_hHe2_R_-387 | CCTAGCTGTGACTTTGGGCA |
| Exon 2 | Sequencing | Seq_hHe2_R_-152 | TGGAAAGAAGAGGAGCAGGAC |
| Human | Fwd PCR | PCR_hHe3_F_+238 | AGGCTGGATGTTCAGGTTCTT |
| HAO1 | Rev PCR | PCR_hHe3_R_-212 | TCCCAAAGCCAAAGCCCTTA |
| Exon 3 | Sequencing | Seq_hHe3_F_+186 | AGCAGAAATAACTCCAGTAGCCA |
| Human | Fwd PCR | PCR_hHe4_F_+324 | GCTGGCTGAAAATCGTGTCAA |
| HAO1 | Rev PCR | PCR_hHe4_R_-348 | TCCTTGGGGCTTCTCTTTGG |
| Exon 4 | Sequencing | Seq_hHe4_F_+174 | ACTGATTAAGACCACTAGAGTATCACA |

PCR products were purified and concentrated using DNA clean & concentrator 5 (Zymo Research) and 40 ng of PCR product subjected to Sanger sequencing (ELIM Biosciences).

Figure 19:
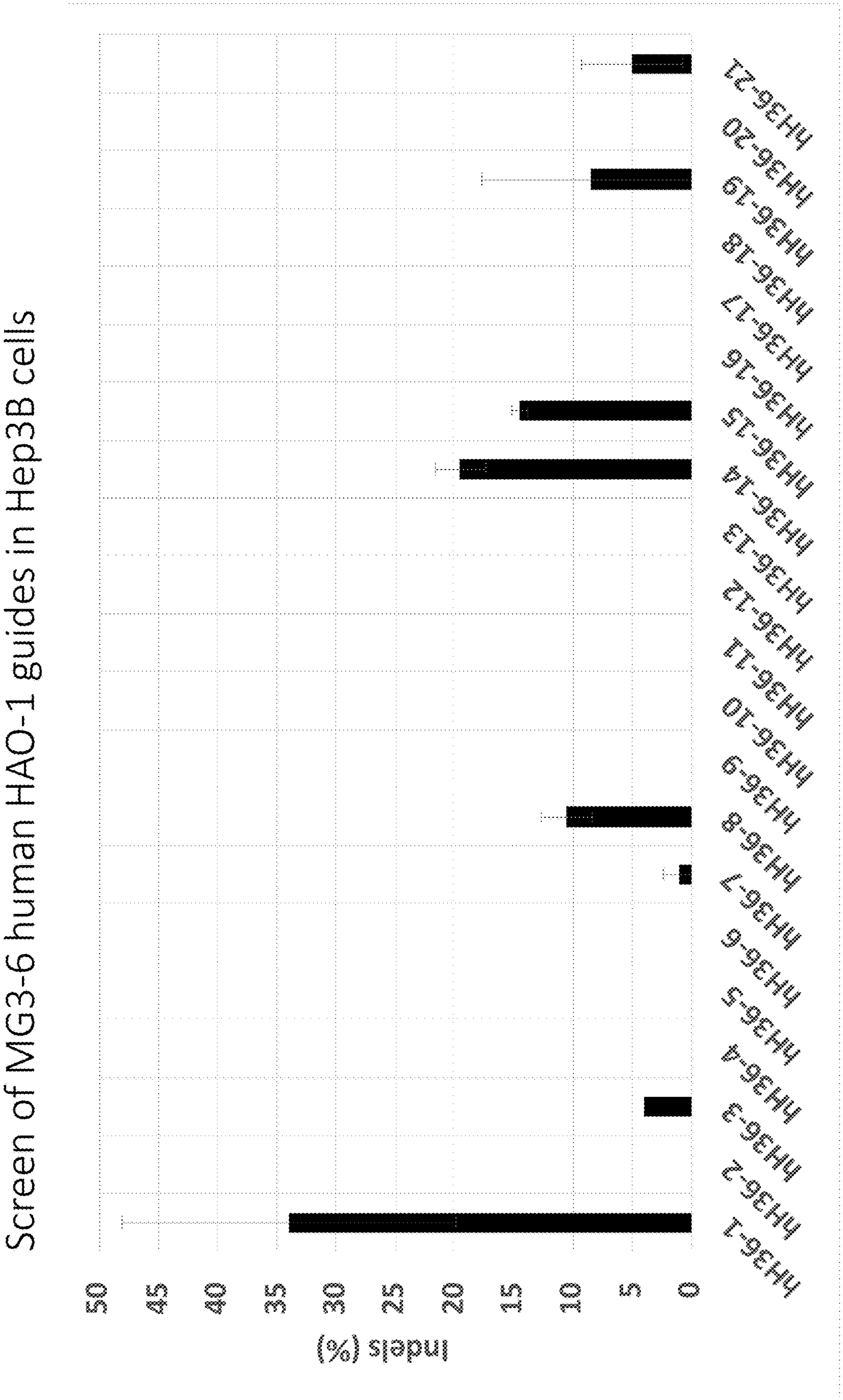
FIG. 19 depicts the activity of chemically modified MG3-6 human HAO-1 guides in Hep3B cells when delivered as mRNA and gRNA using Lipofectamine Messenger Max.

The Sanger sequencing chromatograms were analyzed for insertions and deletions (INDELS) at the predicted target site for each sgRNA by an algorithm called Tracking of Indels by DEcomposition (TIDE) as described by Brinkman et al. (Nucleic Acids Res. 2014 Dec. 16; 42(22): e168. Published online 2014 Oct. 9. doi: 10.1093/nar/gku936). From this screen guides hH364-1, 14, and 15 were identified as having the highest editing activity in Hep3B cells (FIG. 19 and Table 19).

TABLE 19

Editing activity of MG3-6 guides at human HAO1 gene delivered by mRNA transfection

| Guide Name | PAM | Spacer Sequence | Editing Activity in Hep3B (Average % indels) | Spacer Sequence SEQ ID NO: |
|---|---|---|---|---|
| hH36-1 | ACAGGTT | AATTAGCCGGGGGAGCATTTTC | 34.0 | 11773 |
| hH36-2 | ATAGACT | CCCAGACCTGTAATAGTCATAT | 0.0 | 11774 |
| hH36-3 | ACAGGTC | CCAAAGTCTATATATGACTATT | 4.0 | 11775 |
| hH36-4 | CCAGACC | CAAAGTTTCTTCATCATTTGCC | 0.0 | 11776 |
| hH36-5 | ACAGATC | GATGCTCCGGAATGTTGCTGAA | 0.0 | 11777 |
| hH36-6 | ACAGATC | CTCTGTCCTAAAACAGAAGTCG | 0.0 | 11778 |
| hH36-7 | GAGGGTC | TGTCGACTTCTGTTTTAGGACA | 1.0 | 11779 |
| hH36-8 | GGGGGCT | GGGTCAGCATGCCAATATGTGT | 10.5 | 11780 |
| hH36-9 | ACAGGCT | TCATGCCCGTTCCCAGGGACTG | 0.0 | 11781 |
| hH36-10 | AGGGACT | ACTCAACATCATGCCCGTTCCC | 0.0 | 11782 |
| hH36-11 | CTGGGCC | GAACGGGCATGATGTTGAGTTC | 0.0 | 11783 |
| hH36-12 | CAGGACC | AGTTGCAGCCAACGAAGTGCCT | 0.0 | 11784 |

TABLE 19-continued

Editing activity of MG3-6 guides at human HAO1 gene delivered by mRNA transfection

| Guide Name | PAM | Spacer Sequence | Editing Activity in Hep3B (Average % indels) | Spacer Sequence SEQ ID NO: |
|---|---|---|---|---|
| hH36-13 | AAGGACC | TTGGCTGCAACTGTATATCTAC | 0.0 | 11785 |
| hH36-14 | ATGGGCT | GCTAGTGCGGCAGGCAGAGAAG | 19.5 | 11786 |
| hH36-15 | CAAGGCC | GGCAGGCAGAGAAGATGGGCTA | 14.5 | 11787 |
| hH36-16 | ACAGATT | AACCGTCTGGATGATGTGCGTA | 0.0 | 11788 |
| hH36-17 | GTGGACT | GAGGAAAATTTTGGAGACGACA | 0.0 | 11789 |
| hH36-18 | ATAGACC | TGCTGCATATGTGGCTAAAGCA | 0.0 | 11790 |
| hH36-19 | ATGGGTC | TTGATATCTTCCCAGCTGATAG | 8.5 | 11791 |
| hH36-20 | GAAGACT | TGGGAAGATATCAAATGGCTGA | 0.0 | 11792 |
| hH36-21 | AGAGGTT | AATTGTTGCAAAGGGCATTTTG | 5.0 | 11793 |

Example 27—Gene Editing Outcomes at the DNA Level for Human GPR146

Figure 20:
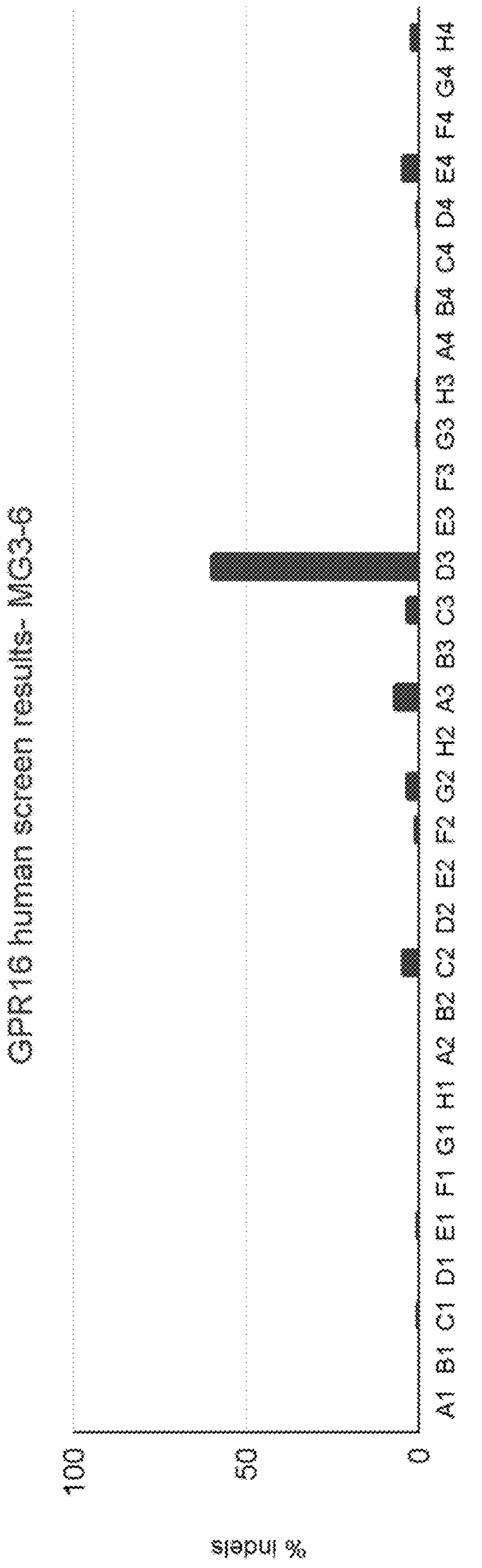
FIG. 20 depicts the gene editing outcomes at the DNA level for human GPR146 in Hep3B cells.

Nucleofection of MG3-6 RNPs (104 pmol protein/120 pmol guide) (SEQ ID NOs: 11374-11405) was performed into Hep3B cells (100,000) using the Lonza 4D electroporator. Cells were harvested and genomic DNA prepared three days post-transfection. PCR primers appropriate for use in NGS-based DNA sequencing were generated, optimized, and used to amplify the individual target sequences for each guide RNA (SEQ ID NOs: 11406-11437). The amplicons were sequenced on an Illumina MiSeq machine and analyzed with a proprietary Python script to measure gene editing (FIG. 20).

TABLE 20

Guide RNAs and Sequences Targeted for Example 25 When Targeting GPR146

| SEQ ID NO: | NAME | SEQUENCE |
|---|---|---|
| 11374 | MG3-6-human GPR146-A1 | mA*mG*mC*rUrGrCrArGrCrUrGrGrUrUrCrArArCrGrGrCrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 11375 | MG3-6-human GPR146-B1 | mG*mG*mU*rGrGrArGrGrArGrCrUrGrCrCrUrGrCrCrUrGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrUxmU*mU*mU |
| 11376 | MG3-6-human GPR146-C1 | mC*mC*mU*rGrCrCrUrGrCrCrArGrGrArCrCrUrGrCrArGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 11377 | MG3-6-human GPR146-D1 | mG*mG*mG*rGrCrUrGrUrCrArCrUrGrUrUrGrUrCrGrCrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrUrCrCrArArUrArGrGrArGrCrGrGrGrCrGrGrUrArUrGrU*mU*mU*mU |
| 11378 | MG3-6-human GPR146-E1 | mG*mG*mG*rCrCrUrGrGrUrGrGrUrGrGrGrCrGrUrGrCrCrArGrUrUrGrArGrArArUrCrGrArArArGrArUrUrCrUrUrArArUrAr |

TABLE 20-continued

Guide RNAs and Sequences Targeted for Example 25 When Targeting GPR146

| SEQ ID NO: | NAME | SEQUENCE |
|---|---|---|
| | | ArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11379 | MG3-6-human GPR146-F1 | mU*mG*mG*rUrGrCrUrGrGrCrCrArArCrCrUrArCrArCrArGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11380 | MG3-6-human GPR146-G1 | mG*mU*mA*rCrUrUrUrGrUrCrArArCrArUrGrGrCrArGrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11381 | MG3-6-human GPR146-H1 | mG*mC*mG*rGrCrGrArArGrUrCrCrArCrGrUrGrGrCrArCrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11382 | MG3-6-human GPR146-A2 | mA*mC*mU*rArCrArUrCrGrArGrCrGrUrGrCrArCrUrGrCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11383 | MG3-6-human GPR146-B2 | mC*mG*mU*rCrCrGrCrArGrGrGrArGrGrArCrArCrGrCrCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11384 | MG3-6-human GPR146-C2 | mG*mG*mA*rCrArCrGrCrCrCrCrUrGrGrArCrCrGrGrArCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11385 | MG3-6-human GPR146-D2 | mG*mG*mC*rCrGrGrCrUrGrGrArGrCrCrCrUrCrGrGrCrArCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11386 | MG3-6-human GPR146-E2 | mG*mU*mG*rGrCrCrArCrCrGrUrGrUrGrCrArCrGrCrArGrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11387 | MG3-6-human GPR146-F2 | mA*mA*mG*rCrCrCrGrUrGrGrArCrGrCrArCrArCrUrArCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11388 | MG3-6-human GPR146-G2 | mC*mC*mU*rGrGrGrCrUrArCrUrGrCrArCrUrUrUrGrUrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11389 | MG3-6-human GPR146-H2 | mG*mC*mU*rGrArUrGrArArArArArGrCrUrGrCrCrCrUrGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11390 | MG3-6-human GPR146-A3 | mC*mU*mG*rCrGrGrGrArCrCrGrGrCrArCrUrGrCrUrCrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |

TABLE 20-continued

Guide RNAs and Sequences Targeted for Example 25 When Targeting GPR146

| SEQ ID NO: | NAME | SEQUENCE |
|---|---|---|
| 11391 | MG3-6-human GPR146-B3 | mG*mU*mG*rGrUrGrUrCrArCrArArArGrCrUrGrCrUrGrGrAr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |
| 11392 | MG3-6-human GPR146-C3 | mU*mA*mG*rCrCrCrCrArGrGrUrArGrUrGrUrGrCrGrUrCrCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |
| 11393 | MG3-6-human GPR146-D3 | mA*mG*mA*rUrGrArUrGrArCrCrGrUrGrUrGrCrCrCrCrArGr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |
| 11394 | MG3-6-human GPR146-E3 | mG*mG*mC*rCrArCrCrArGrCrArGrCrCrUrGrUrGrUrGrCrCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |
| 11395 | MG3-6-human GPR146-F3 | mG*mC*mG*rUrGrUrUrGrUrArCrArCrGrCrUrGrGrCrCrArUr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |
| 11396 | MG3-6-human GPR146-G3 | mA*mG*mU*rGrCrArCrGrCrUrCrGrArUrGrUrArGrUrGrGrUr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |
| 11397 | MG3-6-human GPR146-H3 | mC*mC*mA*rCrCrArGrUrGrArGrGrArCrArCrArUrUrGrArArG rUrUrGrArGrArArUrCrGrArArArGrArUrUrCrUrUrArArUrArAr GrGrCrArUrCrCrUrUrCrCrGrArUrGrCrUrGrArCrUrUrCrUrCr ArCrCrGrUrCrCrGrUrUrUrCrCrArArUrArGrGrArGrCrGrGr GrCrGrGrUrArUrGrU*mU*mU*mU |
| 11398 | MG3-6-human GPR146-A4 | mU*mG*mA*rArGrGrGrGrArUrCrUrGrCrArGrUrGrCrCrArCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |
| 11399 | MG3-6-human GPR146-B4 | mC*mA*mC*rArGrCrGrCrCrCrArCrCrGrGrGrArGrCrUrCrGr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |
| 11400 | MG3-6-human GPR146-C4 | mU*mC*mG*rGrGrGrGrGrCrCrGrArGrCrArGrGrUrGrCrArCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |
| 11401 | MG3-6-human GPR146-D4 | mA*mC*mA*rGrGrGrGrCrCrArGrGrGrCrGrCrUrGrArGrCrAr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrUmU*mU*mU |
| 11402 | MG3-6-human GPR146-E4 | mA*mU*mG*rGrUrCrArUrGrCrUrGrGrCrCrUrUrGrCrUrGrUr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |
| 11403 | MG3-6-human GPR146-F4 | mA*mG*mC*rArCrCrArGrCrArGrGrGrCrGrUrUrGrUrArGrCr GrUrUrGrArGrArArUrCrGrArArArGrArUrUrCrUrUrArArUrAr |

TABLE 20-continued

Guide RNAs and Sequences Targeted for Example 25 When Targeting GPR146

| SEQ ID NO: | NAME | SEQUENCE |
|---|---|---|
| | | ArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11404 | MG3-6-human GPR146-G4 | mA*mG*mG*rCrCrCrArCrUrGrGrCrArCrGrCrCrCrArCrCrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11405 | MG3-6-human GPR146-H4 | mG*mA*mC*rArArCrArGrUrGrArCrArGrCrCrCrCrArGrCrUrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11406 | MG3-6-human GPR146-A1 | AGCTGCAGCTGGTTCAACGGCA |
| 11407 | MG3-6-human GPR146-B1 | GGTGGAGGAGCTGCCTGCCTGC |
| 11408 | MG3-6-human GPR146-C1 | CCTGCCTGCCAGGACCTGCAGC |
| 11409 | MG3-6-human GPR146-D1 | GGGGCTGTCACTGTTGTCGCTG |
| 11410 | MG3-6-human GPR146-E1 | GGGCCTGGTGGTGGGCGTGCCA |
| 11411 | MG3-6-human GPR146-F1 | TGGTGCTGGCCAACCTACACAG |
| 11412 | MG3-6-human GPR146-G1 | GTACTTTGTCAACATGGCAGTG |
| 11413 | MG3-6-human GPR146-H1 | GCGGCGAAGTCCACGTGGCACT |
| 11414 | MG3-6-human GPR146-A2 | ACTACATCGAGCGTGCACTGCC |
| 11415 | MG3-6-human GPR146-B2 | CGTCCGCAGGGAGGACACGCCC |
| 11416 | MG3-6-human GPR146-C2 | GGACACGCCCCTGGACCGGGAC |
| 11417 | MG3-6-human GPR146-D2 | GGCCGGCTGGAGCCCTCGGCAC |
| 11418 | MG3-6-human GPR146-E2 | GTGGCCACCGTGTGCACGCAGT |
| 11419 | MG3-6-human GPR146-F2 | AAGCCCGTGGACGCACACTACC |
| 11420 | MG3-6-human GPR146-G2 | CCTGGGGCTACTGCACTTTGTG |
| 11421 | MG3-6-human GPR146-H2 | GCTGATGAAAAAGCTGCCCTGC |
| 11422 | MG3-6-human GPR146-A3 | CTGCGGGGACCGGCACTGCTCC |
| 11423 | MG3-6-human GPR146-B3 | GTGGTGTCACAAAGCTGCTGGA |
| 11424 | MG3-6-human GPR146-C3 | TAGCCCCAGGTAGTGTGCGTCC |
| 11425 | MG3-6-human GPR146-D3 | AGATGATGACCGTGTGCCCCAG |

TABLE 20-continued

Guide RNAs and Sequences Targeted for Example 25 When Targeting GPR146

| SEQ ID NO: | NAME | SEQUENCE |
|---|---|---|
| 11426 | MG3-6-human GPR146-E3 | GGCCACCAGCAGCCTGTGTGCC |
| 11427 | MG3-6-human GPR146-F3 | GCGTGTTGTACACGCTGGCCAT |
| 11428 | MG3-6-human GPR146-G3 | AGTGCACGCTCGATGTAGTGGT |
| 11429 | MG3-6-human GPR146-H3 | CCACCAGTGAGGACACATTGAA |
| 11430 | MG3-6-human GPR146-A4 | TGAAGGGGATCTGCAGTGCCAC |
| 11431 | MG3-6-human GPR146-B4 | CACAGCGCCCACCGGGAGCTCG |
| 11432 | MG3-6-human GPR146-C4 | TCGGGGGGCCGAGCAGGTGCAC |
| 11433 | MG3-6-human GPR146-D4 | ACAGGGGCCAGGGCGCTGAGCA |
| 11434 | MG3-6-human GPR146-E4 | ATGGTCATGCTGGCCTTGCTGT |
| 11435 | MG3-6-human GPR146-F4 | AGCACCAGCAGGGCGTTGTAGC |
| 11436 | MG3-6-human GPR146-G4 | AGGCCCACTGGCACGCCCACCA |
| 11437 | MG3-6-human GPR146-H4 | GACAACAGTGACAGCCCCAGCT |

r = native ribose base, m = 2'-O methyl modified base, F = 2' Fluro modified base, * = phosphorothioate bond

Figure 21:
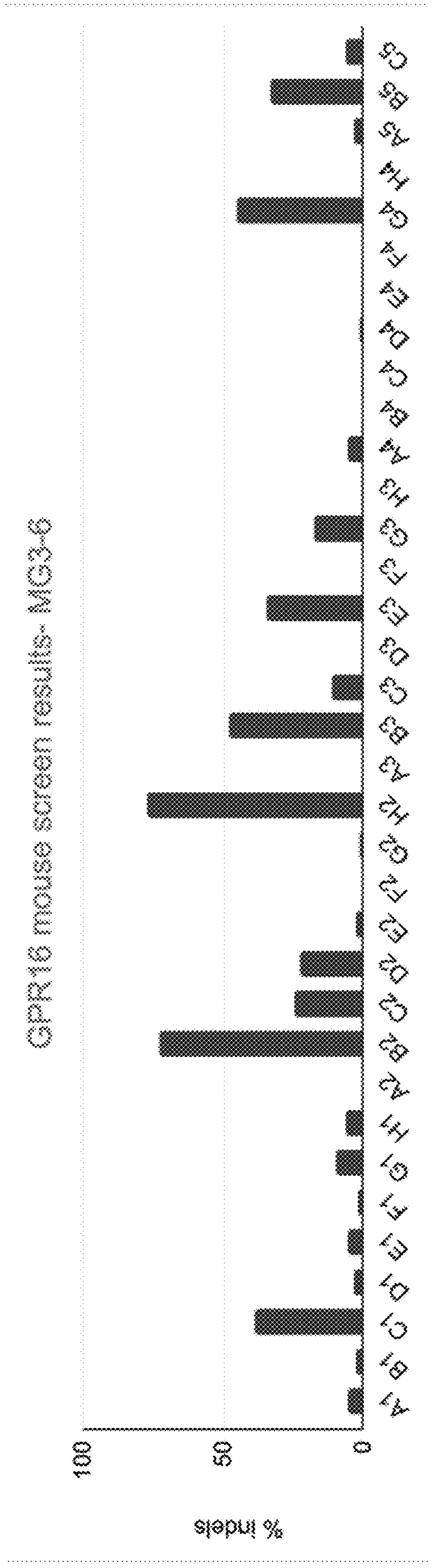
FIG. 21 depicts the gene editing outcomes at the DNA level for mouse GPR146 in Hepa1-6 cells.

Example 28—Gene Editing Outcomes at the DNA Level for Mouse GPR146 in Hepa1-6 Cells Nucleofection of MG3-6 RNPs (104 pmol protein/120 pmol guide) (SEQ ID NOs: 11438-11472) was performed into Hepa1-6 cells (100,000) using the Lonza 4D electroporator. Cells were harvested and genomic DNA prepared five days post-transfection. PCR primers appropriate for use in NGS-based DNA sequencing were generated, optimized, and used to amplify the individual target sequences for each guide RNA (SEQ ID NOs: 11473-11507). The amplicons were sequenced on an Illumina MiSeq machine and analyzed with a proprietary Python script to measure gene editing (FIG. 21).

TABLE 21

Guide RNAs and Sequences Targeted for Example 25 When Targeting GPR146

| SEQ ID NO: | NAME | SEQUENCE |
|---|---|---|
| 11438 | MG3-6-mouse GPR146-A1 | mG*mU*mG*rGrCrCrCrArCrUrCrArArCrArGrCrArCrArGrCrG rUrUrGrArGrArArUrCrGrArArArGrArUrUrCrUrUrArArUrArAr GrGrCrArUrCrCrUrUrCrCrGrArUrGrCrUrGrArCrUrUrCrUrCr ArCrCrGrUrCrCrGrUrUrUrUrCrCrArArUrArGrGrArGrCrGrGr GrCrGrGrUrArUrGrU*mU*mU*mU |
| 11439 | MG3-6-mouse GPR146-B1 | mC*mC*mG*rCrUrGrUrGrCrCrGrGrArArCrCrUrGrCrGrCrCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 11440 | MG3-6-mouse GPR146-C1 | mG*mC*mC*rGrGrArArCrCrUrGrCrGrCrCrUrGrGrGrCrUr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |

TABLE 21-continued

Guide RNAs and Sequences Targeted for Example 25 When Targeting GPR146

| SEQ ID NO: | NAME | SEQUENCE |
|---|---|---|
| 11441 | MG3-6-mouse GPR146-D1 | mU*mC*mU*rCrGrCrUrGrCrUrCrUrArCrCrUrGrGrGrGrCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 11442 | MG3-6-mouse GPR146-E1 | mG*mG*mG*rGrGrCrArGrGrGrGrUrCrCrCrUrGrUrGrArGrCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 11443 | MG3-6-mouse GPR146-F1 | mU*mA*mC*rUrUrCrGrUrGrArArCrArUrGrGrCrCrGrUrGrGr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 11444 | MG3-6-mouse GPR146-G1 | mG*mG*mC*rArCrUrGrGrCrArCrCrUrGrCrGrUrArCrCrUrGr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 11445 | MG3-6-mouse GPR146-H1 | mU*mG*mU*rUrGrGrGrCrCrCrUrGrCrCrCrArCrUrCrCrArGrG rUrUrGrArGrArArUrCrGrArArArGrArUrUrCrUrUrArArUrArAr GrGrCrArUrCrCrUrUrCrCrGrArUrGrCrUrGrArCrUrUrCrUrCr ArCrCrGrUrCrCrGrUrUrUrUrCrCrArArUrArGrGrArGrCrGrGr GrCrGrGrUrArUrGrU*mU*mU*mU |
| 11446 | MG3-6-mouse GPR146-A2 | mG*mG*mG*rCrCrCrUrGrUrGrGrArGrCrCrUrCrArGrCrArGr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 11447 | MG3-6-mouse GPR146-B2 | mU*mG*mU*rGrCrUrCrArUrCrGrGrCrUrArCrGrUrGrGrUrGr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 11448 | MG3-6-mouse GPR146-C2 | mA*mA*mU*rCrGrGrGrArArGrGrArArGrArCrArCrArCrCrCrG rUrUrGrArGrArArUrCrGrArArArGrArUrUrCrUrUrArArUrArAr GrGrCrArUrCrCrUrUrCrCrGrArUrGrCrUrGrArCrUrUrCrUrCr ArCrCrGrUrCrCrGrUrUrUrUrCrCrArArUrArGrGrArGrCrGrGr GrCrGrGrUrArUrGrU*mU*mU*mU |
| 11449 | MG3-6-mouse GPR146-D2 | mA*mC*mA*rCrCrCrCrUrGrGrArCrCrArGrGrArCrArCrCrArG rUrUrGrArGrArArUrCrGrArArArGrArUrUrCrUrUrArArUrArAr GrGrCrArUrCrCrUrUrCrCrGrArUrGrCrUrGrArCrUrUrCrUrCr ArCrCrGrUrCrCrGrUrUrUrUrCrCrArArUrArGrGrArGrCrGrGr GrCrGrGrUrArUrGrU*mU*mU*mU |
| 11450 | MG3-6-mouse GPR146-E2 | mC*mC*mU*rGrGrArCrCrArGrGrArCrArCrCrArGrCrArGrGr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 11451 | MG3-6-mouse GPR146-F2 | mA*mG*mC*rArGrGrCrUrGrGrArCrCrCrCrUrCrGrGrUrGrCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 11452 | MG3-6-mouse GPR146-G2 | mA*mC*mA*rCrArGrUrGrCrUrGrArCrGrUrCrArCrGrGrGrGr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrUrCrCrArArUrArGrGrArGrCrGr GrGrCrGrGrUrArUrGrU*mU*mU*mU |
| 11453 | MG3-6-mouse GPR146-H2 | mA*mG*mG*rGrGrCrArUrUrArUrCrUrGrGrGrCrArUrCrCrUr GrUrUrGrArGrArArUrCrGrArArArGrArUrUrCrUrUrArArUrAr ArGrGrCrArUrCrCrUrUrCrCrGrArUrGrCrUrGrArCrUrUrCrUr |

TABLE 21-continued

Guide RNAs and Sequences Targeted for Example 25 When Targeting GPR146

| SEQ ID NO: | NAME | SEQUENCE |
|---|---|---|
| | | CrArCrCrGrUrCrCrGrUrUrUrCrCrArArUrArGrGrArGrCrGr GrGrCrGrGrUrArUrGrU*mU*mU*mU |
| 11454 | MG3-6-mouse GPR146-A3 | mU*mC*mU*rGrGrGrCrArUrCrCrUrArCrArGrGrUrUrGrCrUrG rUrUrGrArGrArArUrCrGrArArArGrArUrUrCrUrUrArArUrArAr GrGrCrArUrCrCrUrUrCrCrGrArUrGrCrUrGrArCrUrUrCrUrCr ArCrCrGrUrCrCrGrUrUrUrCrCrArArUrArGrGrArGrCrGrGr GrCrGrGrUrArUrGrU*mU*mU*mU |
| 11455 | MG3-6-mouse GPR146-B3 | mG*mC*mC*rArUrCrArCrCrUrGrCrUrGrUrArUrCrCrCrCrGrG rUrUrGrArGrArArUrCrGrArArArGrArUrUrCrUrUrArArUrArAr GrGrCrArUrCrCrUrUrCrCrGrArUrGrCrUrGrArCrUrUrCrUrCr ArCrCrGrUrCrCrGrUrUrUrCrCrArArUrArGrGrArGrCrGrGr GrCrGrGrUrArUrGrU*mU*mU*mU |
| 11456 | MG3-6-mouse GPR146-C3 | mU*mC*mA*rGrCrCrGrCrCrGrGrArGrCrUrUrGrCrCrGrGrGr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |
| 11457 | MG3-6-mouse GPR146-D3 | mG*mU*mG*rGrUrGrUrCrArCrArGrArArCrUrGrCrUrUrGrAr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |
| 11458 | MG3-6-mouse GPR146-E3 | mC*mU*mU*rGrArGrArArGrGrCrCrArGrGrArArCrUrUrGrGr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |
| 11459 | MG3-6-mouse GPR146-F3 | mC*mG*mU*rGrArCrGrUrCrArGrCrArCrUrGrUrGrUrGrCrCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |
| 11460 | MG3-6-mouse GPR146-G3 | mA*mG*mG*rCrUrCrArArGrUrArGrUrArArGrGrUrGrUrCrCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrUmU*mU*mU |
| 11461 | MG3-6-mouse GPR146-H3 | mG*mC*mC*rArCrCrArGrCrArGrCrCrUrGrUrGrCrArCrCrGrG rUrUrGrArGrArArUrCrGrArArArGrArUrUrCrUrUrArArUrArAr GrGrCrArUrCrCrUrUrCrCrGrArUrGrCrUrGrArCrUrUrCrUrCr ArCrCrGrUrCrCrGrUrUrUrCrCrArArUrArGrGrArGrCrGrGr GrCrGrGrUrArUrGrU*mU*mU*mU |
| 11462 | MG3-6-mouse GPR146-A4 | mA*mG*mU*rGrCrCrArGrGrGrCrArUrArCrArArCrArCrArGrG rUrUrGrArGrArArUrCrGrArArArGrArUrUrCrUrUrArArUrArAr GrGrCrArUrCrCrUrUrCrCrGrArUrGrCrUrGrArCrUrUrCrUrCr ArCrCrGrUrCrCrGrUrUrUrCrCrArArUrArGrGrArGrCrGrGr GrCrGrGrUrArUrGrU*mU*mU*mU |
| 11463 | MG3-6-mouse GPR146-B4 | mA*mG*mG*rGrCrArCrGrCrUrCrGrArUrGrUrArGrUrArGrUr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrUxmU*mU*mU |
| 11464 | MG3-6-mouse GPR146-C4 | mU*mG*mA*rArCrArGrGrArUrGrArGrCrArGrUrGrUrCrArCr GrUrUrGrArGrArArUrCrGrArArArGrArUrUrCrUrUrArArUrAr ArGrGrCrArUrCrCrUrUrCrCrGrArUrGrCrUrGrArCrUrUrCrUr CrArCrCrGrUrCrCrGrUrUrUrCrCrArArUrArGrGrArGrCrGr GrGrCrGrGrUrArUrGrU*mU*mU*mU |
| 11465 | MG3-6-mouse GPR146-D4 | mA*mG*mU*rGrUrCrArCrArUrGrGrGrCrCrUrCrArCrUrGrCrG rUrUrGrArGrArArUrCrGrArArArGrArUrUrCrUrUrArArUrArAr GrGrCrArUrCrCrUrUrCrCrGrArUrGrCrUrGrArCrUrUrCrUrCr ArCrCrGrUrCrCrGrUrUrUrCrCrArArUrArGrGrArGrCrGrGr GrCrGrGrUrArUrGrU*mU*mU*mU |

TABLE 21-continued

Guide RNAs and Sequences Targeted for Example 25 When Targeting GPR146

| SEQ ID NO: | NAME | SEQUENCE |
|---|---|---|
| 11466 | MG3-6-mouse GPR146-E4 | mG*mG*mG*rCrCrUrCrArCrUrGrCrUrGrArGrGrCrUrCrCrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11467 | MG3-6-mouse GPR146-F4 | mC*mA*mC*rArGrGrCrCrCrArCrCrUrGrGrArGrUrGrGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11468 | MG3-6-mouse GPR146-G4 | mA*mU*mG*rGrUrCrArUrGrGrUrGrUrUrCrUrUrGrCrUrGrGrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11469 | MG3-6-mouse GPR146-H4 | mG*mA*mG*rCrArUrUrArUrArGrCrCrUrArArGrCrUrCrArCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11470 | MG3-6-mouse GPR146-A5 | mC*mU*mG*rCrCrCrCrCrArGrGrUrArGrArGrCrArGrCrGrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11471 | MG3-6-mouse GPR146-B5 | mG*mA*mG*rArGrGrArCrCrCrArCrArGrCrCrCrCrArGrGrCrGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11472 | MG3-6-mouse GPR146-C5 | mU*mC*mA*rGrCrCrArCrGrCrUrGrUrGrCrUrGrUrUrGrArGrUrUrGrArGrArArUrCrGrArArArGrArUrUrCrUrUrArArUrArArGrGrCrArUrCrCrUrUrCrCrGrArUrGrCrUrGrArCrUrUrCrUrCrArCrCrGrUrCrCrGrUrUrUrCrCrArArUrArGrGrArGrCrGrGrGrCrGrGrUrArUrGrU*mU*mU*mU |
| 11473 | MG3-6-mouse GPR146-A1 | GTGGCCCACTCAACAGCACAGC |
| 11474 | MG3-6-mouse GPR146-B1 | CCGCTGTGCCGGAACCTGCGCC |
| 11475 | MG3-6-mouse GPR146-C1 | GCCGGAACCTGCGCCTGGGGCT |
| 11476 | MG3-6-mouse GPR146-D1 | TCTCGCTGCTCTACCTGGGGGC |
| 11477 | MG3-6-mouse GPR146-E1 | GGGGGCAGGGGTCCCTGTGAGC |
| 11478 | MG3-6-mouse GPR146-F1 | TACTTCGTGAACATGGCCGTGG |
| 11479 | MG3-6-mouse GPR146-G1 | GGCACTGGCACCTGCGTACCTG |
| 11480 | MG3-6-mouse GPR146-H1 | TGTTGGGCCCTGCCCACTCCAG |
| 11481 | MG3-6-mouse GPR146-A2 | GGGCCCTGTGGAGCCTCAGCAG |
| 11482 | MG3-6-mouse GPR146-B2 | TGTGCTCATCGGCTACGTGGTG |
| 11483 | MG3-6-mouse GPR146-C2 | AATCGGGAAGGAAGACACACCC |

TABLE 21-continued

Guide RNAs and Sequences Targeted for Example 25 When Targeting GPR146

| SEQ ID NO: | NAME | SEQUENCE |
|---|---|---|
| 11484 | MG3-6-mouse GPR146-D2 | ACACCCCTGGACCAGGACACCA |
| 11485 | MG3-6-mouse GPR146-E2 | CCTGGACCAGGACACCAGCAGG |
| 11486 | MG3-6-mouse GPR146-F2 | AGCAGGCTGGACCCCTCGGTGC |
| 11487 | MG3-6-mouse GPR146-G2 | ACACAGTGCTGACGTCACGGGG |
| 11488 | MG3-6-mouse GPR146-H2 | AGGGGCATTATCTGGGCATCCT |
| 11489 | MG3-6-mouse GPR146-A3 | TCTGGGCATCCTACAGGTTGCT |
| 11490 | MG3-6-mouse GPR146-B3 | GCCATCACCTGCTGTATCCCCG |
| 11491 | MG3-6-mouse GPR146-C3 | TCAGCCGCCGGAGCTTGCCGGG |
| 11492 | MG3-6-mouse GPR146-D3 | GTGGTGTCACAGAACTGCTTGA |
| 11493 | MG3-6-mouse GPR146-E3 | CTTGAGAAGGCCAGGAACTTGG |
| 11494 | MG3-6-mouse GPR146-F3 | CGTGACGTCAGCACTGTGTGCC |
| 11495 | MG3-6-mouse GPR146-G3 | AGGCTCAAGTAGTAAGGTGTCC |
| 11496 | MG3-6-mouse GPR146-H3 | GCCACCAGCAGCCTGTGCACCG |
| 11497 | MG3-6-mouse GPR146-A4 | AGTGCCAGGGCATACAACACAG |
| 11498 | MG3-6-mouse GPR146-B4 | AGGGCACGCTCGATGTAGTAGT |
| 11499 | MG3-6-mouse GPR146-C4 | TGAACAGGATGAGCAGTGTCAC |
| 11500 | MG3-6-mouse GPR146-D4 | AGTGTCACATGGGCCTCACTGC |
| 11501 | MG3-6-mouse GPR146-E4 | GGGCCTCACTGCTGAGGCTCCA |
| 11502 | MG3-6-mouse GPR146-F4 | CACAGGGCCCACCTGGAGTGGG |
| 11503 | MG3-6-mouse GPR146-G4 | ATGGTCATGGTGTTCTTGCTGG |
| 11504 | MG3-6-mouse GPR146-H4 | GAGCATTATAGCCTAAGCTCAC |
| 11505 | MG3-6-mouse GPR146-A5 | CTGCCCCCAGGTAGAGCAGCGA |
| 11506 | MG3-6-mouse GPR146-B5 | GAGAGGACCCACAGCCCCAGGC |
| 11507 | MG3-6-mouse GPR146-C5 | TCAGCCCACGCTGTGCTGTTGA |

r = native ribose base, m = 2'-O methyl modified base, F = 2' Fluro modified base, * = phosphorothioate bond

Figure 22:
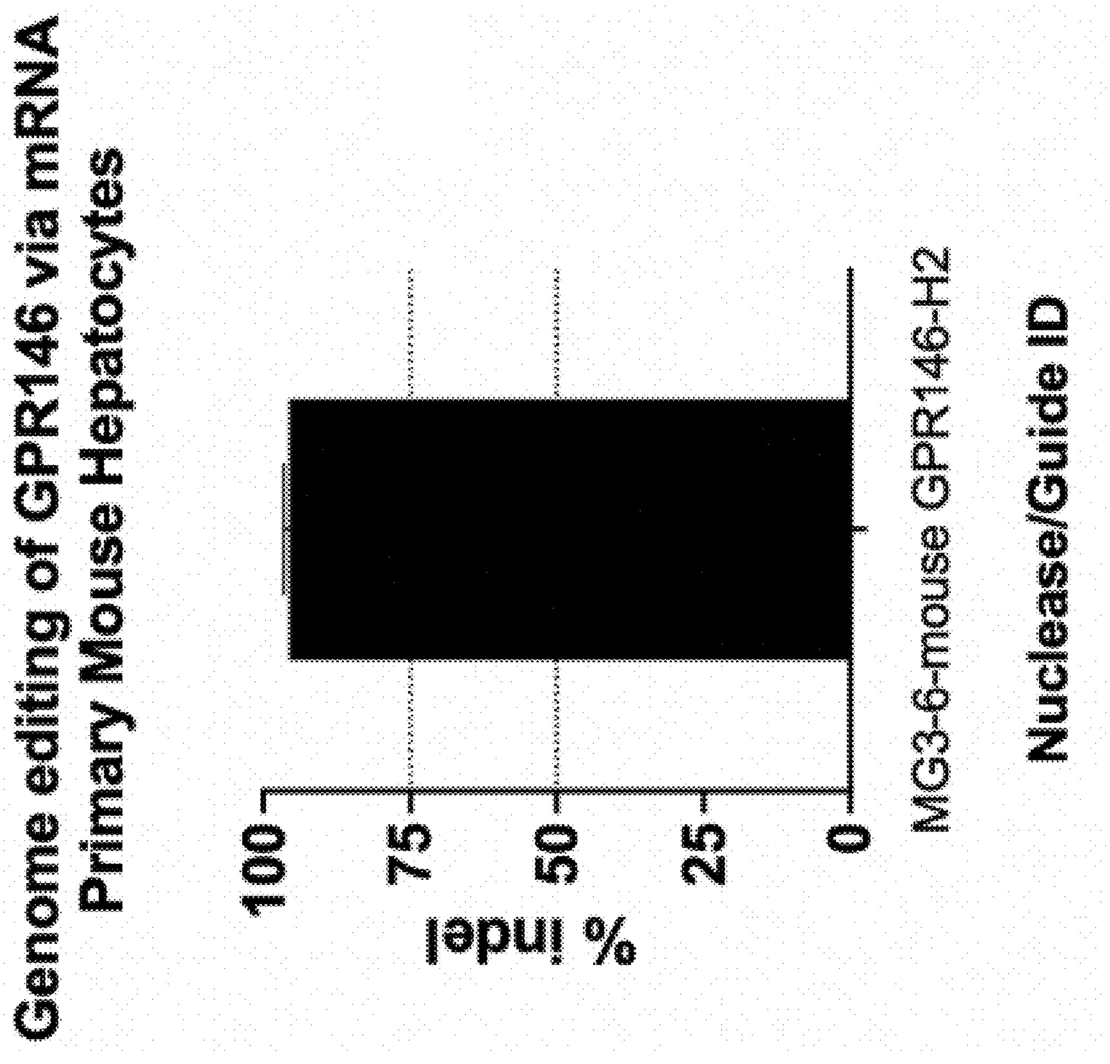
FIG. 22 depicts the gene editing outcomes at the DNA level for mouse GPR146 in primary mouse hepatocytes.

Example 29—Gene Editing Outcomes at the DNA Level for Mouse GPR146 in Primary Mouse Hepatocytes Lipofection with MessengerMax of MG3-6 mRNA and guide (0.42 ug mRNA, 1:20 nuclease:guide molar ratio) was performed in primary mouse hepatocytes (1E5 viable cells/guide) using the guide RNAs described in Example 29 above. Cells were harvested and genomic DYNA prepared three days post-transfection. PCR primers appropriate for use in NGS-based DNA sequencing were used to amplify the individual target sequences for each guide RNA. The amplicons were sequenced on an Illumina MiSeq machine and analyzed with a proprietary Python script to measure gene editing (FIG. 22). The results indicated that the GPR146-H2 sgRNA was highly effective for editing in mouse hepatocytes.

Figure 23:
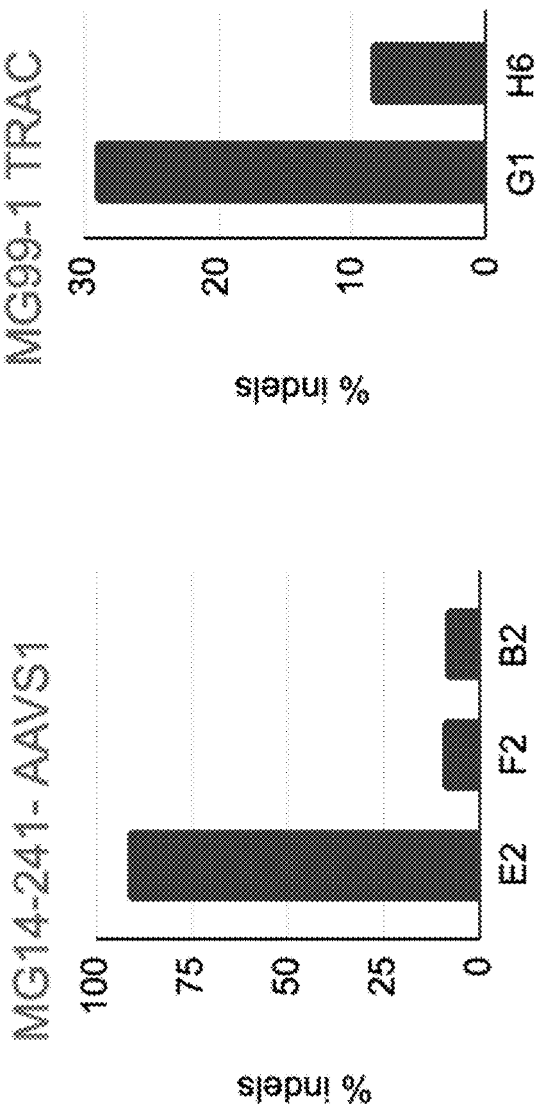
FIG. 23 depicts the gene editing outcomes at the DNA level for TRAC and AAVS1 in K562 cells.

Example 30—Gene Editing Outcomes at the DNA Level for TRAC and AAVS1 in K562 Cells Nucleofection of MG14-241 and MG99-1 mRNA along with the matching guide RNA (500 ng mRNA/150 pmol guide) was performed into 200,000 human lymphoblasts (K562 cells) using the Lonza 4D electroporator. Cells were harvested and genomic DNA prepared three days post-transfection. PCR primers appropriate for use in NGS-based DNA sequencing were generated, optimized, and used to amplify the individual target sequences for each guide RNA. The amplicons were sequenced on an Illumina MiSeq machine and analyzed with a proprietary Python script to measure gene editing. (FIG. 23).

TABLE 22

Guide RNAs and Sequences Targeted for Example 30

Figure 24:
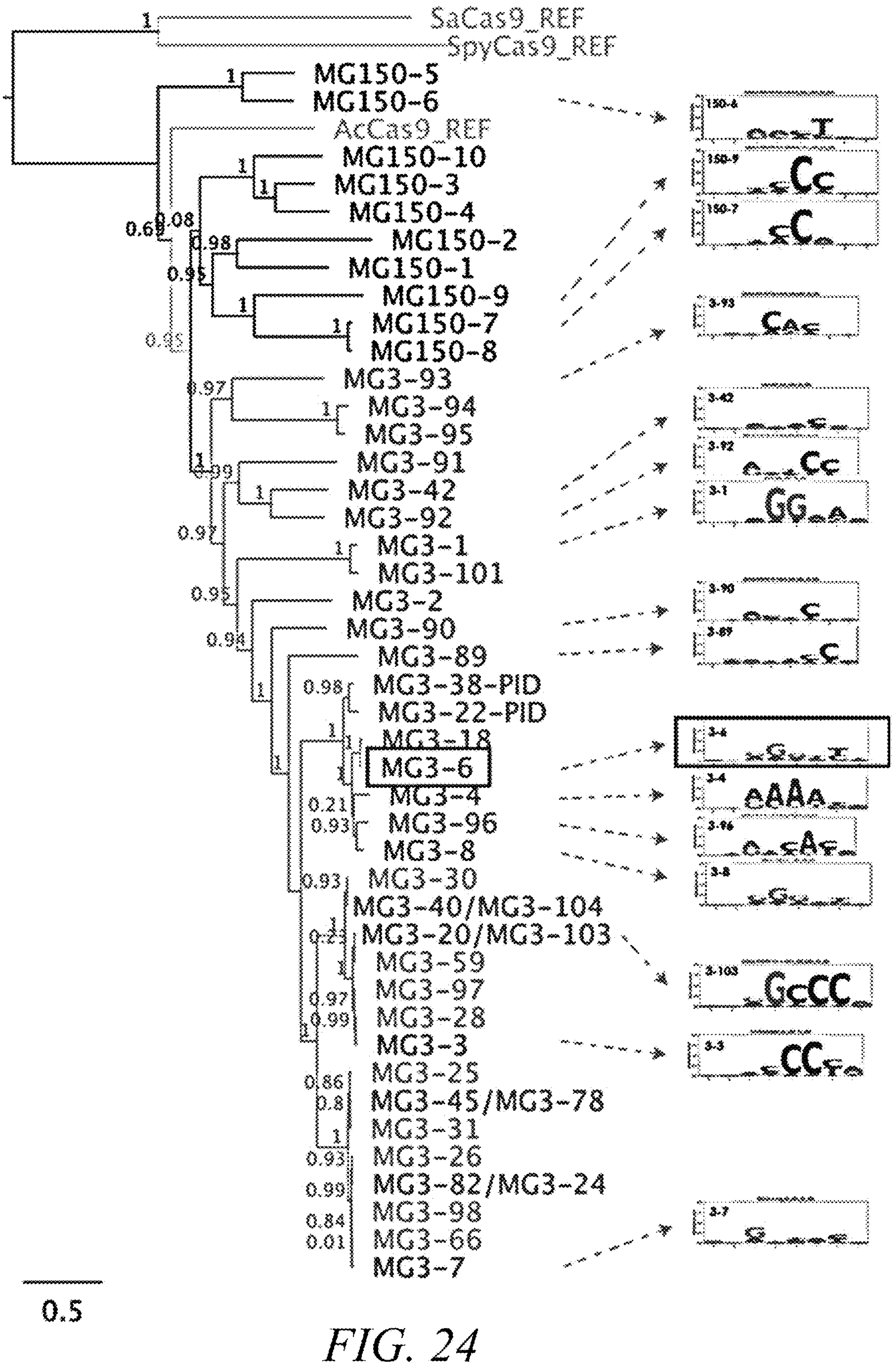
FIG. 24 depicts phylogenetic analysis of nucleases from the MG3 and MG150 families. PAM SeqLogo representations are shown for some active candidates. Reference SaCas9 and SpyCas9 sequences were included.
Figure 25:
FIG. 25 depicts phylogenetic analysis of nucleases from the MG15 family. Active candidates are highlighted with circles. Reference SaCas9, SpyCas9, and AcCas9 sequences were included as outgroup.
Figure 26:
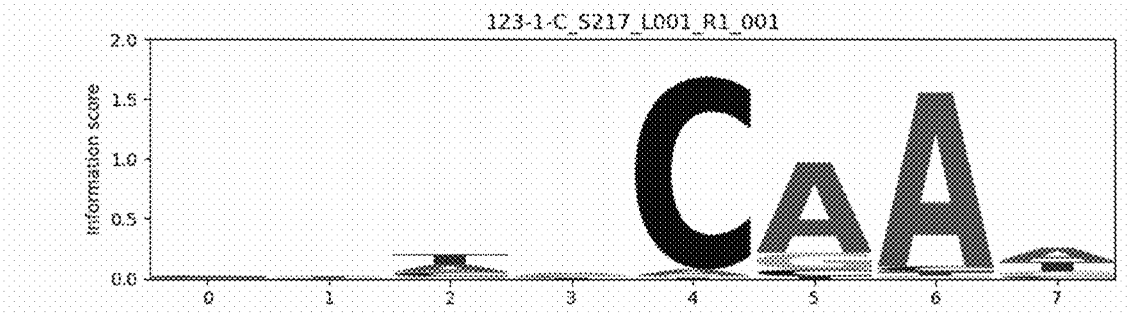
FIG. 26 depicts SeqLogos of the PAMs for MG123-1, MG124-2, MG 125-1 and MG125-2.
Figure 26:
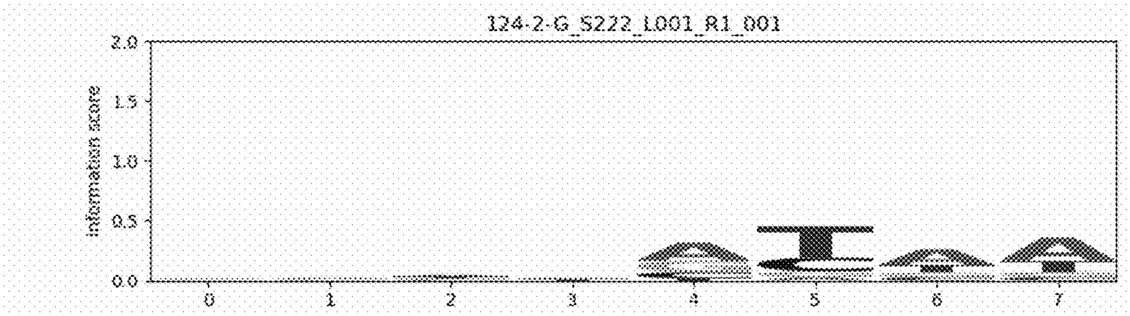
Figure 26:
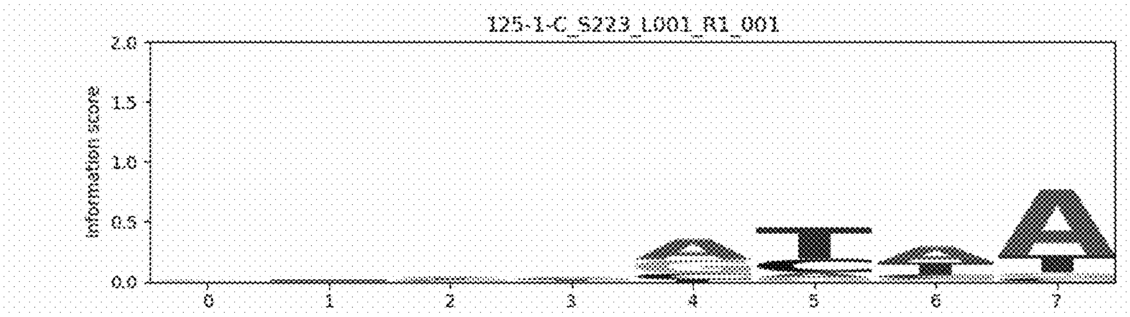
Figure 26:
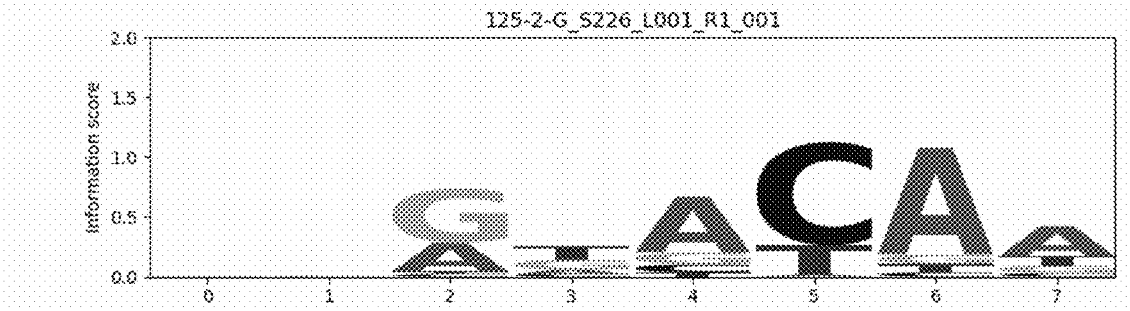
Figure 27:
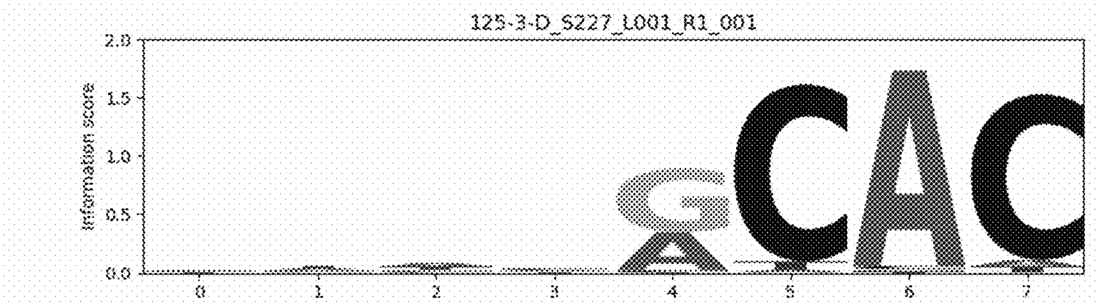
FIG. 27 depicts SeqLogos of the PAMs for MG125-3, MG125-4, MG125-5, and MG150-5.
Figure 27:
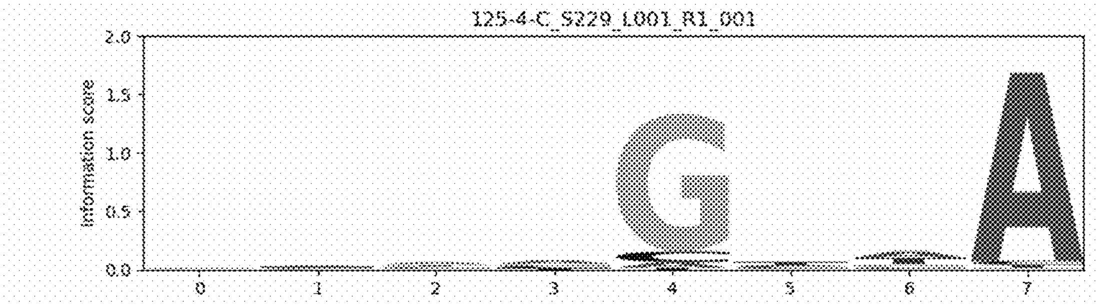
Figure 27:
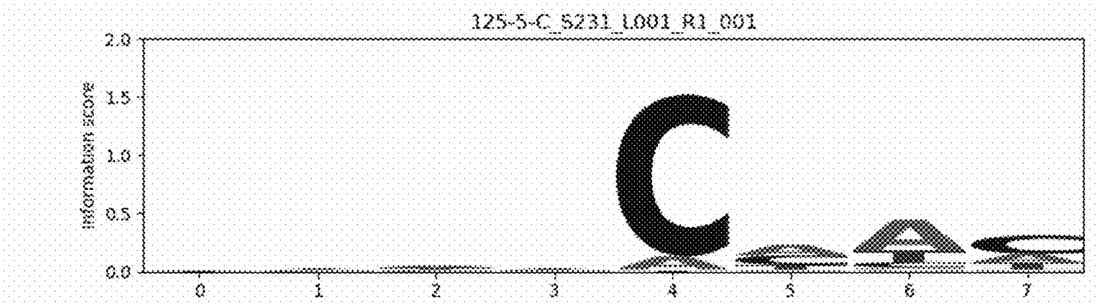
Figure 27:
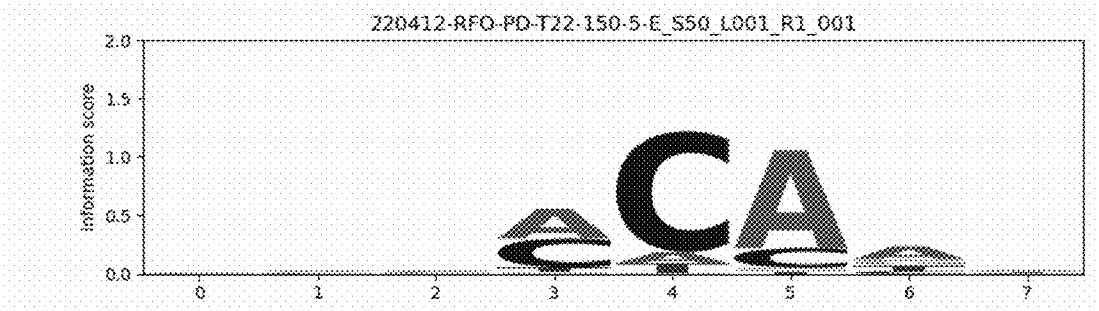
Figure 28:
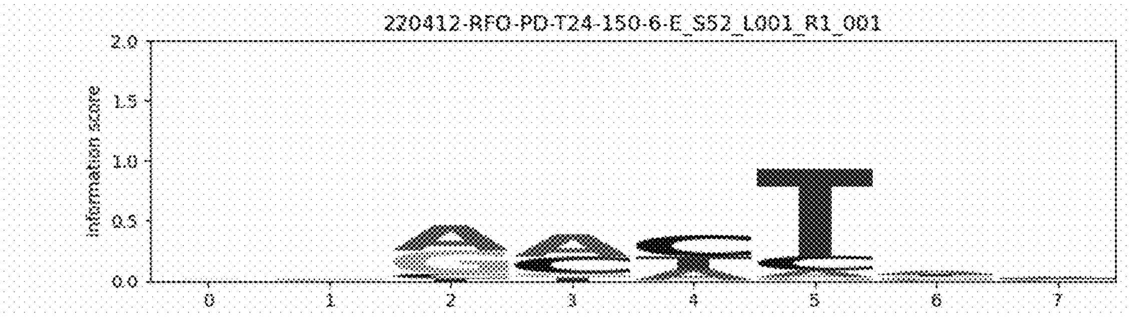
FIG. 28 depicts SeqLogos of the PAMs for MG150-6, MG150-7, MG150-8, and MG150-9.
Figure 28:
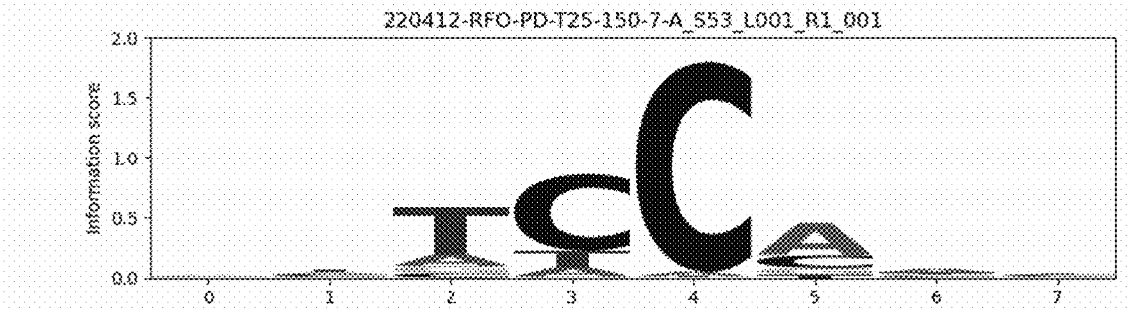
Figure 28:
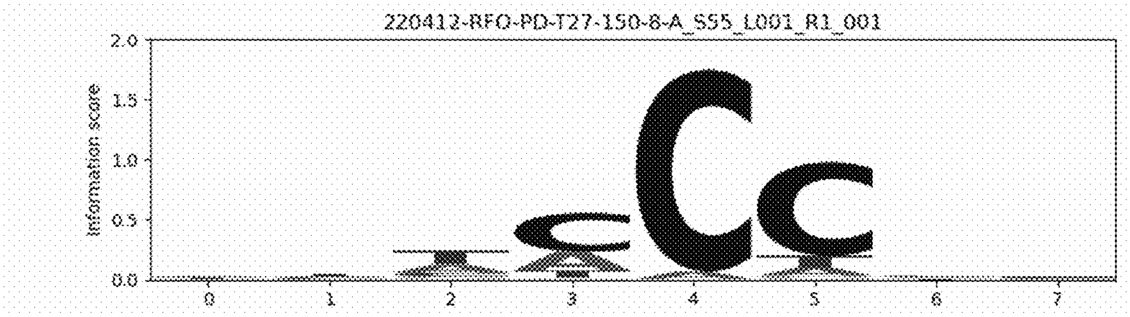
Figure 28:
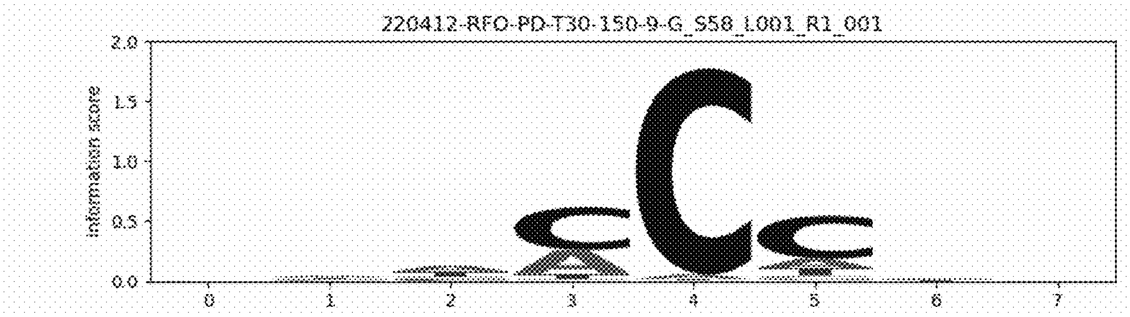
Figure 29:
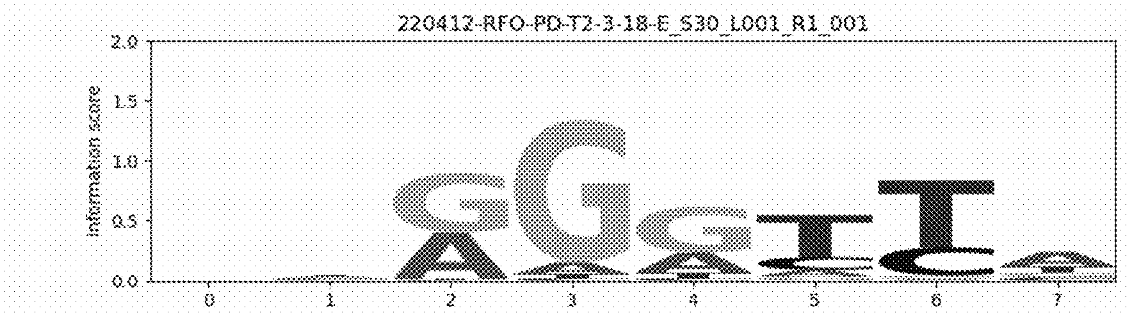
FIG. 29 depicts SeqLogos of the PAMs for MG3-18, MG3-89, MG3-90, and MG3-91.
Figure 29:
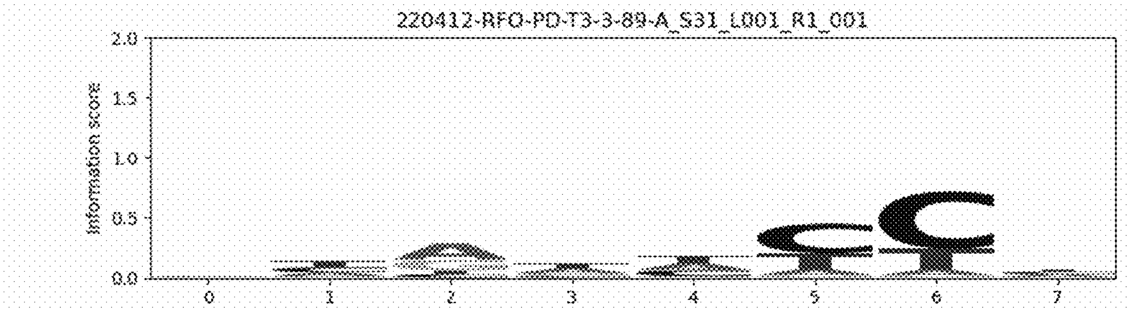
Figure 29:
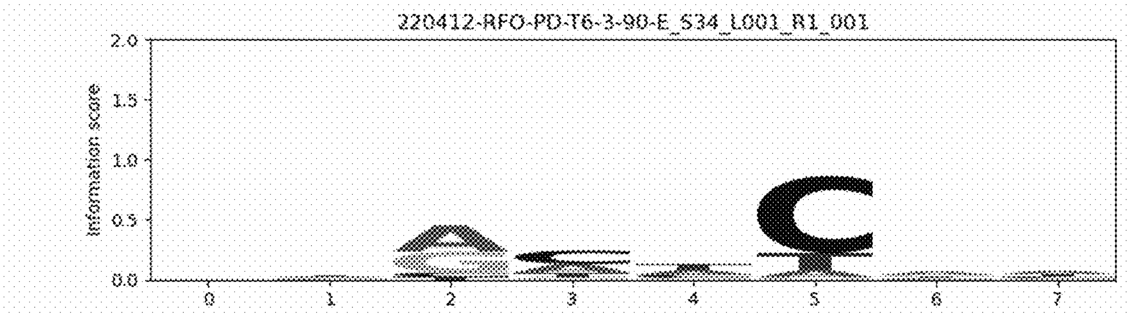
Figure 29:
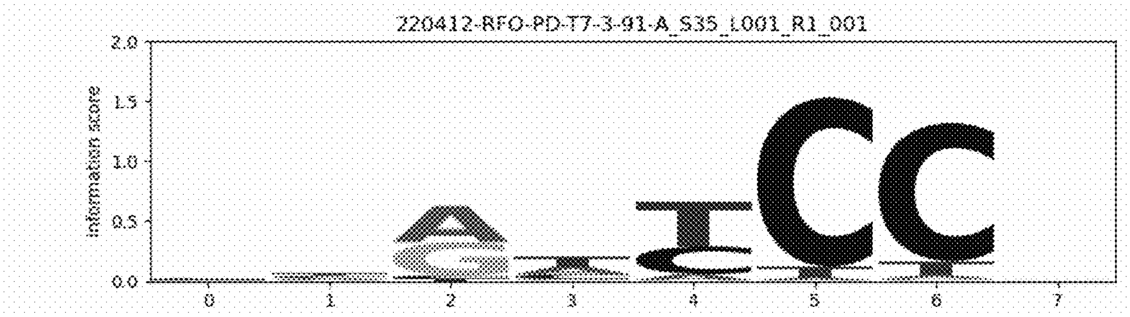
Figure 30:
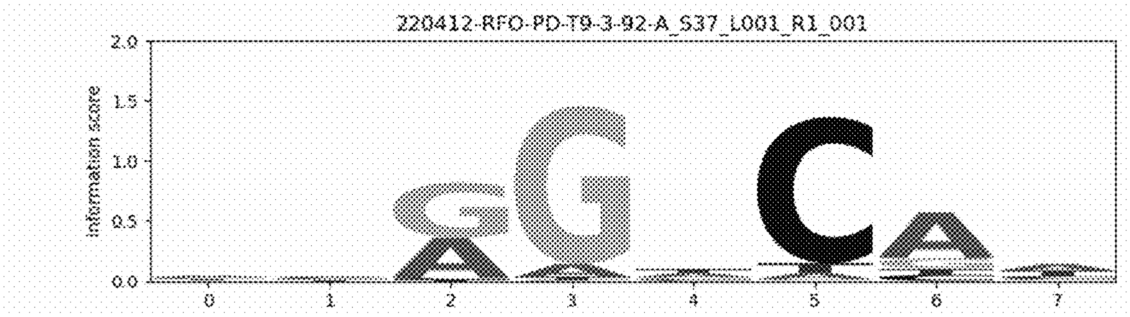
FIG. 30 depicts SeqLogos of the PAMs for MG3-92, MG3-93, MG3-95, and MG3-96.
Figure 30:
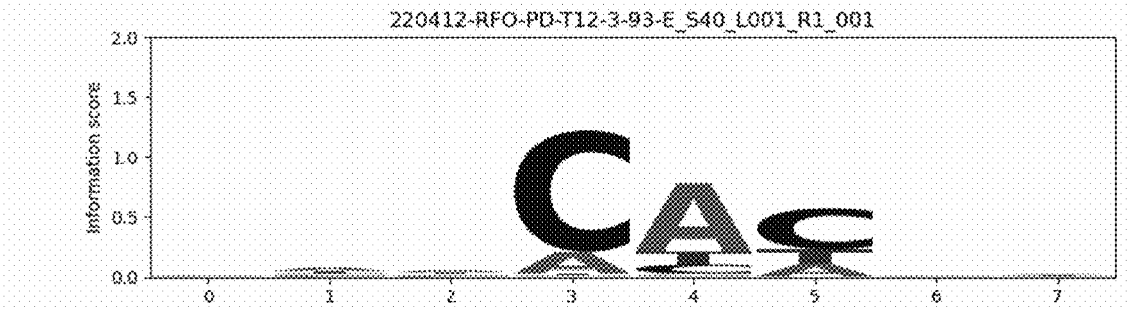
Figure 30:
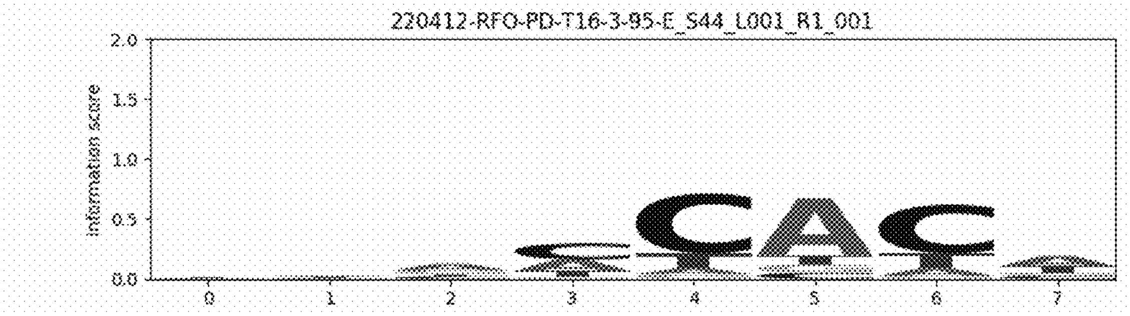
Figure 30:
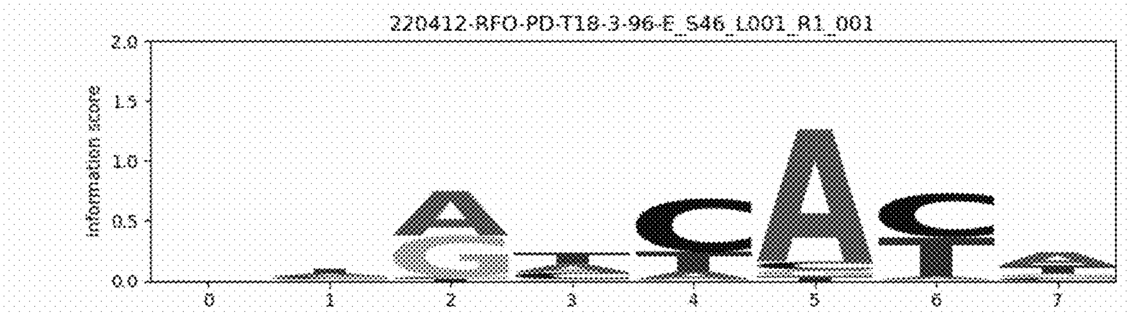
Figure 31:
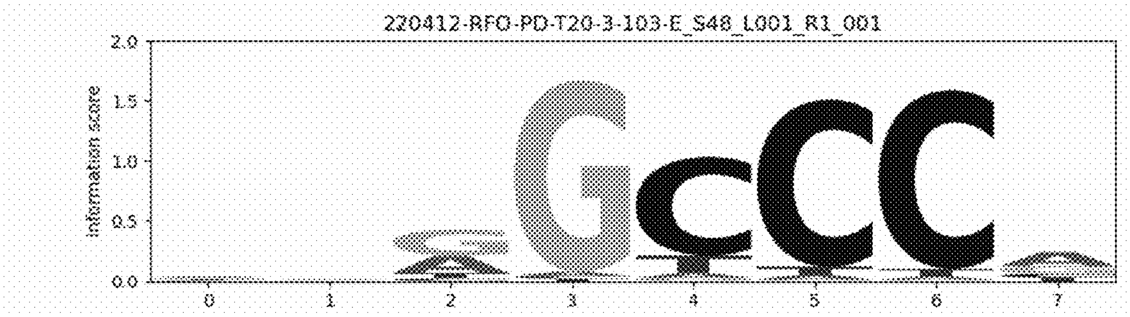
FIG. 31 depicts SeqLogos of the PAMs for MG3-103, MG15-130, MG15-146, and MG15-164.
Figure 31:
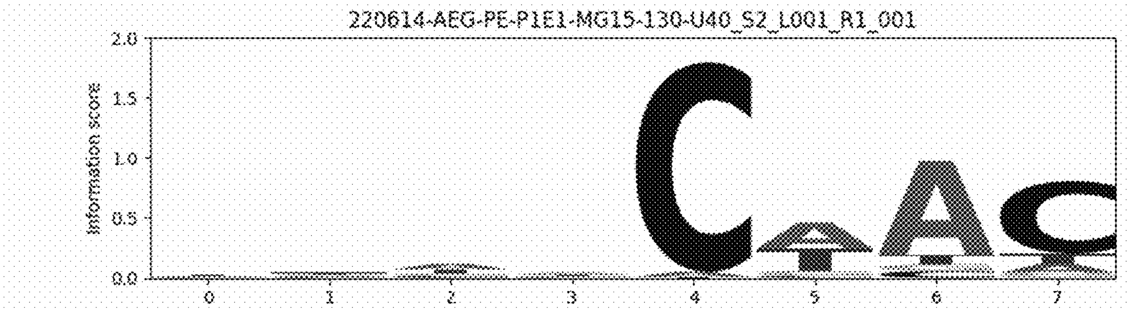
Figure 31:
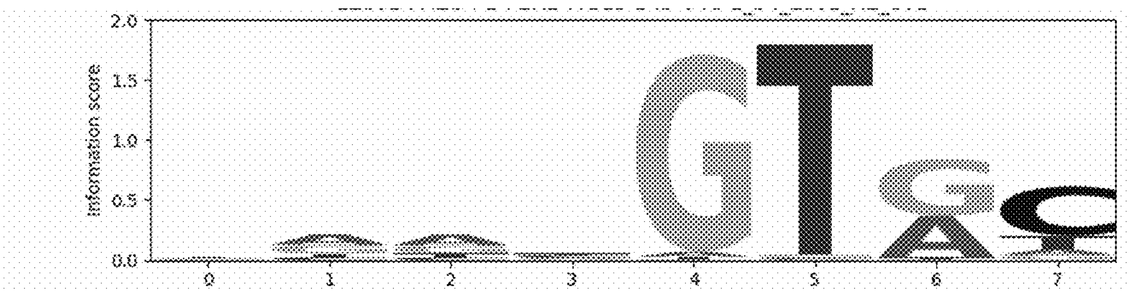
Figure 31:
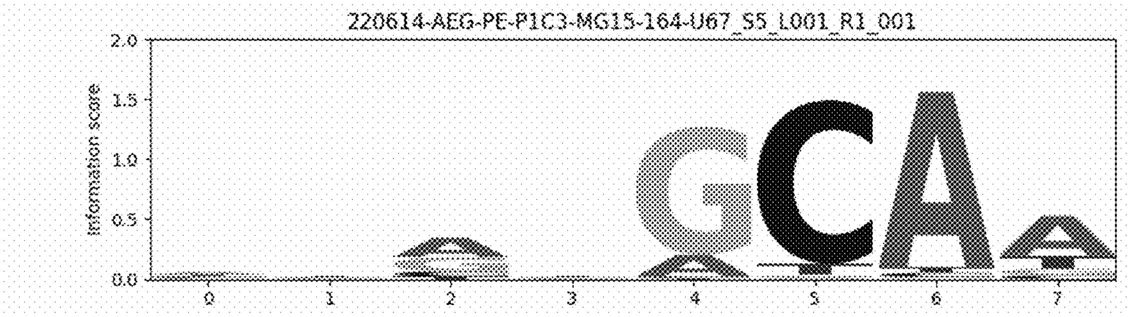
Figure 32:
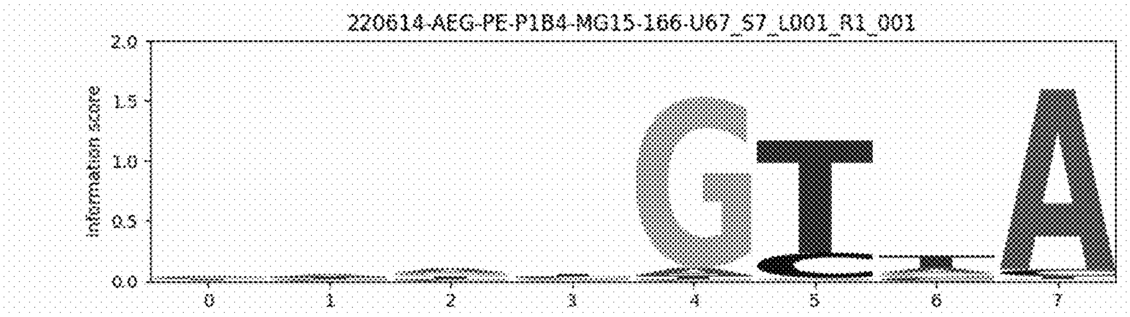
FIG. 32 depicts SeqLogos of the PAMs for MG15-166, MG15-171, MG15-172, and MG15-174.
Figure 32:
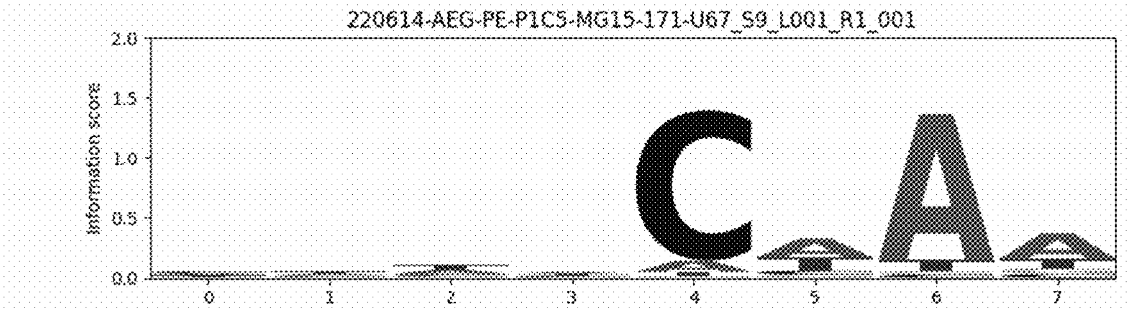
Figure 32:
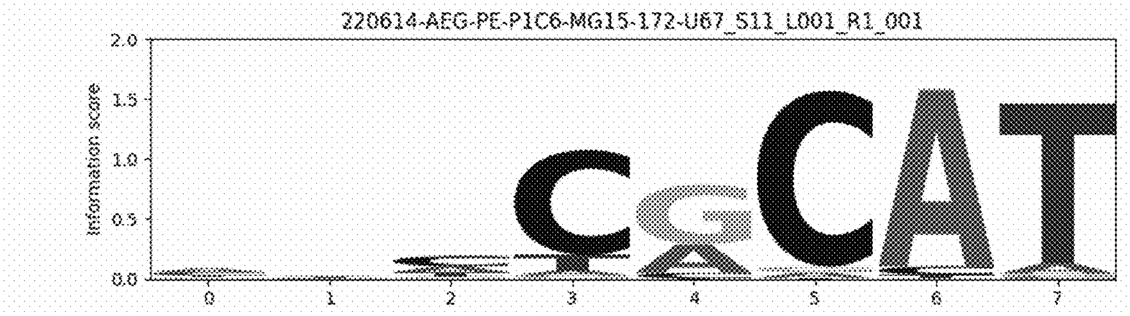
Figure 32:
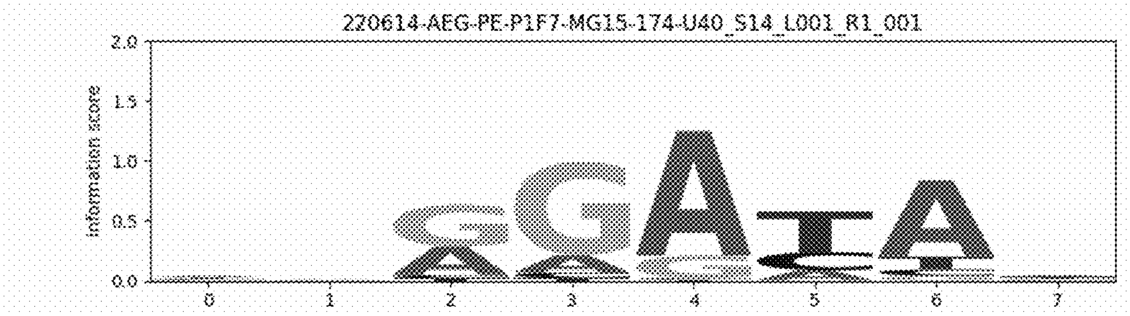
Figure 33:
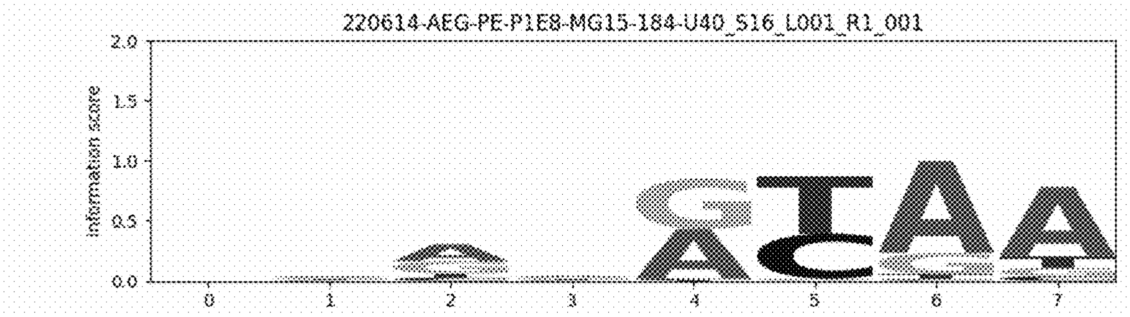
FIG. 33 depicts SeqLogos of the PAMs for MG15-184, MG15-187, MG15-191, and MG15-193.
Figure 33:
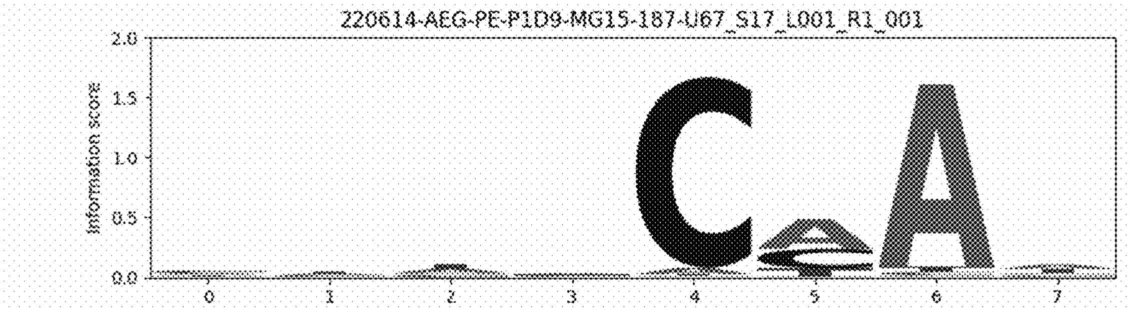
Figure 33:
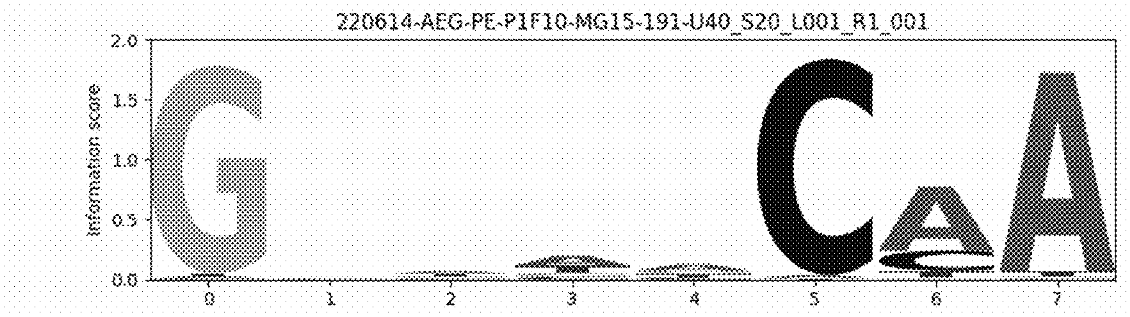
Figure 33:
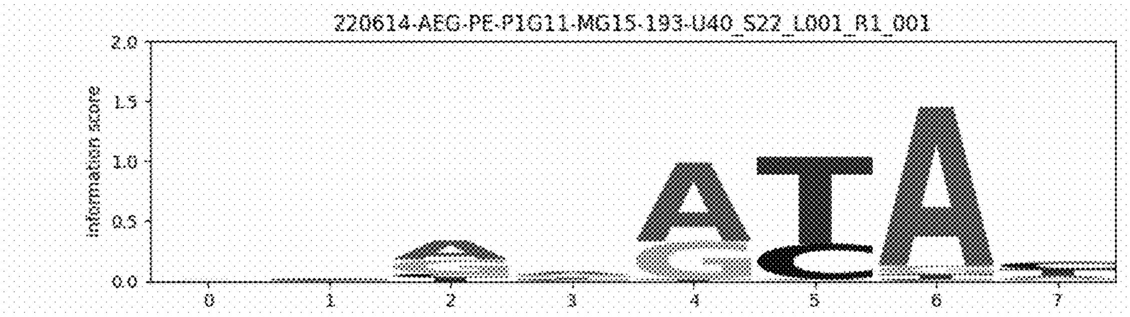
Figure 34:
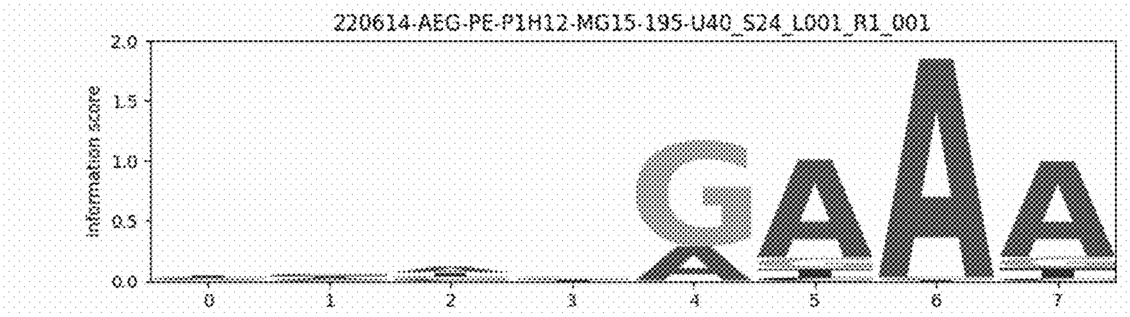
FIG. 34 depicts SeqLogos of the PAMs for MG15-195, MG15-217, MG15-218, and MG15-219.
Figure 34:
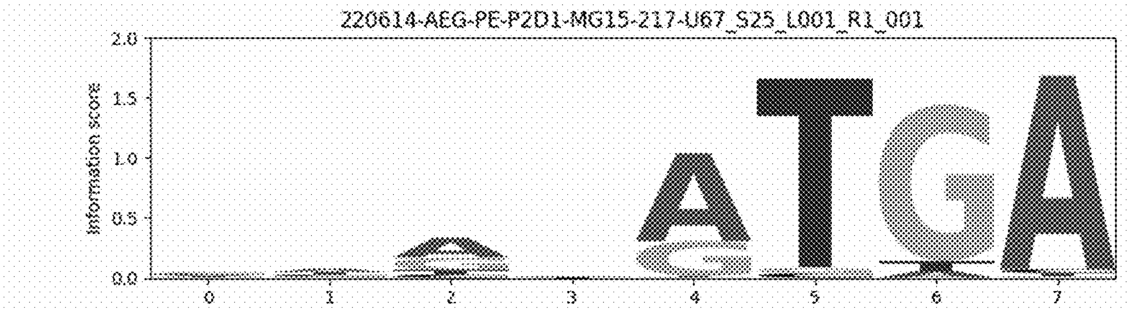
Figure 34:
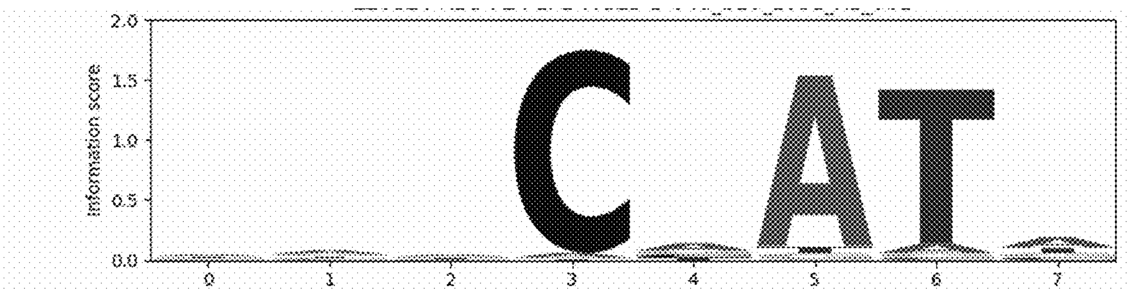
Figure 34:
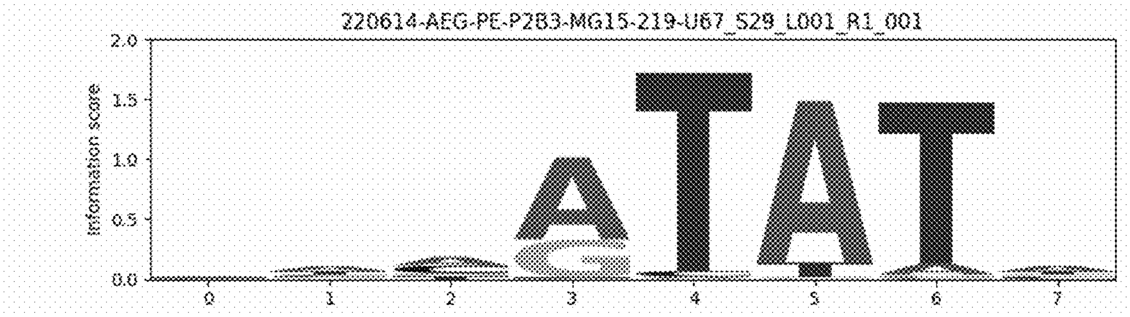
Figure 35:
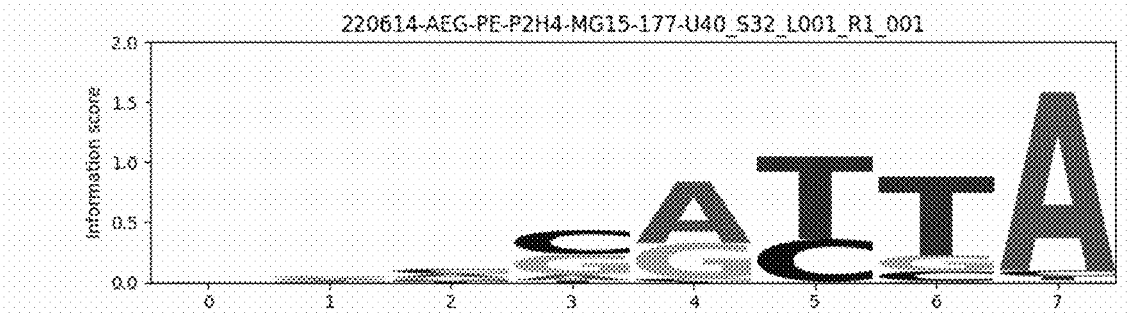
FIG. 35 depicts a SeqLogo of the PAM for MG15-177.

| SEQ ID NO: | NAME | SEQUENCE |
|---|---|---|
| 11508 | MG14-241-AAVS1-E2 | mU*mG*mG*rCrArCrArGrGrCrCrCrCrArGrArArGrGrArGrUrCrUrUrGrCrCrGrGrArArArCrGrGrCrUrArGrArCrArArGrGrGrArArUrCrGrCrUrUrUrUrArCrGrCrGrArUrUrArCrCrCrGrCrArArGrGrUrArArGrCrCrCrGrUrCrArGrCrArCrCrCrUrUrGrGrUrGrUrCrGrGrCrGrGrGrCrGrArUrCrCrUxmU*mU*mU |
| 11509 | MG14-241-AAVS1-F2 | mC*mC*mA*rCrUrArGrGrGrArCrArGrGrArUrUrGrGrUrGrUrCrUrUrGrCrCrGrGrArArArCrGrGrCrUrArGrArCrArArGrGrGrArArUrCrGrCrUrUrUrUrArCrGrCrGrArUrUrArCrCrCrGrCrArArGrGrUrArArGrCrCrCrGrUrCrArGrCrArCrCrCrUrUrGrGrUrGrUrCrGrGrCrGrGrGrCrGrArUrCrCrUxmU*mU*mU |
| 11510 | MG14-241-AAVS1-B2 | mA*mG*mG*rArGrArArCrGrGrGrGrUrGrUrCrCrArGrGrGrUrCrUrUrGrCrCrGrGrArArArCrGrGrCrUrArGrArCrArArGrGrGrArArUrCrGrCrUrUrUrUrArCrGrCrGrArUrUrArCrCrCrGrCrArArGrGrUrArArGrCrCrCrGrUrCrArGrCrArCrCrCrUrUrGrGrUrGrUrCrGrGrCrGrGrGrCrGrArUrCrCrUxmU*mU*mU |
| 11511 | MG14-241-AAVS1-E2 | TGGCACAGGCCCCAGAAGGA |
| 11512 | MG14-241-AAVS1-F2 | CCACTAGGGACAGGATTGGT |
| 11513 | MG14-241-AAVS1-B2 | AGGAGAACGGGGTGTCCAGG |
| 11514 | MG99-1-TRAC-G1 | mG*mA*mC*rArCrCrUrUrCrUrUrCrCrCrCrArGrCrCrCrArGrGrUrGrUrUrUrArGrUrUrCrUrCrUrGrArUrGrArArArArUrCrArGrUrArArGrUrUrCrUrArArArArUrArArGrGrCrArUrUrArUrGrCrCrGrUrGrGrGrGrUrArUrGrGrUrGrGrUrArUrCrCrUrCrGrUrUrCrArArArUrArUrCrCrArCrCrGrUrUrUrCrUrArArArArArArArUrCrGrCrGrCrGrCrCrGrCrCrGrGrCrGrUrGrCrU*mU*mU*mU |
| 11515 | MG99-1-TRAC-H6 | mC*mC*mC*rGrGrCrCrArCrUrUrUrCrArGrGrArGrGrArGrGrArUrGrUrUrUrArGrUrUrCrUrCrUrGrArUrGrArArArArUrCrArGrUrArArGrUrUrCrUrArArArArUrArArGrGrCrArUrUrArUrGrCrCrGrUrGrGrGrGrUrArUrGrGrUrGrGrUrArUrCrCrUrCrGrUrUrCrArArArUrArUrCrCrArCrCrGrUrUrUrCrUrArArArArArArArUrCrGrCrGrCrGrCrCrGrCrCrGrGrCrGrUrGrCrUxmU*mU*mU |
| 11516 | MG99-1-TRAC-G1 | GACACCTTCTTCCCCAGCCCAGGT |
| 11517 | MG99-1-TRAC-H6 | CCCGGCCACTTTCAGGAGGAGGAT |

r = native ribose base, m = 2'-O methyl modified base, F = 2' Fluro modified base, * = phosphorothioate bond Example 31—Novel Type II CRISPR Effectors are Active Nucleases with Diverse PAM Requirements Novel nucleases of the MG3, MG15, MG150, MG123, MG124, and MG125 families were identified from phylogenetic analysis. The MG150 family of nucleases is more closely related to the MG3 family than to any other family identified (FIG. 24), and a new group of divergent effectors expanded the MG15 family of nucleases (FIG. 25). In vitro cleavage activity assays show that nucleases reported here generally have preference for cleavage at positions three or four from the PAM (Table 23). In addition, PAM sequence determination for Type II nucleases indicates diverse PAM requirements, as shown by the SeqLogo images from NGS data. (FIGS. 26-35)

TABLE 23

Cut sites of MG Family Variants

| Candidate | Cut Site from NGS | Candidate | Cut Site from NGS |
|---|---|---|---|
| MG1-2 (SEQ ID NO: 6) | 3 | MG71-2 | 2 or 3 |
| MG1-4 (SEQ ID NO: 1) | 4 | MG72-1 | 3 |
| MG1-5 (SEQ ID NO: 2) | 4 | MG73-1 (SEQ ID NO: 11720) | 3 |
| MG1-6 (SEQ ID NO: 3) | 4 | MG73-2 (SEQ ID NO: 11721) | 3 |
| MG1-7 (SEQ ID NO: 4) | 4 | MG74-1 (SEQ ID NO: 11722) | 3 |
| MG14-1 (SEQ ID NO: 678) | 1 or 3 | MG86-1 (SEQ ID NO: 11723) | 3 |
| MG14-241 (SEQ ID NO: 914) | 3 | MG86-2 (SEQ ID NO: 11724) | 3 |
| MG14-244 (SEQ ID NO:917) | 3 | MG87-1 (SEQ ID NO: 11725) | 3 |
| MG14-246 (SEQ ID NO: 919) | 3 | MG87-2 (SEQ ID NO: 11726) | 3 |
| MG14-248 (SEQ ID NO: 921) | 3 | MG87-3 (SEQ ID NO: 11727) | 3 |
| MG14-5 (SEQ ID NO: 681) | 3 | MG88-1 (SEQ ID NO: 11728) | 3 |
| MG15-1 (SEQ ID NO: 930) | 1 or 3 | MG88-2 (SEQ ID NO: 11729) | 3 |
| MG15-115 (SEQ ID NO: 1042) | 3 | MG88-3 (SEQ ID NO: 11730) | 3 |
| MG15-135 (SEQ ID NO: 1062) | 3 | MG89-2 (SEQ ID NO: 11731) | 3 |
| MG15-54 (SEQ ID NO: 981) | 3 | MG89-3 (SEQ ID NO: 11732) | 3 |
| MG15-66 (SEQ ID NO: 993) | 3 | MG94-1 (SEQ ID NO: 11733) | 3 |
| MG15-94 (SEQ ID NO: 1021) | 3 | MG94-2 (SEQ ID NO: 8748) | 3 |
| MG16-1 (SEQ ID NO: 11718) | 1 or 3 | MG95-1 (SEQ ID NO: 8782) | 3 |
| MG16-2 (SEQ ID NO: 1093) | 3 | MG95-2 (SEQ ID NO: 8783) | 3 |
| MG16-3 (SEQ ID NO: 11734) | 3 | MG96-1 (SEQ ID NO: 8786) | 3 |

TABLE 23-continued

| Cut sites of MG Family Variants | | | |
|---|---|---|---|
| Candidate | Cut Site from NGS | Candidate | Cut Site from NGS |
| MG17-2 (SEQ ID NO: 7700) | 3 | MG98-1 (SEQ ID NO: 8819) | 3 |
| MG18-1 (SEQ ID NO: 1354) | 1 or 3 | MG98-2 (SEQ ID NO: 8820) | 3 |
| MG2-4 (SEQ ID NO: 11735) | 1 or 3 | MG99-1 (SEQ ID NO: 11748) | 3 |
| MG2-5 (SEQ ID NO: 323) | 3 | MG100-1 (SEQ ID NO: 8960) | 3 |
| MG2-55 (SEQ ID NO: 371) | 3 | MG100-2 (SEQ ID NO: 8961) | 3 |
| MG2-7 (SEQ ID NO: 321) | 3 | MG111-1 (SEQ ID NO: 9037) | 3 |
| MG21-1 (SEQ ID NO: 1512) | 1 or 3 | MG111-2 (SEQ ID NO: 9038) | 3 |
| MG21-2 (SEQ ID NO: 11736) | 3 | MG112-3 (SEQ ID NO: 11749) | 3 |
| MG21-3 (SEQ ID NO: 1513( | 3 | MG116-1 (SEQ ID NO: 9150) | 3 |
| MG21-97 (SEQ ID NO: 1607) | 3 | MG123-1 (SEQ ID NO: 11750) | 3 |
| MG22-1 (SEQ ID NO: 1656) | 1 or 3 | MG124-2 (SEQ ID NO: 11751) | 3 |
| MG22-2 (SEQ ID NO: 11737) | 3 | MG125-1 (SEQ ID NO: 11752) | 3 |
| MG22-3 (SEQ ID NO: 1657) | 3 | MG125-2 (SEQ ID NO: 11753) | 3 |
| MG23-1 (SEQ ID NO: 1756) | 3 | MG125-3 (SEQ ID NO: 11754) | 3 |
| MG23-2 (SEQ ID NO: 11738) | 3 | MG125-4 (SEQ ID NO: 11755) | 3 |
| MG23-3 (SEQ ID NO: 1757) | 3 | MG125-5 (SEQ ID NO: 11756) | 3 |
| MG3-1_long (SEQ ID NO: 424) | 3 | MG150-5 (SEQ ID NO: 7363) | 3 |
| MG3-3 (SEQ ID NO: 11739) | 3 | MG150-6 (SEQ ID NO: 7364) | 3 |
| MG3-4 (SEQ ID NO: 11740) | 3 | MG150-7 (SEQ ID NO: 7365) | 3 |
| MG3-42 (SEQ ID NO: 429) | 3 or 4 | MG150-8 (SEQ ID NO: 7366) | 3 |
| MG3-6 (SEQ ID NO: 426) | 3 | MG150-9 (SEQ ID NO: 7367) | 3 |
| MG3-7 (SEQ ID NO: 422) | 3 | MG3-18 (SEQ ID NO: 11757) | 3 |
| MG3-8 (SEQ ID NO: 428) | 3 | MG3-89 (SEQ ID NO: 11758) | 3 |
| MG4-2 (SEQ ID NO: 11741) | 2 or 3 | MG3-90 (SEQ ID NO: 11759) | 3 |
| MG4-5 (SEQ ID NO: 432) | 1 or 3 | MG3-91 (SEQ ID NO: 11760) | 3 |

TABLE 23-continued

| Cut sites of MG Family Variants | | | |
|---|---|---|---|
| Candidate | Cut Site from NGS | Candidate | Cut Site from NGS |
| MG40-1 (SEQ ID NO: 5718) | 3 | MG3-92 (SEQ ID NO: 11761) | 3 |
| MG40-2 (SEQ ID NO: 5719) | 3 | MG3-93 (SEQ ID NO: 11762) | 3 |
| MG40-3 (SEQ ID NO: 5720) | 3 | MG3-95 (SEQ ID NO: 11763) | 3 |
| MG40-4 (SEQ ID NO: 5721) | 3 | MG3-96 (SEQ ID NO: 11764) | 3 |
| MG40-5(SEQ ID NO: 5722) | 3 | MG3-103 (SEQ ID NO: 11765) | 3 |
| MG40-6 (SEQ ID NO: 5723) | 3 | MG15-130 (SEQ ID NO: 1057) | 3 |
| MG43-3 (SEQ ID NO: 8359) | 3 | MG15-146 (SEQ ID NO: 1073) | 3 |
| MG44-1 (SEQ ID NO: 11742) | 3 | MG15-164 (SEQ ID NO: 1091) | 3 |
| MG46-1 (SEQ ID NO: 11743) | 3 | MG15-166 (SEQ ID NO: 11766) | 3 |
| MG47-1 (SEQ ID NO: 5751) | 3 | MG15-171 (SEQ ID NO: 7605) | 3 |
| MG47-2 (SEQ ID NO: 5752) | 3 | MG15-172 (SEQ ID NO: 7606) | 3 |
| MG48-1 (SEQ ID NO: 5769) | 3 | MG15-174 (SEQ ID NO: 7608) | 3 |
| MG48-3 (SEQ ID NO: 5771) | 3 | MG15-184 (SEQ ID NO: 7618) | 3 |
| MG49-1 (SEQ ID NO: 5805) | 3 | MG15-187 (SEQ ID NO: 7621) | 3 |
| MG49-2 (SEQ ID NO: 5806) | 3 | MG15-191 (SEQ ID NO: 11767) | 2 |
| MG50-1 (SEQ ID NO: 5824) | 3 | MG15-193 (SEQ ID NO: 11768) | 3 |
| MG51-1 (SEQ ID NO: 5827) | 3 | MG15-195 (SEQ ID NO: 11769) | 3 |
| MG52-1 (SEQ ID NO: 5831) | 2 | MG15-217 (SEQ ID NO: 11770) | 3 |
| MG6-3 (SEQ ID NO: 11744) | 1 | MG15-218 (SEQ ID NO: 11771) | 4 |
| MG6-5 (SEQ ID NO: 11745) | 3 | MG15-219 (SEQ ID NO: 11772) | 4 |
| MG7-1 (SEQ ID NO: 11746) | 3 | MG15-177 (SEQ ID NO: 7611) | 3 |
| MG71-1 (SEQ ID NO: 11747) | 3 | | |

Embodiments

The following embodiments are illustrative in nature and are not intended to be limiting in any way:

1. A method of editing a B2M locus in a cell, comprising contacting to said cell
   (a) an RNA-guided endonuclease; and
   (b) an engineered guide RNA, wherein said engineered guide RNA is configured to form a complex with said endonuclease and said engineered guide RNA comprises a spacer sequence configured to hybridize to a region of said B2M locus,
      wherein said region of said B2M locus comprises a targeting sequence having at least 85% identity to at least 18 consecutive nucleotides of any one of SEQ ID NOs: 6387-6468.
2. The method of embodiment 1, wherein said RNA-guided endonuclease is a class 2, type II Cas endonuclease.
3. The method of embodiment 1, wherein said RNA-guided endonuclease comprises a RuvCIII domain comprising a sequence having at least 75% sequence identity to SEQ ID NO: 2242 or SEQ ID NO: 2244.
4. The method of embodiment 3, wherein said RNA-guided endonuclease further comprises an HNH domain.
5. The method of embodiment 1, wherein said engineered guide RNA comprises a sequence having at least 80% identity to any one of SEQ ID NOs: 6305-6386.
6. The method of embodiment 1, wherein said region of said B2M locus comprises a sequence at least 75%, 80%, or 90% identical to at least 19 of the non-degenerate nucleotides of any one of SEQ ID NOs: 6388, 6399, 6401, 6403, 6410, 6413, 6421, 6446, and 6448.
7. A method of editing a TRAC locus in a cell, comprising contacting to said cell
   (a) an RNA-guided endonuclease; and
   (b) an engineered guide RNA, wherein said engineered guide RNA is configured to form a complex with said endonuclease and said engineered guide RNA comprises a spacer sequence configured to hybridize to a region of said TRAC locus,
      wherein said region of said TRAC locus comprises a targeting sequence having at least 85% identity to at least 18 consecutive nucleotides of any one of SEQ ID NOs: 6509-6548.
8. The method of embodiment 7, wherein said RNA-guided endonuclease is a class 2, type II Cas endonuclease.
9. The method of embodiment 7, wherein said RNA-guided endonuclease comprises a RuvCIII domain comprising a sequence having at least 75% sequence identity to SEQ ID NO: 2242 or SEQ ID NO: 2244.
10. The method of embodiment 9, wherein said RNA-guided endonuclease further comprises an HNH domain.
11. The method of embodiment 7, wherein said engineered guide RNA comprises a sequence having at least 80% identity to any one of SEQ ID NOs: 6469-6508.
12. The method of embodiment 7, wherein said region of said TRAC locus comprises a sequence at least 75%, 80%, or 90% identical to at least 19 of the non-degenerate nucleotides of any one of SEQ ID NOs: 6517, 6520, and 6523.
13. A method of editing a HPRT locus in a cell, comprising contacting to said cell
   (a) an RNA-guided endonuclease; and
   (b) an engineered guide RNA, wherein said engineered guide RNA is configured to form a complex with said endonuclease and said engineered guide RNA comprises a spacer sequence configured to hybridize to a region of said HPRT locus,
      wherein said region of said HPRT locus comprises a targeting sequence having at least 85% identity to at least 18 consecutive nucleotides of any one of SEQ ID NOs: 6616-6682.
14. The method of embodiment 13, wherein said RNA-guided endonuclease is a class 2, type II Cas endonuclease.
15. The method of embodiment 13, wherein said RNA-guided endonuclease comprises a RuvCIII domain comprising a sequence having at least 75% sequence identity to SEQ ID NO: 2242 or SEQ ID NO: 2244.
16. The method of embodiment 15, wherein said RNA-guided endonuclease further comprises an HNH domain.
17. The method of embodiment 13, wherein said engineered guide RNA comprises a sequence having at least 80% identity to any one of SEQ ID NOs: 6549-6615.
18. The method of embodiment 13, wherein said region of said HPRT locus comprises a sequence at least 75%, 80%, or 90% identical to at least 19 of the non-degenerate nucleotides of any one of SEQ ID NOs: 6619, 6634, 6673, 6675, and 6679.
19. A method of editing a TRBC1/2 locus in a cell, comprising contacting to said cell
   (a) an RNA-guided endonuclease; and
   (b) an engineered guide RNA, wherein said engineered guide RNA is configured to form a complex with said endonuclease and said engineered guide RNA comprises a spacer sequence configured to hybridize to a region of said TRBC1/2 locus,
      wherein said region of said TRBC1/2 locus comprises a targeting sequence having at least 85% identity to at least 18 consecutive nucleotides of any one of SEQ ID NOs: 6722-6760 or 6782-6802.
20. The method of embodiment 19, wherein said RNA-guided endonuclease is a class 2, type II Cas endonuclease.
21. The method of embodiment 19, wherein said RNA-guided endonuclease comprises a RuvCIII domain comprising a sequence having at least 75% sequence identity to SEQ ID NO: 2242 or SEQ ID NO: 2244.
22. The method of embodiment 21, wherein said RNA-guided endonuclease further comprises an HNH domain.
23. The method of embodiment 19, wherein said engineered guide RNA comprises a sequence having at least 80% identity to any one of SEQ ID NOs: 6683-6721 and 6761-6781.
24. The method of embodiment 19, wherein said region of said TRBC1/2 locus comprises a sequence at least 75%, 80%, or 90% identical to at least 19 of the non-degenerate nucleotides of any one of SEQ ID NOs: 6734, 6753, 6790, and 6800.
25. A method of editing a HAO1 locus in a cell, comprising contacting to said cell
   (a) an RNA-guided endonuclease; and
   (b) an engineered guide RNA, wherein said engineered guide RNA is configured to form a complex with said endonuclease and said engineered guide RNA comprises a spacer sequence configured to hybridize to a region of said HAO1 locus, wherein said region of said HAO1 locus comprises a targeting sequence having at least 85% identity to at least 18 consecutive nucleotides of any one of SEQ ID NOs: 11802-11820.

26. The method of embodiment 25, wherein said RNA-guided endonuclease is a class 2, type II Cas endonuclease.

27. The method of embodiment 25, wherein said RNA-guided endonuclease comprises a RuvCIII domain comprising a sequence having at least 75% sequence identity to SEQ ID NO: 2242.

28. The method of embodiment 27, wherein said RNA-guided endonuclease further comprises an HNH domain.

29. The method of embodiment 25, wherein said region of said HAO1 locus comprises a sequence at least 75%, 80%, or 90% identical to at least 19 of the non-degenerate nucleotides of any one of SEQ ID NOs: 11806, 11813, 11816, and 11819.

30. The method of embodiment 1 wherein said RNA-guided endonuclease is a Cas endonuclease.

31. The method of embodiment 2, wherein said class 2, type II Cas endonuclease comprises an endonuclease having at least 75% sequence identity to any one of SEQ ID NOs: 421-431.

32. The method of any one of embodiments 1-4, 30-31, wherein said RNA-guided endonuclease comprises a sequence at least 75%, 80%, or 90% identical to SEQ ID NO: 421.

33. The method of any one of embodiments 1-4, 30-32, wherein said engineered guide RNA comprises a sequence having at least 80% identity to any one of SEQ ID NOs: 6305-6386.

34. The method of any one of embodiments 1-4, 30-32, wherein said engineered guide RNA comprises a sequence at 80%, or at least 90% identical to any one of SEQ ID NOs: 6306, 6317, 6319, 6321, 6328, 6331, 6339, 6364, and 6366.

35. The method of embodiment 7, wherein said RNA-guided endonuclease is a Cas endonuclease.

36. The method of embodiment 8, wherein said class 2, type II Cas endonuclease comprises an endonuclease having at least 75% sequence identity to any one of SEQ ID NOs: 421-431.

37. The method of any one of embodiments 7-10, 35-36, wherein said RNA-guided endonuclease comprises a sequence at least 75%, 80%, or 90% identical to SEQ ID NO: 421.

38. The method of any one of embodiments 7-10, 35-37, wherein said engineered guide RNA comprises a sequence at 80%, or at least 90% identical to any one of SEQ ID NOs: 6477, 6480, and 6483.

39. The method of embodiment 13, wherein said RNA-guided endonuclease is a Cas endonuclease.

40. The method of embodiment 14, wherein said class 2, type II Cas endonuclease comprises an endonuclease having at least 75% sequence identity to any one of SEQ ID NOs: 421-431.

41. The method of any one of embodiments 13-16, 39-40, wherein said RNA-guided endonuclease comprises a sequence at least 75%, 80%, or 90% identical to SEQ ID NO: 421 or SEQ ID NO: 423.

42. The method of any one of embodiments 13-16, 39-40, wherein said engineered guide RNA comprises a sequence at 80%, or at least 90% identical to any one of SEQ ID NOs: 6552, 6567, 6606, 6608, and 6612.

43. The method of embodiment 19, wherein said RNA-guided endonuclease is a Cas endonuclease.

44. The method of embodiment 20, wherein said class 2, type II Cas endonuclease comprises an endonuclease having at least 75% sequence identity to any one of SEQ ID NOs: 421-431.

45. The method of any one of embodiments 19-22, 43-44, wherein said RNA-guided endonuclease comprises a sequence at least 75%, 80%, or 90% identical to SEQ ID NO: 421 or SEQ ID NO: 423.

46. The method of any one of embodiments 19-22, 43-45, wherein said engineered guide RNA comprises a sequence at 80%, or at least 90% identical to any one of SEQ ID NOs: 6695, 6714, 6769, and 6779.

47. The method of embodiment 25, wherein said RNA-guided endonuclease is a Cas endonuclease.

48. The method of embodiment 26, wherein said class 2, type II Cas endonuclease comprises an endonuclease having at least 75% sequence identity to any one of SEQ ID NOs: 421-431.

49. The method of any one of embodiments 25-28, 47-48, wherein said RNA-guided endonuclease comprises a sequence at least 75%, 80%, or 90% identical to SEQ ID NO: 421.

50. The method of any one of embodiments 1-24, 30-46, wherein said cell is a peripheral blood mononuclear cell (PBMC).

51. The method of any one of embodiments 1-24, 30-46, wherein said cell is a T-cell or a precursor thereof or a hematopoietic stem cell (HSC).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

TABLE 24

Listing of additional protein and nucleic acid sequences referred to herein not included in the sequence listing

| Category | SEQ ID: | Description | Type | Organism | Sequence |
|---|---|---|---|---|---|
| MG123 active effectors PAM | 11518 | MG123-1 3' PAM | Nucleotide | artificial sequence | nnnnCAAa |
| MG124 active effectors PAM | 11519 | MG124-2 3' PAM | Nucleotide | artificial sequence | nnnnATAA |
| MG125 active effectors PAM | 11520 | MG125-1 3' PAM | Nucleotide | artificial sequence | nnnnATAA |
| MG125 active effectors PAM | 11521 | MG125-2 3' PAM | Nucleotide | artificial sequence | nnGTACAA |
| MG125 active effectors PAM | 11522 | MG125-3 3' PAM | Nucleotide | artificial sequence | nnnnRCAC |
| MG125 active effectors PAM | 11523 | MG125-4 3' PAM | Nucleotide | artificial sequence | nnnnGnnA |
| MG125 active effectors PAM | 11524 | MG125-5 3' PAM | Nucleotide | artificial sequence | nnnnCnnn |
| MG150 active effectors PAM | 11525 | MG150-5 3' PAM | Nucleotide | artificial sequence | nnnMCMnn |
| MG150 active effectors PAM | 11526 | MG150-6 3' PAM | Nucleotide | artificial sequence | nnRMYTnn |
| MG150 active effectors PAM | 11527 | MG150-7 3' PAM | Nucleotide | artificial sequence | nnwMCrnn |
| MG150 active effectors PAM | 11528 | MG150-8 3' PAM | Nucleotide | artificial sequence | nnwMCCnn |
| MG150 active effectors PAM | 11529 | MG150-9 3' PAM | Nucleotide | artificial sequence | nnnMCMnn |
| MG3 active effectors PAM | 11530 | MG3-18 3' PAM | Nucleotide | artificial sequence | nnRGGTY |
| MG3 active effectors PAM | 11531 | MG3-89 3' PAM | Nucleotide | artificial sequence | nnRwwYYn |
| MG3 active effectors PAM | 11532 | MG3-90 3' PAM | Nucleotide | artificial sequence | nnRmwYnn |

TABLE 24-continued

Listing of additional protein and nucleic acid sequences referred to herein not included in the sequence listing

| Category | SEQ ID: | Description | Type | Organism | Sequence |
|---|---|---|---|---|---|
| MG3 active effectors PAM | 11533 | MG3-91 3' PAM | Nucleotide | artificial sequence | nnRwYCCn |
| MG3 active effectors PAM | 11534 | MG3-92 3' PAM | Nucleotide | artificial sequence | nnRGnCAn |
| MG3 active effectors PAM | 11535 | MG3-93 3' PAM | Nucleotide | artificial sequence | nnCACnn |
| MG3 active effectors PAM | 11536 | MG3-95 3' PAM | Nucleotide | artificial sequence | nnnMYAY |
| MG3 active effectors PAM | 11537 | MG3-96 3' PAM | Nucleotide | artificial sequence | nRwYAYn |
| MG3 active effectors PAM | 11538 | MG3-103 3' PAM | Nucleotide | artificial sequence | nnRGCCCn |
| MG15 active effectors PAM | 11539 | MG15-130 3' PAM | Nucleotide | artificial sequence | nnnnCwAC |
| MG15 active effectors PAM | 11540 | MG15-146 3' PAM | Nucleotide | artificial sequence | nnnnGTRY |
| MG15 active effectors PAM | 11541 | MG15-164 3' PAM | Nucleotide | artificial sequence | nnRnRYAW |
| MG15 active effectors PAM | 11542 | MG15-166 3' PAM | Nucleotide | artificial sequence | nnnnGYTA |
| MG15 active effectors PAM | 11543 | MG15-171 3' PAM | Nucleotide | artificial sequence | nnnnCWAW |
| MG15 active effectors PAM | 11544 | MG15-172 3' PAM | Nucleotide | artificial sequence | nnCCRCAT |
| MG15 active effectors PAM | 11545 | MG15-174 3' PAM | Nucleotide | artificial sequence | nnRGAYA |
| MG15 active effectors PAM | 11546 | MG15-184 3' PAM | Nucleotide | artificial sequence | nnRnRYAA |
| MG15 active effectors PAM | 11547 | MG15-187 3' PAM | Nucleotide | artificial sequence | nnnnCAAn |
| MG15 active effectors PAM | 11548 | MG15-191 3' PAM | Nucleotide | artificial sequence | GnnnnCMA |

TABLE 24-continued

| Listing of additional protein and nucleic acid sequences referred to herein not included in the sequence listing | | | | | |
|---|---|---|---|---|---|
| Category | SEQ ID: | Description | Type | Organism | Sequence |
| MG15 active effectors PAM | 11549 | MG15-193 3' PAM | Nucleotide | artificial sequence | nnRnRYAY |
| MG15 active effectors PAM | 11550 | MG15-195 3' PAM | Nucleotide | artificial sequence | nnnnGAAA |
| MG15 active effectors PAM | 11551 | MG15-217 3' PAM | Nucleotide | artificial sequence | nnRnRTGA |
| MG15 active effectors PAM | 11552 | MG15-218 3' PAM | Nucleotide | artificial sequence | nnnCnAT |
| MG15 active effectors PAM | 11553 | MG15-219 3' PAM | Nucleotide | artificial sequence | nnnRTATW |
| MG15 active effectors PAM | 11554 | MG15-177 3' PAM | Nucleotide | artificial sequence | nnnSRYTA |
| MG71 effectors | 11711 | MG71-2 effector | protein | unknown | MFDNLDASKVNDFNAVFSEVENYVRDEMGIEDWSCQNIDELAKVLCDVNLGRTTKQKAMQSLLPAQTKQQKAIIQLFSGGKAKLAELFVDEELDECEKKSVSFQDDDLNEFEPVLTAALGERYEGLLRFKAIYDWSLLAKILHLDTSKKDEDEQHLLSECKMQVYEDHKRDLAVLKSMLKGKPLYNKIFRQDGDISYEKYAKGIKGRNQIDFCKDLKKQLEGIAEYKKIMQEITSIDDAKTEEERLLFRITNGFAFPKQTTKDNGHIPIQVHLAELKCILDNAEGYLPFLGETDNNGLSVREKIEQIVKFRIPYYVGPLAGTRMSREQGRCWVVRKNEKIYPWNFTEIVNLEESAEKFITNMTAKCTYLVGEDVLPKESLLYSEFMVRNAINNITVDGERLPVDVLEKIFKQLFLAKTSKVTKKTLERFFRQENISFQNIGGIDDKINASMKSYNDFRRIFGEDYIQLHRDEIENIIRWITLFCDEKKCWSLK |
| MG73 effectors | 11712 | MG73-1 effector | protein | unknown | MTKILGLDLGIASVGYAVVNLDEQKFDGGEILTAGVRIFEAAENPKDGASLSAPRREARALRRILRRKTIRLQQIRNLFIKYQILTTEELNHLYASPLPSVWEIRTLSLYEKQPLQHIARALLHIAKRRGFRSMRKSAEEKNYETGQLLQGISLLQNLLKQSGRQTIGEFLYHLPQSEPKRNKAGSYNHSIARSMLEEEVRLILEKQRTYGNTALSSEFEQEFRAIAFDQQPLKPSSPGKCTFLPDEDRAPKQAYTAELFAALSKINHIRIVSQGTSRALSADERQIALDLCLEKENNNFAQLRKLLELQENEFFNISYIIPRAKQNTDYQPEKKTAVYKMTGYHALRKALKDHKPLWTTYMDNPNGGLDQIAVVLATFKSDKEIINALEKLQFPSELIEAVKSLSFSGFMHLSLKAMRNINPFLLEGHTYDKACELAGYNFQAAKRNAGLTKLPPLTEEENFSITSPVVKRSIAQTRKVVNALNRKYGPFDAVHIELAREMGRNWAQRKELTQQQKENQEERDLIKAQGIEGLFPKNSLDIKKIRLWKEQGGYCIYSNQYIKPEQILEEGYCQVDHIIPYSRSFDNTLSNQVLCLTKENQDKRNDIPFDYFQRIQRDWDSFVTLVNASPTMRPNKKQKLLRTELSEEDLAGFKDRNLNDTRFISSFVRKYLLQNLQLTNKYKQGVFCRNGKITADLRNMWGLSKIREQDDKHHALDAIVLACCSNAMMQQISTQYTHNKETAALKIKPLFPWPWKEFRTDVENALLSIFVSRPPRKKITGAFHKETYYSAKHLARGFKTLKTDINTLTAEKLAKQRDLEIKYYGVERNKKLYDAIEQALLARTDAKQPLKVYLGPAQTPVKKIKLIMEG |

TABLE 24-continued

| Listing of additional protein and nucleic acid sequences referred to herein not included in the sequence listing | | | | | |
|---|---|---|---|---|---|
| Category | SEQ ID: | Description | Type | Organism | Sequence |
| | | | | | NKGVPVLKGTAVAENGAMPRVDVFYKNGTYFLVPVYTIDFTKEKLPLI SIPDNQPMDVRDFRFSLYKDDYVQIKNKTGETFEGYFKQYNAQTGQIY LETHDRSDSYTVSGKPASEKKFSKSTFVDFTKYQIDILGNQHRVEKEKY TGITRKNKGFGG |
| MG89 effectors | 11713 | MG89-2 effectors | protein | unknown | MSYVLGLDLGIASVGWSIVEPGNRIIDLGVRVFKKAETDKEGDPLNLIR RESRLSRRRLYRRAHRLSRLLNFLISSGLIHSKDEVLKNVYNENPWALR TLGLNSVLTNNQLARVIYHICKHRGFYWASSADDGQADNGKIKKSLSS NQLVMKEKGYKTVGQMIFTEYPNCQRNKSGEYSKSLPRTDLDKELRA IFKAQQSFSNPIVTKDFINAIVGCGDRKTGFLWEQRPALQGEDLLKMV GHCRFEKDELRAPAANFYSEQLVWLTKINNLRVYDEDSQERPLTREER DLILNMPLEMKSDIKYSSLTSAFEKANLWKSGQFKYKSVDYEQKTQKK KNTAKSVDITKSSKKNPEDKVFYKSSHLHEIRKALGSSLSEEWEKIRTE VLSGKYDRYNRIAYVLTVYKEDSDVIEQLSPYESRTLIEALLPVRFSGFV ALSEKSLKKIIPHMVLGKRYDEACSEANYKHYKQNQAEFKKLKYLPPL FSGREPNGTLIFNEEIGDIPRNPVVLRVINQTRKVVNAIVKKYGSPKSVH IELARDLAKSRAERNEIEKRNEEAASRHIKERDEFEKLFGSKCLNGTNL LKYRLYKEQDCKSMYSSKEIDHKRLFEKGYVQIDHILPYSRSYDDSQSN KVLVLTNENQDKGNRIPFEYFEAKQHGFSWYEFEQWVKSCKNLNQKK KRNLLRCSLSKDAKKDFLERNLNDTRYACRFVKNYIDSFLCLSENSDNS GCVVVAGQLTAYLRNCWGLNKVREENDRHHALDATVIACCTRKIVQ KVGAWSKSREMNSYNSSYVDPDSPVDEDEKLLQKLYVNTRKPDFPKP WECFRSEVESRVFESALEKLKEKLKLQCSYTESELKNVRTLFVSRACE KIGKGALHGDTVYRQTSEMRKENVAVKKVSLKKLKYARIEAIVDADT RNKNLCDALKKRYEEYARKIGKKIEDFVDKDIAKIFADDNPLHMPNSD GQEDPCNPIVKSVRVKEAFSGVPIRNGVAGNSTIIRVDLFKKDGKYYCI PVYAWNKTLPNRAYVSGKKETDWALVDDSFEWCFSIRQNELLKIKLK GETIFGYYNGFDRDRGSFNILLHDRQDGKDHKQGLIRKGIKTAISITKY DVDVLGNYYLSKPEKRLELA |
| MG73-1 sgRNA | 11714 | MG73-1 sgRNA | Nucleotide (RNA) | unknown | (N24)GUUAUAGUGGGAAAUCACUAUAAUAAGUGAAAUCGCAAGGCU CUGUUCUUGAACAUCCUUUAUUAUAAAACUCCUGCCAAUCGGUUG GGAGUUUU |
| MG89-2 sgRNA | 11715 | MG89-2 sgRNA | Nucleotide (RNA) | unknown | (N24)GUUGUAGCUUCCUUGAAGAAAUUCAACGUUGUUACAAUAAGG UUUUCGAAAGAUUACCGAACCCGCCCUCACUUAGGUGAGGGCUUU U |
| MG99 effectors | 11716 | MG99-1 effector | protein | unknown | MRDLSYRIGLDIGIGSIGWAVVSSETEDHPARIENFGTRIFDSGEDPKTR ESLCQARRADRGVRRLERRRAFRKEMLKNHFQNIGLLNNTENDDYES CRDDDVYLLKVKGLDGKLEAAELFKCLAHTCNHRGYKDFYEPEDDDE NEESGVNEKAANLFEKEFAASGKRTVSEYLVEKYFNNGFVKFRNRSGS DAPYMLIRRSLLKDEAEKIIKKQSEYYPCLGGINAERTVSIIFSQRDFED GPGDPNDPHRRYHGFLETLGRCPYYKDEKRGFRGTVISDVFAVTNTLS QYVFFEKETGECRLDPKIANELVSYLLTNAGLTMTEVKKILKSHGYEL KKSEKSDDKAISKAVKFLSIAKKCVEEAGKSWEALISEDQFDAANLSTL HRIGELISKFQTPSRRVQEMKKAGIDGDLIKAFSGKKISGTSSVSYKYM TDSINAFLSGDIYGNFQANFIKENAAVKEEERSYKLEPRHIDDPEVRDN |

TABLE 24-continued

| Category | SEQ ID: | Description | Type | Organism | Sequence |
|---|---|---|---|---|---|
| | | | | | RVVFKAINETRKVVNAIIDIYGSPEDIVIEVASELGKSVEARIEETKRQR ANEKENDRIKSEIAKLLSIDVQSVKTTMIERYKLYNIQEGKCAYSLEPL GDLKDVVENVNKVYEIDHIVPFSLILDNTLNNKALVFTRENQTKGQRT PLMYLSEEKAKEFLAFSNHLFSKKTGGISKTKLEYLKLETIYGEAAAEK LNAWKSRNINDTRYITKYIAGLFDKQLIFAGDKKQHVFTVKGSVTQKF RREWFRGTEWGKDEKDRTTYLNHALDALVAANLTKAYIEIGSDAIKLS QIYRAHRYQITEEYESYLDKCVKKMSKYYGFSEGYTKKLLSKPERIPSF VPRLKEEVAVRENDSDSEAFDKGVSKLYSAEAPFIDPPHIPITSHKQNKK FKGCIADSNPIRVEEIDGEAHKIRRIDIKTLSAKKLKDLYTGDVSLREEL AAMLDGKPESYTVGDSLKESGKEFFLSKSGAVIRKVSVDDGIVSNYYR KEIKDGQYSTLGMLKYYCIEVYKDAKGKTRIYGIRFVDVVKKNKKLY QKAESYPEDYASHVMYLFTGDFVRITDKKGKLKFEGFYQAVKNINSSI LYFSPVNLANTVIKGISLTDNIEKYYVDILGRIGGKIRCSEPLQSTAEKK SL |
| MG14 sgRNA | 11717 | MG14-241 sgRNA | Nucleotide (RNA) | unknown | N(20)GUCUUGCCGGAAACGGCUAGACAAGGGAAUCGCUUUUACGCG AUUACCCGCAAGGUAAGCCCGUCAGCACCCUUGGUGUCGGCGGGC GAUCCUUUU |
| MG16 effectors | 11718 | MG16-1 effector | protein | unknown | MIKNILGLDLGVGSIGWALIQTEDDQPKQIIGMGSRIVPLTKDDSDQFT KGQAISKNAERTARRTTRKGYDRYQLRRALLTQVLRQNGMLPECMD ENMIDLWKLRSDAATEGKQLTLQQIGRVLYHINQKRGYKHAKSDDNG DSKQTKYVEAVNLRYKEIQEKNVTVGQHFYAELLNSKVESGNGPYYTF RIKDKVFPRAAYIAEFDQIMGVQKEYYPNVLTDELIETLRNRIIFYQRPL KSCKHLVGLCEFEMRPYKKDGKIVYGGPKCAPRTSPLAQLCAMWET VNNITLTNRNNERLEISNEQRRQLVQFLCTHETLKLTDLYKILGITKKD GWYGGKAIGKGIKGNVTLNQLRKALDGKYSQWLEMPIERIDVVDRNT AEAFWAVSPKVEETPLFQLWHAVYSLQNVEELTKTLQNRFSITDPQVI DALCKIDFVKPGYANKSHKFIRRLLPYLMEGMMYSEACACIQINHSNS MTKAEREARPLAERIELLQKNALRQPVIEKILNQMINLVNRLQQEYGPI DEARVELARELKQSREERKDAFDRNNKNEKRNKEISALISEQGIRPSRS RIQKYKMWEESEHRCMYCGKVVNLSEFLNGADVEIEHIIPRSILFDDSF SNKVCACRDCNREKDNMTAMDYMASKPEGEFEAYKQRVDEAFNAHR ISKTKRDHLLWRRADIPQDFIDRQLRLSQYIATKAVEILQQGIRQVWTS GGGVTDFLRHQWGYDEILHTLNLPRYRQVEDLTEMVHYEHAGQEHD EERIKNWSKRIDHRHHAIDALTVALTRQSYIQRLNTLEASHEHMEKLV KEANTPYKEKKSLLEKWVALQPHFSVEEVTTQVDGILVSFRAGKRVTT PARRAVYHGGKRTIVQRGIQVPRGALTEDTIYGKLGDKFVVKYALDH PSMKPENIVDPTIRLLVENRITALGKKDAFKTPLYSAEGMEIKSVRCYT SLSEKGVVPIKYNEKGNAIGFAKKGNNHHVAIYKDQSGQYQEMVVSF WDAVERKLYGVPTVITNPKTVWDELLEKELPQDFLEKLPKDNWQYVL SMQENEMFVLGMEEDEFNDAIDTQDYNTLNKHLYRVQKLSHADYTFR FHTETKVDDKYDGVENGRNTSMSLKALVRIRSFNGLFTQFPHKVKIDI MGRITKA |
| MG16-1 sgRNA | 11719 | MG16-1 sgRNA | Nucleotide (RNA) | unknown | N(22)GUUGUGUAUGGAAACAUACACAAUAAGGAUUAUUCCGUUGUG AAAACAUUCAGGGUGGGACGCAAGUCUCGCCCUUUU |

TABLE 24-continued

Listing of additional protein and nucleic acid sequences referred to herein not included in the sequence listing

| Category | SEQ ID: | Description | Type | Organism | Sequence |
|---|---|---|---|---|---|
| MG73 effectors | 11720 | MG73-1 effector | protein | unknown | MTKILGLDLGIASVGYAVVNLDEQKFDGGEILTAGVRIFEAAENPKDGASLSAPRREARALRRILRRKTIRLQQIRNLFIKYQILTTEELNHLYASPLPSVWEIRTLSLYEKQPLQHIARALLHIAKRRGFRSMRKSAEEKNYETGQLLQGISLLQNLLKQSGRQTIGEFLYHLPQSEPKRNKAGSYNHSIARSMLEEEVRLILEKQRTYGNTALSSEFEQEFRAIAFDQQPLKPSSPGKCTFLPDEDRAPKQAYTAELFAALSKINHIRIVSQGTSRALSADERQIALDLCLEKENNNFAQLRKLLELQENEFFNISYIIPRAKQNTDYQPEKKTAVYKMTGYHALRKALKDHKPLWTTYMDNPNGGLDQIAVVLATFKSDKEIINALEKLQFPSELIEAVKSLSFSGFMHLSLKAMRNINPFLLEGHTYDKACELAGYNFQAAKRNAGLTKLPPLTEEENFSITSPVVKRSIAQTRKVVNALNRKYGPFDAVHIELAREMGRNWAQRKELTQQQKENQEERDLIKAQGIEGLFPKNSLDIKKIRLWKEQGGYCIYSNQYIKPEQILEEGYCQVDHIIPYSRSFDNTLSNQVLCLTKENQDKRNDIPFDYFQRIQRDWDSFVTLVNASPTMRPNKKQKLLRTELSEEDLAGFKDRNLNDTRFISSFVRKYLLQNLQLTNKYKQGVFCRNGKITADLRNMWGLSKIREQDDKHHALDAIVLACCSNAMMQQISTQYTHNKETAALKIKPLFPWPWKEFRTDVENALLSIFVSRPPRKKITGAFHKETYYSAKHLARGFKTLKTDINTLTAEKLAKQRDLEIKYYGVERNKKLYDAIEQALLARTDAKQPLKVYLGPAQTPVKKIKLIMEGNKGVPVLKGTAVAENGAMPRVDVFYKNGTYFLVPVYTIDFTKEKLPLISIPDNQPMDVRDFRFSLYKDDYVQIKNKTGETFEGYFKQYNAQTGQIYLETHDRSDSYTVSGKPASEKKFSKSTFVDFTKYQIDILGNQHRVEKEKYTGITRKNKGFGG |
| MG73 effectors | 11721 | MG73-2 effector | protein | unknown | MNKILGIDMGIASLGYAVVNIDDENFVNGDILASGVRIFDVAESPDGSSLAAPRRAARSVRRILRRKVMRIKAIKQLFLDENLLSPQELDLLSKQDFKTLYQATPEGQPIPSVWEIRARALDNPCSLVDICRALLHIAKRRGFRSMRKSEKLTGEAGKLLKGVEEMQKKLQESNFRTIGELLFHLPATEPKRNKDGSYSHSVARSLLEEEVHLILQVQRAKGANALSQEFETQFCKIAFLQNPLQPSDPGFCTLEPTEPRAPKNAYTAELFAALCKINHIYLEEDGQSHALSAAQRALALEKCFSTQKTNYKQLRELFNLPNDIKFNISYTAPAKKKSKKKEEAQSPEQAVQAPQEYDAEKNTTLYNMAGFHALKKALKSSPLWAEYQTNPNGILDKIAEVLSRYKSDGEIRQHLTALGLPAEAVEKLQNVNFSGFMNLSLVAMNKIIPFLKEGFRYDVACKKAGYNFQAPQQNKGLSKLPPLTEEDNHTITSPVAKRSLAQARKVINALNKKYGPFDAVHIEVAREIGKSFEKRKEIEAEQKAHAEERARLKEVGIDGIIPQTETDLKKLRLWKEQDGRCMYSLQYIEPRKILEEGYCQVDHIIPYSLSFDNSLNNQVLCLTSENQHKKNQIPYEYFHSGKAQITWEDFEGYVNSLQNIRMAKKHRLLKQELTEDDLQGFKERNLSDTKLISRFMKNYLLANLRLTGKYKQGVFCVNGKHTSTLRGFWRLQKIREDGDKHHALDAIVIACCTNRLMQYISTKYRQNRELELQRKEVAVPWPFPHFKHAVENSLLSIFVSRPPRKKVTGALHKNTFFSAKHIKKGIKTLRTDIQKLTLDSLKKQRELEVKYFGVERNKPLYDLIETALNNRPNDKTPIQVQMPTKNGGFVPVRHIKLISESTSGIPVLGGTALAENDSMPRVDVFLEDGQYYVVPVYTMDFAKGVLPLVAQPSGRLMKKENFVFSLYKDDYVNLVNKQGETWEGYFKQLNAQTGQIYLESHDRSAQYTVSGKPSNQKKIASSTLKLIEKYQIDIFGGKHLVKKEKYIGIIRKNKGFGG |
| MG74 effectors | 11722 | MG74-1 effector | protein | unknown | MQVHDDVILGLDIGVGSLGWALLEEDLQTGEQRLLQRQTPQGETTYALGVRLFHVPENAKTKELLNVKRRTARMQRRTTARRAQRMRRVRALL |

TABLE 24-continued

| Listing of additional protein and nucleic acid sequences referred to herein not included in the sequence listing | | | | | |
|---|---|---|---|---|---|
| Category | SEQ ID: | Description | Type | Organism | Sequence |
| | | | | | DSLGVPGVRDADAFHLGKGRGAQCDPWQLRREGLERRLEAREWAVV<br>LLHIAKHRGFRSNSKTDRSGSDKEMGQVLQAVSNLQQEVEASGLTVG<br>ALLASRERRRNRADHTGAPRYDLCMLRSLQENEVDILFTRQRELGNPL<br>AGEEVRCRYAELAFAQRPLAPVSHMVGPCAFLEGERRAPRFAPTAELF<br>RYVQALCNMRLRQETGEETPLSEEQRQAACAVFGSVQSVTYKKLRQV<br>LRLPAGCRFAGLSYGVTEKGNVQDPEKADVVMRTGKCCQGTACLRGI<br>LGDAYEALHEQRLDEADAARLAATGALSAPAAALLARGMAGLRLTDA<br>VARIVSELNDLDQIRAVLALLPLAAPRIAALSQAAGEGKLGIFQGTARL<br>SLRAMEAILPHMLACGEYAAACELAGFDPRAAQKTDVTDIRNPVVLRV<br>FREVRRQFSAICREFGFLPGRVHVELLREVGKSGEERNRISRGLERRTK<br>EKEAARKAVAQLLGKSPETVSAGEVQRYELWRQQDGKCAYYMLWR<br>HAGGERAYGDAMPQGSIPPDWLADGVNAVQVDHILPRSRTFDNSFHN<br>LCLCCHAANQAKGGRTPWEWLGAAQPQAWHDFEQWVQSLPLKGLK<br>KRNYLLRDLNAEVQGRFHARNLTDSGYVARLTLRWLEEEYARHDVP<br>MQDADGRTRRRFFARPGQVTDFLRRHWGVQALKKIDGQRSGDRHHA<br>LDALLVAACSEGMLQRMVRAFQREENGPERLHIPCPWQDFSATVGRA<br>LGSVFVSRVERGRTKGPLHEETLRAIREERQPDGETRRVLYERKAVAR<br>LTAADLDKIKDAARCPDVVAALRRWLDAGKPGDALPRSAHGDIIRHVR<br>VCAGEFSSGVVLQRGSGQAQASNGGMVRTDIYSRDGKFYMVPVYAKD<br>VADKRLPLRACVAAKAEKDWREMTADYRFLFSLTPDCYVLTENRKGE<br>VKEGYFAGANRNTSAISLSLAHDKQNVIQGIGITTLKRFEKYRVDRFGR<br>LSLVRREADPRGRS |
| MG86 effectors | 11723 | MG86-1 effector | protein | unknown | MKKILSFDLGITSIGYSVLTEDEAQKYSLLDYGVSMFDKPTDKDGNSK<br>KLLHAQALSTKKLYKLRKERKKNLALLFEKYALAKASKLLEQEKKNL<br>YMYKWQLRAKKVFEERLSIGEIFTILYHIAKHRGYKSLDSGDLLEELC<br>VELGIKIDVKKEKKDDEKGKIKQALSTIESLRKEYPKKTVAQIIYEVEL<br>QKERPVFRNHDNYNYMIRREHINDEIATIIRKQKEFGNFENIDSEVFIVD<br>IIAAIDDQKESTNDMSLFGKCEYYPKEHVAHQYSLLSDIFKMYQAVANI<br>TFNKEKIKITKEQIRLLTEDFLNKIKKGKSVKELKYKDVRKILKLDESV<br>KIFNKEDSYQRAGKKVEHTITKFHFVDNLSKIDKSFIEDIFNADESYVL<br>MREIFDVIHKEKSPKRIYEQLKSKVSSEAVIIDLIRYKKGSSLNISSYAMA<br>KFLPYFEEGMTLDAIKEKLDLGRKEDYSVYKKGIKYLHISTYEKDDDL<br>EINNHPVKYVVSAVLRVVKHLHAKHGTFDEIKVESTRELSLNDKVKKE<br>IDKANKAREKEIEKIISNDEYQKIAKEYGKNIHKYARKILMWEAQERFD<br>VYSGKSIGIDDIFSNRVDVDHIVPQSLGGLYVQHNLVLVHRDENLQKSN<br>QLPMNYITDKEAYINRVEHLFSEHKINWKKRKNLLASNLDEIYKDTFES<br>KDLRATSYIEALTANILKRYYPFIDEKKSVDGSAVRHIQGRATANIRKV<br>LGVKTKSRESNIHHGVDALLIGVTNPSWLQKLSNIFRENFGKIDDEARK<br>NIKKALPYIDGVEVKDIVKEIEQKYNSYGEDSIFYKDIWGKAKTVNFW<br>VSKKPMISKVHKDTIYADKGNGIFTVRESIIAKFINLKITPTTFPEDFMK<br>KFHKEILEKMYLYKTNSNDVICKIVQQRAEEIKELLWSFEFLDVKNKE<br>EMQEAKANLESLVHRELFDNNGNVVRKVKFYQTNLTGFKVRGGLAT<br>KEKTFIGFRAFKKDKKLEYKRIDVSNFEKIKKSNDGSFKVYKNDIVFFV<br>FDEEKYKGGKIVSFLEDKKMAAFSNPKYPANIQAQPESFLTIFKGKANS<br>HKQVSVGKAKGIIKLKVDILGNIESYQVLGNAKSKLLDEIKSIVSH |

TABLE 24-continued

| Listing of additional protein and nucleic acid sequences referred to herein not included in the sequence listing | | | | | |
|---|---|---|---|---|---|
| Category | SEQ ID: | Description | Type | Organism | Sequence |
| MG86 effectors | 11724 | MG86-2 effector | protein | unknown | MKKILSLDLGITSIGYSVIEEFGNDRYSLIDYGVSMFDKATDKDGNSKKLLHSASTSTSKLYDLRKKRKKDLAQLFHNFGLGDKNSLLSQEKQNIYKNKWYLRCHKAFKEKLNINELFTIFYTLAKHRGYKSLDSSDLLEELCEKLNIPLETKTKKDDERGKIKKALKTIEELKQNSTKTVAQIIYEIELKKENPTFRNHDNYNYMIRREYIDQEIEKIIKTQKDFGLFDDKFDIDNFIEKLKDIITYQNPSTNDMRLFGNCEYYEDEKAAHQYSVISDIFKMYESVSNITFNTKPSIKITKEQINKIADDFFTKIKKGKNIADIKYKDIRKILALSDDTKIFNKDDSYISKGKKVEHTIIKFHFVNNLSKFDNSFIVENLNSLENLKEIFEVLQFEKDPTAIYEKLKDKIEDKQTIINLIKHKSGNSLNISAKAMVEFIPYFKDGLTTDKIKEKLELNRCEDYSKFYKGIKYLNIRQFEQDDNLDINNHPVKYVVSATLRVIKYLHIVCGTFDEIRVESTRELSQNEETKKAIEKANKELEKQINDIVQNKEYQNIAQHYGKNLQKYARKILLYEAQNRRDIYTGEGIEFEDIFTKKVDIDHIVPQSVGGLSVKHNLVLVFRDTNIQKSNQLPMNFVKDKQDFINRVEHLFSEHKINWKKRKNLLATNLDEIYKDTFESKSLRATSYIEALTAQILKRYYPFKDKEKQENGKAVSYIQGRATSNIRKILKVKTKTRDTNIHHAIDAILIGLTNQSWLQKLSNTFRENFGKIDEEARANIKKDMPIFEIIIDDEVKYLEPKELVELIEKNYNYDGENSIFYKDIWGKIKSVNFWVSKKPMVSKIHKDTIYSKKDDGIYTVRENIINHFINLKITPKTSSKKFEEEFNKKILNKMYLFKTNPKDAVCKAIIKRANDIKTLLDSFIDIDTKDKEAMNNAKTKLDELIHKDIPDNNGKPIRKIKFYQTNLTGFDVRGGLATKEKTFIGFKAQIINGKLNYTRIDVANIDKIKKENDNSFKVYKNDLVFFIYTDGTNKGGKIVSFLEDKRIAAFSNPRFPSSIGFQPHFFVTIFNGKANSHKQHSLNKAIGIIKLNLDILGNIKSYQKIGSCESELLEFIKKVIKD |
| MG87 effectors | 11725 | MG87-1 effector | protein | unknown | MEKYIIGLDLGINNVGWSVVDAQTNKIKYLGVKQFEASDSAKDRRTQRNTRRRLKRRETRKTDILKILSNINFPNNLTIDTMLIETRCKGINEQISKQDITNILCYMATHRGYIPFGDEEVSFVDLDGKYPCEYYYEMFKSSTNNKYRALRNTVKNEENINEVKKMLETQRKYYPEITNETIENIVTTLQRKRKFWEGPGSINALTDYGRFKTPEDVVEYLDKKKENPEYEKYIFEDLIGKCSVIPNEKCVSQINFYAEKFNLLNDFINISFKSIEELNNKDDFYETQVKTYKLRESGLNKVFDYCMSKDTLTIKGLFKDLFATTIDNISGYRQDGHDPNKPEMSTMNTFRSIRKTFKECNANMDIFKPENTDLYNEIINYMMLVPGQVELINMLSTIMPLSENDKEALKKVFKSKKTNLKYHSLCEKILIRACNDMLSLQKNYMQVYKLKDYGKESRKEFVKRYEESNKGEKLMNPTFIDDIISSPQVKKTLRQSVKVINEIIKNEKSLPDVIVVESTKDTLNSEKMRKVYIDINKKQKALHDKAIKTLSSIGYSEKDISKKKIEKLMLYEEFDGLCPYCNNQITLKYLINGSDEIEHILPRSNSFDDSFDNRTVSCANCNKNKNNQTPLEFLKGNEKESFIERIKSNKNISEFKKENFLFAGDISKYRTRFFNRNLRDTAYATKEMINQINIFNLYLESKNKDERIKTLSTPGQITHSIRKRYDLEKDRDTDIPYHHAIDASILALLPTTKIGSKVVMFQNDNKFFLNENNKDKMTEIGLELKYYDTSEGKIEYDDYIADFKNINDTSNIFMYSPEVKKEPNKGLFNANMYKVIKIDDKYYKIDQINDIYNLSDSDKKLLPKLFDDAKNETLLCKLQHKEFYEKLKNIYIKYSDSKNSPFEDYQREINNLSKEDKFDYLKHGLKMSENAPSVKRLRYYTPISEPYLIDKKSINKKDGTYLAFDSLAQAGIEVYYNETKNCFAFVPIPSVCYNLKTRKVNRKHKLYKRYKELNLKDYKVKYIVTLYNGNTIEVLKKDNTIIKGVVSSYHKTNDKIVLKNGSYFTKSDLEFSIIDYNPIGKSQKRLTKRIK |

TABLE 24-continued

Listing of additional protein and nucleic acid sequences referred to herein not included in the sequence listing

| Category | SEQ ID: | Description | Type | Organism | Sequence |
|---|---|---|---|---|---|
| MG87 effectors | 11726 | MG87-2 effector | protein | unknown | MKKYTIGLDLGINNVGWAKYDLETKKVIDKGVVRFKESSTAQDRRIIR<br>GSRRLRKRKQHRVERLAIQLSNINFCTSRSYEPELLNKRIKGLNESLSE<br>QEITNIIYWFAIHRGYIPFDEEKPEREVHKFAEDEYPCQYIFDYYKEYG<br>VYRGQCDLISLKDNLKELKQILLTQQKYHSKLTDEVIDNILYIIQSKREF<br>WEGPGASKENQLSPYGRYRTLEDLEKYKADPTYHQYLYEMLIGKCEL<br>SIDKDGFMDQVAPKCNFYAEEFNFYNDFINMSVKEPSQIDEEYRNKITL<br>KGKFTEDTIEEIKKEIISTKKVSLDKLVKKILGLELKDIQGYRIDKKYKP<br>EISQFEFYKYLLKSFKDEKLNPSWLENDDKTIYNQIVYILTVAPSTYAIE<br>DMLKDRVKEVEFKKEEIDVLIDIKKKKNPDLKYHSLSERILKKALDDIK<br>RHNCEYNFMQIMKRLEYEKEMKEYFQNNYSTKTQSPYTIEDQYIDHLI<br>ANPQVKKTLRKAIKIINAIIKEEKNYPETIVIESATSLNSKERKKQIEEEQ<br>KTFNQLNKEVKKELEDNGYEATDKNMQLLINWKETNESCIYCGESISL<br>KEVLITEIEHILPKSKSMDNSHNNTTCSCLKCNKEKNNRTPYQYLTSKN<br>MYEGFKNRVMNQYDKMSQDKKSNLLFEGDIDKYSIKFINRNLRDTSYA<br>SVALVQELKKYNEYLGAKEGYKINIITSPGQLTSKIRQYLKIKDKDRTY<br>LYHHVVDAMILASIPDTEIGKVLIEAQNDSQYWFKDKNKENKYKEEVY<br>NMLNNVWLSNRDQIQKFNQDCDNMPDNNKEGLIKRSYEVLKNPVRQF<br>SQYTEYAKYIKQNDVYYKISQIDNIYNLLIRKKDGSADKDKKLLDELFD<br>LSNKKNKTLLCEKKDPKLYQKLKNIYEKNSFSINPFVDESKYMYGLED<br>GDKFDCLKQGIRKTDNSNSPLVIKLRYLEKVTNPYIKNNITTRRKNLYN<br>EFTINKPKKDTLIGLDGLKQVSTRIFYSYEDKKFIFLPICAISFVNGKLN<br>KKEKNYQTTYNRLIGNKNVKEMGNIYVGEWVGVYKKNGEYFEGRYK<br>GYHKTSNVLEYYINGLDTLSCATIGSSDLRIIIYTTDILGNRHIRLDTQKE<br>I |
| MG87 effectors | 11727 | MG87-3 effector | protein | unknown | MTKNYSIGIDMGVNNIGWSILNNDTKKLENYGVRLFPTSNDAKERREV<br>RNTRRRLKRKETRLDDTLYLLKKYGFNEDNTIEENLIEKRVKGLNEKL<br>EKQDIVNILCYMIKHRGYIPFGDEEVTLVDLNGKYPCEFYYEMYKNGG<br>KYRNRKMTVRITDNEKEIKKILETQSKYYKNINQDFINKYLNILTRKRK<br>YWEGPGSINDLTPFGRFKTQEDVENYLEEKRKNPSYEKYIYEDLIKKC<br>DYELEERCCCKLNIYYELFNMYQDFINVSFKNIEELENKDCFYETKNGL<br>YKLNKKGLLMVKDYCMNNFKLKYTDILKKLFNTDKDNISGYRIDKDH<br>KPEFSTLNSYRKIMLEFTEKGFDTTWVSDYNCYNEIMEKMTLTPGGVE<br>FIKEIENNKLVPYKFNEEEKSLFKELKEYFNKKTLLSYGSLSQKILQKAI<br>NDMLDLEKNFMQVSRIKDYGKEARENFIKQYKKTSNKLEINASFVDDII<br>ASPQVKKSLRQAIKIINAIIEKEGCLPVSIAIESTKELNSDKKKKEIEKEQ<br>KIQENLRKQASNYLSTVFGDSSVTETNILKVMLYNETNGHCAYCNKPL<br>SINDIFADNIQVDHILPISKSENDSENNKIISCKKCNDDKKNNTPYQFLKN<br>KNYFEEFEKRVLENKNISDYKKDNLLYKDDLDKYKTRFFNRNLRDTAY<br>ATTELINQIEIFNNYLEILDKKRINTLSVPGQITSSIRNRYVKNEDKTSLE<br>KNRDAGVFHHAVDASIVVSVSDTHIGQIMLKAQNDKEYWIKNKSNYDD<br>IYKYLINLRIDDTINQIEKINNENIKVSKQVSKNPQGKLANSNIYKMIKK<br>DNEQYIINQIDNIYTFDFKKDENKKLFEKLLNEENNEFTLLCYDNDKNT<br>FNYIKKIYNEYKNEKGNPFVNYLIDKGEIPDGNSFDYDITGIRMVTKKG<br>NGPIIKRLRYYSKKNDLYILNKKNINKKDSNYLALDSLKQFCVKVYVD<br>NDNKKFVFLPIYTISLDPKTKKVNENDEFYKLFYNKYIGNKNVTFFADI<br>YNGNKLEITKKDGTIVSGYYSTFNKANNKLILNNGDTFTLSDKKISIIHT<br>DILGNEKKG |

TABLE 24-continued

| Listing of additional protein and nucleic acid sequences referred to herein not included in the sequence listing | | | | | |
|---|---|---|---|---|---|
| Category | SEQ ID: | Description | Type | Organism | Sequence |
| MG88 effectors | 11728 | MG88-1 effector | protein | unknown | MKYKIGLDLGSTSLGWAVVELNEADQITSLVDMGVRIFPDGRDAKSH KPINVIRREHRQMRRRGDRVLLRKKRVLQLIHKYGLDFDISADIKLED PYVLRARAVSDKLSSAELGRVLFHLALRRGFKSNRKETRGDSGGKLK KATLALHDAIGDKTLGEFQVDSKRYRFADQFDGNKIKDGALYPTRDM YLDEFNRICSVQNMSDDMRQQFEYAIFHQRPLVPPEIGTCMFELDQPR AYKFEPVFQRFRVLQQINQLRIINNGEIKELTAEQREKLQDALLATFCG VKRDKSGRPKITFAEVKKLLGLSRNTKFNLESEKRKDMDVDATAFAFA ECELADFWRACTDNVKSQVLAHLNDDELSDSDLVDYLAHEYGISQDK AEKLIQQPFEDGVANLSVCAMQKMLPFLEQGHLYHIAAKEAGYDHAD RGIVHLDTLPYYGDVMALRPSLVQDKMGRYRTMNATVHIALNQLRAV VNDLIARFDGEPYAINIEMGRDVSAGADERAEIEKQQAANKRENDRIAT ELVAMGVRVCRENIQKYKLWENLGKSPLDRRCVYTGEIISKEKLFSPE FEIEHILPFSRTLDDSMANKTISAAVANRFKGNRSPDEAFSDPKSPWKY EDVVARAQNLPDATKWRFNRGAMDVFLQGKECIARAMNDTRFMTRM AVTYLQHVCADKNRVNGMPGRLTASLRDEWHLNWWKNKAEESKYR GNHIHHAIDAFVIACTDENILRKLADAKSDMHTPFPGFDYFDFKMRCE NTIISYRQSQKNPKDAHSTVGCLHEDTAYNLECFEDGGCGVNAVMSHR EELPTTDKDKKAFAKDFKNVNPKTLQMFLNDAGVANEEPDIAIKFLD WCAMRNIRKVRMYKTGVDVTTYVPVFRTKKQRDVYRAAYLNWYVN TGVASGIVDKKLRAVQQEKEKHLLQEFQDAAKQAYKWYVGGNNFCA EIFEIRDDDTRYPKLRGRWQVEILSNYNAQLNAGAPLWRHKYATAKRI MSLRINDMVMAEFSKDDPKLPKGLVETVAHQCAIEKTDKVNVVFRVK KLNSSGTVYLRPHFIAKEDADTKSWIASATSLQEHKARKVCVSPSGKIL GLK |
| MG88 effectors | 11729 | MG88-2 effector | protein | unknown | MNYRLGLDMGATSIGWSIYDVETEKLLDTGVRIFDDGREDKSKASLCV KRRNARGARKLNNRRHIKTQELLKILTTLGLFPQEQNKREDLKNDNP YKLRKEALDRQLSTYELGRTLMQLAKRKGFKSNRKDNREEGGKLKK GFAELKDIMQKENARTYGEFLYNCMQRNPDKPIRLKNTFDESGKYKG GLFPFREIYVNEFEQIWHKQKEYYPQILTDENKEKLKNIIFFQRPLKEA EEGECQFEKGEKRIPRAHPLFQEFRIWQNVLNLTFSAENEPDYKPLEK VQELIKLLMNPQEVKPNKQGIIIYANLKKALGLDKNGVFNFERQNNRD TDLEKGLLVNTTQNAINESEFLAPYWNNFSDAQKGELINVIMRPHNYIP FPKTRISIEEEDDLIINYVRKRFNLPQEAAEELLFDIDLEDDFGSLSEKAI SKILPFMKQGTPYHDACQSAGYHHSYKEYEHIDKLPYYGEILGQSCLG KKNNPKCVEEEFGKINNATVHVALNQIRHLINEHIMRYGKPYDIAVEYA RDLNASTQERLAMTDTRDKNELENQRIIKELQSKLGNHPYSKNDIQKY KIWKKLPFYDKNPLIRECPFSGEQIPLSELLNGQKFQIEHLIPFSRSLDD SLNNKVIATVEANRYKGNRTPFEAFGQSKDGYNWKDIQHRAKKLSVE QQWRFAPDAMQRFEKQEGPIVRSLIDTRYMTRLLQDYLQPIVKEDGK QRVQAVVGQLTSLVRKAWGLNVYKEKADKDKYREFHNHHAIDAIVIS AINRAQIKDVVGILAHVRDDIREEYKDELFQLSDNNVPEDKKREIKKEI RDVTAKREIAIAKKYFPLPKSFNIPDILQQVAAINISHKPNLKNIKQKDS TIGQLHQDTAYGLQKFVDDKSLKAIFKTKKAGDEASDDKTTPKDITQY IPMFRNKEDKKAYYDAFREWFKFNGKAASMDAKTKEDKKLKAEIAQ KEQAAIQTLRQTALKAFKWFVGGNNFCAEIYEINPNNKIEGVASKDRG EWKTEIVSNYNATVRNSRGEDIAYWRYKYPNAKRIMSLRGNDMVMAT |

TABLE 24-continued

| Category | SEQ ID: | Description | Type | Organism | Sequence |
|---|---|---|---|---|---|
| | | | | | FSREQAFDEKFPKGIQEYVREKFQQKSDCQELDILFRVKKMGSNGICF TPHNIAKENADTKSWIASAGAMQKYRVRKIHISYMGRIQNA |
| MG88 effectors | 11730 | MG88-3 effector | protein | unknown | MKYKFAFDLGSTSCGWAVVNTDEDGNVVGLADMGVRIFPDGRNAKT KEPLQVARRNARGARVRNDRILQRRHKIIDLLKENGMIYDCSDERENP YKLRSDAVDKEITLKQLGRIMYNLSLRRGFKSNRKPTQKENDSDLKKA TEKLKQELKGQTLGQYLWGKMKKNLDKEKENKGKDVKNKIGKVRF SNLFDGNKIKDGSVYPSREMYEDEFNRIWSKQAEFHDILTDELKGKFY NAIFFQRPLKPQQRGFCMFEDGELRIYKAHPLFQRFRALQTINQMEID DKPLTEEQREALKKELFEEFKTKNTKAGTVSFSDIRTILGLKKGVKINL EKNDDDENDGDNTRADKTPEDKDNKKDDDKEYDNIYADKTAYLLSRP ECFGEKWFEIPFDEQCSIVDILTDCVYNNIEEKKKYDEQQEQNGKHILE DDEIKQFLQEHYNLDDEQCNAIMNAPLEEGTGSLSQKAIEKILPYLEEG QLYNDACKSAGYHHSLFDGDVEMLGELPYYGDVLKKSCVQDKDGNY RITNISVHVALNQLRLVVNELIKKYGNPDFVAVEIARDLKMGTEELKN LNNKQNSNKKENDKITKAIKEANGNPNNAKDREKFKLWELCQKRCVY TGKQISATELFSDRVHVDHILPFSRTFNNGFFNKVVCFGDANEDKGNST PYEAFKNGYQGQSYEEILDRVKKIVEAMKEKKMFKKKTVKDKDGKK KKVDIDEFSWRFKEDAMEKFKEQEGLIARQLNDTKYMSRLAVQYLKH ICKVEYYTDEEGKEHRKNNCYGLPGTMTDFCRKGWGVNWLKDKSNK EGYRSSHAHHAVDAFVVACMTRGQLQKIASMANWIEEHGGQCQDDK LYLSILFKKCKKPFDTFDRERIYELCDKMPISFKPKLKDPKQENSTVGA LCEDTAYSLLEFDKGLNGVFVKREDVGSLVLKDLPNIIDTQADKLIKEY VETEEAFNKFKEYCEKNGIKKIRCKSFADVSTYIPIFKTKEERDEYHKA YEDWFIFEGRSPANETEEQKQERKEKEQELLKIVQQKALKAYKWFVG GNNFCADVYQISPRDKVYTDKKEQGSWKVEVLSNYMATLNKGQALW RKKHPTARLVMRLKIDDMVMGENFTKEEAEQKLQQEIEKWEKSKEM KKYKDKLTEWEKTHEGKEPKKPEKPKSINEIIIEKCNKEKTSSTSFLFR VKKISSDGSVYIRPDFITKEESDKKSVKLSASSYQKYKIRKVFVSPAGKL VDNGFSDKWNDTKCN |
| MG89 effectors | 11731 | MG89-2 effector | protein | unknown | MSYVLGLDLGIASVGWSIVEPGNRIIDLGVRVFKKAETDKEGDPLNLIR RESRLSRRRLYRRAHRLSRLLNFLISSGLIHSKDEVLKNVYNENPWALR TLGLNSVLTNNQLARVIYHICKHRGFYWASSADDGQADNGKIKKSLSS NQLVMKEKGYKTVGQMIFTEYPNCQRNKSGEYSKSLPRTDLDKELRA IFKAQQSFSNPIVTKDFINAIVGCGDRKTGFLWEQRPALQGEDLLKMV GHCRFEKDELRAPAANFYSEQLVWLTKINNLRVYDEDSQERPLTREER DLILNMPLEMKSDIKYSSLTSAFEKANLWKSGQFKYKSVDYEQKTQKK KNTAKSVDITKSSKKNPEDKVFYKSSHLHEIRKALGSSLSEEWEKIRTE VLSGKYDRYNRIAYVLTVYKEDSDVIEQLSPYESRTLIEALLPVRFSGFV ALSEKSLKKIIPHMVLGKRYDEACSEANYKHYKQNQAEFKKLKYLPPL FSGREPNGTLIFNEEIGDIPRNPVVLRVINQTRKVVNAIVKKYGSPKSVH IELARDLAKSRAERNEIEKRNEEAASRHIKERDEFEKLFGSKCLNGTNL LKYRLYKEQDCKSMYSSKEIDHKRLFEKGYVQIDHILPYSRSYDDSQSN KVLVLTNENQDKGNRIPFEYFEAKQHGFSWYEFEQWVKSCKNLNQKK KRNLLRCSLSKDAKKDFLERNLNDTRYACRFVKNYIDSFLCLSENSDNS GCVVVAGQLTAYLRNCWGLNKVREENDRHHALDATVIACCTRKIVQ KVGAWSKSREMNSYNSSYVDPDSPVDEDEKLLQKLYVNTRKPDFPKP |

TABLE 24-continued

Listing of additional protein and nucleic acid sequences referred to herein not included in the sequence listing

| Category | SEQ ID: | Description | Type | Organism | Sequence |
|---|---|---|---|---|---|
| | | | | | WECFRSEVESRVFESALEKLKEKLKLQCSYTESELKNVRTLFVSRACE<br>KIGKGALHGDTVYRQTSEMRKENVAVKKVSLKKLKYARIEAIVDADT<br>RNKNLCDALKKRYEEYARKIGKKIEDFVDKDIAKIFADDNPLHMPNSD<br>GQEDPCNPIVKSVRVKEAFSGVPIRNGVAGNSTIIRVDLFKKDGKYYCI<br>PVYAWNKTLPNRAYVSGKKETDWALVDDSFEWCFSIRQNELLKIKLK<br>GETIFGYYNGFDRDRGSFNILLHDRQDGKDHKQGLIRKGIKTAISITKY<br>DVDVLGNYYLSKPEKRLELA |
| MG89 effectors | 11732 | MG89-3 effector | protein | unknown | MDLIFGLDLGIASVGWSVVDDENKRIVDLGVRAFKAAETEDKGKSLNL<br>VRRTSRLSRRRIYRRANRLNSLLNYLIKSGLISSKDEILNNEHHENPWNL<br>RVKGLDGVLSNNQLARIIYHICKHRGFYWSSSAEETEDTEKGKIKKCL<br>AQNSLALTNEHFRTIGETILNKYPDAQRNKADEYTKSISRVLLNEELKQ<br>ILTVQKEVFHNPLLTDDFFKAILGTGDKKSGFLWKQKPPLQGEQLLK<br>MVGHCRFEKDELRSPKANYFAERHVWLTKLLNLRIYSEDCEDRALTV<br>EEISIVINKIYEQKSDIRYSSLTTAFVKSGIWPKNHQYKYKGLNYDQLTS<br>SKKKKVEDTASTSEDSTDTKKTAKKTNPESKIFYKSSCYQNIKDAYMSN<br>SLEQEWNILSTQISQGNYDRYNRIAYILSIYKDDEEVKKHLLDCGEKSE<br>VAEALLKIRFNGFSALSEKALKKIVPIMEQGKRFDVACSEAGYAHYKQ<br>SQDSKEKRKYLPPLFSGREPNGTLIINSELDDLPRNPVVMRVINQTRKV<br>VNALVKKYGSPKSVHIELARDLSKTFEERIDIQKRQEEIKERRQKEQEE<br>FDRIFGVGIRSGKNLEKYSLYKQQDCKSIYSGETIDLGRLFEQGYVEVD<br>HVLPYSRSFNDSQDNKVLVLTKENQNKGNMLPYEYFMSHNLDWNQFE<br>ARVLSNKKLRKNKRCNLLKKSLNRNSKKEFLDRNLNDTRYACRFVKN<br>FIDKYLRLSDKADKSGCVVVSGQLTAYLRKHWGLNKNRSENDRHHAV<br>DATVVACCSRRMVQLIGYWSKHKERQYLKDSQSDPDLESDEELLLKK<br>SIGSQKLYFPYPWVKFRKELNLRVFSSDIEELKNELSLFESYTEEDISKV<br>KTLFVSRAIQKIGRGALHADTVRSQTEEMNKEKVAVSRVKLSELSYDR<br>ISKIVDSDTRNKNLCNALKRRFEAYCKSNNINEISKLKAKDSAKIFTTNN<br>PMHMPNSNGEEDPLNPVVRTVRVKETFSGVPIRHGIAGNGDIFRVDIFF<br>KEGKYYLVPIYAIAKELPNRACVAKKHESEWTVIDDTYQWCFSVTQYD<br>LIKIELKKETYFGYFNGFDRATGAVNIILHDRSTEKYKKGLIRSIGLKTA<br>KSVTKYRVDVLGNYYLAGAEKRLELA |
| MG94 effectors | 11733 | MG94-1 effector | protein | unknown | MRKKIRYVIGLDIGIASVGWAALLLDENDNVCGIVRAGVHTFDEAVVG<br>QSKITGAAYRRGYRSGRRSIRRKVNRIQRVKNLLQRLNIISKKDLEEYF<br>SGAVENIYYLRCAAIQNEPAYILNNKELAQLLIYYAKHRGYKSNTSYEQ<br>KTDDSKKVLSALSENKKYMLEKGYQTAGEMLYRDEKFRRKRYGSSEE<br>CELLLVRNSGDDYSHSISRELLVEEVHVIFARQRELGNKLTTKELEDQF<br>VEIMQSQRNYDEGSGEGSPYGGNLIEKMVGECTFEKGEKRACKASYTS<br>ERFVLLEKLNHLRIQSKNGDVRALTEEERDAIIKLAYKNKDVKYKALR<br>TILKLNPDERFGGLTYSRGDIENSTEGKSVFVSLEYWYEIKKVLGLFYD<br>DLDNEETQQLLDSIGTILTCYKSDDLRRRKFEQLHLEQEKIEHLLALNY<br>TKFQNLSFKAMKNIMPELEKGLSYTEACSNAGYGDKETIEGKNKYISK<br>ELLNNTLDSIMNPTVKRAVRRTIRILNELIKQYGSPVEVHVEMARDLTH<br>SQTVTNKMKKRQDENKAEKEEAKRFICENFGKTEAQVSGKDILRYRL<br>WKSQNQIDIYSNTMIPVSDILDYEKYEVDHIIPYSCSFNDSFNNKMLVRK<br>KDNQDKKNRTPYEYIGSDEKKWEAFATCANTYVMNYGKRKNMLTKV<br>PASNTGEWMSRNLNDTRYTTKVVTDLIRKHLKFEAYVDQKRKKHIYPI |

TABLE 24-continued

Listing of additional protein and nucleic acid sequences referred to herein not included in the sequence listing

| Category | SEQ ID: | Description | Type | Organism | Sequence |
|---|---|---|---|---|---|
| | | | | | NGGITAKLRYEWGLEKDREKSDKHHAQDAVVIACCTDGMIQRLSRQYMLQEIGIVTWKNHKLVDRRTGEIVEETNLPWECFREEVEMFMADSPEDYIEKAKKNGYKGEAPKPIFVSRLPQKKTTGKINEDTLRSVRIDSKGKARFVNKTKLQDLKLVEVDGKKQIKDYYRPEDDKLLYDKLLERLVKNDDAKVVFAEPFYKPKKDGSDGPIVRSVKTYGKTVKNQVLVGDGVAERGGIYRCDVFKRKDEYYAVVVYYRDLYIGNLPNNAAHFDIEMKKGEFEFSLYKDDLIRFVKDGKEQYAYYKYINANNSQITYTEHDTSKETKCTTIRTLDKFQKMNVDLLGNIYSSDKEEREWN* |
| MG16 effectors | 11734 | MG16-3 effector | protein | unknown | MATKKILGLDLGTNSIGWALIETEDSNPKSILAMGSRIVPLSTDDSTQFAKGQAITKNADRTQKRTARKGLNRYQMRRAMLTEELRRHGMLPERTDENIMDLWRLRSDAATDGKQLSLPQIGRVLYHINQKRGYKHSKADNSANTKQTKYVEAVNQRYRDIQACHQTIGQYFYEQLLSSAVQTPSGSYYTYRIKDKVLPREAYIAEFDQIMKVQRVFYPDVLTDELVDTLRNHIIFYQRPLKSCKHLVSLCEFEKRPFKREDGQIVYSGPKCAPRTSPLAQFCTVWEAVNNITLTNRQNETFEITQEQRVAMADFLNQHDKMGVKDLQKILGISPKDGWWAGKAIGKGLKGNTTFTQLREALGNLPNAEHLLKMKLSMVDAAVDTTTGELIRQVSPQVEEEPLFRLWHLVYSLQNEDELRKALRKQFGIDDEEVLDKLCKIDFVKPGYANKSHKFIRKLLPYLMEGYQYHEACAHIGVNHSDSLTAEQNAARPLLDKIPLLEKNELRQPVIEKILNQMINVVNALKAEYGDIDDVRIELARELKSSKDEREAAFKRNNENERQNKIYENRIREYGIQPSRSRIQKYKMWEESNHLCFYCGKPVNVTDFLAGAEVEIEHIIPQSVLFDDSYSNKVCACRACNQAKGNLTAREFMEKHSKEEYDSYLRRVDDAFNAHRISKTKRDHLLWRKEDIPQDFIDRQLLQSQYIAKKAAEILRQGYRNVYATSGSVTDFLRHQWGYDEILHRLNLPRYQQVEGLTEDVTYDHCGQEHQQERIKGWTKRLDHRHHAIDALTIALTQQSVIQRLNTLNNSREQMFDELGKRTDTPEYTEKRSLLEKWVDAQPHFSVQEVTDKVDGILVSFRAGKRAATPAKRAVYQNGKRHIVQTGLQVPRGALSEETVYGKLGNKYVVKYPLGHQSMKMDDIVDPTIREIVRTRLNAFGGKAKDAFAEPLYSDAAHQMQIKTVRCYTGLQDKAVVPVRFNAQGEPVGFVKMGNNHHIAIYRDAKGQYQESVVSFWQAVERKRYGIPVVIEQPHEVWDKLINSDNIPQDFLETLPHDDWQFVVSLQQNEMFILGMDDADFEAAMEQKDYRTLNKYLYRVQKISSKEYCFRYHTETSVDDKYDGVINKSISMELQKLKRLTSISAFFSQHPHKVRVNLLGEVSAL |
| MG2 effectors | 11735 | MG2-4 effector | protein | unknown | MNSTRSTPLVLSFDIGYASIGWSVAEVVDPANNLQAGVVTFPSDDVLNSERAGHRRARRNIAARRNRVQRLKLASVGAGFVTAEEIETLDRMERKSAPEWRHCPWFLAARVLGESPESTLTGLQLFHVLRWYAHNRGYAPPSWGLFDEADGEQEEDFEKVRNAEKAMHEFGADTMAQTWCALLDADPTAGRWPEPRHWAKGENMAFPRERVQAEVTRLLVAHVGKLPGVTSDFVRCLIDDWEHHPKIRSWLQGADPRTGKLRDYALPKRYEGGLLFGQHIPRFDNKIIPWCPFTLKEDTNSGKISGRNVPKKHSRAFLDFKVAMRLNDLALSELGESGGRLSAGQRMTLFKRIEGYGDVTVRQFADLVAEVCAIPKPDLTTRIPEREGSDRPFELRPERKALIAILTGGRSLPSWPLIHSIWDCFEDAEAVLRPVFHGKPTSWADLIEQAKAPDVLLERLEELFRLGKGKPSRSKKAQPPPDFEVLLRCKITITKAHGRARYCSDKLRAATDEALGGLDPRRAPTTETSDDAGCLYLNERQRDLQDRLPLSKLINNHLVRHRLLIFRRLLQDLVNTYANGDRERIDAIVVEVARDLNEYSGKNTKQRVALFQEKQRPFND |

TABLE 24-continued

Listing of additional protein and nucleic acid sequences referred to herein not included in the sequence listing

| Category | SEQ ID: | Description | Type | Organism | Sequence |
|---|---|---|---|---|---|
| | | | | | AAEAFAQALIDDAQYTPEQAQALATYANVRRFRLMREQNFECPFTGR HLSAEDIAKDRVDFEHIIPRSLKPTDSLDAMVITYRAVNQAKRNRTAMR FIKDMAGERLDADDAGWSYHTPQQFETAVNRMRPKGRLNTAAKRSQ ANRCDALLVEDYEPREADFLQRDLTQTGYLMKYAVGEARKFFRSAPR QPRFIHLEGRVTTFFKKAWRLTETLAPISPLFLREYADPRTGRWQSTV RPKAELRRFTQLHHALDALTLGLATALVPGIERKELRRALSLRQAKGD DATLLRSDPKLGEALRWRTEDRFEAAPLSGKLESAVRRALAEGRVVQ HVPAKRQGMKVDSNFFGFVEFDETGRLRVRQKMRSPTTRRREIKTTV KNGKNLHTLSHLSLDPKSWLGAPDHPLRRKQLEHGLRTENDLANPKL GNIRGMLPIRENWGIALITKDGSPRLDVIPYINVHQWLEVLALENGGGS PVVLRKGHLVGFDAEKCPEEYCGAWMLLGVKDGRSGTTLELIRPWM VAPRKGGTKESSAKQAIKPASGYSEKEGKASGVFLQRSADVFLKLGLR PLDHDLTGIAAF |
| MG21 effectors | 11736 | MG21-2 effector | protein | unknown | HNTSGVYDLTVARTFIEEEAHKLFAAQRQFGNAFATENIENEYCEILLS QRHFSDGPGGERTFKFDLRGNCTFEKDELRAFKACYTFEFFKLLQDIN HLRIIPEYRKGSNKQTRPLTPEERQKIIDLCLKSSSIDFSKLRKELKLAD DEIFNRVGYDVKKKKSKKKDAEEQPEEQLTPEQQRTKCEEATKFTQM QSYHEMRKALDKVAKGTISKFSHDKLDEIGEILSLYKADDKRRERLEQ IGLSNEEIEALLPLTFTKAGNLSLGAMRKLIPYLEQGLTYDKACEIVYG DHRAQYKGERMPLLSFGKLKEEGALDSVNNPVVLRAIAQTFKVVNAII RRYGSPQAIHIELARDMKRNFADRQDIKSKQKDNWSENNRRREKVEEI KGSVATGQDIVKMKLYEDQNGVCLYSGKQLELHRLFEVGYAEVDHIV PYSKCFDDSYNNKVLVFSSENQRKGNRLPLEYMLAEGDEDKLDDYVTL VEANIKNTRKKQRLLKPCLTEQDITDWKARNLTDTQYITKAVADILRN YLAFEEDSPFIKKPVRSINGAVTDQVRKRLGLQKHREEGDLHHAMDA AVIAVTTDGYINRISRYTQRREFGKRIGCYKDKQTGEKVEIERQKGQA PLYIDPETGEKLTEQVFDHKYAPTFPAPWKEFTKELKARMAPNADEAI RQLYLPSYGSEEIKPIFVSQMPDRKISGQAHAETIRSARIDVDESGKERII AVAKTPLTSLKLDKDGEIDGYYMPSSDRLLYEELKNRLIKTKTSGKTY GNAEQAFKEPVYKPKKDGSQGPRVYKVKTWKPTTSNVKVAGGIAKK GDIVRVDIFHITGGKDQGYYFVPIYVADTIKNTLPKHAVVTNFKSSKVE WKEMDDSNFIFSLYKGDLIHIELCADCRDKDSNNKIRKAKDMYVYYDG |
| MG22 effectors | 11737 | MG22-2 effector | protein | unknown | MKNILGLDLGTNSIGWAWIQSKVPQQTDDCPSSSEYLMPDCATIRMAG SRVLPMDGKMLSGFESGLAVSKTKERTTYRMARRVNERFQLRRERLN RVLRILGFLPAHYEACLDRYGKIDEEKNVTIPWVPTADGKRKFLFYAS FLEMKERFHEHHPNLEKIPLDWTLYYLRTKALQQAITKEELAWVLHS FNQKRGYNQSRDEVKDEDASQKEEYVKVKVVSVVDSGEKKKGKTSYI VTTESNLQFTTENAAAPSWLDKEREFIVTTKLNPTGLPKMNQEGRIDC TVRIPKEEDWELKKKRTEALIADSHMTVGEYIFHSLLDNPDAKIKGAK VGTIDRHFYKEELIAILKKQAAFHPELKDAERYAECVSALYASNEMHR NILSAWDMPRLIVNDIIFYQRPLKSKKSDIAECPFESRYFMDKEKKLQK QGIKCIPTSHPHFQEYRIWQFLSNLRVLRREVRENGRYMTDVDVSAHY LTDKVKVELYEWLAGKANVKQKELLSKLRMSEKEFRWNYVEDNIYP CGETRSLLSTRLKKAKLPLSLLDSPSSDGSHTFEFELWHILYSVSDLAEL RKALRRFARKHDFTAEQQEAFVETFVKCPPFKKDYGAYSDKALVKLL SLMRIGKYWNADRIDTNTRRRIACLLDGEACDSISLRTREKVAERGLQ |

TABLE 24-continued

| Listing of additional protein and nucleic acid sequences referred to herein not included in the sequence listing | | | | | |
|---|---|---|---|---|---|
| Category | SEQ ID: | Description | Type | Organism | Sequence |
| | | | | | QSIEQFQGLPQSLACYVVYDRHAEASEVVRWESPADLQQFTRQFKQYS LRNPIVEQVVLETLRVVHDLWEEIQKDGGTIDEIHLEMGRDLKNTAEQ RARIMRRNRENEMTNFRIKLLLQELHDCQPDIEGIRPYSPSQQELLRLY EETVWESESGKLGGKEASKDIPDDIKKIRDLLSKPSDKPIPQSAIQRYRL WLDQKYLSPYTGRPIPLARLFTADYEIEHIIPRSIFFDDSYANKVICESAV NKLKNNRLGMQFIREMDGRVETVKLGEGRETSILSVDGYVDLVNDLF RNNPRKRNNLLAEEITEDFCHRQLSDTRYIARYIKGILSNIVRQRAADG TLEQEATSKNLIVCTGQITDRVKQDWGLNDVWNHIITPRFERLNRMTG SNDYGEWCCKEGKRYFQTRVPLHLQIGFNKKRIDHRHHAMDAIAIAC VNRNVVNYLNNAAAHATDRMDLRMRICRPSGNGQTKKEIRSPWKNFA HDAECALQAITVSFKQNVRIITKATNTYEGYDASGKKVRRCQTSSDHY SIRKPLHKDTVYGEVVLPVVNQVPLKKALLRVNRIVNGKLRKKIQEM QSSGLTDKQIVDFFMKTCADSPEWNSINFKKIEVRAYSNEEGQTRMAAI RTAIDESFSEKVIGSITDVSIQRILLNHLRECNGDSEEAFSPEGIETMNRN IVRLNGGKPHLPIYKVRLGEAMGKKFAVGQRGNKGKKFVITAKNTNL FFAVYANDEGKRSFETIDLHCALEMQKQGSSVAPPINENGDKLLFVLSP NDLVYVPSESELQHDIDSEDLKLDHVFKVVSFSENRCCFVPHSMSSPIAA GFEFNSPNKIEVVSRLGLFEQDKETVSIKNICLPIKMDRLGHLHLVKI |
| MG23 effectors | 11738 | MG23-2 effector | protein | unknown | MSEKIPYYIGLDMGTNSVGWAVTDENYKILRGKGKDMWGVRLFDEA QTAAERRTNRVSRRRRQREVARIGLVKEYFADALNAVDPGFMVRLEE SKYWLEDRSEENQQKFALFNDKDFTDKEYYTVYPTIFHLRKELIESTE QHDVRLVYLAILNLFKRRGHFLNKSLESDGETMSMAEAYAALVDEAA ALEITLPMPIDAKKLEEVLSQKGVSRKFVEQDTNEFFGFSKKASEAREL VKLMCGLTGKMRNIYGEELIDDDNKKLALSFRSNDYEEKMNEVAELV GDENMRLLEAVKEVHDIALLANILSGEQYLSVARVKQYNKHKEDLQQ LKRVLRTYDKAAYKKMFRVMGKDNYSAYVGSVNYKEHKERRNAGA GKDGESFRKAVEKVIDALPEEAQLDQDVIEIREKIKNEAFLPKQLTSAN GIIPNQVHLRELKRILENASGYLPFLNEIDESGLTVKERIAQLYEFQIPY YVGPLSKQNSKNAWANRRPGEEKGRILPWNFEQKIDVNQAAEDFIKR MVRHCSYLDAEFTLPKQSLMYEKYMVLNELNNLRINGEKPTVLQKQQ IYNELFGKGKRITQKALINYLKDEGIVEKDSEPIISGIDGDFKASLSTFG KLRTVLKEEARKDSSQEMMDQIVFWATVYGDDKRFIRARIEEHYSEIL DDHAIKQLLGMKFNGWGNLSKAFLEMEGASKEDGVYRSVIQALWET NDNLMELLGQRYTYKEELEKRVQTKEKPLAEWTIDDLDGMYLSPSVK RMVWQTLKIIREITEVRGSAPSKIFVEMARDDAQTKAKNKGKRTKSRK DELLECYKDDKAWKDELTSVDDGELRAKKLYLYYLQMGRCMYSGEA IDLASLMSGNTMYDIDHIHPRHFVKDDSLENNLVLVKKDKNAHKSDNY PLESEIRNKQFGFWKSLLDKGLITKTKFTRLIRSEDFSPEELAGFINRQL VETRQGTKAITKILQQAFPDDDMEVVFTKAGVAAKLRHDFDLVKVRC VNDTHHAHDAYLNIVAGNVYNAKFTSNPLRFIKNEVKKGNASYHMDKI FFRDVKRGNKLVWQAPNNEEKTPGTIAIVREQLARRTVLQTRRSYMA HGILSDATIYSKDTAKTESYRPVKSSDERLSDVKKYGGMTSIKNTAYAL VEYTVKGKTIRSLEGVPIYLGNCSKDDKKLLQYLQEILQRENKNKQVE NVSVRMYPIRQRSYLKVDGYYYYLGGATGSSVYLLDAMSVYLSKEDM GYVKKVEKAVAQQRYDECTKEGEFVLTREKNMDLYNKLVDKFSHGV FIKRKASILKTLEEGIDVFSELNIEKQCGIIMQIFAWITTSQQNVNLTDIG GVAHAGTLLISKKLSTSREALLIEQSLTGLWSKTTDLLTV |

TABLE 24-continued

Listing of additional protein and nucleic acid sequences referred to herein not included in the sequence listing

| Category | SEQ ID: | Description | Type | Organism | Sequence |
|---|---|---|---|---|---|
| MG3 effectors | 11739 | MG3-3 effector | protein | unknown | MSADSLNYRIGVDVGDRSVGLAAIELDDDGFPLKKLAMVTFRHDGGK<br>DPATGKTPKSRKETAGVARRTMRMRRRKKKRLKDLDKKLRDLGYFV<br>PRDEEPQTYEAWSSRARLAESRFEDPHERGEHLVRAVRHMARHRGW<br>RNPWWSFSQLEEASQEPSETFGRILERAQHEWGERVSDNATLGMLGA<br>LAANNNILLRPRRYEHNPKTGKNAEKLNVRGQEPILLDKVRQEDVLAE<br>LRRICKVQGIEDQYPELAHAVFTQVRPYVPTERVGKDPLQPMKIRASR<br>ASLEFQEFRIRDAVANLRIRVGGSERRPLTEEEYDRAVDYLMEYSDTTP<br>PTWGEVADELEIAENTLIAPVIDDVRLNVAPYDRSSAIVEAKLKRKTQA<br>RQWWDDDANLDLRSQLILLVSDATDDTARVAENSGLLEVFESWSDEE<br>KQTLQDLKFDSGRAAYSIDTLNKLNAYMHEHRVGLHEARQNVFGVSD<br>TWRPPRDRLDEPTGQPTVDRVLTIVRRFILDCERAWGRPQKIVVEHAR<br>TGLMGPSQRADVLKEIARNRNANERIRQELREGGIEAPNRADIRRNSII<br>QDQESQCLYCGKEIGVLTAELDHIVPRAGGGSSKRENLAAVCRACNAS<br>KGSRPFAVWAGPARLERTIQRLRELQAFKTKSKKRTLNAIIRRLKQRE<br>EDEPIDERSLASTSYAATSIRERLEQHENDDLPDGFAPVAVDVYGGSLT<br>RESRRAGGIDKSIMLRGQSDKNRFDVRHHAIDAAVMTLLNPSVAVTLE<br>QRRMLKQENDYSSPRGQHDNGWRDFIGRGEASQSKFLHWKKTAVVL<br>ADLISEAIEQDTIPVVNPLRLRPQNGSVHKDTVEAVLERTVGDSWTDK<br>QVSRIVDPNTYIAFLSLLGRKKELDADHQRLVSVSAGVKLLADERVQIF<br>PEEAASILTPRGVVKIGDSIHHARLYGWKNQRGDIQVGMLRVFGAEFP<br>WFMRESGVKDILRVPIPQGSQSYRDLAATTRKFIENGQATEFGWITQN<br>DEIEISAEEYLATDKGDILSDFLGILPEIRWKVTGIEDNRRIRLRPLLLSS<br>EAIPNMLNGRLLTQEEHDLIALVINKGVRVVVSTFLALPSTKIIRRNNL<br>GIPRWRGNGHLPTSLDIQRAATQALEGRD |
| MG3 effectors | 11740 | MG3-4 effector | protein | unknown | MSTDPKNYRIGVDVGDRSVGLAAIEFDDAGFPIQKLALVTFRHDGGLD<br>PTKNKTPVSRKKTRGDARRTMRMNRRRKQRLRDLDMMLTNLGYTVP<br>EGPEPETYEAWTSRALLASIKLANVDELNEHLVRAVRHMARHRGWAN<br>PWWSIDRLENASREPSETFEIILARARELFGEKVPADPTLGMLGALAAN<br>NEVLLRPRDGKKKKTGYVRGTPLLVAKVRQEDQLAELRRICEIQGIEG<br>QYDALRSAIFTHKMAYVPTERVGKDPLNPSKNRTIRASLEFQEFRILDS<br>VANLRVRTDSRSKRELTEAEYDVAVEFLMSYTANEQPSWADVAEVIGV<br>PGNRLIAPVLEDVQQKTAPFDRSSAAFEKAMGKKTEARQWWESTDDD<br>QLRSLFISFLVDATDDTEEAAAEAGLPELYMSWPAEEREVLSDIDFEKG<br>RVAYSQETLSKLSEYMHEYRVGLHEARKAVFGVDDTWRPPLDKLDEQ<br>TGQPTVDRVLTILRRFVLDCERQWGRPRAITVEHARTGLVGPAQRQEI<br>LNEQKKNRENNELIRGDLRKSGVENPSRAEVRRHLIVQEQESQCLYCG<br>AVIRTDTSELDHIVPRAGGGSSRRENMAAVCHYCNSKKKRTLFYDWA<br>GPVKLQETVDRVRQLEAFKDSKKAKMFKNQIRRLKQTEADVPIDERSL<br>ASTSYAAVAVRERLEQHFNEGLAPDDKSRVVLDVYAGAVTRESRRAG<br>GIDERILLRGERDKNRFDVRHHAIDAAVMTLLNRSVALTLEQRSQLRR<br>AFYELELDKLDRDQLKPGEDWRNFTGLYEASQNKFSEWKKAATVLGD<br>LLAEAIEDDAIAVVSPLRLRPQNGSVHDDTINAVKKLTLGSAWPADAV<br>KRIVDPEIYLAMKDVLGKLKELPEDSARSLELSDGRYIEADDEVLFFPK<br>KAASILTPRGAAEIGNSIHHARLYSWLTKKGELKFGMLRVYGAEFPWL<br>MRESGSRDVLHMPIHPGSQSFRGMQDGVRKAVESGEAVEFGWITQDD<br>ELEFDPEDYIAHGGDDELNRLLRVMPERRWRVDGFYNAGTLRIRPALL |

TABLE 24-continued

Listing of additional protein and nucleic acid sequences referred to herein not included in the sequence listing

| Category | SEQ ID: | Description | Type | Organism | Sequence |
|---|---|---|---|---|---|
| | | | | | SAEQLPSELQKKVADKTLSDVELILLRAVQRGLFVAISSFLPLESLKVIR<br>RNNLGFPRWRGNGNLPTSFEVRSSALRALGVEG |
| MG4 effectors | 11741 | MG4-2 effector | protein | unknown | MLREPGNSVKSKIMGQQAKRRSYVLGLDIGTHSVGWALLKFRDGRPC<br>GVERAGVRIFEPGVEEVAFERGRAEPPGQKRRQARALRRQTERRARR<br>KAKLLHILQRAGLLPKGEADEILPALDRDILARHSAAWPGARDALPYW<br>LRSGALDHRLEPHEFGRALYHLGQRRGFLSNRRAPMRKNEEDGKVKA<br>GISTLKEQMEKAGARTLGEFFAGLDPHQERIRQRYTSREMYEQEFEAV<br>WSAQAAHHPAILTDDLKARVHHAVFHQRPLHNQSYLAGSCTLEPDRK<br>RTPWACLIAQRFRMLQKLNDTRVLPASGPERPLSDEERQTVLTELDRK<br>KELKFDRVRKLLGLSADSSFNWESGGEDRLVGNTTNARLAKVFGKRW<br>WSLSPDDRDQVVEDVRSYEKAEALARRGREHWGLDEKAAGELSKLSL<br>EDGYCRLSRQAIERLLPGMEKGTAYMELVRKLYPDRWAAGKPVDLLP<br>ALAETDLDMRNPVVRRCLTELRKVVNAVVRHYGKPSAIRIELARDLRK<br>SAKQREQTWRRNRRNQQDREAAAEKLLQEARIANPSRADVEKVLLAE<br>ECGWHCPYTGHGFGMADLFGPHPHFDVEHIVPFSRSLDNSFLNKTICE<br>ARENRDRKRNHTPYEAYGADAERWDQIIARVQSFRGTASREKLRRFQ<br>QHEVEDLDGVAQRELNDTRYASLLAVQYVGMLYGGAVDAGHVRRVQ<br>AAKGGTTGYLRDMYGLGFVLGEGRKERSDHRHHAVDAVAIALTDPA<br>ALKSISQAASDERRGGRVSFGAVALPWVDFIGDVQAAIEAINVSHRPSR<br>KVNGALHEETFYGPRGMDGDGRPTGYVQRKPVERLSAKEIPNIPDPAV<br>REAVQAKLDEVGGTPAQAFKDPANHPVRKRGIPVHKVRLRLNINPVQ<br>VGSGATERHVLTGSNHHMEIIEVRDAKGGKKWTGRLVHRLEAKRRA<br>LGRETIVDRAVQAGRQFQFSLSPGDMIELTGEDGERKLHVVRSISEGRI<br>EYVDARDARKKADIRASGDWRKPAVGSLLRLHCRKVVVTPFGEIRYA<br>ND |
| MG44 effectors | 11742 | MG44-1 effector | protein | unknown | MEKFYLGADIGTNSVGIACTDENYELIRAKGKDCWAVRLFDESKTAET<br>RRNFRTSRRRLERRKQRISWLQALFAPYINDETFFIRLNNSQFLPEDKD<br>EILQADKNALFGDEGYTDKNYHVEFPTIYHLREKLIEGGKYDLKLYYL<br>TIHHIVKYRGHELFEGATMEEIRDIKRLFENLNAVWEATYAENVPHINL<br>AKSDEAKEILLDTKKGLRDKQIALEKLFGENTALMKESIKAMLGGKIS<br>PETLFGEEYKDEKSFSFKDMDEEAFDALQSTYGDNFECLNALRSIYNFV<br>AFEKLLCGHKNISSAMIAVYNKHAADLSLLKSFIRSERPNDYNKIFKSTT<br>EKANYVNYIGYTKKGGEKKKVAKCKSDDEFFAYMKKYLSSLDDIKDG<br>ATRDKILGEIENGSFLPKILHSDKGLFPRQVNEAELKAIASNMVKYYPE<br>TKEIADKIIPLFEYRIPYFVGPLAGVNSWAVRKSGEITPWNIGEKIDLAA<br>SNEEFMRKMTSKCSYIFGEDVLPKCSIIYQKFDVLNQLNKLRVNDRPLT<br>VDLKKGIFNELFLKYPKVSDKKIKDYLIRNGHFSPTDGEITLSGKDGEF<br>KASMSSYIQLKRILGDFVDKDLENGGEVCENIILWHTLNTDKKIVYDLI<br>EKRYKNIPEIADSVKALKGLSFKNFGRLSKKFLVDLYSADNETGELVNI<br>LDVLYETNENLNEILNDEKYAFGKLVDEANGVADSKITYEDIEKLYVSP<br>AVRRGIWQTVTMIDEYVEAIGRTPDKIFVEVTREDGVKGDAGRTQPRK<br>RQLQEKYKNVSKTYADVISELGDEKYSDMKLRQERLFLYFRQLGKCM<br>YSGQRIDLDRLDTDTYDVDHILPRTFIKDDSLDNKVLVLRSKNAEKADR<br>YPLPQGFSDQQDFWKMLLDKNLIAKTTYDRLTRTEPLGDNDYKDFINR<br>QKVITDQTVKAVAELMKRKYPTAKIVYSKAKNVNDFKNKFDIFKCRET<br>NDLHHARDAYLNVVVGNVYDTVFSNPLDMFRKDGDMWRTYNLKKLF |

TABLE 24-continued

| Listing of additional protein and nucleic acid sequences referred to herein not included in the sequence listing | | | | | |
|---|---|---|---|---|---|
| Category | SEQ ID: | Description | Type | Organism | Sequence |
| | | | | | TRDVKGAWDCSRIARIKSICGSHTMAVTRYAYCNKGEFYNQTVYGKD DAGVSSPRKSNGPLSDTKKYGGYKSQTTAYFAIVSSLDKKDNRVKTIEA VPVLVAYRLKNNPKAVEEYFNSYLKSPEVLIPKIKNKQLVSYNGSLVYI AGVTGDRISVHNATQLFTDNKMDEYVNGLLKLLDMDAKKMLVGDEP RYVIKTNRNKEEKLVIDKEKNVELYGYLKNKLCDKIYSGLSAFATFAK NIENGKEKFIDLTIVEQAKVLIQILMMFKRKDILSDLTLIGGSSHSGKIL FNKKIDDVNFEIIHLSPAGLRVIKNKV |
| MG46 effectors | 11743 | MG46-1 effector | protein | unknown | MKENYYLGLDIGTNSVGYAVTDGGFNLLKYKGEPMWGSHVFEEGKQ CSDRRMHRTARRRLDRRQQRVHLTQEIFAKAISEVDERFFVRLKESAL FREDTSGRDTYIFFQDENYTDKEYHRDYPTIHHLIKELMEDTTPHDVRL VYLAVAWLMAHRGHFLSEVNKDNITELLDFDSIYGNLMELFTTPPWIC SDKEEFKNILLLHQTIKNKERKFWGLLYEGKKPKTDEEDYINKEGMIR LLSGGTVEAGKLFNQKEFQEKISISLKKSEEDFQLLLDEMDEEDSEYLI RLRALYDWALLVDSLHGCSSISEAKVQDYAQHEADLKMLKNFVRKYC PNEYAAIFKNAEKENYASYVYNIPKGKRTKEYKKKITQEEFCDYLKKK LKDIQIEEEDQEIYQDMMFRLETYTFMPKQVTGDNRVIPYQLYYDELK KILENAENYLPFLKKVDEQGISNKTKLLSIFEFRIPYYVGPLCSASKYA WLKRKAEGKIYPWNFEEKVDLDQSEKAFINRMTNNCSYLPGETVLPQ NSLLYCKFTVLNEINNIKINGIPISVECKQEIYRLFEENKKVTVDKIKKY LISNNYMEKEDVLGGIDITIKSSLKPQHDFKRLLHSKILNEKEVEQIIECI TYSEEKSRVLRRLEREFPKLSDEDRRYLSKLKYSGFGRLSREFFTGIHG ANKETGESFSIIQALWDTNDNLMQLLSDRYTFKDSIEEEQRQYYEEHP MTVESLLEEMYVSNAVKRPIYRTLDVIKDIQSVCKAAPKKIYIEMARG QEEGSNRKRSRKDQILELYKNMDKGEVRELSKQLEDCSDRELRSEVLF LYFMQLGRSMYSGKPIDIEKLKTNAYDVDHIYPQCRVKDDSLSNKVLV LSEENRAKGDKYPISAVIRQNMGEMWRVYHEKGLISDEKYRRLTRVS AFSNAEKMEFINRQLVETRQSTKALTRIFRYIFPETEIVFVKAGLVSDFR NEVLKCAKSRIVNDLHHAKDAYLNIVAGEVYHARFTSKFFKIDQDEYS VKTKAIFGNKVWNGKELVWDGEKDIARVKKILTKNSVHYTRYAFERK GGLFDQQPLRAASGLIERKAGLDTEKYGGYNKSTASYFLLVKYAEAG KKPKQDVMFVPIDLMESEQIIKSESYAKYYVRNAIAHIIGKSREIVQEVS FPLGMRKMKVNTLLTLDGFEAILASKSNGGKTLVFGSMMPLFVNNKK EIYIKRLESFSKKKKQNNFLFVDEVYDKITKEENRELFLFLINKVEEEP YCLIFGSQLQVLHDKENEFENLNLEQQVETLLNLLSIFKTGRTTGCDL KLLGGAGQAGIFTESSKLSNWKKSYKDVRIVDISAAGLHRKTSQNLLE LL |
| MG6 effectors | 11744 | MG6-3 effector | protein | unknown | MKKVLGIDLGVASIGWGIIETDEKNENGRILKSGVRIFQGNEQRADAA PGESSNADRRNKRSVRRQRDRRTRRKINLYVTLKKNGLAPNKSEWDK WVSINPYTIRAKALDEKVSLHEFGRALYHLNQRRGYKSNRKAGSDKE GAVKEGISKVRNHMAKHNARTIGEYFHEIYDNHLQNDTEHDDFDWRI RDKYTHRKMFKEEFDALWDAQSVFHKELTNDLGEVLKKIIFHQRKM KSQSHLIGKCELETDKKRIAKAHLLFQEFRVLKNINNLSISDENGFPIKL TEGDRKLFKEIFDKKDKVSWSQLKTALINSGTIGNKNAVFNLERGGRK NIEGNRTNAALSHKKAFGEKWYELEDDFKKHVVDVLIHVDKPEIVKNL ALNKWDRTEEQAEYITHKLTLEQRYGGFSEKAIKKLLPYLKKGMEES SAIKKAGYSLFEQNPGKMNQLPMPDQTIKNPVVYHALIELRKVVNGIIR |

TABLE 24-continued

Listing of additional protein and nucleic acid sequences referred to herein not included in the sequence listing

| Category | SEQ ID: | Description | Type | Organism | Sequence |
|---|---|---|---|---|---|
| | | | | | EYGMPDVIRVELARDLKAGYERRQKMTKKMRELEKKNDKAYKALQ KEPFNIQYPGYNDIIWFNLWEECDKTCPYTGKTIPAEAFNSGEFQIEHIL PFSRSLDNSYANKTLCEADFNRKKGNRTPWECVEAGIMEEDTMLQRIR NLPWNKRNKFTQKEIDEDKFLNRQLSDTRYISKEASSYLKHLSCERVE VVKGQTTSLLRHLWGLNGVLNKEGPDMKNRDDHRHHAIDAIVVAFTN RSTLKRLSDENKRIGTAEWMDADESGRATNDEIKRRLGGRIDLSEPWP TFRNDVEVSINNITVSHRVNRKVSGALHEETYYGPTDEPAPKNKEMMV LRKSVHQLSKKDLGLIRDETIRQIVNDEVQKRMDNGESQANAIASLEA DPPFIISPKAKVPIRKVRLLMKKDPQIMHYFENKNGEEDRAALYGNNH HIAIYETSDKNGVKKQIGIVIPMMEAARRVKDGDPIVMKDYRPDHTFL YSLAKNDMIFNHEDEQIYRVQKINSDGTIMFRQNNVAMKGQSDPGVYF KSGSRLGASKIKISPIGEIFPAND |
| MG6 effectors | 11745 | MG6-5 effector | protein | unknown | MDSYTLGLDIGSNSIGWSLIKEDKNPTIIDIGVRVFPEGIDRDTKGAEISK NKTRRNARSSRRMHQRRSYRKSKLVKISREQGILPQEDKELDKLFLKD PYELRAKGIDEKISLFEFGRALFHLNQRRGFLSNRKSGKSKEDGVVTKS ASELQSTIKKTGCRTLGEYLNKLDSTEERRRSYYTFRSMYEEEFEKLW EKQKEFYPKILNDDLKKVIKDETIFFQRPIRWDRDTIRDCDLEPGEKVC PRSDWHARRFRILQDINNLEIYNTDGSSDKLSDERRKVLLEELLNKKD MTFGALRKKYGLFESQTFNLEEGSADKKKAKLKGDEFAAQMRSAKIL GKKGWEKLNESQRIEINDLIVDDDIEDNELVKILIDKYRFSQTQAEATL DISLPSKYSSFSKVALQKLLIYMEKGKLVHEAIQAVYGKPQAITNKGEI MDFLPMPEDLRNPIANRGLFEVRKLVNAIIREYGKPKKINIEMAREVK GSKRERDEIHLKQYKNERINEEARKTLIDDFKIPNPSRDDIIKYKLWVE CNKVCPYTGKSISQHQLFGPNPEFQIEHIIPYSRCLDDSYMNKTLCFVD ENKEKGNETPYEYYSEKIPKQYEQILQRIRTLPYPKRRRFSQQEVKLDN FIERQLNDTRYISREVVKYLKKLGVIVKGTRGQVTSELRHQWGLNNIL DLAGEGLKNRDDNRHHSIDAAVTAVIGNEHLRELARTKFRKNNKEFK QPWPDFREELEEKIKHINVSYRVQRKVSGALHEETSYGPTGRKDEKGQ DIFVYRKKLEDLTISMVNKIVDLVVRDIVKKRLVERGIDPEKDKKIPKE VWNEPLYMKTTKSDKKVQIRKVRIQDVFNNMIMLKDKKGKPCRAVA PGNNHHIEIFEYKDKKGGKKRDGRVITMFDAVQRSQKRESVVKRDYG DGKEFVCSLATNEMFIMDNVDGNTELYRIQKITQSGNNKTIILRPHTYA GKLSDSDKPPLIQRKSPNTLKGHKVTVDMLGRFHMAND |
| MG7 effectors | 11746 | MG7-1 effector | protein | unknown | MSNKTILGLDLGVSSIGWAIIERNDENGRIVKSGVRVIPSSKSELSVFKD FDKGKPASFSKERTEKRGIRRSYFRKKLRRAKLIEHLKENNMFDPELL GPKYSIDVWEWREKATKEKITLAQLGRVLLHINQKRGYKSNRKAIVD EESDSNWLNAINDNSKLLREKGITVGEYFYQEGKLHERKPKVKFALHF RMKVRIFNRKDYLDEIEQIWKKQSEFYPELTDELKESIIDHTIFYQRPL KSAKHLLSECRYEKMHKVIARSNPLFQLFRVLEKVNNLRAEDAFGNNR EITDEEKLKIIEACTSAQSWKLLDKKKNLSKSKIKSILGLGKDYEINLDS IEGSKTLHSIWEVLMKSWGEAGDWIDFDWSIQGNDFSKQKSYQLWHA LYSIDEPQYLRKKLCEGFGFDLDTARLLMNIRLESDYGALSARAIKRIIP ELLKFPKDATKAIENAGYKFTDSETKEERESRELKDRIEHLKKGALRN PVVEKVLNQLVTLVNAIYAHPELPNPDEIRVELARELKSGAKERRRAE LGMARAAKDNDRIRELLQTEFGIPYPGRRDILRYRFWEEQDMRCVYS GDVIPRNKLFVGEEYELDHIIPRARLENDSNSNLVLVKSSENKDKSDMT |

TABLE 24-continued

| Listing of additional protein and nucleic acid sequences referred to herein not included in the sequence listing | | | | | |
|---|---|---|---|---|---|
| Category | SEQ ID: | Description | Type | Organism | Sequence |
| | | | | | AADYMKSKGEKAFEEYLVRVKNLYDKGAKKKAGERGSGINKGKRNF LIMKKEEIPQDFIERQLRESQYIVKEAVKLLKEVCRDVTTTTGKITDLL KHQWGANDVFRNIQVPKYRKWGMTETIVDRKTGEVIERIIDWSKRKD HRHHALDAIIVACTRQSYIQQLNRLNVLYENDYESLKSYRKFELPWPSF HNDLISSLESLLVSFRNKRRVATMNKNRIKVGGKKKYIVQKTLTPRDA FHLETTYGRRLVNNYKLVKLNKKFSMELAELVIDPDLKEKILNRLMEF GNDPQKAFANLKKNPFKWKNENLEEVLIYDEVFTTRKKLDEKENNPSE IIDPEVREIVTQRLKEFDNNPKKAFADIENKPVWYNKDKQIRIKTVNTR AKASDLYPVRTKENGNPKDFVFTRNNHHITVYQKEDGKYYDKVTSFW EAFELKKAKMPIYKENDDAAKAVLHLKINDMVLVDLNPEDLDQNDPE FFNTLSEHLYRVQKLASGDVTFRHHLETELSNKNTEVRVTNAESLYNR VVMYPLDVLGLPK |
| MG71 effectors | 11747 | MG71-1 effector | protein | unknown | MDNLILRREKMLVTKIKNTYPQISDDEIKAIKKLKYKDWGRLSATLLN SSTIAYEDKAFGELVTIISALRHTNKNFMELLSSYCSYDFIGKIKEFNGS RQSSNGKLTYKDVEELYVSPSAKRSIWQTLTILEEIKKIMGCEPKRIFIE MARSKEESKRTDSRLKKLQDLYKKCREENIDFMPRKDEFNALKTQLSS KKEEDLRSDKLYLYYTQMGRCMYTGERIELASLYDNNLYDIDHIYPRS KTKDDSLSNRVLVKKQVNAAKTDIYPLDAAIRTKMHSFWKLLYDKGFI DERKYERLTRSTQLRDEELAGFISRQLVETRQSTKAVAAILKTAYQNSE VVYVKAGNVSDFRQQFKFVKCRDVNDLHHAKDAYLNIVVGNCYHVKF TANPLNFITKNQDNRRYSLKPEIFYKFSIKRDGEIAWLGGEDGTMATV ARTMHKNNILFTRQPLEGKGELFKQNPLKAKSGQLPLKAGLSVEKYG GYDSLTTAYFALVKSEGKQGSVQLSIEGIPLVYAKQGEKAVQDYLTEV VQLCKPEIKIPKIKKYSLFKINGFPMHISGRTGKQLVFYGAGQLCIADD VADYLKKALKHETDIAEKEKTLADQNADDIQKQKAQKGLDFYEQKW GISGAVNVQLYDMFIAKSANNLYKNRPASQTITLKEKREHFVKLTLSK QIHIIKEILNLFKCASASADFKLIDKGTSCGTLKISNNITKLKECILINQSP TGVFEQEVDLMKL |
| MG99 effectors | 11748 | MG99-1 effector | protein | unknown | Same as SEQ ID 11716 above |
| MG112 effectors | 11749 | MG112-3 effector | protein | unknown | MGYNKVVLGLDVGVGSIGWGLVQLDEEKYADEKQDGTVEEKYKITD GKIIAAGVRRFQLPQDRQKKSLALIRGTARRSRRTIKRRARRLKRLIEL GKEFNLLGNDFDRDKFLIPKKGDKKEKWDTWRFRKEALERKLTDEEF FRVLYHIAKHRGAYFQTRAERLELEKDSKAAKDQGEKGEEKQDNEKK KEREKMKKGLKRIQELLKRSQYKTVGAMFYEMFKNGRKRNAPDKYS NSIRRELLHDEINEIFKAQRALGNEKADPDLEKQYLRAVLMQEKGPDD EKMQKMIGRCEIIKELCSQAGKECTADCPDLNRCRCAPKESYTAERFV LFNRLNSLKIIGGQAIDLAKHRDNIEKLAYTHDKIDFSQIRKELCLTDKP HLRFNLCSYSEKNPEYEKTLKYEVSNGQLQFGPEHRVQMDNFDTGET KVFDKEIRAIFQKRLATTPNYKKINVRYSDIRKELQGPQVDLAGFKFTA LKKEYTKSSAQLESEFFTKPKNKGKNFNGDAAYIKQFEDDAIFVELKG YHKIRKVLENRDGTWEKLKSDGTRIDTIAEALTYCKKDETRTAYLKER GITDESVIDAALTLNMEKIATYSKEAMVKLLEHMEKGLLVNDAKARC GYDKFEHKKQAYLAPYSGFFENNPVVARVIAQTRKVVNAIVRKYGEQ YPIDQIHIEVATELANSEKTRKRIKDAQDKNKDEKSRARSICEEFGINSD EGQNLTMVRLLDEQGHFCPYTGKAIVLRSTGAANEVHINDCEIDHIIP |

TABLE 24-continued

| Category | SEQ ID: | Description | Type | Organism | Sequence |
|---|---|---|---|---|---|
| Listing of additional protein and nucleic acid sequences referred to herein not included in the sequence listing | | | | | |
| | | | | | MSRSENDGMNNKILCCAKANQDKRNRIPFEWFEETHGPNSQQWFEFT<br>RRVEKMYDVPYSKKKNLLRKSWTDEEMKKFMDRNLNDTRYATRHIA<br>DYLRKYFDFSNRRDDIKDVSRIKLRSGGVTAFLRYLCGLNKNRDENDL<br>HHATDALITACATDGHVFLVSNLSKQIEEKGKNWYKHFGMEKFKPLR<br>PWETVREDILEATQKIFVSRMPRHKVTSAAHEDEVWSFDEKKRTKKA<br>QKKKKSSIPKDTARVMKINNGYAKIGEIVRADVFEDGKHKNYVVPIYA<br>VDIFSKKPLPDKYLKKNNTPYDEWPSAAADNLTFKFSLFKDDLITINGT<br>PYYVDFVEGTQANIKVRNINGSKFESTNEKTRKFGYRNIELKKFSVDM<br>LGNYKEVKEEKRLGNEGVKWTKKRPKK* |
| MG123 effectors | 11750 | MG123-1 effector | protein | unknown | MRILGLDLGIASCGWALIDQAKDGEEGRILALGVRCFDAPEDSKDRTP<br>NNQARRQHRGLRRVLRRRRQRMQELRHLFLAHGLLASAGPDALALP<br>GIDPWAMRAEALDRALAPCELAVALGHIARHRGFRSNRNQRSNEAED<br>RTMLAAIAARQERTGHYRTIGEAFARDPEFARRKRNRDGDYGRSILRE<br>EHEREVRLIFARQRALGSQCATEALEQAFTDIAFFQRPLAASEDRVGPC<br>PFEPGERRSARFAPSFELFRFLARLTTLRIGTRREERALTAEEIARAEQG<br>FGTQQGMTFKRLRKLLNLAEAEGFIGISPEDEGRDVVNRSPGNGCMR<br>GSAALRQAIGEGAWLRLLSTPERLDAIAFVLSFAAAKEFPERLAALGIE<br>EDVIAAVLAGVEQGMFDHFAGAGHISAKACRKIIPGLRRGLVYSEACQ<br>EAGYDHARRPETSLSDVANPVARKAIGETLKQVRAIVAEYGLPERIHIE<br>LARDVGKSAEERAEIARGIEKRNRERDRLRRIFVETVGREPAGSEDML<br>RFELWLEQAGRCLYTDHCIPPDAIVAADNRVQVDHILPWSRFGDDSFA<br>NKTLCFATANQEKRGRTPFEWLGADQERWNRFVAVVEGCKGMKGR<br>KKRIYLLKDAVSSEEKFRTRNLNDTRYAARIVLEHLAHFYPEDGSRRVF<br>ARPGALTDRLRRGWGLQDLKKKLEPDGEKRHEDDRHHALDALIVAA<br>TSESALQRLTRAFQEAETRGSHRDFSALTSPWPGFVDQAQEAFKTILVS<br>RAERGRARGEAHEATIRQVRKDEDGPVVYERKSVEALTEKDLARVKD<br>PERNAALIESLRAWIAAGKPKASPPLSPKGDPIAKVRLRTDKKPAIEVR<br>GGVAERGEMVRVDVFRARNRHGRWEFYLVPIYPHQVADKVRWPTPP<br>DRAVQGNTPEEQWPVMDAGYEFLFSLHQRSFIEVEKRDRTVITGYFM<br>GLDRHTGSIAISTPHSTKALARGIGARTLMRFEKFRVDRLGRTFAVRQ<br>ETRTWHGVPCT* |
| MG124 effectors | 11751 | MG124-1 effector | protein | unknown | MTLTLGLDIGTNSIGHALVETDEQGNVISLKHIGVRIFSDSRTDKEKKP<br>LNEARRTARQARRQRERKKSRMKAVLRVLREHGLDPQDSLLESPYAA<br>RAAALTGPLSRSQVGRAIWHIAKHRGPRLVRKDDKEQGVIKEGIRSLE<br>TEMLAQKARTYGELLERIRLNGGSVRLRANSEGSYNRYPSRQVMEAEF<br>NHLWESQVPHHPEVMTEALRERLITAIFYQRPLKPVYPGRCTLEPDEY<br>RMPKAMPMAHEFRIRSEVANLTLKQGDEVRTLTANERQIVVDGLLNS<br>EKLTFTAIAKLLGFRAGVKFNLEGDDGDGGKARNYLIGDLTSSKIRSV<br>WPNFSKMPENMRLSLILALLDIDDELELKCKLRSDFGISPEVVDQLSSL<br>MLPAGYINLSQKAVRAVLPYLQQGMGYAQACAAAGYHHSDHRPEEL<br>TPILPFYNELPGMKRYLGQEQKGKPGRISNPTVHVALNQVRKVYNTLV<br>EVFGVPDCVNIEVTRELKQTAKQKIAANKQNAANKKVRDAFKEKFPE<br>RANSDQDLVRWRLWNELPEERKVCVYSGKEITLNDLFSPRVEIDHIIPH<br>SISFDNSPSNLVLCAQGANRLKTNKTPHEAFAPGLHKEFNWSAIEQRVF<br>ELAADKCGTWAKKKLRFKPDYLDVGGDFATRQLNDTAYLSKVVRIYL<br>GHSCPKVLAVRGAVTAICRKEWGLDRLLRDTVSDHADLFCLSSVKSTG |

TABLE 24-continued

Listing of additional protein and nucleic acid sequences referred to herein not included in the sequence listing

| Category | SEQ ID: | Description | Type | Organism | Sequence |
|---|---|---|---|---|---|
| | | | | | VFMAPHHVTGGSHDIREDCSVNKLLKFGAEVVRVDPIGRFQTPGEIRRIEPRGPKVNFQNLRTTTRKPLTSLTANSISQIKDDGLRTKITAHIKEVNPKLLTDTLNREAKVELSRLLGEFGQKHSVGRVRIVANKSGVIVRHGAANQHTKVLIADTNHHGDVVVRDGKVKMLLTTYAELNHPPEVEAGWTLKMRLHKGDMIRVPGYVYNKYPKKPNYGKDRSDHRHHAVDAFVIACITPSLLRKISRSIALSKYNQLHEFPEPYERFKQELKTHLRKLVVSNKLDHSISAPIFTETNYGFTA* |
| MG125 effector | 11752 | MG125-1 effector | protein | unknown | MRPYGIGLDIGISSVGWAAIALDHQDSPCGILDMGARIFDAAENPKDGASLAAPRREKRSQRRRLRRHRHRNERIRRMLLKEGLLSEAELTGLFDGALEDIYALRTRALDEALTKQEFARVLLHLSQRRGFRSNRRATAAQEDGKLLDAVSENAKRMADCGYRTVGEMLYRDAVFAKHKRNKGGEYLTTVSRAMIEDEVKLVFASQRRLGSAFASEALEQGYLDILLSQRSFDEGPGGNSPYGGAQIERMIGKCTFYPEEPRAARACYSFEYFSLLQKVNHIRLQKDGESTPLTSEQRLQLIELAHKTENLDYARIRRALQIPDAYRENTVSYRIESDPAAAEKKEKFQYLRAYHTMRKAIDGASKGRFALLSQEQRDQIGTVLTLYKSQERISEKLTEAGIEPCDIAALESVSGFSKTGHISLRACKELIPYLEQGMNYNEACAAAGIEFHGHSGTERTVVLHPTPDDLADITSPVVRRAVAQTVKVINAVIRRYGSPVFVNIELARELAKDFTERKKLEKDNKTNRAENERLMRRIREEYGKMNPTGLDLVKLRLYEEQAGVCPYSQKQMSLQRLFEPNYAEVDHIIPYSISFDDSRRNKVLVLAEENRNKGNRLPLQYLTGERRDNFIVWVNSSVRDYRKKQKLLKPTVTDEDKQQFKERNLQDTKTMSRFLMNYINDHLQFGVSAKERKKRVTAVNGIVTSYLRKRWGITKIRGDGDLHHAVDALVIACATDGMIRQITRYAQYRECRYMQTDTGSAAIDEATGEVLRIFPYPWEHFRKELEARLSSDPARAVNALRLPFYLDSGEPLPKPLFVSRMPRRKVSGAAHKDTVKSPKAMAEGKVIVRRALTDLKLKNGEIENYFDPGSDRLLYDALKARLAAFGGDGAKAFREPFYKPRHDGTPGPLVKKVKLCEPTTLNVAVHGGKGVADNDSMVRIDVFRVEGDGYYFVPIYIADTLKPVLPNKACVAFKPYSEWRTMDDRDFIFSLYPNDLIRVTHKSALKLSRVSKESTLPESIESKTALLYYVSAGISGAAVSCRNHDNSYEIKSMGIKTLEKLEKYTVDVLGEYHKVEKERRMPFTGKRS* |
| MG125 effector | 11753 | MG125-2 effector | protein | unknown | MLSYAIGLDIGISSVGWATVALDGEDRPSGIIGMGSRIFDAAEQPKTGDSLAAPRREARSARRRLRRRRHRKERIRALILREGLLNETQLAALFDGQLEDIYALRVRALDEAITAEALARIMLHLSQRRGFLSNRKTAASKEDGELLAAVSANRARMQAHGYHTVGEMLLKDESYREHRRNKGGAYISTVGRDMIVEEVRQIFAAQRTFGNVAASEALEANYLEILLSQRSFDAGPGEPSPYAGSQIENMVGKCTLEPDESRAARATYSFEYFALLEAVNHIRLTGAGVSAPLTAEQRERLIALAHKTADLSYAKIRKELNIPAEQRFNAVSYGKSDSPDEAEKKTKLKQLKAYHQMRGAFEKASKGSFVLLTKEQRNAIGQTLSIYKTGDNIRRSLRDAGLSEEQIAIVEGLSFSGFGHLSVKACDKLIPCLEQGMNYNDACAAAGYAFRAHEGQEKKKLLPPLNAEAKDTITSPVVLRAVSQTIKVVNAIIRERGGSPTFINIELAREMAKDFSERTQIKHEHDENRKQNERLMERIKNEYGKSAPTGLDLVKLKLYEEQAGVCAYSLRQMSLEHLFDPNYAEIDHIIPYSISFDDGYKNKVLVLAKENRDKGNRLPLEYLNGKRREDFIVWVNSAVRDWKKKQRLLKEHITQEDEAKFKERNLQDTKTASRFLLNYIADNLAFAPFQTERKKHVTAVNGSVTAYLRKRWGITKTRANGDLHHAVDALVIACTTDGLIQKVSRYAQYQENRYSADGGLVVDLHTGEV |

TABLE 24-continued

Listing of additional protein and nucleic acid sequences referred to herein not included in the sequence listing

| Category | SEQ ID: | Description | Type | Organism | Sequence |
|---|---|---|---|---|---|
| | | | | | VAQFPEPWAHFRQELDARLSDDPARAVRGLGLAHYATGEIRPRPLFVS<br>RMPRRKITGAAHKETIKSPRALDEGLLITKTPLDALKLDKDSEIAGYYK<br>PESDRLLYEALKERLRQFGGDGKKAFAEPFRKPKHDGTPGPLVTKVK<br>LCEPTTLSVAVHGGLGAANNDSMVRIDVFHVEGDGYYFVPIYIADTLK<br>PELPNKACVAGKKPSEWKRMNPNDFVFSLFPNDLIYVSHRKGICLSLV<br>NKESTLPASREEKCTFLYLVKGKSSTASLECRNHDNTYHIKSLGIKTLE<br>KIEKYTVDVLGEVHKIEKEPRMPFTNMEG* |
| MG125 effector | 11754 | MG125-3 effector | protein | unknown | MYPYAIGFDIGITSVGWAVVALDGEDKPFGIINMGSRIFDAAEQSKTGA<br>SLAAPRREARSMRRRLRRHRHRLERIRHLLVAENVISQAELDALFEGK<br>LEDIYTLRVKALDTAVSHADFARILLHIAQRRGFKSNRKSSTSKEDGEL<br>LAAVSANRALMAEKGYRTVGEMLLKDPQYSGSKRNKGGKYLATVGR<br>DMVEEEVRAIFKAQREQGQAFAATELEEQYLEILLSQRSFDEGPGEGS<br>PYRGSQIEKMIGKCTLEAGEPRAAKASYSFEYFTLLQNINHLRLICGGE<br>SRPLSDAQREFLIALAHKTKDLNFSRIRKELDIPADTTFNAVSYKSADGY<br>EDAEKKAKFCYLKAYHQMKAAFNKLSKGHFDSLARQQKNELGRVLS<br>TYKTSANIRPRLAAAGLSEMEIDIAETMSFSKFGHISVKACDKLIPFLEK<br>GLKYNDACAAAGYDFKGYDSETRTRLLHPTEDDFADVTSPVVRRAISQ<br>TAKVLNAIIRERGNSPTFINIELAREMARDFTERSKMKKDMDENHARN<br>ERIMERIRTEYGKEHPTGQDLVKFKLWEEQHGECAYSQKHLSLKHLF<br>DPDYAEVDHIIPYSISFDDGYKNKVLVLAEENRNKGNRLPLLYLQGERR<br>ADFIVWVENSIHDYRKKQRLLKETITAEDEKGFKERNLQDTKTMSRFL<br>LNYISDHLEFSDFSTGRKKHVTAVNGAITSYLRKRWGIAKIRENGDLH<br>HAVDALVVVCTTDGMIQQLSRYSTLRECEYVQTEAGSIAVSMHTGEVL<br>KRFPYPWPEFRRELEARLGDDPRRAVISQRFPVYANGDIPVRKLFVSR<br>MPRRKVTGAAHKETIKSPKALNDGIVVVKRALTDLKLDPKTGEISNYY<br>MPQSDRLLYEALKEALKKHGGDAAKAFAAPFHKPKSDGTPGPVVNKV<br>KLCEPTTLNVAVLNGAGVADNDSMVRIDVFRVENDGYYFVPIYIADTL<br>KAELPNKACTRGKPYAEWREMDAEDFLFSLYPNDLIRVTSQKGLTLSK<br>AQKESTLPDTYETKQEMLYYTSASINTAAVACRTHDNSYEIKSMGIKTL<br>EKLEKFTVDVLGEYHKVEKEPRMAFCRK* |
| MG125 effector | 11755 | MG125-4 effector | protein | unknown | MRSYAIGLDIGITSVGWATLALDGNENPCGIIGMGARIFDAAEQPKTGE<br>SLAAPRRAARSSRRRLRRHRHRNERIKNLMVSKGVLSSDELETLFDGR<br>LEDIYALRVKALDGKVSRSEFARILLHLSQRRGFRSNRKNPSSKEDGAL<br>LKAVSENAERMEKHGYRTVGEMLLCDEAFKQHKRNKGGNYLTTVTR<br>DMVADEARAIFAAQRSFGSEYASEEFENEYLEILLSQRSFDEGPGGNSP<br>YGGSQIERMIGRCTFFPEERRAARATYSFEYFSLLQKVNHIRIVINGAA<br>ERLTAEQRNTVIELAHTTKDLSYAKIRKALKLSDGQLFNIRYSDKASAE<br>DTEKKEKLGVMKAYHQMRSAFEKQSKGRFDFVTTPQRNDIGTALSLY<br>KTSDKIREYLKDSGFDEIDMDAVESIGSFSKFGHISVKACDMLIPFLERG<br>MNYNEACAAAGLNFKAHDTGEKTRFLHPTEDDYEDITSPVVRRAISQT<br>VKVINAIIRKEGGSPTFINIELAREMAKDFTERNKLKKENDENRAKNEK<br>LLERIRTEYGKSDPSGLDLVKLRLYEEQGGVCMYSLRQMSLEKLFSPN<br>YAEVDHIVPYSKSFDDSRKNKVLVLTEENRNKGNRLPLQYLTGQRRDD<br>FIVWVNNNVRDYRKRRLLLKETLTDEDELGFKERNLQDTKTMSRFLL<br>NYISDNLEFAESTCGRKKKVTAVNGAVTAYMRKRWGITKIREDGDLH<br>HAVDAVVIACTTDGMIQRVSKYARLRECRYMPTEEGSLVIDDGTGEVL |

TABLE 24-continued

Listing of additional protein and nucleic acid sequences referred to herein not included in the sequence listing

| Category | SEQ ID: | Description | Type | Organism | Sequence |
|---|---|---|---|---|---|
| | | | | | HQFPYPWRDFRKELEARIGTDPARTINDLRLPFYMSSGMPLPEPIFVSRMPKRKVTGAAHKDTVKSPKELDKGCVVVKRPLTDLKLKDGKIENYYNPQSDRLLYDALKKALIEHGGDANKAFAGEFHKPKSDGTPGPIVSKVKLLEPTTLNVPVHGGAGVADNDSMVRVDVFLTKGKYNLVPIYVADTLKPELPNKAIAAHKPYSEWPEMSDDDFIFSLYPNDLVCVTHKKGIKLTVTNKNSTLPPTVEGKSFMLYYISTNISGGSIKGITHDNTYEIGGLGAKTLEKLEKYTVDVLGEYHKVGKEVRQPFNIKRR* |
| MG125 effector | 11756 | MG125-5 effector | protein | unknown | MRPYAIGLDIGITSVGWAALALDADENPCGIIDLGSRIFYAAEHPQTGESLAAPRREARGSRRRLRRHRHRNERIRSLMLEERLISQDELETLFDGRLEDIYALRVKALDEIVSRTDFARILLHISQRRGFKSNRKNPTTKEDGILLAAVNENKQRMSEHGYRTVGEMFLLDETFKDHKRNKGGNYITTVARDMVADEVRAIFSAQRELGASFASEEFEERYLEILLSQRSFDEGPGGNSPYGGSQIERMVGRCTFFPDEPRAAKATYSFEYFTLLQKVNHIRIVENGVSSKLTDEQRRIIIELAHTTKDVSYTKIRKALKLSDKQLFNIRYTDNLPAEDSEKKEKLGLMKAYHQMRSAIDRISKGRFAMMPRAQRNAIGTALSLYKTSDKIRKYLTDAGLDEIDINSADSIGSFSRFGHISVKACDMLIPFLEQGMNYNEACAAAGLNFKGHDAGEKSKLLHPKEEDYEDITSPVVRRAIAQTIKVINAIIRKEGSSPTFINIELAREMAKDFRERNRIKKENDDNRAKNERLLERIRTEYGKNNPTGLDLVKLRLYEEQSGVCMYSLKQMSLEKLFEPNYAEVDHIVPYSISFDDSRKNKVLVLTEENRNKGNRLPLQYLKGRRREDFIVWVNNNVKDYRKRRLLLKEELTAEDESGFKERNLQDTKTMSRFLLNYIADNLEFAESTRGRKKKVTAVNGAVTAYMRKRWGITKIREDGDCHHAVDAVVIACTTDAMIRQVSRYARFRECEYMQTESGSVAVDTGTGEVLRTFPYPWPDFRKELEARLANDPAKVINDLHLPFYMSAGRPLPEPVFVSRMPRRKVTGAAHKDTIKSARELDNGYLIVKRPLTNLKLKNGEIENYYNPQSDKCLYDALKNALIEHGGDAKKAFADEFRKPKSDGTPGPIVNKVKLLESATMCVPVHGGKGAAYNDSMVRVDVFLSGGKYYLVPIYVADTLKPELPNKAVTRGKKYSEWLEMADENFIFSLYPNDLICATSKNGITLSVCRKDSTLPPTVENKSFMLYYRGTDISTGSISCITHDNAYKLRGLGVKTLEKLEKYTVDVLGEYHKVGKEVRQPFNIKRRKACPSEML* |
| MG3 effector | 11757 | MG3-18 effector | protein | unknown | MSTDMKNYRIGVDVGDRSVGLAAIEFDDDGLPIQKLALVTFRHDGGLDPTKNKTPMSRKETRGIARRTMRMNRERKRRLRNLDNVLENLGYSVPEGPEPETYEAWTSRALLASIKLASADELNEHLVRAVRHMARHRGWANPWWSLDQLEKASQEPSETFEIILARARELFGEKVPANPTLGMLGALAANNEVLLRPRDEKKRKTGYVRGTPLMFAQVRQGDQLAELRRICEVQGIEDQYEALRLGVFDHKHPYVPKERVGKDPLNPSTNRTIRASLEFQEFRILDSVANLRVRIGSRAKRELTEAEYDAAVEFLMDYADKEQPSWADVAEKIGVPGNRLVAPVLEDVQQKTAPYDRSSAAFEKAMGKKTEARQWWESTDDDQLRSLLIAFLVDATNDTEEAAAEAGLSELYKSWPAEEREALSNIDFEKGRVAYSQETLSKLSEYMHEYRVGLHEARKAVFGVDDTWRPPLDKLEEPTGQPAVDRVLTILRRFVLDCERQWGRPRAITVEHTRTGLMGPTQRQKILNEQKKNRADNERIRDELRESGVDNPSRAEVRRHLIVQEQECQCLYCGTMITTTTSELDHIVPRAGGGSSRRENLAAVCRACNAKKKRELFYAWAGPVKSQETIERVRQLKAFKDSKKAKMFKNQIRRLNQTEADEPIDERSLASTSYAAVAVRERLEQHFNEGLALDDKSRVVLDVYAGAVTRESRRAGGIDERILLRGERDKNRFDVRHHAVDAAVMTLLNRSVALTLEQRSQLR |

TABLE 24-continued

Listing of additional protein and nucleic acid sequences referred to herein not included in the sequence listing

| Category | SEQ ID: | Description | Type | Organism | Sequence |
|---|---|---|---|---|---|
| | | | | | RTFYEQGLDKLDRDQLHPGEDWRNFTGLYPASQKKFLEWKDAATAL<br>GNVLAEAIEDDSIAVVSPLRLRPQNGSVHDETIDPVKKQTLGSDWPADA<br>VKRIVDPEIYLAMKDALGKLKELPEDSARSLELPDGRFVEADDEVLFFP<br>ENAASILTPRGVAEIGGSIHHARLYGWLTKKGELKVGMLRVYGAEFP<br>WLMRESGSRNVLSMPIHRGSQSFRDMQDTTRKAVESGEAVEFAWITQ<br>NDELEFDPDDYIAHGGKDELRQFLGFMPECRWRVDGFKKNYQIRIRPA<br>MLSREQLPSDIQRRLESKTLTKNESLLLKALDTGLVVAIGGLLPLETLK<br>VIRRNNLGFPRWRGNGNLPTSFEVRSSALRALGVEG |
| MG3 effector | 11758 | MG3-89 effector | protein | unknown | MSAPLNYRLGFDVGERSVGFAAVEYDDQGYPLKFLAIGSYLHDGGMD<br>PTTNKNPKSRKETRGVARRTMRMRRQKIKRLKKTDKVLRELGYQVS<br>HYTDEPQTYEAWYSRRLLATQKLSSEELNDHMVRAVRHMARHRGWR<br>NPWWSLTQLESASAEPSETFVQMFEKAQERWADELILPIEETTLGMLG<br>ALSDDNKVLLRPRTYDSKKEKHKEKLNVKGEEPVFFAKVRQEDILREL<br>RIICVRQGVESQYEELRKALFDQIRPHVPQENVGRDPLDPSQYRALRAS<br>LEFQRYRILDALANLGVREGRGKPRSLTGEERTQAWKFLSTYRDQKN<br>APTWGDVAEAMGVEPALLVAPVIDEVRLNKAPYFSSLVAVEKKLKKK<br>HQIYKWWVEASVESRGLLIRVLADATNATLDEASEAGLLELIEGLPEE<br>EREVLDGLSFETGRAAYSADTLTKLADYMEEHLAEGIGVHEARKAVF<br>GVDDSWQPPKATLEEATGQPTVDRVLTIVRRVVLSAQRQWGDPAEIM<br>VEYARTGLMGPAQLAEVKREIAKNRKERDRIRQDLKDGGVSEPKKRH<br>IMAHRIVQDQNCQCMYCGAMITAASCELDHIVPRAAGGSSRRENLAG<br>VCRDCNASKGGRMFADWAADNPRGVSLKDTLGRLRSWEPFKKADKK<br>RLLKLIERRLKQSVMSPEQIDERSLAPTAYAATAIRERLRRHFEDDAKP<br>IPRKDVVKAYAGGLTRESRRAGLIDEKLLLRGSRDKSRLDVRHHAIDA<br>AVLTMLNVPVARTLEERRLMKRERDLSARDNDWRDYTGTAEDKPKF<br>VQWKQAAGEMADLLIDAVDQDSIAVINPLRLRPQNGAVHDDTIRPLEE<br>RALGAEWDPATIKRVVDPSIYLALVDALGKSKSLPADSQRELVLDDGT<br>LMSADDSIALFSTNAASILTPRGAAEIGGSVHHVRLYAWRDRKGEIEVG<br>MQRVFGAEFPWLMRESGVKDVFKVPVHRGSQSYRDLQDGVRKQIESG<br>AAVEIGWITQGDEIQLNLDEVRDSMRSKELLTFLEIFPETRWRVDGLPD<br>NRRLRMRPVLLASEGIEEFLKNAPEDIQTIVVNFFKNGALLSVSKVLAL<br>TETKIIRYNHLGFPRWRGVGRPVSLDIQRAAREALEGKK |
| MG3 effector | 11759 | MG3-90 effector | protein | unknown | MSQEATKYRIGIDVGDRSVGLAAFEFDDAGFPLRKLAMVTYRHDGGL<br>DPTQNKSPKSRKETAGVARRVRRLRKRRKERLKKLDLKLLELGYPLP<br>EGEEAQTYQAWKSRALLTSQKIEDKAEQAEHLVRALRHMARHRGWR<br>NPWWQFGQLDSAPVPSETMVENLNHARLLWPGYITDQTTVGELGALA<br>ASPDILLRPRTRDIKKKPNGLHHQEGVRAVLGSKVRQEDLLAEVKKIW<br>QVQELPVSHYEELARALFEQVRPYVPAQNVGRDPLPGRHHLPRAPRAS<br>LEFTEFRIRQAVANLRVREGREKVPLTSGQHIAAVNYLMNYADKQPPT<br>WGDVAEQIGVEPTRLVAPVIDDVRLNKAPYNHSTSVFTRALPKKSEAM<br>QWWNSADVSLRSLLIIFLSDPTEEATAAADESGLSAIFESWPEKEREKL<br>EGLDFESGRAAYSIQSLIDLNQYMEEHQSDLHTARKEVFGVDDSWQPP<br>RENLHEPTGQPAVDRVLTIVRRFVMACERKWGKPDRIVIEHARTALM<br>GPTQRHEVLREIQRNRDANERIREELRADGLTSPTRADVRRHRVVQNQ<br>DCKCLYCGTMITTATAELDHIVPRAGGGSSKIDNLVAVCRGCNADKGR<br>IPFAVWAEQTSREGVSLDDALNRLWSFDKVVYKGVAGRKLKAQIARR |

TABLE 24-continued

Listing of additional protein and nucleic acid sequences referred to herein not included in the sequence listing

| Category | SEQ ID: | Description | Type | Organism | Sequence |
|---|---|---|---|---|---|
| | | | | | LRQAEEDEPIDERSLESTAYSAVAIRHRLETYFNTSRGLNRGDDGFTFIDVYAGALTREARRAGGIDEQILLRGQRDKNRFDVRHHAVDAAVMTVLDHSVARTLAQRNLIYREDRLKRRENQDDTRWREFTGLGGEAQEKFLVWKQKSYVLADLLAEAIAEDSIPVINPLRLTPRNGSVHKDTLSSLDKMYLGGSWSSKDIARVVDPDIYLALMELLGRATTLDEDPQRSLTVKGKVLQADQEIKLFPESAASILAGTGAVKIGDSLHHARLYAWPTKKGHEIGMLRVFGAEFPWLFKTYGTKNALTVPIHPGSQSYRDMKDTLRKKIESGEAREIGWITQGDEIEIKIESYLQENDELGRFINLIPENRWKIDGENDNGRLRLRPILLSYEEIPESYGEDVLGAKNHQLIRKVLERGAIITAGKILGAEGTKVLRRNHLGAPVWQGQQEARSLDISRAITEKLEG |
| MG3 effector | 11760 | MG3-91 effector | protein | unknown | MSMISTNDDRVEGMHMARYGERKYRVGIDVGDRSVGLAFIEFDEQDMPSELLRMFTVRHDGGIDPTTNKTPKSRKETAGVARRVRKMRKRRTKRLQELDALLMASGFPIVDVSVGETYECWQARAAAVEGFITDEQTRLETVSRAIRHMARHRGWRNPWLTWQGFRELEVPTANHRKNIESANSKLHLDLEDTSTLGQIAASASASNWMLRPRNGQKRKEASNPVLVAQVQQADQLAELYKILEVQRIDSTITEKIARAVFDQVRPYVPKGNIGLDELPGMGAYYRASKASLAFQEFRVRAAVANLRVKNSPRGQERLRLDPQDAQAVAEYLLTWREDQPPQWGDVANALSIDENLLVIPVFEDAFLKLAPYDRTSSDLEQRLSSSANKKKLAGVREWWDSADTQMRELFIEFITSPNESVYEEADESGFSDVFNGWSDEAKEVLLGMQFESGRSAYSVESLRRLNLRLRTGEVDLHEARRLEFGVDDTWRPSLPSIDERTGQPAVDRVLTIVRRAIMGAVDKWGVPEAVVVEHARSGFMGASARNDYLNEVSRRTATRAKLREIVKQQGVERPSDGDIHKWECINRQRCTCAYCGNEITFTTAEMDHIVPRAGGGSNVRENLVAVCRRCNSEKRNIPFAIFAESDAHPYTSLNETLTRVRNWDWSRDRSEQRLKNRMLQRLKRRESDPEIDERSLASTAYAAVEVRQRIAEYLGRITGEDELNRVQVYTGGATREARRAGKIDARIRIRGKDEKDRFDVRHHAIDAAVMATLNHSVAFTLRERAEMKRSATMNRYLDPNEEWKDYSGRTSSAQKRFTVWRQQAHRLADLIVDAVEADSVPVAQQLRLSASRGSVHKDTVSALVRKQLGAPWTAQEILQIVDPEIYVHLRDLAAQNKGVLELDPSRRIQLLSGVWISGSELVEVFPKAAASMKVSSGSVEIGEQIHHARVYAWRGTKGEFQYGILRVFTAELPWLQRQAQSKDLFTMNIDDRSMSYRDLLQTVRKKIESDEARCIGWLTQNDELVLNVEVLRQGSDKIAHFLSTYPESRWKLDGFPENRRFRIRPLYLSREGSDHLDPICAEILEKGAIVGTSNLLSNVHQIIRRDSLGFERWRSQGGLPASWSVPDSTADTVETGLK |
| MG3 effector | 11761 | MG3-92 effector | protein | unknown | MAQRRYRVGIDVGDRSVGAALVAFDDDGIPERVLHAVSYRHDGGIDPTTNKTPQSRKHTAGVARRVRRMRARRTKRLAALDRALIELGLPVRDVSDGETYEPWRMRARCVEGFIEDDAERRDAVSRALRHIARHRGWRNPWHSVRRERLESVPTATHQKNVAAAQAVFPGEIAADATVGQLGEVASRFNHMIRPRTGKKNPKQKTAVLNERVMQADQMAEVVAIWTTQRMPEAELNAVLELVFGQERPVVKAENIGRDELPGMGHLPRAPKASFEFQEFRIRATAATIGVRARQGSSKAERLDADAVDAVSHWLLEWDADDDPTWADVAVEALNLDPRFIKAPVFDDVRRMTAPVNRTARILRKALKKRHNAPVRTWWESASAESRAALVAFLVDPTDENEDLLDRTGLSDVVAAWPEEVLDDLTNLNYEVGRAAYSRESLSKMNTIMAEQRVGLHDARKIAFGVDDTWAPALPQLSEPTGQPTVDRVLPIVRRIVMAAYERYGVPEAVYIEHARSALLGPAARAEHQREVNANRREREKNRQILIEQGIDDPNRSDIRRWHQVQLQ |

TABLE 24-continued

| Category | SEQ ID: | Description | Type | Organism | Sequence |
|---|---|---|---|---|---|
| | | | | | NCLCLYCGQTISAAAGGAELDHVVPRAGGGSNRRENLVAVCRQCNSE KGKLPFAVFAARTQREGVSVEAALERVRGFQWRPADRAVKRGLVHR LKQTAADDPIDERSLESTAYSAVEVRRRLERFYSDHASPEAPRPEIFVFG GSITSEARKAGGIDAIIRLRGKDVKDRFDARHHAVDAAVMTLVDRSVA RTLQQRSDMRYAHRLTGSEPAWREHAGDSAAAQSRFAEWKKKSYRL AELLREAISADAIPVIFPLRLGVNRGSVHKDTVRAAVPKRLGDAWSAAE LDAVVSPAAHMALSSVFDGAAELPHDDGRMLTVRKRRLHADDTISLLP GHAAAIEVNGGVVEIGESIHHARLVAWRDRKGVIQFGMVRVFTAEIPF MQRLAGKKDVFSIPVHPSTLSYRGVQLRVRKALDAGIAVELGWITQGD EIEIGLDDVASMTPEFRQFIAEIPEQRWRVDGFKDGGRLRVRPALLSAE GDAAVSDLVSKTLDKGSFVNAAGFIGAPSSVVIRRSALGVPRWRSAQG HLPVSFSPYQRAENLL* |
| MG3 effector | 11762 | MG3-93 effector | protein | unknown | MNEGVIQYRIGIDVGQNGVGLAAIAFEAGNPSEVLAMVTHRHDAGLDP AAAKQGYSRKKTSGVARRTRRLRRNRARRLKKLDEILTSLGLEVPAH EVPQTWEAWEARAELQEFPIDNEQELHEKLVLAVRHMARHRGWKNP WWSWNTLWEAPTPTSNMNEIRDNARKVFADLPPTATIGQIGFVAAAT NRLLRPRKDTTKAKTKRPTPVLNAKVMQEDQLAELRSYWDKQNLPD EWLEKIAKAVFYQTRPKVKPELVGHDDLPGMTKLPRASRSSLEFQEFR IRAAIANLKVKVPGSRQENFLSVGDKNRIVDLLMGWDDDEAPTWADV AEELNISVRDLKRPEFDDSPLRVAPYDRSSNAIRNKLVSLRKDGKEALE WWDTADRDQRSLFATWLGDQSQHDDAFLETSGLSDIIASWSEGVMEK IDSLSLEPGRAAYSIESLKILNRHLAEGDNLHEARKHGFNVDDSWTPSL PRFEDRTGQPVVDRVIRIVHRFINGCVYKWGVPESIVIEHVRSGLLGPE ALLDYKRETTRHRNEREQIARDLKDQGISERPSSGDITRMRIVQEQQG VCLYCGTAINIHCELDHIVPRAGGGSNFRENLAAVCRECNRLKGKTPF ARWARETSQEGVSLEGALDRVKNFSVNGSTADLRNLKRRVSQRLRQT DEDQPIDERSMASTAYAALEVRDRVREFTSRFTDTDIPVEVYRGSITSAA RKAGHIDKLILLRDKDIKDRGDFRHHAIDAAVMTVINRSNSQVFAIREA MRSAHAMTGSEPNWKDFRGNSPRQEEKFIEFETRAAHLARIIRERIDA DRIPVISPLRLKPETGKVHADTIVPFDYKALESEWTDKDIVRVVDNELY LALVDALGGKKVLPTDKISVIDQDLAKDHRQVALYGTPSPQIPVRGGS AAISDSLHHFRVYAWKDKKGAIQFGQQRVFGAEFRAMWGDPRQVDV FTAPVPRWAFAHREMPPKVKAAIEAGNAKQIGWYTRNDEIELDLSEL MAQSNVLGEFLRELPEKSWRIRGSHSLSRLSLSPLYLSSEGTDLSEQSRP VQDAVSKGIPVSASSILDSESMIIRRGPLGIPKWNGGNATSYSFRQVAEE VLGTD |
| MG3 effector | 11763 | MG3-95 effector | protein | unknown | MTNHSPAGSISSTDWVLGVDLGQRSVGLAAVALDPDGTPTEILASNVV RIDGGLLPGSEESPVSRKAAAGMARRVRRLHRRRRARLKALDRRLMD LGFPVDDGPETYESWLDRARLVEGRIANETERKRATSRAVRHIARHRG WRNPWLSWSAFAELSTPSDNHRRNLAAAAERFDRETEGWTVGQLGA AGTDPRITIRPRTAKDSRRIVHGEAALLEHRVLQEDQLAELRQIWTTQ EWDPAELPELEKAVFTQAEPFVPPGNVGRDALPGMQTHPRAPRASLEF QRFRIQSVVGNLRVPVTERSGDLRPLTPEERERVTGLLERWHEREGHV PGERPTWRDVAEAVGVSLRNLRGRDTSDYATATPPTMETLDRLKAGI AALKPAAVRRDVAAWFDEAEDDQISAFVSYLADSTDASNEALDEAGLT DIITGWDEAALEKLGDLPLEPGRAAYSLESLNRLTGRMQADAVDLQEA |

TABLE 24-continued

Listing of additional protein and nucleic acid sequences referred to herein not included in the sequence listing

| Category | SEQ ID: | Description | Type | Organism | Sequence |
|---|---|---|---|---|---|
| | | | | | RKREFGVDDSWTPPTPSIETPTGMPAVDRNLVAVRRFVMSMVSQFGM PQLVVIEHVRESFLGVTAVEELRRQQRLDRRRRETAAKEVAAASGKEP RAADVRRYSLIQRQNGQCAYCGTAIGLRNSELDHIVPRAVGGASTRAN LLAVCRACNNLKGKQPFAVWAAADTRTDEDGEKLVSVEAALARTRS WMAPRPSIRERNELREIRQRLRQRESDEPIDERSMESTAYAATALVERV QNYLESQTPEGVQTPPVRVYRGSITASARKSSGVDKVIRLRGKSMKHR GDFRHHAIDAAVCALITPSVARTLAIRESLRTAHRFTGDEHDWKSFTG DSPQARAEHTAWTARMQTLAKLLRDAVDADQVPVSIPLRLGRRVGRV HEDKVRPFDSRPLGGTWSAKELERIVDRRLYTALHHVAASATSGVEVT PELCTELGSSMGATVKLYGSPAAQIPVRGGSARLGAIHHARLYAWRGT RGIEFGMMRVFAGELTAMWPSPATDVLTAPVPEWSMSYRRTAPAVM QQLRSDTAVQVGWIAPGDEIVVLPPREGARASSLDSLVSSVGEDRWTV TGFERATTINVAPRLLSAEGISEETPKAVTSVLNRPGRLAASSLLPRIRVI RRDALGRERRRGGGRLPSSFVPFEVAEQRLQGD |
| MG3 effector | 11764 | MG3-96 effector | protein | unknown | MSTDMKNYRIGVDVGDRSVGLAAIEFDDAGFPIQKLALVTFRHDGGLD PTDNPKSRKETRGEARRRMRMTRRRKQRLCDLDKVLENLGYTVPEGP EPETYEAWTSRALLASIKLASADELNEHLVRAVRHMARHRGWANPW WSLDQLERASQEPSETFEIILARARELFGEKVPANPTLGMLGALAANN EVLLRPRAEKKKKTGYVRGTPLLAAQVRQIDQVAELRRICEVQDIEEQ YETLRNAIFAHKVAYVPTERVGKDPLAPSKNRTIRASLEFQEFRILDSV ANLRVRTDSRAKRELTEGEYDAAVEFLMGYTAKEQPSWADVAEEIGV PGNRLIAPVLEDVQQKTAPFDRSSAAFEKAMSKKTEARQWWESNDDD QLRSLFIMFLADATNDTEEAAAVAGLPELYMSWPAEEREALSNIDFEK GRVAYSHETLSKLSEYMHEYRVGLHEARKAVFGVDDTWRPPLAKLEE PTSQPTVDRVLTILRRFVLDCERQWGRPQAITVEHARIGLMGPVQRQK ILNEQKKNRGENERIRNELRESGVENPNRAEVRRHLIVQEQECQCLYC GTMITTTTSELDHIVPRAGGGSSRRENLAAVCRYCNGKKNRKLFYEW AGPVKMQETIDRVRQLRAFKDSKKAKMFKNQIRRLKQTEADEPIDERS LASTSYAAVAVRERLEQHFNEGLTLDDKSRVVLDVYAGAVTRESRRAG GIDERILLRGERDKNRFDVRHHAVDAAVMTLLNRSVALTLEQRSQLRR AFYEQGLDKLDRDQLKPEEDWRDFIGLYPASKEKFLEWKKTATVLGD VLAEAIEEDSIAVVSPLRLRPQNGSVHKETIAAVKKQTLGSSWSADAVK RIVDPEIYLAMKDALGKLKELPEDSARSLELSDGRYIEADDEVLFFPEN AASILTPRGVAEIGGSIHHARLYSWLTKKGDLKVNVLRVYGAEFPWL MRESGSSDVLRMPIHPGSQSFRDVQEETIEMIEGGFAKEIAWITQNDEL EFDPVEYINLPGRSDKLTRFLIYMPETRWRVDGFPESRNLRIRPLMLSQ EDLPSEIKKHKEEKQLSDEEKLLVEALEKGLIITSSKLLGLKSIKVIRRN NLGFPRWRGNGNLPTSFEVRSSALRALGVEG |
| MG3 effector | 11765 | MG3-103 effector | protein | unknown | MSADSLNYRIGVDVGDRSVGLAAIEFDDDGFPIKKLAMVTFRHDGGM DPATGKTPKSRKETAGVARRTMRMRRRKKKRLKDLDKKLRDLGYFV PRDEEPQTYEAWSSRARLAESRFEDPHERGEHLVRAVRHMARHRGW RNPWWSFSQLEEASQEPSETFGRILERAQHEWGERVSDNATLGMLGA LAANNNILLRPRRYEHNPKTGKNAEKLNVRGQEPILLDKVRQEDVLAE LRRICKVQGIEDQYPELAHAVFTQVRPYVPTERVGKDPLQPMKIRASR ASLEFQEFRIRDAVANLRIRVGGSERRPLTEEEYDRAVDYLMEYSDTTP PTWGEVADELEIAENTLIAPVIDDVRLNVAPYDRSSAIVEAKLKRKTQA |

TABLE 24-continued

Listing of additional protein and nucleic acid sequences referred to herein not included in the sequence listing

| Category | SEQ ID: | Description | Type | Organism | Sequence |
|---|---|---|---|---|---|
| | | | | | RQWWDDDANLDLRSQLILLVSDATDDTARVAENSGLLEVFESWSDEEKQTLQDLKFDSGRAAYSIDTLNKLNAYMHEHRVGLHEARQNVFGVSDTWRPPRDRLDEPTGQPTVDRVLTIVRRFILDCERAWGRPQKIVVEHARTGLMGPSQRADVLKEIARNRNANERIRQELREGGIEAPNRADIRRNSIIQDQESQCLYCGKEIGVLTAELDHIVPRAGGGSSKRENLAAVCRACNASKGSRPFAVWAGPARLERTIQRLRELQAFKTKSKKRTLNAIIRRLKQREEDEPIDERSLASTSYAATSIRERLEQHENDDLPDGFAPVSVDVYGGSLTRESRRAGGIDKSIMLRGQRDKNRFDVRHHAIDAAVMTLLNPSVAVTLEQRRMLKQENDYSSPRGQHDNGWRDFIGRGEASQSKFLHWKKTAVVLADLISEAVEQDTIPVVNPLRLRPQNGSVHKDTVEAVLERTVGDSWTDKQVSRIVDPNTYIAFLSLLGKKKELEADHQRLVSVSAGVKLLADERVQIFPEEAASILTPRGVVKIGDSIHHARLYGWKNQRGDIQVGMLRVFGAEFPWFMRESGVKDILRVPIPQGSQSYRDLAATTRKFIENGQATEFGWITQNDEIEISAEEYLATDKGDILSDFLTVLPENRWKVVGIGDNRRFKIRPLLLSNEIIPDTLNGRSIKSEERDLIVSVLDKGVRVVASTLLTLPSTKIIRRNNLGIPRWRGNSHLPTSLDIQRAATQALEGRD |
| MG15 effector | 11766 | MG15-166 effector | protein | unknown | MKYIIGLDMGITSVGFASMMLDDNDEPCRIIHMGSRIFEAAENPKDGSSLAAPRRENRSMRRRLRRKRHRKERIKNLIIQNNMMTADEIDAIYNSGKELPDIYKVRAEALDRKLDTEEFVRLLIHLSQRRGFKSNRKVDAKEKGSEAGKLLSAVKSNKELMVERNYRTIGEMLYKDEKFAEFKRNKADDYSNTFARSEYEEEIREIFRAQQEYGNPYATEELKDSYLEIYLSQRSFDEGPGGDSPYAGNQIEKMVGSCTLEPDEKRAAKATFSFEYFNLLTKVNSIKVVSSAGKRSLNEDERKRVIKLAFAKNAISYASIRKELNLGDGERFNISYSQSDKSIEEIEKKTKFTYLTAYHTFKKAYGSVFNEWSAEKKNHLAYALTAYKNDNKIKKYLTENGFDAVETDIALTLPSFSKWGNLSEKALNKIIPYLEQGMLYHDACTAAGYNFKADDTDKRMYLPAHEKEAPELGDITNPVVRRAISQTIKVVNAIIREMGESPCFVNIELARELSKNKAERSKIEKGQKENQARNDRIMERLRNEFGLLSPTGQDLIKLKLWEEQDGICPYSLKPIKIENLFDVGYTDIDHIIPYSLSFDDTYNNKVLVMSSENRQKGNRIPMQYLDGKRRDDFWLWVGSSNLSRRKKQNLLKETLSDDDLSGFKKRNLQDTQYLSRFMLNYLKKYLTVAPNATGRKNTIQAVNGAVTSYMRKRWGIQKVREDGDTHHAVDAVIISCVTAGMTKRISEYAKYKETEYQNPETGEYFDVNKNTGEVINRFPMPYAWFRNELLMRCSEDPSRILHEMPLPNYATDEAVAPIFVSRMPKHKVRGSAHKETIRQSFEEDGKKFTVSKTPLTDLKLKNGEIENYFNPESDVLLYNALKERLIAFGGDAKKAFEAPFHKPKSDGSEGPLVKKVKLICKSTLTVPVLKNTAVADNGSMVRVDVFFVEGEGYYLVPIYVSDTVKKELPNKAIVAHKPYEEWKEMREENYVESLYQNDLIGIKLKKEMKFSLVQKNSTLPKNINVKDGLFYYKGTNISGANISVINNDNTYTVESLGVKRIPVIEKYQVDVLGNVSKVGKEKRVRFQ* |
| MG15 effector | 11767 | MG15-191 effector | protein | unknown | MKYIIGLDMGISSVGFATMMLNEKDEPCRIMHMGSRIFEAAEHPKDGSSLAAPRRENRSMRRRLRRKCHRKERIKNLIVSNNILTADEIDTIYNSGKDLTDIYQIRAESLDRKLNTEEFVRLLIHLSQRRGFKSNRKVDAKEKGSEAGKLLSAVNSNKELMTEKNYRTIGEMLYKDDKFAVFKRNKADDYTNTFAREEYEEEIQKIFSAQQEYGNQYATDELKEGYLEIYLSQRSFDEGPGGNSKYAGDQIEKMVGFCTLEPDEKRAAKATYSFEYFNLLTKVNSFKILSAEGKRSLNENERQKIIKLAFNKNAISYASLRKELSVGYSERFNISYSQSD |

TABLE 24-continued

Listing of additional protein and nucleic acid sequences referred to herein not included in the sequence listing

| Category | SEQ ID: | Description | Type | Organism | Sequence |
|---|---|---|---|---|---|
| | | | | | KSIDEIEKKTKFTYLTAYHTFKKAYGSALIEWSTEKKNHLAYALTAYK NDNKIKNCLTEHGFNETECEIALTLPSFSKWGNLSEKALNKIIPYLEQG MLYHDACTAAGYNYKADDTDKRMYLPAHEKEAPELENISNPVVRRAV SQTIKVINAIIREIGESPCFVNIELARELSKNKTERNKIEKGQKDNQARN DRIMERLRNEFGLISPTGQDLIKLKLWEEQDGICPYSLQAISIERLFEAG YTDIDHIIPYSISFDDTYNNKVLVMSSENRQKGNRIPMQYLQGKRRDEF WLWVDSSNLSRRKKQNLLKETLSDDDLSGFKKRNLQDTQYLSRFMLN YLKKYLKLAPNATGRKNTIQAVNGAVTSYMRKRWGIQKVRENGDTH HAVDAAVISCVTAGMTKRISEYAKYKETEYQYPENGEYFDVDKRTGE VINRFPMPYPWFRNELLMRCSENPSRILQEMPLPNYAADEAVDPIFVSR MPKHKAKGSAHKETIRKAFEEDGKKYTVSKVPLEDLKLKNGEIENYF NPKSDTLLYNALKSRLIEFCGDAKKAFEAPFYKPKSDGSKGPLVKKVKI VNKATLTVPVLKNTAVADNGSMVRVDVFFVEGEGYYLVPIYVADTVK KELPQKAIIANKTYENWKEMKEENFVFSLYPNDLIRIKSKKEMKFNLV NKESTLAPHYQSKDAYVYYKGSDISTAAITAITHDNTYKLRGLGVKTLL AIEKYQVDVLGNIIKIGREKRMRFR* |
| MG15 effector | 11768 | MG15-193 effector | protein | unknown | MNYRLGLDIGITSVGWAVLEHDSSEEPFRIADLGVRIFDRAEHPKDGSA LALPRREARSSRRRIRRHRHRLERIKALLESQGIITIEKLQEVYHGSKEL TDIYELRCLGLDNLLTQEEWARVLIHLAQRRGFKSNRKKEIKENKKEK NEDGKLLAAVRDNQALMQEKNYRTIGEMFYRDDKFSLNKRNKSELYS HTVGREQILDEIAQLFTAQRRLGNSYAGEKVEQLYTDIVSRQRSFDEGP GTPSPYAGNLIERMRGKCTFEKEEPRAAKACYSFELFNLLQKINSLRID DKNSASRPLNKEERQLLIQSAHEKADIKYTDLRKKLQLSPEQRENTLSY GRDDVEEIEKKNKFNYLKAYHDIRIALDKVSKGRIKQLPVEHIDMIGEI LTLYKNEDRITSKLRKTGLTEYDIEELLSLSYSGFGRLSLKAIKNILPYL QEGHIYSEASTLAGYNFRGHDNVVKQMYLPANNEQLQDITNPVVRRA VSQTIKVINAVIRKYGSPQLICIELSREMGKNFFDRKRIEKQIKENTDLN DAVRNKIIEYGHLNPTGLDIVKMKLWQEQDGRCAYSGEPISIQDLFDA GIADVDHIIPYSVSFDDSYANKVLVKSSENRQKGNLLPLEYMKNNPNKQ EKFIVWVNTNVRNFRKQQRLLKKTITEEDRNKWKERQLNDTKYISRF MLNYIRDYLEFAPAENIGKRKVISVNGNITAYMRKRWGLKKDRLAGD LHHAQDAVVVACVTEGMIQKITRYSQYCEAKNNRSHFVDYETGEVIDT LRNRFGADFVEPWDNFKIEMVSRLSDDPALRIDAYKLDNYLDLKDIKPI FISRMPNRKNKGAAHQETIRSSRLTGEGLVVSKINITKLKLDADGEIAN YYNPKSDMRLYNALKNRLQQFNGNGEAAFKEPVYKPAAPGKTISPVK KVKVIDKSNLNVAVGKGVAANGDMLRIDVFKKGDGYYWVPIYVADTV KETLPNKACVHSKPYELWKEMDDNDFIFSLYPNDLIRFIPNNGEEAFM YYIKAGISTASITVESHDRSQSIPSLGVKTLKILEKWNVDVLGNRTLVKN EKRQYYPGQTTR* |
| MG15 effector | 11769 | MG15-195 effector | protein | unknown | MKYGIGLDIGIASVGSAIVLLDGSDEPYKIYRLSSRVFPKAETDKGESLA SDRRNNRGMRRRLRRRRHRKERIRNLIYDVFDVNEDYITEIYAESGLK DIYQIRYEALDRKLDKDEFIRLLIHLSQRRGFKSNRKSDVGKKDDGKLL DAVKKNTELRQKMYRTIGEMLYCDDRFADSKRNTEGNYKNTFSRSEY GEEIKCIFENQRAFGNEYATEDFEEKFIGIIMSQRSFDEGPGPGKDSKYS GNLIERLVGKCTFEREEMRAPKASYTFEYFNLLSKINAIKIVSANNTRC LTEEQRAIIKNLAFSKNDLSYKSLRKALGLNEDELFNISYTDSDTNKKK |

TABLE 24-continued

| Listing of additional protein and nucleic acid sequences referred to herein not included in the sequence listing | | | | | |
|---|---|---|---|---|---|
| Category | SEQ ID: | Description | Type | Organism | Sequence |
| | | | | | AKNKKGTADKFSERDAVEDKTKFSYLKAYHTFKKAYGDEYDRWSTD<br>KKNYLGYVLTVFKTDKNVELKLRERNFSDDEINIAQTIPSFSKLGNLSV<br>KAMNKMIPFLENGEIYNKAAEMAGYNFKADDKCAGMYLPANESKAPE<br>LGDIANPVVRRSVSQTIKVINAIVREMGESPVYVNIELARDLAKSHDER<br>EKIEKNNNANRQKNDKLMEELRKEFKLANPKGEDLIKLKLWNEQNGR<br>CMYSYEPIVRERLFEPGYAEIDHIIPYSISFDDTMSNKVLVKAKENRDK<br>GDRLPLQYMTGKKADDFRVRVSNSILSRKKKNNLLKEQLTEEDRKSF<br>KQRNLQDTQYISRFMMNFIKKYLKFAGEAKIVAVNGRATDYMRKRW<br>GIRKIRADGDTHHAVDACVVACATHGMVQRISEYSKYKETEYIDDDGR<br>IYDINKKTGELTDRFPMPYPMFRKELEMLTSNDPQRILSQSKFPNYSGD<br>EQLEPIFVSRMPQHKVTGAAHEDTLRKPVTENGQNYVVQKVKLTKLK<br>LNDNGEIENYYMPQSDKLLYNALKERLAEYGGDGEKAFKNLTEPFRK<br>PKSDGTPGPIVTKVKTIEKQTCGVPLADNTTIADNGPMVRVDVFYVAG<br>EGYYLVPIYVSDTVKKELPNRACVANKPYSEWKVMDDKNFLFSLYNN<br>DLVKITFKREKKFSLVNKDSTLDKEHRTKSELLYYKGTNIHTASITVIT<br>HDNTYIFEGMGVKTLISIEKYEVDVLGRVRKVNKEKRMGF* |
| MG15 effector | 11770 | MG15-217 effector | protein | unknown | MRYVLGLDIGIASVGWAVLELDSFDEPFKIIDLNSRIFTKAENPQDGSSL<br>AKPRREARGNRRRLRRRRHRLDRIKHLIYVVGLMSKEGYDKLYTSGF<br>DKDVYTLRAEGLDRSLSAAEWTRVLIHIAKHRGFKSNRKSTTVAGEDG<br>KVLQAVKENQEILSKYRTVGEMFHNDDKFKSRKRNTTDSYILCVSRH<br>MLKDEIKALFTAQRSFNNPFTDEKFEAKYIEIFESQRAFDEGPGSESPYG<br>GNQIEKMIGQCTFEDGEKRAPKASYSFMRFNLLQKVNHIRIKSSSATRA<br>LSEEERSIIIALAYKSPNFTYGSIRKAIKLPYDMTFSDVYYKYEKGLSEE<br>ELIDKNEKSNKIKSLEPYHTIRKALDKVYKNRIEELSEDNINDIAYAFSV<br>YKTNAKISQKLKECGIDNKDIEALINNLGTFAKFGHLSVKACKKINKYL<br>ETGMTYDKACEAAGYDFKGHCGEKTKFLSGAADEIKEIPNPVVKRALS<br>QTIKVINAVVRKYGSPVEVHVELAREMARSKKDRDKINSIMKDNQAAN<br>DRIRGILKNEFNINNPTGIDILKYRLYQEQQGICVYSQKVMDLERVMK<br>DGKYAEIDHILPYSRSFDDSYNNKVLVKTEENRLKRNRTPYEYMQDNE<br>VKYKGFCEIVKSIIHNPTKVSNLLRENYNPQLVKDWKARNINDTRYISK<br>FVYNFLNDHLLLADGMRKRRIIAVNGAVTGYIRKRLGINKIRANGDTH<br>HAVDAVVIACVTQGVISKVTKYSQWQEVFYKNNNTGKLVDYETGEIIT<br>KDNFDEFIDSKFPEPWPLFRKELEARAGTNPKYEIECLRLDTYSPEEVT<br>SLRPMFVSRMPNRKVTGQAHQETIRSSRMANDGMTVSKVPLTSLKLS<br>KDGQSIEGYFSPESDRLLYEALLNRLQGFGGKADKAFTEPFYKPKNDG<br>SKGPIVKAVKITAPSTLNVRINNGKGLADNGSMVRIDVFHITAGKGAGY<br>YLVPIYVADTKKDKLPSKAIVAHKKYDEWKLMDEKDFVFSLYPNDLIY<br>VEKKGNIELSLDKKIEKDSTLPKKISSPQGYFYYVKAGIGDGSVQIKSH<br>DGVYLLPSMGVKTLKLLRKCVVDELGNISFVGKEKRQHF |
| MG15 effector | 11771 | MG15-218 effector | protein | unknown | MNKSVKFGLGLDVGIASIGWATVALDEKGEPYKLLNLGSRIFDKAENP<br>KDGSSLAMQRRQFRSQRRLIRRRRHRLDRVIFLFQKIGLCTNDELNKL<br>FQTPAPKNVYELRVDALDRKLDKQEWIRVLYSVLKHRGFKSNRKNAK<br>SEDGLLLKAIQSNEEIIFNNGYRTVGEMLFKDPLFTNSKRNKGGSYKNC<br>VSRISIQKELDLLFEKQREYGNEFTSDYFKESFLNIFLAQRNFDEGPGAP<br>SCYGGNLIEKMIGYCALKKDKKRAPKASLSFALFSFWSKINNIRYYDSN<br>RCKEYSISTEQARKVLQKALIKSDLNYSDIRKIIGLDDGCYFKDITYTSK |

TABLE 24-continued

Listing of additional protein and nucleic acid sequences referred to herein not included in the sequence listing

| Category | SEQ ID: | Description | Type | Organism | Sequence |
|---|---|---|---|---|---|
| | | | | | KSKKTKKKQQAKNNNESYLSIDGLTLVEDVLTPEKDANEQSVDTILDIE KKSKIKFFNSFISIKKAANGMLDHLNPFDPEDRKIFNRISYAFTVSKNDD GIAGYLNEIDISAEIKESLINNLDGFSQFGHISEEACEKLLPFLENGCDYT SACVEAGYVSSSDDVVGKDLLPARSSELDDIVNPVVRRSVSQLIKVVNSI IRENGKPEYINVEFARDLARSFADRREITKEQEDRKAHNEKVRKIIEET FGRARASSKDILIYKLWMEQESKCIYSGKHIDAHRLFEPGYVEVDHILP FSKSFDDSMTNKVLVFKEENQNKANRTPLEYMRASKPMYVDSYLAMV KFLYKSNFKKLQNLTTEFCGNDREEWSTSNLNDTRYIAKFIHKYIKDH LYPAKTGIKRVRAVNGRITSLLRHFWGIKKIRENGDLHHAVDAAVISV TTDMIIKKFSEASKRHEEYDEKIMVEKPWEMFVDEISARISENPADQVE RLGLSTYSDEEKSSLKTPFVSRMPRHKVTGSVHDSTLRSPVLLKQGINA YVSKREINDKLLKVFDDKKCEFFNMQLDAKFYASLKSYLEDKNENKG EFHKIKKDGSLGPVVRKVKVVENCSSGVFLNNGKAFAKNGDMIRIDVF QVKEGKDKGFYFVPIYVADKVKDKLPSRAVIQGKDPKDWKEMKDEDF IYSLYPNDLIYFSSKKIVGFKNNNKSSEILGVDMSEGYLYYTGADISTASI NVDFVDNSFSKHGLGVKTLKEFRKFTIDVLGNIHEVKKEKRLVFGRK |
| MG15 effector | 11772 | MG15-219 effector | protein | unknown | MNYILGLDIGIASVGWAAVALDANDEPCKILDLNARIFEAAEQPKTGAS LAAPRREARGSRRRTRRRRHRMERLRHLFAREELISAENIAALFEAPA DVYRLRAEGLSRRLDEGEWARVLYHIAKRRGFKSNRKGAASDADEGK VLEAVKENEALLKNYKTVGEMMERDEKFQTAKRNKGGSYTFCVSRG MLAEEIGELFAAQREQGNPHASETFETAYSKIFADQRSFDDGPDANSRS PYAGNQIEKMIGTCSLETDPPEKRAAKASYSFMRFSLLQKINHLRLKD AKGEERPLTDEERAAVEALAWKSPSLTYGAIRKALPLPDELRFTDLYY RWDKKPEEIEKKKLPFAAPYHEIRKALDKREKGRIQSLTPDALDAVGY AFTVFKNDAKIEAALSAAGIDGEDAVALMAAGLTFRGFGHISVKACRK LIPHLEKGMTYDKACKEAGYDLQKTGGEKTKLLSGNLDEIREIPNPVV RRAIAQTVKVVNAVIRRYGSPVAVNVELAREMGRTFQERRDMMKSME DNNAENEKRKEELKGYGVVHPSGLDIVKLKLYKEQGGVCAYSLAAMP IEKVLKDHDYAEVDHILPYSRSFDDSYANKVLVLSKENRDKGNRTPME YMANMPGRRHDFITWVKSAVRNPRKRDNLLLEKFGEDKEAAWKERH LTDTKYIGSFIANLLRDHLEFAPWLNGKKKQHVLAVNGAVTDYTRKR LGIRKIREDGDLHHAVDAAVIATVTQGNIQKLTDYSKQIERAFVKNRD GRYVNPDTGEVLKKDEWIVQRSRHFPEPWPGFRHELEARVSDHPKEM IESLRLPTYTPEEIDGLKPPFVSRMPTRKVRGAAHLETVVSPRLKDEGM IVKKVSLDALKLTKDKDAIENYYAPESDHLLYEALLHRLQAFGGDGEK AFAESFHKPKADGTPGPVVKKVKIAEKSTLSVPVHHGRGLAANGGMV RVDVFFIPEGKDRGYYLVPVYTSDVVRGELPMRAVVQGKSYAEWKLM REEDFIFSLYPNDLVYIEHEKGVKVKIQKKLREISTLPREKTMTSGLFY YRTMGIAVASIHIYAPDGVYVQESLGVKTLKEFKKWTIDILGGEPHPV QKEKRQDFASVKRDPHAAKSTSSG |
| MG3 effectors | 11794 | MG3-42 effectors PI domain | protein | unknown | HGDVLTATIPASTFSFRNTPATLRKKLLAGEAVSVGWLTQNDEIEIEVD EFACGNTSFAKFLTEIPEKRWRVDGFYDNRRLRIRPAYLSAEGLTDNHS KVVHETLEKGQFVNAGALLSASRTLLIRRTALGAPRWKLDSSGLPVSF SPLKLAEEAL |

TABLE 24-continued

Listing of additional protein and nucleic acid sequences referred to herein not included in the sequence listing

| Category | SEQ ID: | Description | Type | Organism | Sequence |
|---|---|---|---|---|---|
| MG3 effectors sgRNA | 11795 | MG3-42 effector sgRNA | Nucleotide (RNA) | unknown | (N22)<br>GTTGGGAATCGTCACTGAAAAGTGACGATTCTCAACAAAAGACTTT<br>TGTCTTGATTTCTTTATCCCCCGGCATTTTGTGCCGGGGGATTCGTT<br>ATT |
| MG3 effectors tracr | 11796 | MG3-42 effector tracr | Nucleotide (RNA) | unknown | GCATCGTTTGAAGAAGTGACGATTCTCAACAAAAGACTTTTGTCTT<br>GATTTCTTTATCCCCCGGCATTTTGTGCCGGGGGATTCGTTATT |
| MG16 effectors | 11797 | MG16-3 effector | protein | unknown | MATKKILGLDLGTNSIGWALIETEDSNPKSILAMGSRIVPLSTDDSTQFA<br>KGQAITKNADRTQKRTARKGLNRYQMRRAMLTEELRRHGMLPERTD<br>ENIMDLWRLRSDAATDGKQLSLPQIGRVLYHINQKRGYKHSKADNSA<br>NTKQTKYVEAVNQRYRDIQACHQTIGQYFYEQLLSSAVQTPSGSYYTY<br>RIKDKVLPREAYIAEFDQIMKVQRVFYPDVLTDELVDTLRNHIIFYQRP<br>LKSCKHLVSLCEFEKRPFKREDGQIVYSGPKCAPRTSPLAQFCTVWEA<br>VNNITLTNRQNETFEITQEQRVAMADFLNQHDKMGVKDLQKILGISPK<br>DGWWAGKAIGKGLKGNTTFTQLREALGNLPNAEHLLKMKLSMVDAA<br>VDTTTGELIRQVSPQVEEEPLFRLWHLVYSLQNEDELRKALRKQFGID<br>DEEVLDKLCKIDFVKPGYANKSHKFIRKLLPYLMEGYQYHEACAHIGV<br>NHSDSLTAEQNAARPLLDKIPLLEKNELRQPVIEKILNQMINVVNALKA<br>EYGDIDDVRIELARELKSSKDEREAAFKRNNENERQNKIYENRIREYGI<br>QPSRSRIQKYKMWEESNHLCFYCGKPVNVTDFLAGAEVEIEHIIPQSVL<br>FDDSYSNKVCACRACNQAKGNLTAREFMEKHSKEEYDSYLRRVDDAF<br>NAHRISKTKRDHLLWRKEDIPQDFIDRQLLQSQYIAKKAAEILRQGYR<br>NVYATSGSVTDFLRHQWGYDEILHRLNLPRYQQVEGLTEDVTYDHCG<br>QEHQQERIKGWTKRLDHRHHAIDALTIALTQQSVIQRLNTLNNSREQ<br>MFDELGKRTDTPEYTEKRSLLEKWVDAQPHFSVQEVTDKVDGILVSFR<br>AGKRAATPAKRAVYQNGKRHIVQTGLQVPRGALSEETVYGKLGNKY<br>VVKYPLGHQSMKMDDIVDPTIREIVRTRLNAFGGKAKDAFAEPLYSDA<br>AHQMQIKTVRCYTGLQDKAVVPVRFNAQGEPVGFVKMGNNHHIAIYR<br>DAKGQYQESVVSFWQAVERKRYGIPVVIEQPHEVWDKLINSDNIPQDF<br>LETLPHDDWQFVVSLQQNEMFILGMDDADFEAAMEQKDYRTLNKYL<br>YRVQKISSKEYCFRYHTETSVDDKYDGVINKSISMELQKLKRLTSISAFF<br>SQHPHKVRVNLLGEVSAL |
| MG86 effectors | 11798 | MG86-1 effector | protein | unknown | MKKILSFDLGITSIGYSVLTEDEAQKYSLLDYGVSMFDKPTDKDGNSK<br>KLLHAQALSTKKLYKLRKERKKNLALLFEKYALAKASKLLEQEKKNL<br>YMYKWQLRAKKVFEERLSIGEIFTILYHIAKHRGYKSLDSGDLLEELC<br>VELGIKIDVKKEKKDDEKGKIKQALSTIESLRKEYPKKTVAQIIYEVEL<br>QKERPVFRNHDNYNYMIRREHINDEIATIIRKQKEFGNFENIDSEVFIVD<br>IIAAIDDQKESTNDMSLFGKCEYYPKEHVAHQYSLLSDIFKMYQAVANI<br>TFNKEKIKITKEQIRLLTEDFLNKIKKGKSVKELKYKDVRKILKLDESV<br>KIFNKEDSYQRAGKKVEHTITKFHFVDNLSKIDKSFIEDIFNADESYVL<br>MREIFDVIHKEKSPKRIYEQLKSKVSSEAVIIDLIRYKKGSSLNISSYAMA<br>KFLPYFEEGMTLDAIKEKLDLGRKEDYSVYKKGIKYLHISTYEKDDDL<br>EINNHPVKYVVSAVLRVVKHLHAKHGTFDEIKVESTRELSLNDKVKKE<br>IDKANKAREKEIEKIISNDEYQKIAKEYGKNIHKYARKILMWEAQERFD<br>VYSGKSIGIDDIFSNRVDVDHIVPQSLGGLYVQHNLVLVHRDENLQKSN<br>QLPMNYITDKEAYINRVEHLFSEHKINWKKRKNLLASNLDEIYKDTFES |

TABLE 24-continued

Listing of additional protein and nucleic acid sequences referred to herein not included in the sequence listing

| Category | SEQ ID: | Description | Type | Organism | Sequence |
|---|---|---|---|---|---|
| | | | | | KDLRATSYIEALTANILKRYYPFIDEKKSVDGSAVRHIQGRATANIRKV LGVKTKSRESNIHHGVDALLIGVTNPSWLQKLSNIFRENFGKIDDEARK NIKKALPYIDGVEVKDIVKEIEQKYNSYGEDSIFYKDIWGKAKTVNFW VSKKPMISKVHKDTIYADKGNGIFTVRESIIAKFINLKITPTTFPEDFMK KFHKEILEKMYLYKTNSNDVICKIVQQRAEEIKELLWSFEFLDVKNKE EMQEAKANLESLVHRELFDNNGNVVRKVKFYQTNLTGFKVRGGLAT KEKTFIGFRAFKKDKKLEYKRIDVSNFEKIKKSNDGSFKVYKNDIVFFV FDEEKYKGGKIVSFLEDKKMAAFSNPKYPANIQAQPESFLTIFKGKANS HKQVSVGKAKGIIKLKVDILGNIESYQVLGNAKSKLLDEIKSIVSH |
| MG86 effector sgRNA | 11799 | MG86-1 effector sgRNA | Nucleotide (RNA) | unknown | (N20)GUUUUAAUACCCGAAAGGGUAUUAAACUAAGGUCACUUUUUA GUGGCUGACUUUAGAGUAUGGCUUUGGCUAUACUCCAUUUU |
| MG94 effector | 11800 | MG94-1 effector | protein | unknown | MRKKIRYVIGLDIGIASVGWAALLLDENDNVCGIVRAGVHTFDEAVVG QSKITGAAYRRGYRSGRRSIRRKVNRIQRVKNLLQRLNIISKKDLEEYF SGAVENIYYLRCAAIQNEPAYILNNKELAQLLIYYAKHRGYKSNTSYEQ KTDDSKKVLSALSENKKYMLEKGYQTAGEMLYRDEKFRRKRYGSSEE CELLLVRNSGDDYSHSISRELLVEEVHVIFARQRELGNKLTTKELEDQF VEIMQSQRNYDEGSGEGSPYGGNLIEKMVGECTFEKGEKRACKASYTS ERFVLLEKLNHLRIQSKNGDVRALTEEERDAIIKLAYKNKDVKYKALR TILKLNPDERFGGLTYSRGDIENSTEGKSVFVSLEYWYEIKKVLGLFYD DLDNEETQQLLDSIGTILTCYKSDDLRRRKFEQLHLEQEKIEHLLALNY TKFQNLSFKAMKNIMPELEKGLSYTEACSNAGYGDKETIEGKNKYISK ELLNNTLDSIMNPTVKRAVRRTIRILNELIKQYGSPVEVHVEMARDLTH SQTVTNKMKKRQDENKAEKEEAKRFICENFGKTEAQVSGKDILRYRL WKSQNQIDIYSNTMIPVSDILDYEKYEVDHIIPYSCSENDSFNNKMLVRK KDNQDKKNRTPYEYIGSDEKKWEAFATCANTYVMNYGKRKNMLTKV PASNTGEWMSRNLNDTRYTTKVVTDLIRKHLKFEAYVDQKRKKHIYPI NGGITAKLRYEWGLEKDREKSDKHHAQDAVVIACCTDGMIQRLSRQY MLQEIGIVTWKNHKLVDRRTGEIVEETNLPWECFREEVEMFMADSPE DYIEKAKKNGYKGEAPKPIFVSRLPQKKTTGKINEDTLRSVRIDSKGKA RFVNKTKLQDLKLVEVDGKKQIKDYYRPEDDKLLYDKLLERLVKNDD AKVVFAEPFYKPKKDGSDGPIVRSVKTYGKTVKNQVLVGDGVAERGG IYRCDVFKRKDEYYAVVVYYRDLYIGNLPNNAAHFDIEMKKGEFEFSL YKDDLIRFVKDGKEQYAYYKYINANNSQITYTEHDTSKETKCTTIRTLD KFQKMNVDLLGNIYSSDKEEREWN* |
| MG94 effector | 11801 | MG94-1 effector PI domain | protein | unknown | KTVKNQVLVGDGVAERGGIYRCDVFKRKDEYYAVVVYYRDLYIGNLP NNAAHFDIEMKKGEFEFSLYKDDLIRFVKDGKEQYAYYKYINANNSQI TYTEHDTSKETKCTTIRTLDKFQKMNVDLLGNIYSSDKEEREWN* |

SEQUENCE LISTING

The patent contains a lengthy sequence listing. A copy of the sequence listing is available in electronic form from the USPTO web site (https://seqdata.uspto.gov/?pageRequest=docDetail&DocID=US12435323B2). An electronic copy of the sequence listing will also be available from the USPTO upon request and payment of the fee set forth in 37 CFR 1.19(b)(3).

What is claimed is:

1. An engineered nuclease system comprising:

a) an endonuclease or a ribonucleic acid encoding said endonuclease, wherein said endonuclease comprises a sequence having at least 80% sequence identity to SEQ ID NO: 1433; and b) an engineered guide ribonucleic acid structure configured to form a complex with said endonuclease, said engineered guide ribonucleic acid structure comprising:

i) a guide ribonucleic acid sequence configured to hybridize to a target deoxyribonucleic acid sequence; and ii) a tracr ribonucleic acid sequence configured to bind to said endonuclease, wherein said engineered guide ribonucleic acid structure comprises a sequence having at least 80% sequence identity to non-degenerate nucleotides of SEQ ID NO: 11145.

2. The engineered nuclease system of claim 1, wherein said engineered guide ribonucleic acid structure comprises a sequence having at least 90% sequence identity to non-degenerate nucleotides of SEQ ID NO: 11145.

3. The engineered nuclease system of claim 2, wherein said engineered guide ribonucleic acid structure comprises the non-degenerate nucleotides of SEQ ID NO: 11145.

4. The engineered nuclease system of claim 1, wherein said tracr ribonucleic acid sequence comprises a sequence having at least 80% sequence identity to SEQ ID NO: 11201.

5. The engineered nuclease system of claim 4, wherein said tracr ribonucleic acid sequence comprises a sequence having at least 90% sequence identity to SEQ ID NO: 11201.

6. The engineered nuclease system of claim 5, wherein said tracr ribonucleic acid sequence comprises the sequence of SEQ ID NO: 11201.

7. The engineered nuclease system of claim 1, wherein said engineered guide ribonucleic acid structure comprises:

a) at least two ribonucleic acid polynucleotides; or b) one ribonucleic acid polynucleotide comprising said guide ribonucleic acid sequence and said tracr ribonucleic acid sequence.

8. The engineered nuclease system of claim 2, wherein said tracr ribonucleic acid sequence comprises the sequence of SEQ ID NO: 11201.

9. The engineered nuclease system of claim 6, wherein said endonuclease comprises a sequence having at least 90% sequence identity to SEQ ID NO: 1433.

10. The engineered nuclease system of claim 9, wherein said endonuclease comprises the sequence of SEQ ID NO: 1433.

11. The engineered nuclease system of claim 6, wherein said endonuclease comprises a RuvC_III domain, wherein said RuvC_III domain comprises a sequence having at least 80% sequence identity to SEQ ID NO: 3253.

12. The engineered nuclease system of claim 11, wherein said RuvC_III domain comprises the sequence of SEQ ID NO: 3253.

13. The engineered nuclease system of claim 12, wherein said endonuclease comprises an HNH domain, wherein said HNH domain comprises a sequence having at least 80% sequence identity to SEQ ID NO: 5068.

14. The engineered nuclease system of claim 13, wherein said HNH domain comprises the sequence of SEQ ID NO: 5068.

15. The engineered nuclease system of claim 6, wherein said endonuclease is a class 2, type II Cas endonuclease.

16. A method of editing a locus in a cell, said method comprising contacting to said cell:

a) an endonuclease or a ribonucleic acid encoding said endonuclease, wherein said endonuclease comprises a sequence having at least 80% sequence identity to SEQ ID NO: 1433; and b) an engineered guide ribonucleic acid structure configured to form a complex with said endonuclease, said engineered guide ribonucleic acid structure comprising:

i) a guide ribonucleic acid sequence configured to hybridize to a target deoxyribonucleic acid sequence; and ii) a tracr ribonucleic acid sequence configured to bind to said endonuclease, wherein said engineered guide ribonucleic acid structure comprises a sequence having at least 80% sequence identity to non-degenerate nucleotides of SEQ ID NO: 11145.

17. The method of claim 16, wherein said engineered guide ribonucleic acid structure comprises a sequence having at least 90% sequence identity to non-degenerate nucleotides of SEQ ID NO: 11145.

18. The method of claim 17, wherein said engineered guide ribonucleic acid structure comprises the non-degenerate nucleotides of SEQ ID NO: 11145.

19. The method of claim 16, wherein said tracr ribonucleic acid sequence comprises a sequence having at least 80% sequence identity to SEQ ID NO: 11201.

20. The method of claim 19, wherein said tracr ribonucleic acid sequence comprises a sequence having at least 90% sequence identity to SEQ ID NO: 11201.

21. The method of claim 20, wherein said tracr ribonucleic acid sequence comprises the sequence of SEQ ID NO: 11201.

22. The method of claim 17, wherein said tracr ribonucleic acid sequence comprises the sequence of SEQ ID NO: 11201.

23. The method of claim 21, wherein said endonuclease comprises a sequence having at least 90% sequence identity to SEQ ID NO: 1433.

24. The method of claim 23, wherein said endonuclease comprises the sequence of SEQ ID NO: 1433.

25. The method of claim 21, wherein said endonuclease comprises a RuvC_III domain, wherein said RuvC_III domain comprises a sequence having at least 80% sequence identity to SEQ ID NO: 3253.

26. The method of claim 25, wherein said RuvC_III domain comprises the sequence of SEQ ID NO: 3253.

27. The method of claim 26, wherein said endonuclease comprises an HNH domain, wherein said HNH domain comprises a sequence having at least 80% sequence identity to SEQ ID NO: 5068.

28. The method of claim 27, wherein said HNH domain comprises the sequence of SEQ ID NO: 5068.

29. The method of claim 21, wherein said endonuclease is a class 2, type II Cas endonuclease.

30. The method of claim 24, further comprising contacting said cell with a deoxyribonucleic acid repair template.

* * * * *